(12) United States Patent
Nobles et al.

(10) Patent No.: US 6,562,052 B2
(45) Date of Patent: May 13, 2003

(54) SUTURING DEVICE AND METHOD

(75) Inventors: Anthony A. Nobles, Fountain Valley, CA (US); Steven E. Decker, Anaheim, CA (US); Benjamin G. Brosch, Mission Viejo, CA (US)

(73) Assignee: Sutura, Inc., Fountain Valley, CA (US)

( * ) Notice: Subject to any disclaimer, the term of this patent is extended or adjusted under 35 U.S.C. 154(b) by 75 days.

(21) Appl. No.: 09/881,550

(22) Filed: Jun. 14, 2001

(65) Prior Publication Data
US 2002/0045908 A1 Apr. 18, 2002

Related U.S. Application Data

(63) Continuation-in-part of application No. PCT/US01/08050, filed on Mar. 13, 2001, and a continuation-in-part of application No. 09/524,211, filed on Mar. 13, 2000, which is a continuation-in-part of application No. 09/471,866, filed on Dec. 23, 1999, which is a continuation of application No. 09/231,177, filed on Jan. 14, 1999, now Pat. No. 6,117,144, which is a continuation-in-part of application No. 09/036,437, filed on Mar. 9, 1998, now abandoned, which is a continuation-in-part of application No. 08/702,315, filed on Aug. 23, 1996, now Pat. No. 5,860,990.

(60) Provisional application No. 60/002,769, filed on Aug. 24, 1995.

(51) Int. Cl.⁷ .............................................. A61B 17/04
(52) U.S. Cl. ..................................................... 606/144
(58) Field of Search ................................. 606/139, 144, 606/145, 146, 147

(56) References Cited

U.S. PATENT DOCUMENTS

| | | |
|---|---|---|
| 4,553,543 A | 11/1985 | Amarasinghe |
| 4,841,888 A | 6/1989 | Mills et al. |
| 5,059,201 A | 10/1991 | Asnis |
| 5,222,508 A | 6/1993 | Contarini |
| 5,304,184 A | 4/1994 | Hathaway et al. |
| 5,374,275 A | 12/1994 | Bradley et al. |
| 5,383,897 A | 1/1995 | Wholey ....................... 606/213 |
| 5,403,329 A | 4/1995 | Hinchcliffe |
| 5,417,699 A | 5/1995 | Klein et al. |
| 5,431,666 A | 7/1995 | Sauer et al. |
| 5,458,609 A | 10/1995 | Gordon et al. |
| 5,462,560 A | 10/1995 | Stevens |
| 5,462,561 A | 10/1995 | Voda |
| 5,470,338 A | 11/1995 | Whitfield et al. |
| 5,476,469 A | 12/1995 | Hathaway et al. |
| 5,476,470 A | 12/1995 | Fitzgibbons, Jr. |
| 5,496,332 A | 3/1996 | Sierra et al. |
| 5,499,991 A | 3/1996 | Garman et al. |
| 5,501,691 A | 3/1996 | Goldrath |
| 5,507,755 A | 4/1996 | Gresl et al. .................. 606/139 |
| 5,527,321 A | 6/1996 | Hinchliffe |
| 5,527,322 A | 6/1996 | Klein et al. |
| 5,540,704 A | 7/1996 | Gordon |
| 5,562,686 A | 10/1996 | Sauer et al. |
| 5,562,688 A | 10/1996 | Riza |
| 5,573,540 A | 11/1996 | Yoon |

(List continued on next page.)

FOREIGN PATENT DOCUMENTS

| | | |
|---|---|---|
| EP | 941698 | 9/1999 |
| WO | WO 97/07745 | 3/1997 |

*Primary Examiner*—Gary Jackson
(74) *Attorney, Agent, or Firm*—Knobbe, Marteens, Olson & Bear, LLP

(57) ABSTRACT

A suturing device and method allows a physician to remotely suture biological tissue. The device includes an elongate body, first and second arms operably connected to the elongated body, whereby each arm mounts an end portion of a suture, and first and second needles, each needle having a distal end and being mounted such that the distal end of the needle is movable to engage respective end portions of said suture. The suturing apparatus further includes an actuator which drives the needles to engage the suture non-simultaneously.

61 Claims, 85 Drawing Sheets

U.S. PATENT DOCUMENTS

| | | |
|---|---|---|
| 5,613,974 A | 3/1997 | Andreas et al. |
| 5,613,975 A | 3/1997 | Christy |
| 5,632,752 A | 5/1997 | Buelna |
| 5,700,273 A | 12/1997 | Buelna et al. |
| 5,779,719 A | 7/1998 | Klein et al. |
| 5,792,152 A | 8/1998 | Klein et al. |
| 5,810,849 A | 9/1998 | Kontos |
| 5,817,110 A | 10/1998 | Kronner |
| 5,836,955 A | 11/1998 | Buelna et al. |
| 5,860,990 A | 1/1999 | Nobles et al. |
| 5,860,991 A | 1/1999 | Klein |
| 5,868,762 A | 2/1999 | Cragg et al. |
| 5,944,730 A | 8/1999 | Nobles et al. |
| 5,954,732 A | 9/1999 | Hart et al. |
| 5,972,005 A | 10/1999 | Stalker et al. .............. 606/144 |

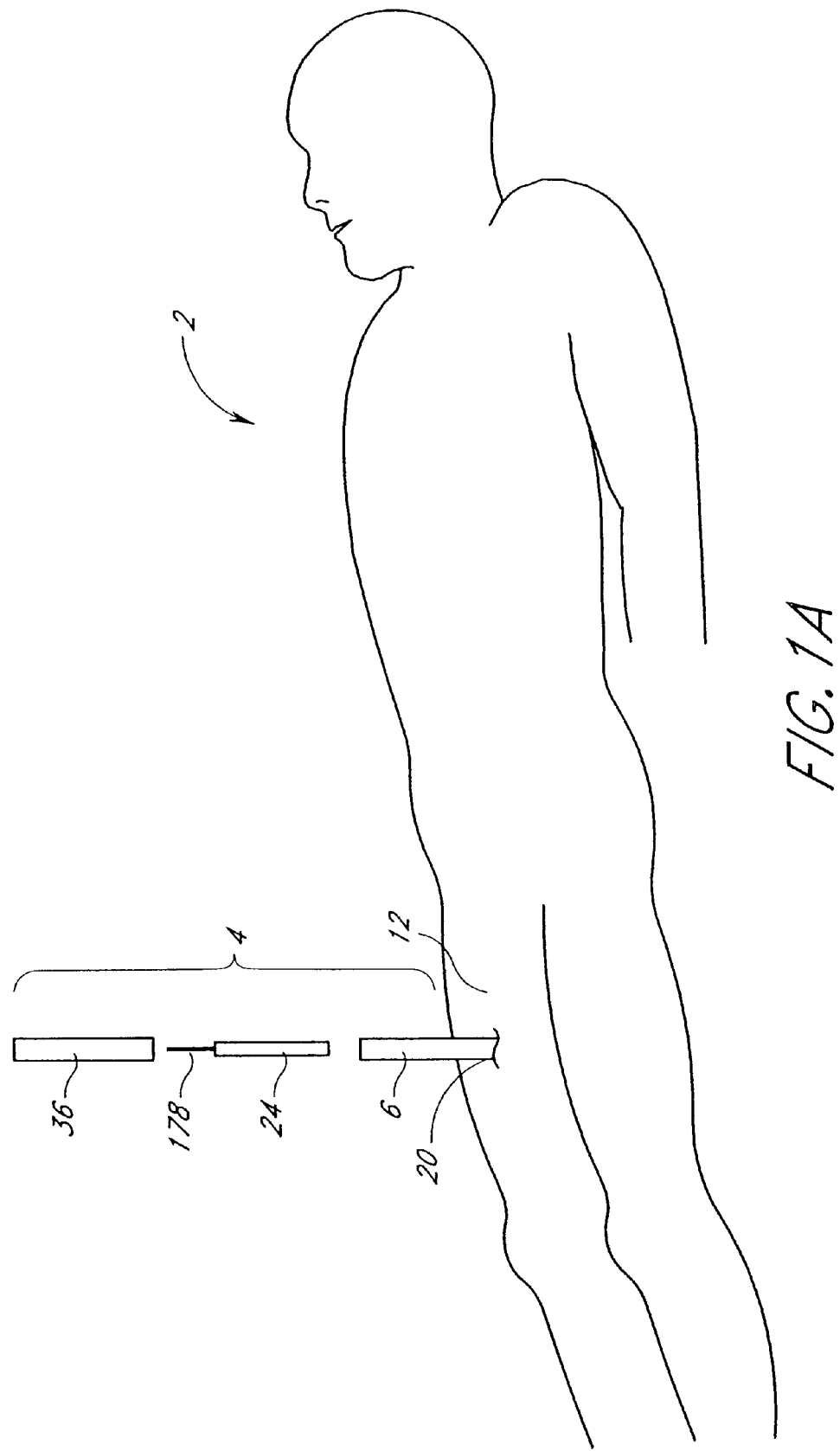

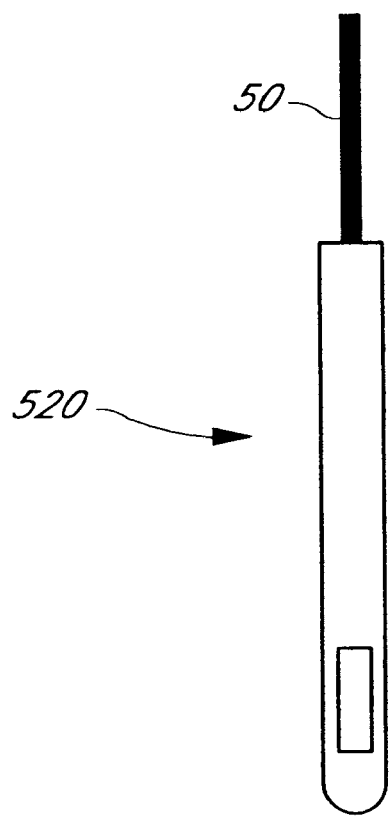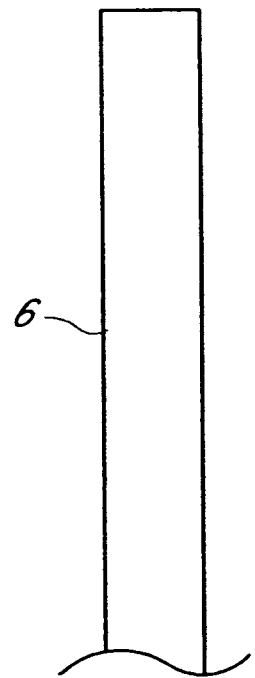
FIG. 1C

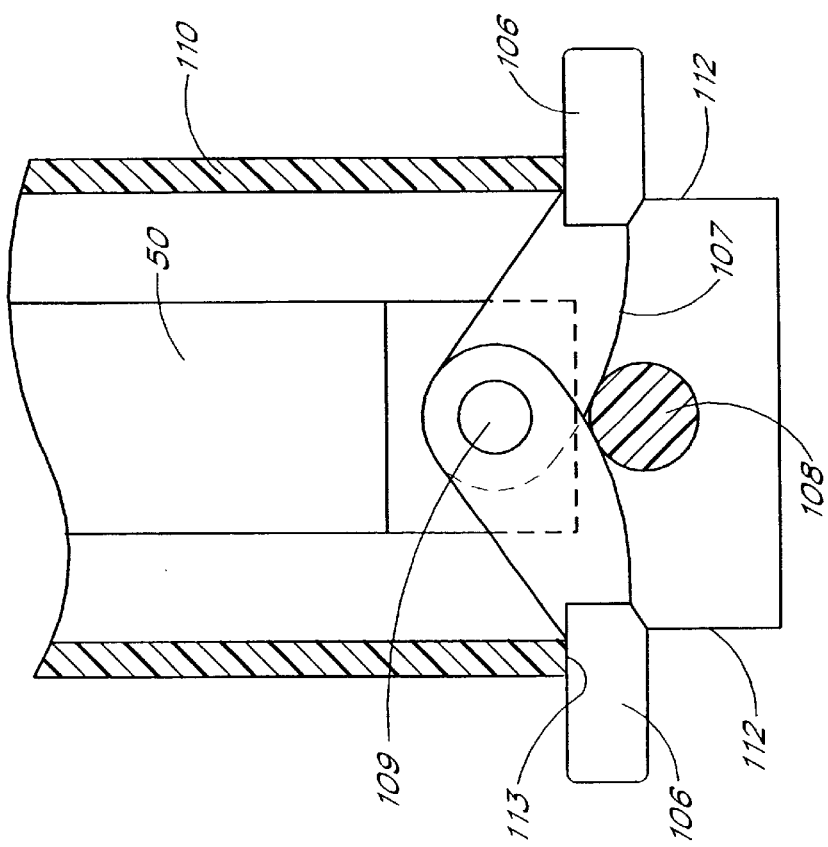
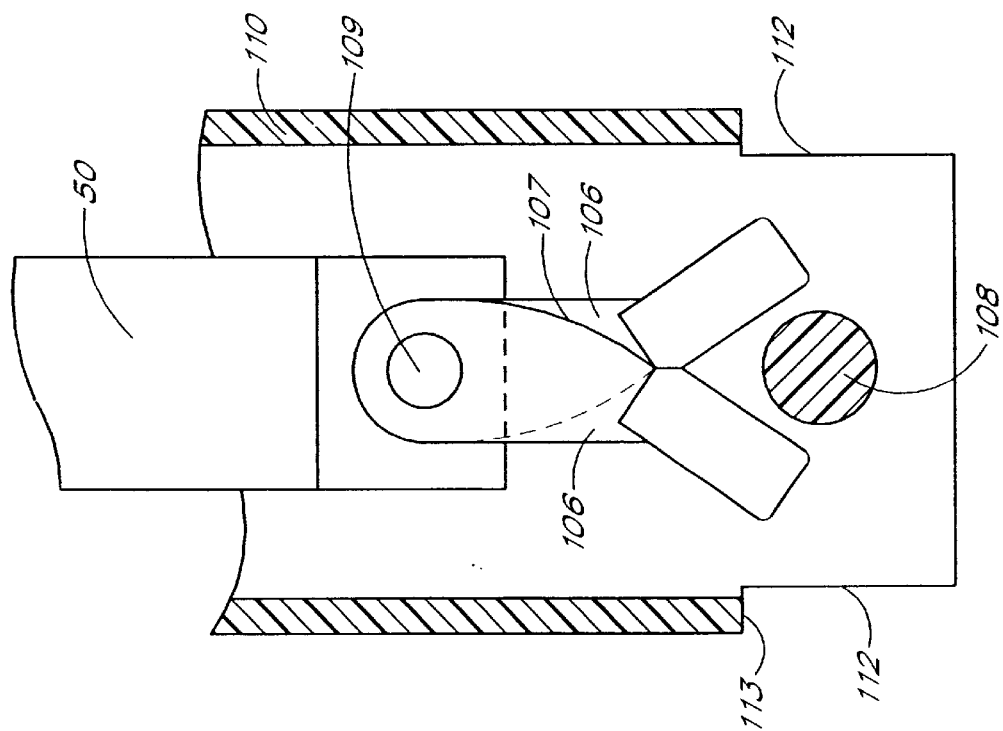

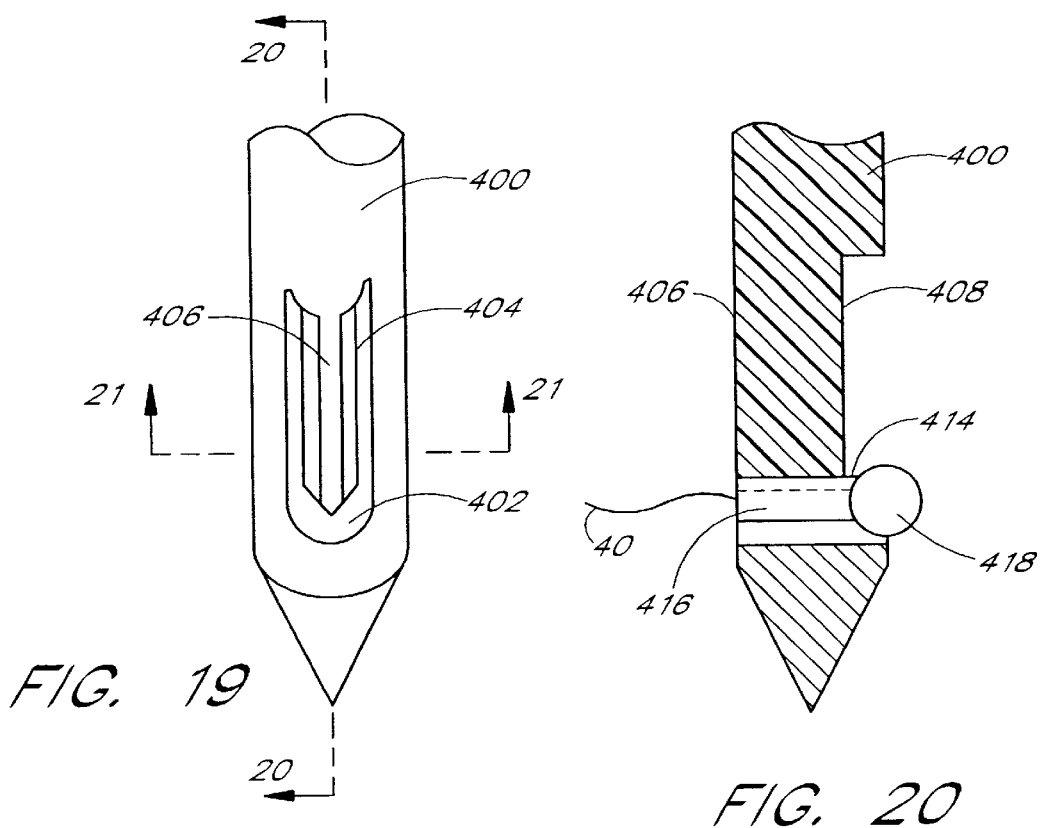
FIG. 19
FIG. 20
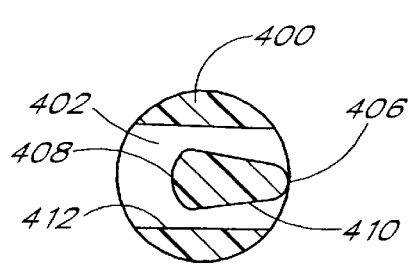
FIG. 21
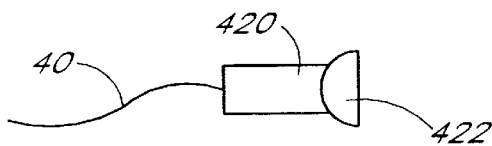
FIG. 22
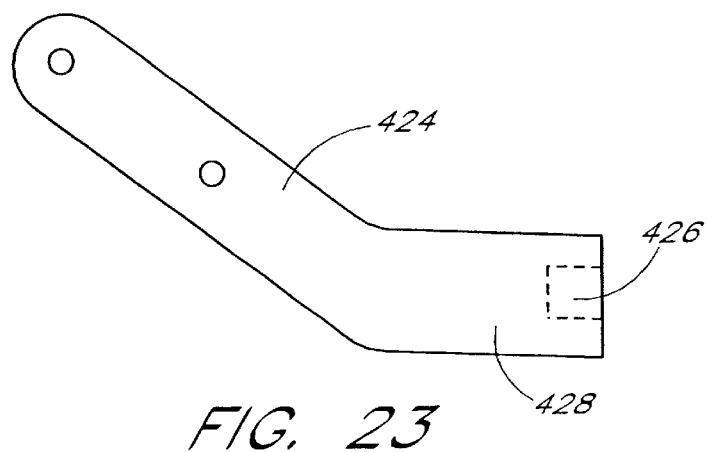
FIG. 23

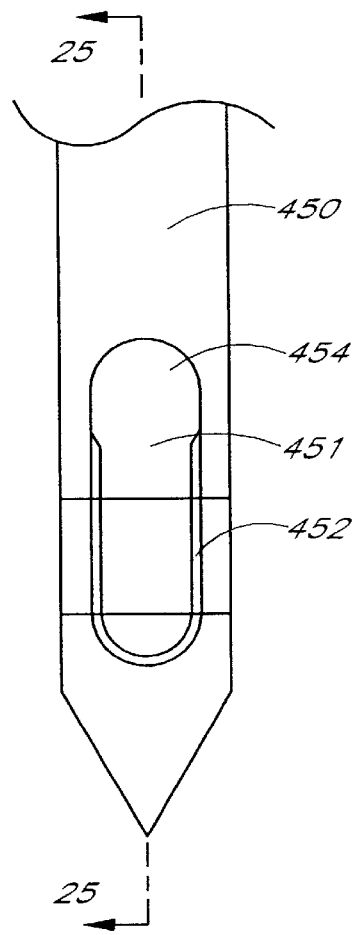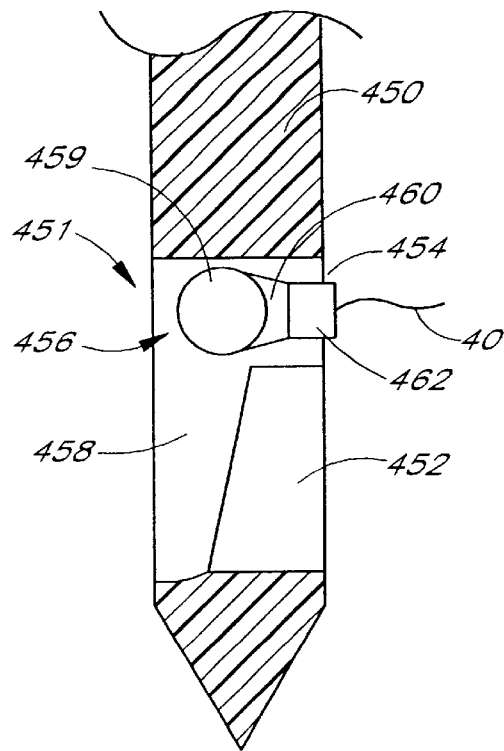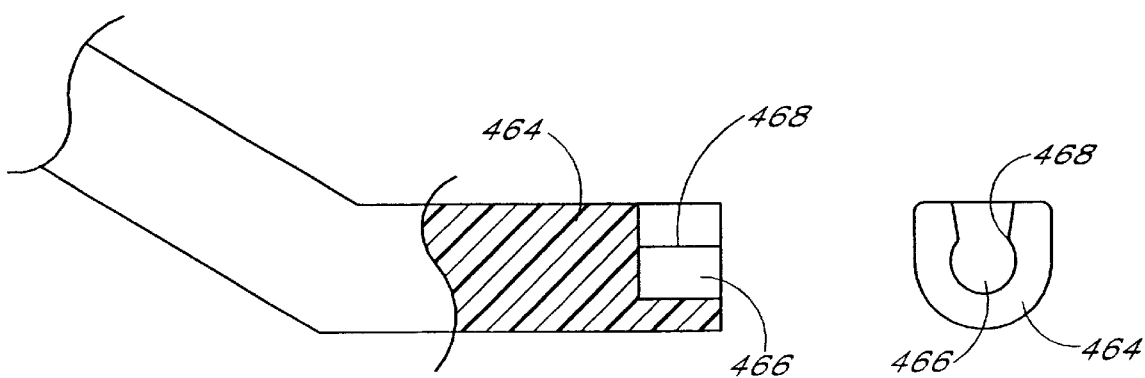
FIG. 24  FIG. 25
FIG. 26  FIG. 27

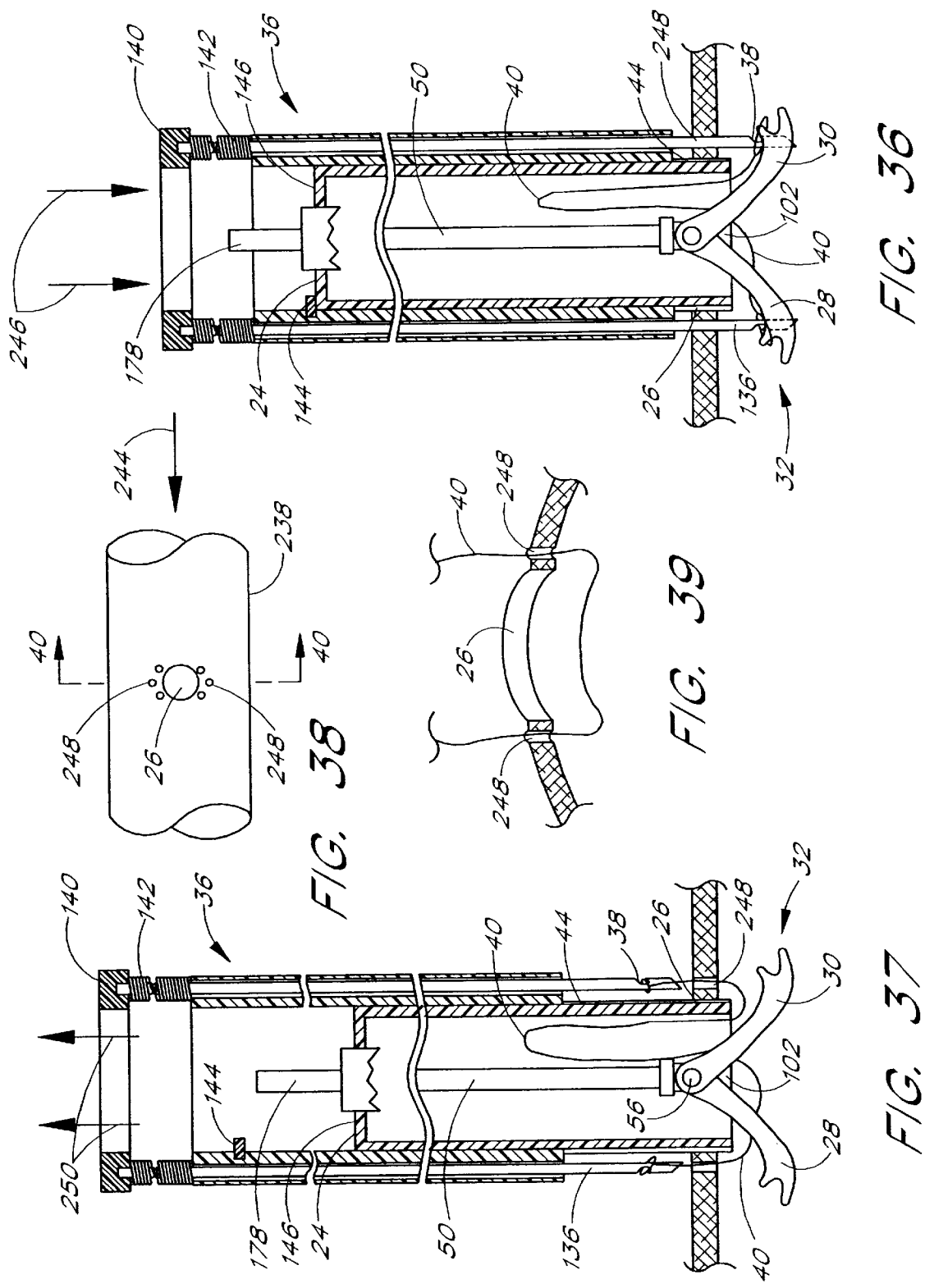

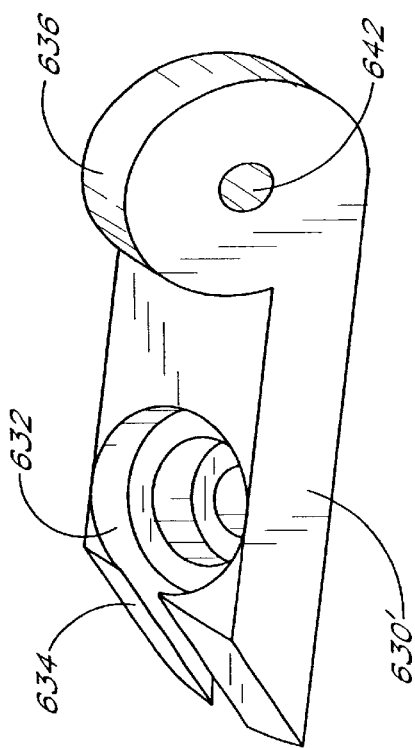
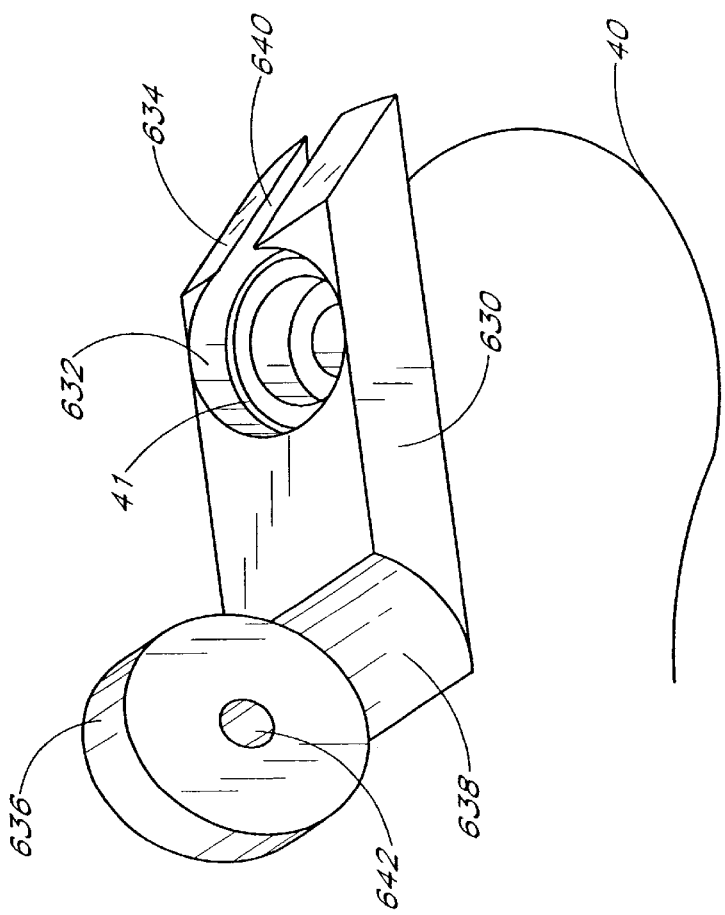
FIG. 53B
FIG. 53A

SUTURING DEVICE AND METHOD

RELATED APPLICATIONS

This application is a continuation-in-part of International Patent Application No. PCT/US01/08050. This application is also a continuation-in-part of and claims priority from U.S. patent application Ser. No. 09/524,211 filed Mar. 13, 2000, which is a continuation-in-part of U.S. patent application Ser. No. 09/471,866 filed Dec. 23, 1999, which is a continuation of U.S. patent application Ser. No. 09/231,177 now U.S. Pat. No. 6,177,144 filed Jan. 14, 1999, which is a continuation-in-part of U.S. patent application Ser. No. 09/036,437 filed Mar. 9, 1998, now abandoned which is a continuation-in-part of U.S. patent application Ser. No. 08/702,315 now U.S. Pat. No. 5,860,990 filed Aug. 23, 1996, which claims the benefit of U.S. Provisional Application No. 60/002,769 filed Aug. 24, 1995.

BACKGROUND OF THE INVENTION

1. Field of the Invention

The present invention relates to suturing devices. Specifically, the present invention relates to suturing devices and methods for suturing biological tissue that may not directly accessible to the physician.

2. Description of the Related Art

Physicians frequently use sutures to close cuts, punctures, incisions and other openings in various biological tissue, such as blood vessels, of the human body.

In an arterial catheterization procedure, a relatively small percutaneous incision is made in the femoral or other artery. A catheter is inserted through the incision and directed along an arterial path to a target area, such as the heart, to perform one or more procedures, such as an angioplasty or angiogram. These procedures are designed to be relatively quick 'outpatient' procedures.

Upon completion of the catheterization procedure, the physician typically creates a 'thrombus patch' by applying direct pressure to the patient's thigh to make the blood around the incision clot. Because the femoral artery must not be completely blocked (occluded) by the applied pressure, the physician commonly applies direct pressure by hand for the first twenty minutes after the procedure. During this time, the physician can feel the pulse to assure the artery is not occluded. Afterwards, the physician usually turns the procedure over to an assistant who applies direct pressure using sandbags, clamps or other devices. A significant problem with this approach is that it is frequently necessary to apply the pressure for an extended period of time, such as twenty-four hours or longer.

Another problem with the thrombus patch method is that the high blood pressure in the artery can cause the thrombus patch to rupture or burst while direct pressure is being applied to the thigh or after direct pressure is removed. This requires the whole process to be restarted. If the patch ruptures and is not restored, the patient may bleed to death. Because thrombus patches frequently burst, the patient frequently must remain in the hospital or catheterization lab overnight for observation. Thus, these 'out-patient' procedures become 'in-patient' procedures, simply because a thrombus patch it is difficult to create. Staying in the hospital increases patient discomfort and hospital expenses, which are often disproportionate to the actual medical procedure performed.

Furthermore, if a thrombus patch cannot be formed, the physician may need to anesthetize the patient, occlude blood flow to the artery, make a large incision in the thigh to allow conventional suturing with a needle, suture the artery with conventional means, restore blood flow to the artery, and suture the incision in the thigh. This results in additional discomfort and expenses for the patient.

While the above problems could potentially be avoided by suturing the blood vessel immediately following the catheterization procedure, the size and location of the artery make suturing difficult. Specifically, the opening in the thigh is typically too small and too deep to provide enough working space for suturing the artery using conventional methods. Thus, in order to suture the vessel according to conventional methods, the opening in the thigh would have to be significantly enlarged, potentially exposing the patient to additional pain, scarring, and health risks.

SUMMARY OF THE INVENTION

The present invention addresses the above problems by providing a suturing device and method for suturing biological tissue, such as, for example, an organ or blood vessel. The device is particularly well suited to suture an opening made in an artery, such as the femoral artery, following a catheterization procedure. The device eliminates the need to apply pressure to a patient's thigh for an extended period of time, and eliminates many of the complications and costs associated with the creation of a thrombus patch.

One aspect of the invention relates to a suturing device comprising an elongate body and first and second arms. Each of said arms has a suture mounting portion which mounts an end portion of a suture. The arms are mounted on the elongate body such that said suture mounting portions are movable away from said body to a first position and towards said body to a second position. The suturing device further comprises first and second needles, each of said needles having a distal end. Each of said needles is mounted such that the distal end of the needle is movable (i) in a proximal to distal direction from a position adjacent said elongate body to a position spaced outwardly from said body, and (ii) towards the suture mounting portion of one of the arms when in said first position, wherein the respective distal ends of the first and second needles engage respective end portions of said suture. The suturing apparatus further comprises an actuator which drives the needles in said proximal to distal direction such that the engagement of the respective end portions of the suture is non-simultaneous.

Another aspect of the invention relates to a suturing apparatus comprising an elongate body and first and second arms. Each of said arms has a suture mounting portion which mounts an end portion of a suture, and each of said arms is operably connected to the elongate body such that said suture mounting portions are movable away from said body to a first position and towards said body to a second position. The suturing apparatus further comprises first and second needles, each of said needles having a distal end. Each of said needles is mounted such that the distal end of the needle is movable (i) in a proximal to distal direction from a position adjacent said elongate body to a position spaced outwardly from said body, and (ii) towards the suture mounting portion of one of the arms when in said first position. The suturing apparatus further comprises an actuator comprising first and second needle drivers connected to drive the first and second needles, respectively, in said proximal to distal direction. Said needle drivers are independently actuable such that the first needle is movable independent of the second needle.

Another aspect of the present invention relates to a device for suturing biological tissue. The device comprises an elongated body and an arm operably connected to the elongated body to move to an extended position away from the elongated body and to a retracted position toward the elongated body. The arm has a mounting portion which mounts a portion of a suture, and has a tissue contacting surface which faces proximally when the arm is in the extended position. The tissue contacting surface has a projecting portion configured to provide intimate contact with said tissue and to thereby inhibit lateral movement of said arm when said tissue contacting surface is pressed against tissue. The device further comprises a needle having a distal end which is movable distally from a position adjacent the elongated body towards said mounting portion of said arm when the arm is in the extended position, such that said distal end engages said portion of the suture mounted by said mounting portion.

Another aspect of the present invention relates to a suturing apparatus comprising an elongated body. The suturing apparatus further comprises an arm operably connected to the elongated body and movable relative to the elongated body to an extended position away from the elongated body and to a retracted position towards the elongated body. The arm has a mounting portion which mounts a portion of a suture. The suturing apparatus further comprises a needle movable relative to the elongated body. The needle has a distal end movable from a position adjacent the elongated body towards the mounting portion of the arm when the arm is in the extended position, such that the distal end engages the portion of the suture mounted by the mounting portion of the arm. The suturing apparatus further comprises a patch which is tethered by the suture.

Another aspect of the present invention relates to a method of suturing. The method comprises providing an elongate body having first and second arms which mount first and second portions, respectively, of a suture. The method further comprises engaging the first and second portions of the suture with first and second needles, respectively, by driving the first and second needles towards the first and second arms, respectively, in a proximal to distal direction. The engaging comprises engaging the first portion of suture with the first needle prior to engaging the second portion of the suture with the second needle.

Another aspect of the present invention relates to a method of occluding a septal defect. The method comprises inserting a distal end portion of an elongated body into an opening in a living being. The method further comprises positioning the distal end portion in a first location adjacent a first tissue portion in proximity to the septal defect. The method further comprises deploying a first needle within the elongated body so as to draw a first end of a suture through the first tissue portion. The method further comprises moving the distal end portion to a second location displaced from the first location and positioning the distal end portion adjacent a second tissue portion in proximity to the septal defect. The method further comprises deploying a second needle within the elongated body so as to draw a second end of the suture through the second tissue portion. The method further comprises using the suture to secure a patch across the septal defect.

Another aspect of the present invention relates to a method of suturing. The method comprises inserting a distal end portion of an elongated body into an opening in a living being. The method further comprises positioning the distal end portion in a first location adjacent a first tissue portion. The method further comprises deploying a first needle within the elongated body so as to draw a first end of a suture through the first tissue portion. The method further comprises moving the distal end portion to a second location displaced from the first location and positioning the distal end portion adjacent a second tissue portion. The method further comprises deploying a second needle within the elongated body so as to draw a second end of the suture through the second tissue portion. The method further comprises using the suture to secure a patch to the first and second tissue portions.

Another aspect of the present invention relates to a method of suspending a biological structure. The method comprises positioning a distal portion of an elongated body adjacent the biological structure to be suspended. The method further comprises positioning a first arm operably connected to the elongated body on one side of the biological structure, the first arm releasably holding a first end portion of a suture. The method further comprises extending a first needle toward the first end portion of the suture in the first arm. The first needle moves on an opposite side of the biological structure such that when the first needle engages the first end portion of the suture, the biological structure is encircled by the first arm, the first needle, and the elongated body. The method further comprises positioning a second arm operably connected to the elongated body adjacent a tissue portion. The second arm releasably holds a second end portion of the suture. The method further comprises extending a second needle through the tissue portion to engage the second end portion of the suture in the second arm. The method further comprises drawing the first end portion and second end portion of the suture toward the elongated body. The method further comprises tying the first end portion and second end portion of the suture to suspend the biological structure to the tissue portion.

Another aspect of the present invention relates to a method of placing a suture around the exterior of a biological structure. The method comprises advancing an elongate suturing device having an elongate body distally towards the biological structure. The method further comprises positioning a first suture portion mounted on the elongate device so that the first suture portion is proximate the biological structure. The method further comprises advancing a suture retrieving member of the elongate device past the biological structure without piercing the biological structure. Advancing the suture retrieving member comprises moving the suture retrieving member with the biological structure between the suture retrieving member and the elongate body. Advancing the suture retrieving member further comprises coupling the suture retrieving member to the first suture portion. The method further comprises drawing the first suture portion away from the biological structure by moving the suture retrieving member in a direction away from the biological structure. The method further comprises drawing a second suture portion away from the biological structure by moving at least a portion of the elongate device from the biological structure, whereby the suture extends in a loop around the biological structure.

BRIEF DESCRIPTION OF THE DRAWINGS

FIG. 1A illustrates one embodiment of the present invention in an exemplary use environment.

FIG. 1C illustrates another embodiment of the present invention in the exemplary use environment of FIG. 1A.

FIGS. 12 and 13 are partial cross-sectional views of another configuration of a spreader for deploying the suture clasp arms.

FIG. 19 is a schematic perspective view of a needle tip and one configuration of a suture catch.

FIG. 20 is a cross-sectional view of the suture catch of FIG. 19 taken along line 19—19 illustrating the position of a suture fitting captured by the suture catch.

FIG. 21 is a cross-sectional top view of the suture catch of FIG. 19 taken along line 20—20.

FIG. 22 is a schematic illustration of another configuration of a suture fitting.

FIG. 23 is a side view of a suture clasp arm used to hold the suture fittings of FIGS. 20 and 22.

FIG. 24 is a rear elevational view of a needle tip with an alternate configuration of the suture catch.

FIG. 25 is a cross-sectional view of the needle tip of FIG. 24 taken along line 24—24 of FIG. 24.

FIG. 26 is a partial cross-sectional side view of an alternate configuration of a suture clasp arm to hold a suture fitting.

FIG. 27 is an end view of the suture clasp arm of FIG. 26.

FIG. 36 is a partial cross-sectional view of the suture introducer housing and suture catch assembly of FIG. 2 illustrating the operation of the suture catch assembly.

FIG. 37 is a partial cross-sectional view of the suture introducer housing and the suture catch assembly of FIG. 2.

FIG. 38 is a schematic view of a vessel illustrating the location of the suture.

FIG. 39 is a schematic cross-sectional view of the vessel of FIG. 38 taken along line 40—40.

FIGS. 53A–53B are perspective views of one configuration of the suture clasp member of FIG. 52A.

FIGS. 87–102 illustrate methods of forming suture ends of a suture which may be used with the suture devices described herein, in which:

FIG. 87 shows a strand of material being brought into a stream of hot gas;

FIG. 88 shows a distal end of the strand being thermally deformed to form a deformed region such as a globule;

FIGS. 89 and 90 show a die for flattening the deformed region;

FIG. 91 shows the strand after the deformed region has been flattened;

FIG. 92 shows the strand after excess material has been cut away from the deformed region;

FIG. 93 shows the strand after an eyelet has been formed in the flattened, deformed region;

FIG. 94 shows a suture in which eyelet portions have been formed at both ends of the suture;

FIG. 95 shows the deformed region placed between two blocks having recessed portions therein;

FIG. 96 shows the deformed region after it has been squeezed between the blocks to form a cylindrically shaped member;

FIG. 97 shows a hole being formed in the deformed region with a hypotube;

FIG. 98 shows the formed hole in the deformed region, resulting in a cup-like member at the end of the strand;

FIGS. 99 and 100 show views of a one embodiment of a surgical needle to be used with the cup-like member of FIG. 98;

FIG. 101 shows the surgical needle having entered the cup-like member and secured to it; and FIG. 102 shows an embodiment having cup-like members at both ends of the suture.

DETAILED DESCRIPTION OF THE PREFERRED EMBODIMENTS

Figure 1B:
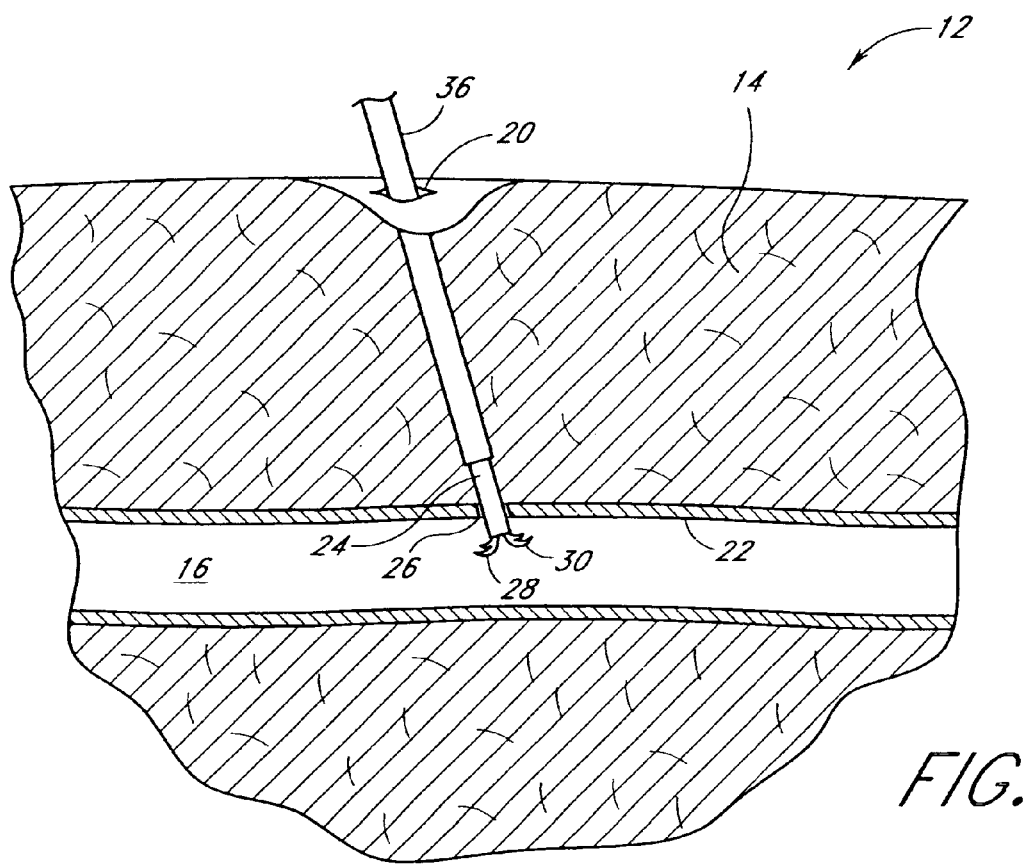
FIG. 1B illustrates a cross-sectional view of the device in FIG. 1A in an exemplary use environment, such as a patient's thigh.

The present invention provides a suturing device for suturing biological tissue. The suturing device may be used to seal a blood vessel following an interventional catheterization procedure, such as an angiogram. FIGS. 1A–1B illustrate one embodiment of the present invention in an exemplary use environment. As depicted by FIGS. 1A–1B, the physician makes an initial incision 20 in the upper thigh 12 of a patient 2. The physician then inserts a needle (not shown) into the incision 20. When blood bleeds back from the insertion, the physician knows the needle has pierced the femoral artery 16. The physician then inserts a guidewire (not shown) through the needle and into the artery. The physician may take the needle out and insert a plastic needle (not shown) over the guidewire once the guidewire is in place. The guidewire may then be taken out.

With this needle in place, the physician can insert a catheter sheath introducer (CSI) 6, also called an introducer sheath. This introducer sheath 6 is typically a single lumen catheter with a valve on its proximal end. The valve is used to prevent extraneous bleed back or to introduce medication into the patient's body. The vessel incision 26 provides access for medical instruments and probes inside the arterial vessel 16. Instruments may be inserted into artery 16 via the introducer sheath 6 to perform various procedures in the body.

In FIG. 1A, the suture assembly 4 consists of the suture catch assembly 36 (described below), the suture introducer housing 24, and the introducer sheath 6. FIG. 1B illustrates a cross-sectional view of the device depicted in FIG. 1A in an exemplary use environment, such as a patient's thigh. After the medical procedure described above, the physician withdraws the CSI 6 and inserts the suture catch assembly 36 and the suture introducer housing 24 through the first incision 20. The suture catch assembly 36 and suture introducer housing 24 pass through the flesh 14 of the patient's thigh 12 and through the second incision 26 into the femoral artery 16. In another method, the physician may first insert the suture introducer housing 24, remove the CSI 6, and then insert the suture catch assembly 36.

Figure 1D:
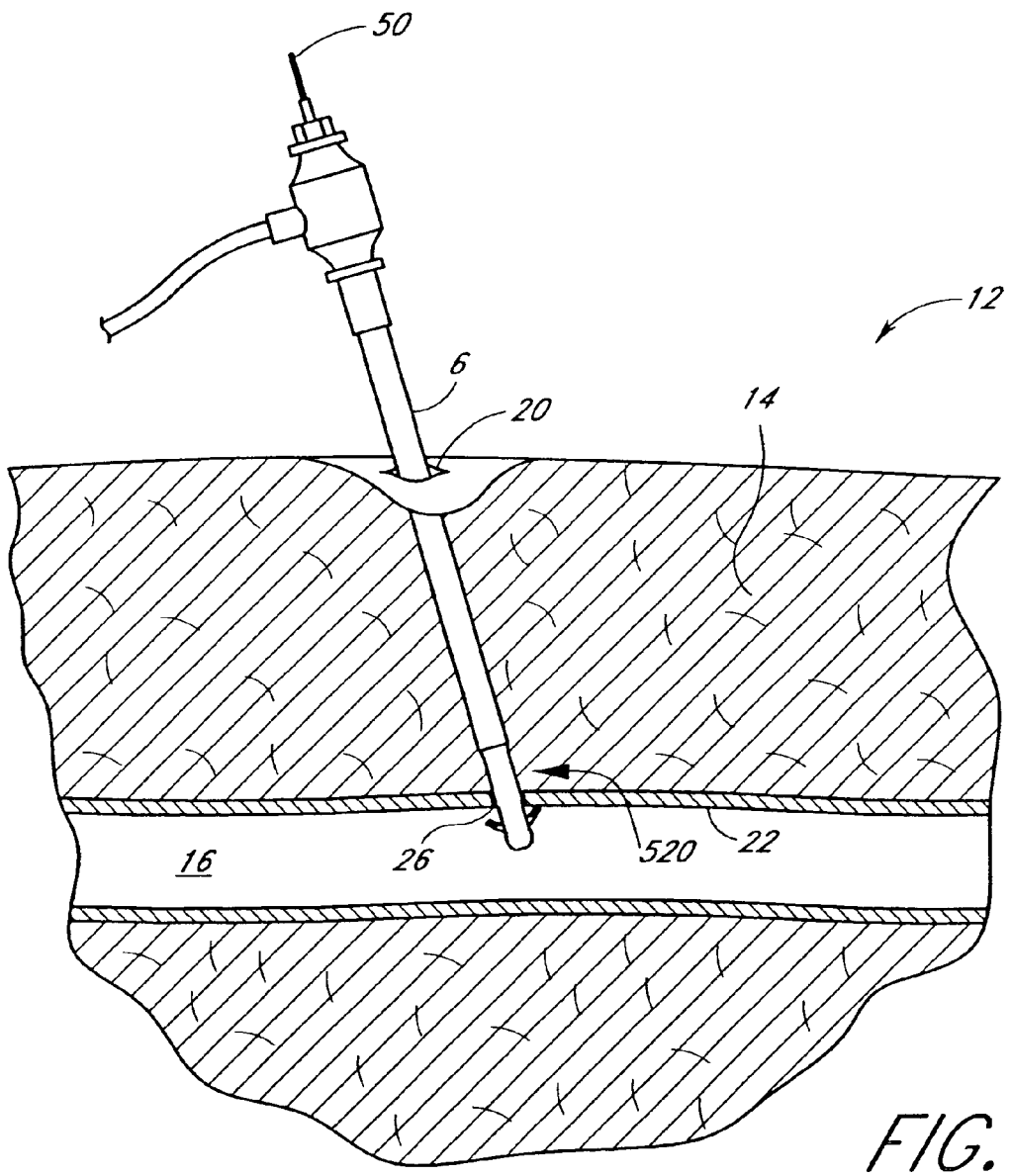
FIG. 1D illustrates a cross-sectional view of the device in FIG. 1C in an exemplary use environment, such as a human thigh.

FIGS. 1C and 1D illustrate another embodiment of the present invention in the exemplary use environment of FIG. 1A. Unlike the device illustrated in FIGS. 1A–1B, the device illustrated in FIGS. 1C–1D does not require the removal of the CSI 6 in order for the device to deploy a suture. Several embodiments of the device shown in FIGS. 1A and 1B will now be described with reference to FIGS. 2–40. The device depicted in FIGS. 1C–1D will thereafter be described in further detail below with reference to FIGS. 41–50.

Embodiments of FIGS. 1A–1B and 2–40

Figure 2:
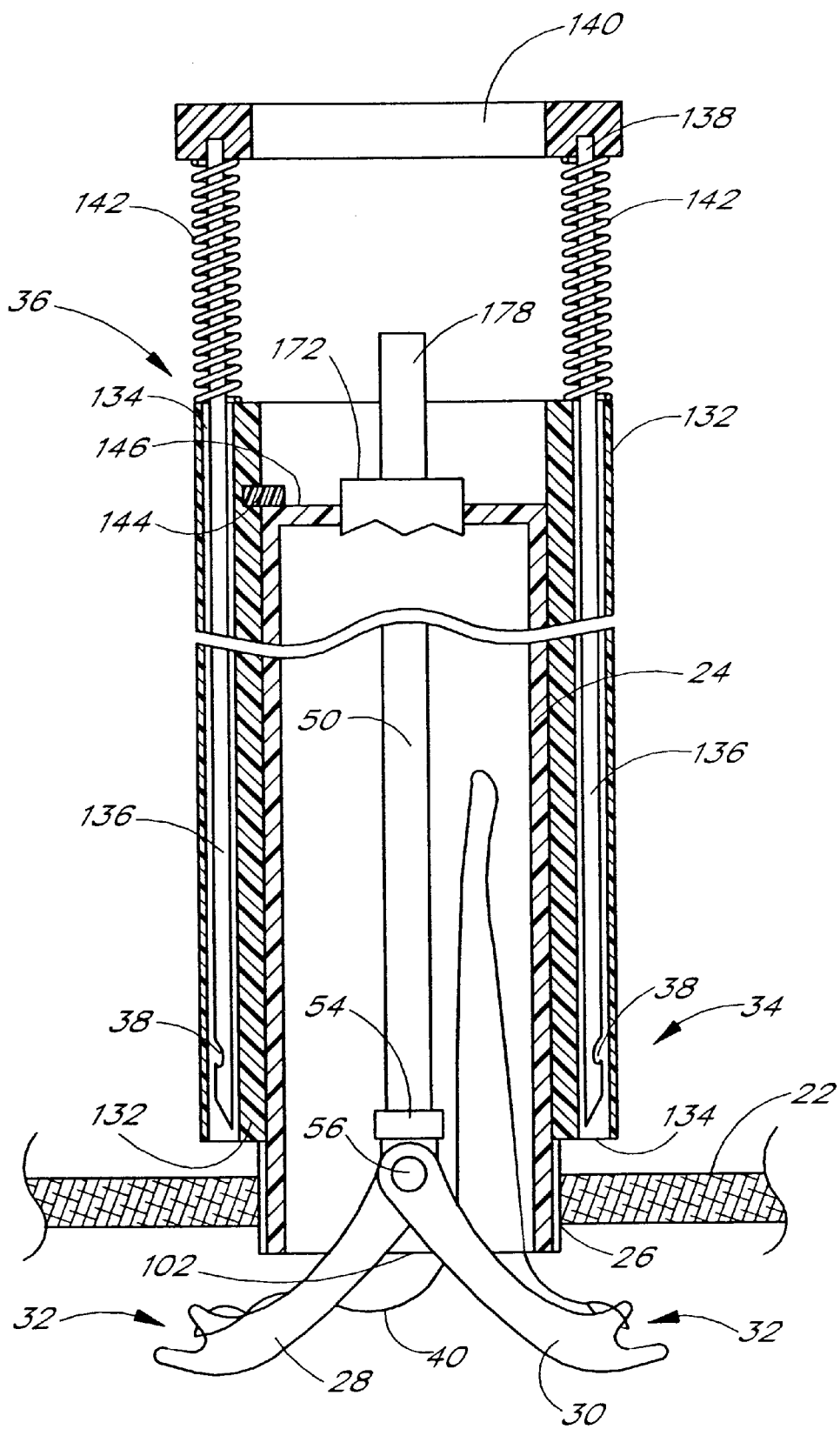
FIG. 2 is a partial cross-sectional view of the suturing device depicted in FIG. 1A having a suture catch assembly and a suture introducer housing.

FIG. 2 shows one embodiment of the suturing device for suturing vessel walls and other biological tissue. Preferably, the device is for use in suturing arterial vessel walls 22. However, the device could be used to suture other tissue such as a patent ductus arteriosus, a patent foramen ovale, a heart defect, a puncture wound, and the like. The suturing device comprises a suture introducer housing 24 for insertion into an opening 26 in the arterial wall 22.

Suture clasp arms 28, 30 are deployably housed in the housing 24 during insertion. After insertion into the vessel 16, the arms 28, 30 are deployed to the position shown in FIG. 2. When deployed, the suture clasp arms 28, 30 extend outside the circumference of the suture introducer housing 24. In certain embodiments, the arms 28, 30 extend from the housing in a symmetric configuration, in which each arm 28, 30 has the same angle with respect to the axis of the housing 24. Alternatively, in other embodiments, each arm 28, 30 can extend from the housing in an asymmetric configuration, in which each arm 28, 30 has a different angle with respect to the axis of the housing 24. Furthermore, in certain embodiments, the arms 28, 30 are spaced equidistantly around the circumference of the housing 24. Equidistant spacing as used herein means that the azimuthal angle between the two arms 28, 30 is 180 degrees, where the azimuthal angle between the two arms 28, 30 is the angle between the plane defined by the axis of the housing 24 and the first arm 28 and the plane defined by the axis of the housing 24 and the second arm 30. Alternatively, in still other embodiments, the arms 28, 30 are spaced non-equidistantly around the circumference of the housing 24 (e.g., the azimuthal angle between the two arms 28, 30 is 90 degrees).

Each arm has at least one suture clasp 32, schematically illustrated, for clasping a suture 40. A penetrating mechanism, generally designated 34, is provided for penetrating the vessel wall 22. The penetrating mechanism 34 is provided on either the suture introducer housing 24 or on a suture catch assembly, generally designated 36. When, as shown in FIG. 2, the penetrating mechanism 34 is part of the suture catch assembly 36, the penetrating mechanism 34 also comprises suture catches 38 for catching the suture 40 and dislodging it from the suture clasps 32. The suture catch assembly 36 operates to pull the suture 40 held by the suture catches 38 through the vessel wall 22. After the ends of the suture 40 are pulled outside the vessel wall 22, the introducer housing 24 can be removed and the suture 40 tied to close the vessel opening 26.

Figure 3:
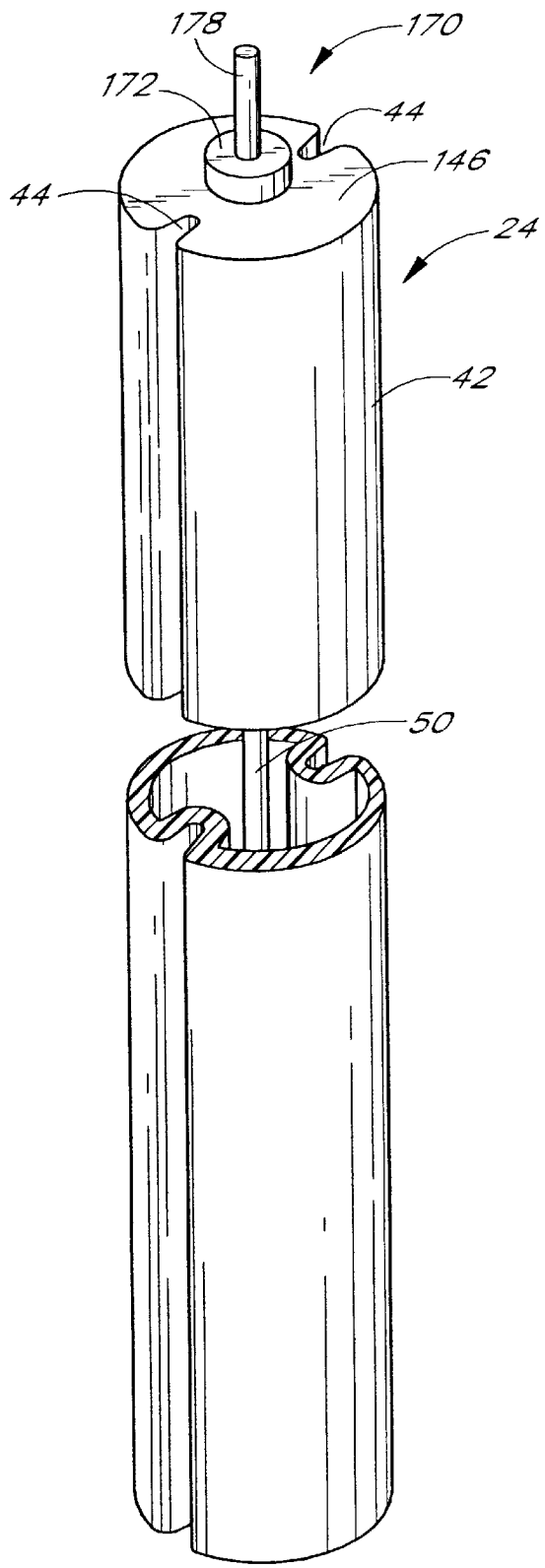
FIG. 3 is a bifurcated perspective view of the suture introducer housing of FIG. 2.

FIG. 3 shows one configuration where the suture introducer housing 24 is a generally cylindrical and thin walled hypo tube. The term "hypo tube" is used to describe a hollow elongated cylindrical member with a thin wall such that the inner diameter and outer diameter vary by a relatively small amount in the range of few thousandths of an inch to tens of thousandths of an inch. The outer surface 42 of the housing 24 comprises a key way groove 44 (exaggerated for clarity) to align the housing 24 with a key 46 (FIG. 17) on the inner surface 48 of the suture catch assembly 36. An arm actuation assembly 170, to be described below, for deploying the suture clasp arms 28, 30 protrudes from the proximal end of the housing 24, and an actuating wire or rod 50 extends from the actuation assembly 170 through the housing 24 to the suture clasp arms 28, 30.

FIG. 2 shows one configuration where the suture clasp arms 28, 30 are attached to the distal end 54 of the actuating rod 50. In this configuration, the arms 28, 30 are pivotally attached to the actuating rod 50 and pivot around pivot shaft 56. The suture 40 is held inside the housing 24 and is positioned underneath the spreader 102, so that it can be removed from the entire housing 24. The arms 28, 30, which are shown in more detail in FIGS. 4A and 4B, terminate with the suture clasps 32 (schematically illustrated). Each arm 28, 30 has an elongated body 58 which attaches to the pivot shaft 56 at one end and to the suture clasp 32 at the other. The length of the body 58 controls how far beyond the circumference of the suture introducer housing 24 the arms 28, 30 extend when they are deployed by the actuating rod 50.

Figure 4A:
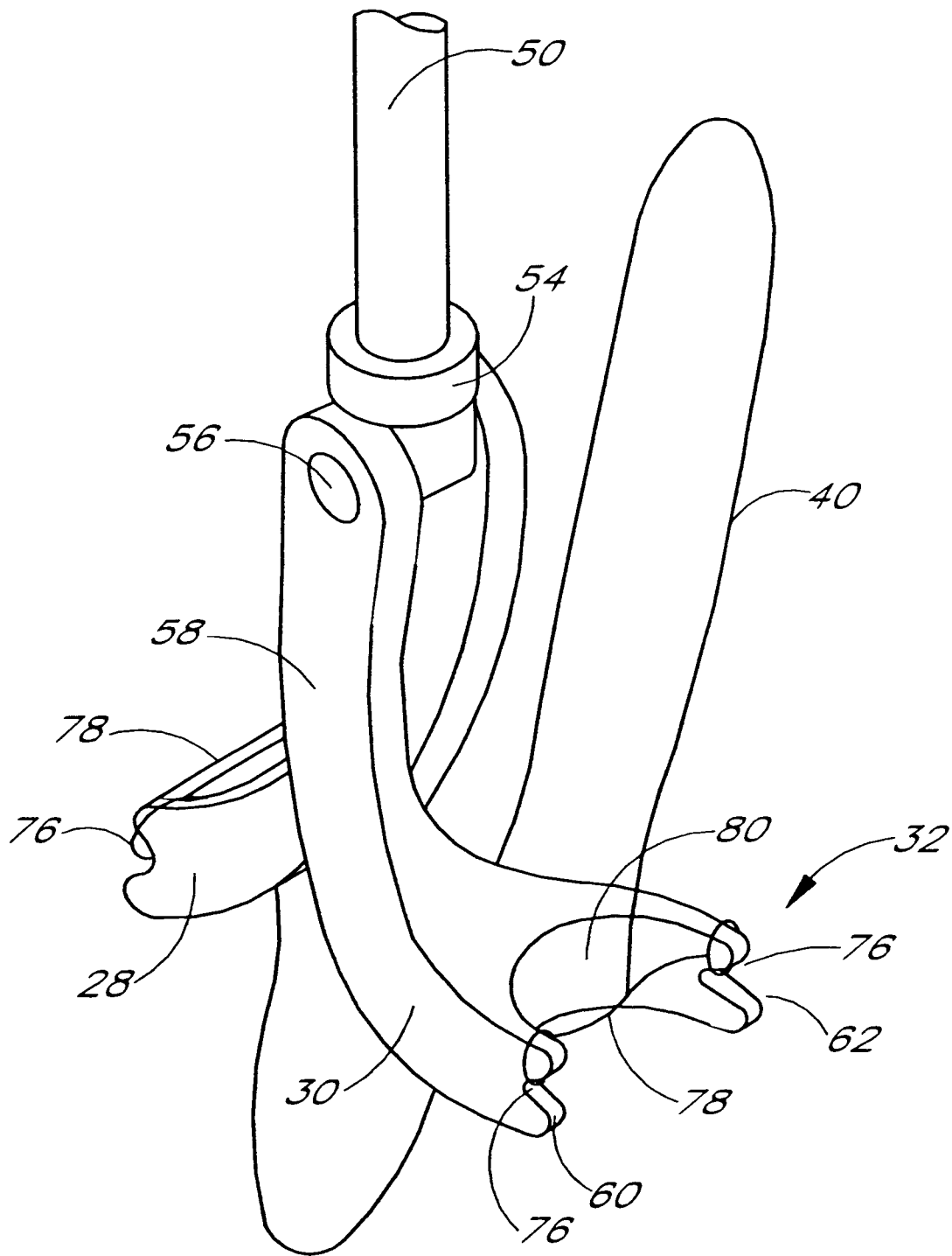
FIG. 4A is a partially schematic perspective view of the suture clasp arms of FIG. 2.
Figure 4B:
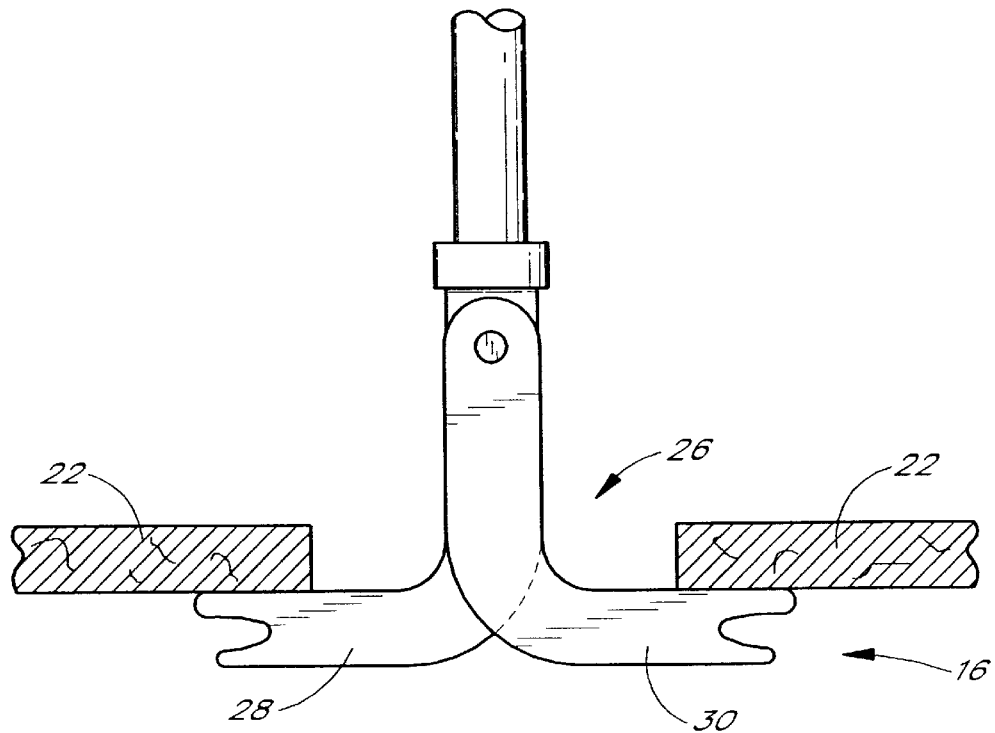
FIG. 4B is a partial cross-sectional view of one configuration of suture clasp arms.
Figure 4C:
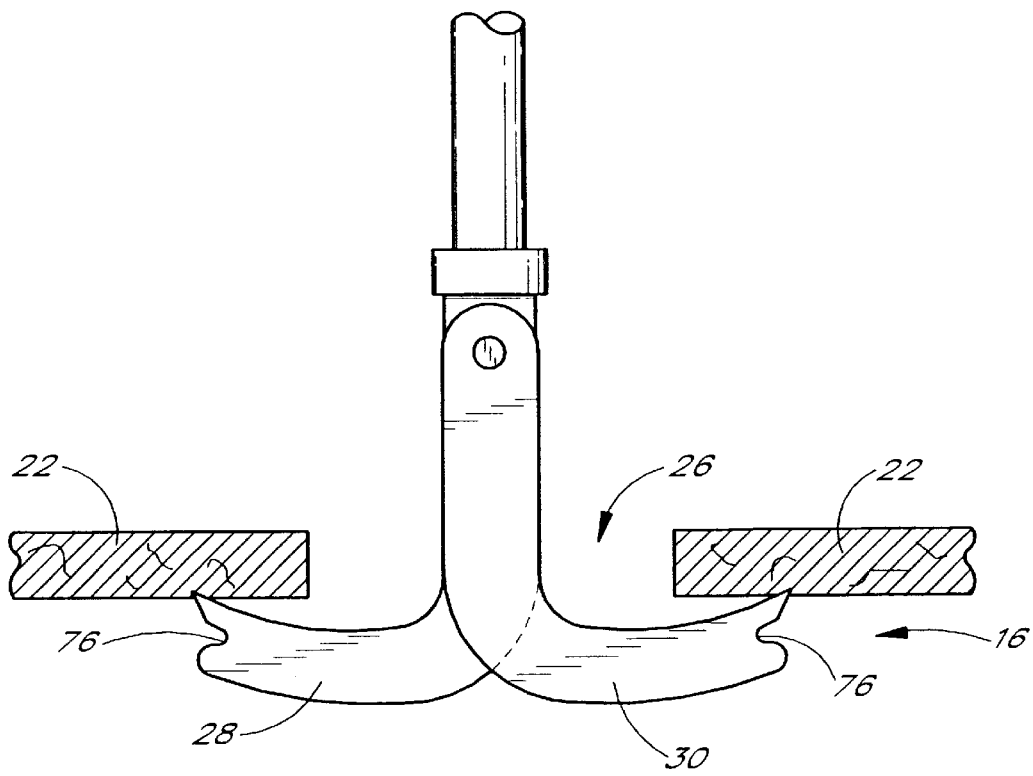
FIG. 4C is a partial cross-sectional view of another configuration of suture clasp arms.

As illustrated in FIG. 4B, the proximal sides of the suture clasp arms 28, 30 near the slots 76 which receives the suture 40 are substantially parallel to the vessel wall 22 when the arms 28, 30 are deployed within the vessel 16. The proximal sides of the suture clasp arms 28, 30 can then provide mechanical support for the vessel wall 22 in the region of the opening 26. In an alternative configuration, as illustrated in FIG. 4C, the proximal sides of the suture clasp arms 28, 30 have an upward curvature near the slots 76, thereby defining a proximally projecting portion on the proximal side of each of the arms 28, 30. In this configuration, the proximal side of the arms 28, 30 provide mechanical support for the vessel wall 22 while the proximally projecting portions provide an improved purchase on the vessel wall 22. This configuration then reduces the probability of slippage of the arms 28, 30 relative to the vessel wall 22 when the arms 28, 30 are deployed within the vessel 16. Other configurations can have multiple proximally projecting portions on each arm 28, 30, or can have proximally projecting portions which are protuberances on the proximal sides of arms 28, 30 without upward curvature. These proximally projecting portions can have various cross-sectional shapes, such as triangular or trapezoidal. Still other embodiments can have relatively small proximally projecting portions which have areas smaller than the area of the proximal side of the arms 28, 30. In addition, other embodiments have proximally projecting portions which are in proximity to the portion of the arms 28, 30 which mount the end portions of the suture, such as the slots 76 illustrated in FIG. 4C. The proximally projecting portions can also be located in proximity to the ends of the arms 28, 30 away from the pivot shaft 56.

Figure 4D:
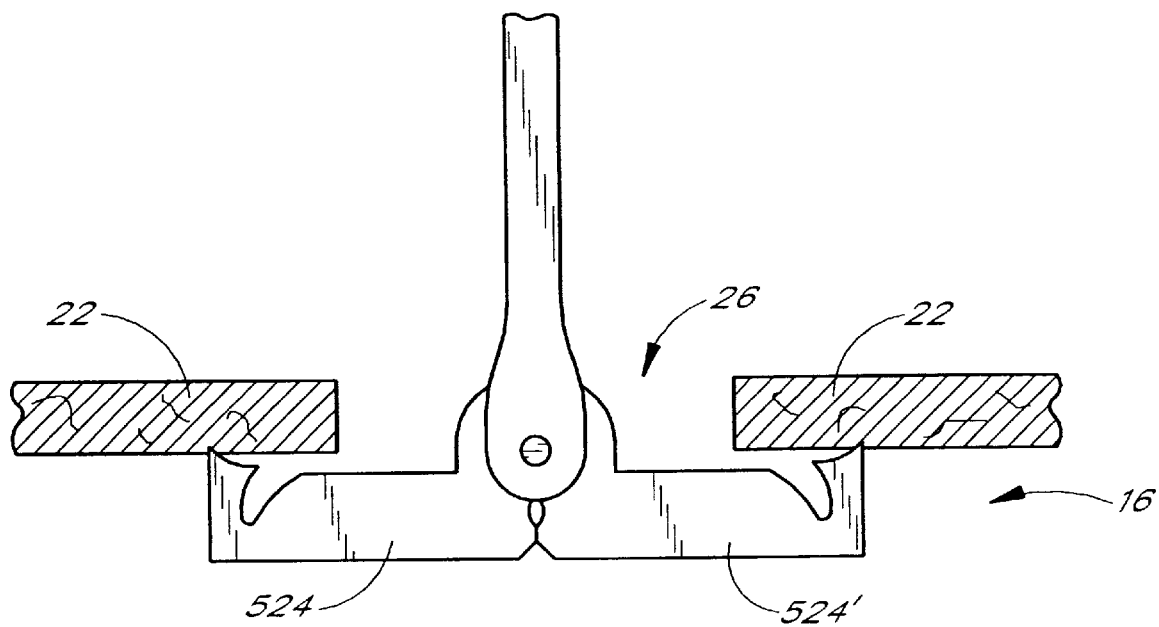
FIG. 4D is a partial cross-sectional view of yet another configuration of suture clasp arms.
Figure 4E:
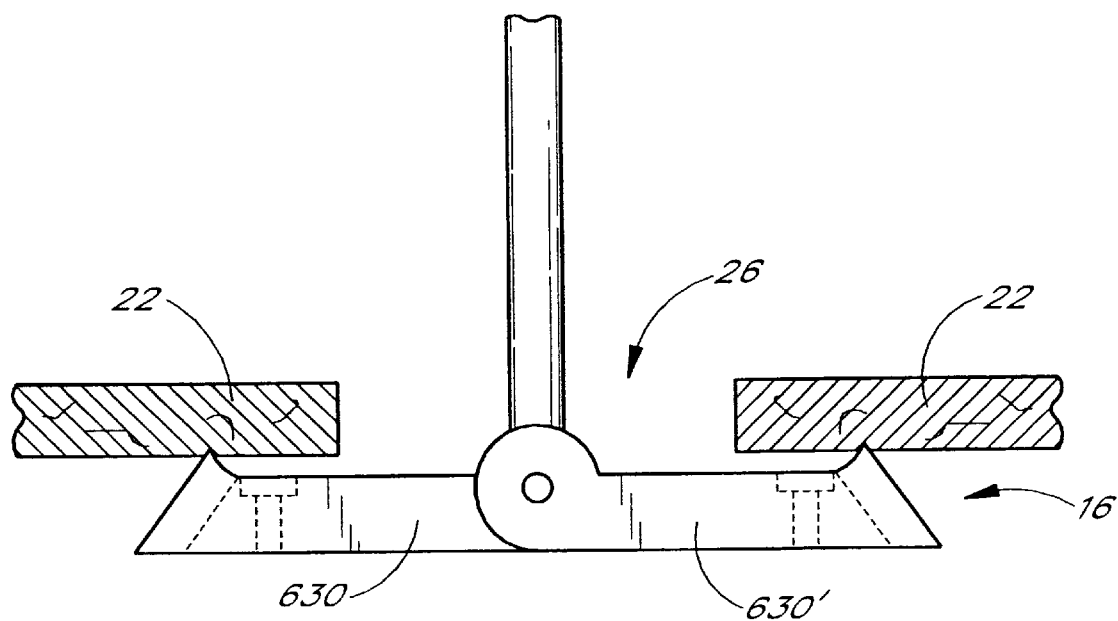
FIG. 4E is a partial cross-sectional view of yet another configuration of suture clasp arms.
Figure 6:
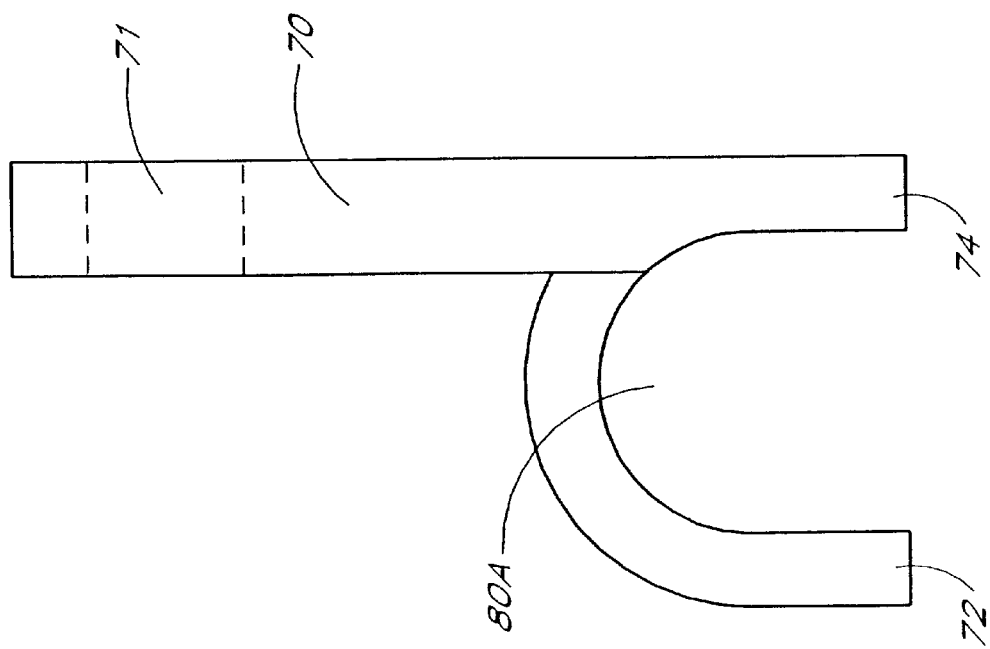
FIG. 6 is an elevational view of another configuration of a suture clasp arm.

Similarly, other configurations of suture clasp arms 28, 30 can have proximally projecting portions on each of the arms 28, 30. FIG. 4D illustrates such proximally projecting portions on arms 28, 30 such as those described below in conjunction with FIGS. 43–47, and FIG. 4E illustrates such proximally projecting portions on arms 28, 30 such as those described below in conjunction with FIGS. 52–56.

Figure 5:
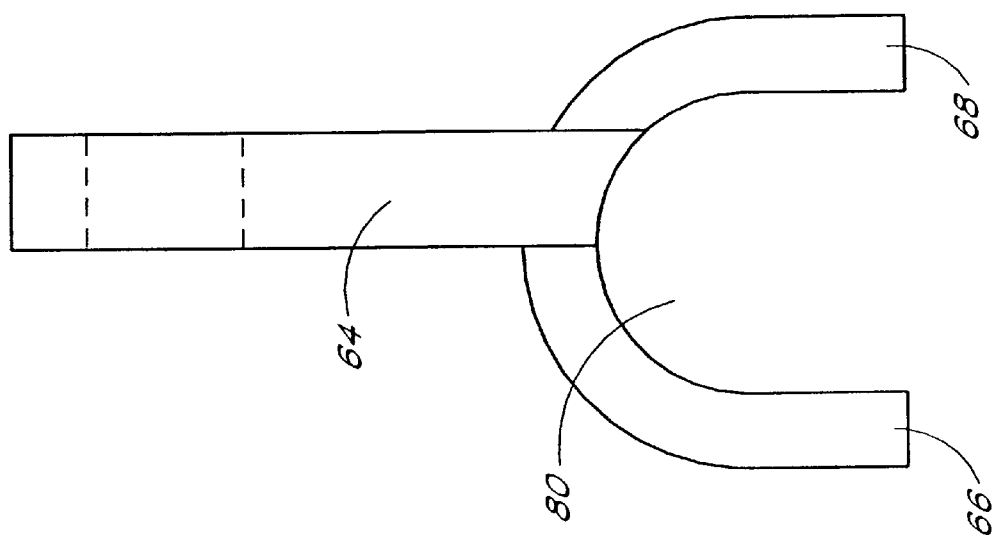
FIG. 5 is an elevational view of one configuration of a suture clasp arm.

FIG. 5 shows an alternate configuration of the arms 28, 30. In FIG. 5, the arms 28, 30 are Y-shaped with an offset body 64, and there is a suture clasp at each tip 60, 62 of the Y-shaped arm. The body 64 is off center from the tips 66, 68, so that a complimentary arm can pivot on the same pivot shaft 56 without interference. Thus, the Y-shape of the arms allows them to pivot beside each other outwardly from and inwardly to their undeployed position without interference from the other arm. The Y-shape of the arm also provides an open area or suture catch receiving area 80 into which the suture catch 30 fits to catch the suture 40. Other arm shapes such as the h-shaped arm shown in FIG. 6 may provide the same or additional benefits. The h-shaped arm has a body 70 with an aperture 71 for attachment to a pivot shaft 56 and each tip 72, 74 of the arm is provided with a suture clasp. The body of the h-shaped arm is positioned all the way to one side of the arm and functions similarly to the Y-shaped arm. The configuration of the suture clasp arm shown in FIG. 6 also has a suture catch receiving area 80A.

Figure 7:
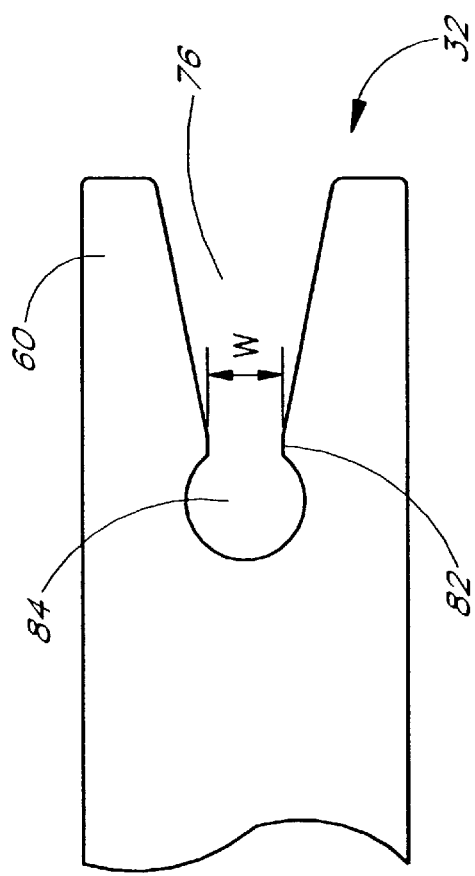
FIG. 7 is an enlarged elevational view of one configuration of a suture clasp.
Figure 8:
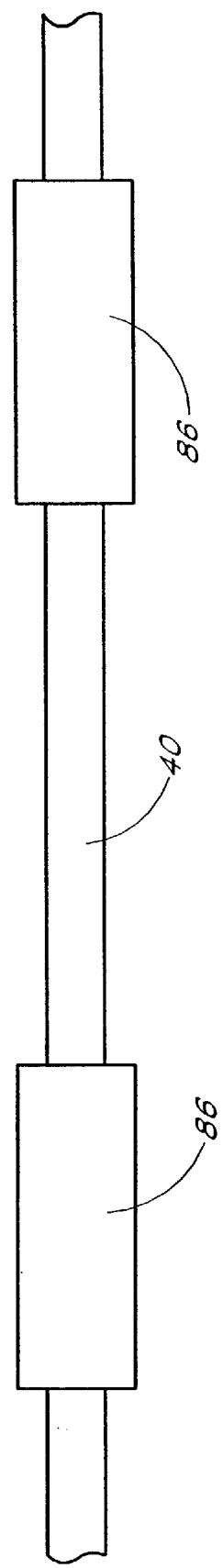
FIG. 8 is an enlarged elevational view of a suture having bands crimped thereon.

FIGS. 7 and 8 illustrate one configuration of the suture clasp 32, which comprises a key hole shaped slot 76 which widens toward the end of the tip to receive the suture 40. As illustrated in FIG. 4, a loop 78 is tied in each end of the suture 40. The loop 78 is sized to fit tightly between the suture clasps 32 on each arm 28, 30. The key hole shaped slot 76 is elongated and narrows away from the end of the tip 60 to a neck 82 having a width W. The end 84 of the slot 76 is circular with a diameter greater than the neck width W. The diameter of the circular end 84 of the slot 76 is sized to receive either the outer diameter of a suture 40, shown in FIG. 8, or the outer diameter of cylindrical bands 86 which are crimped onto the suture 40. The suture 40 or the bands 86 have an outer diameter approximately the same size as the diameter of the end of the slot 76 but smaller than the neck width W. Because the diameter of the bands 86 (or suture 40) is smaller than the width of the neck 83, the bands 86 snap into the end of the slot 76 and are securely held therein until removed by the suture catch 38. In an alternate configuration (FIG. 14), it is desirable for the slots 76 to open upwardly when they are in the deployed position, so that the suture 40 is pulled straight up out of the slots 76.

Figure 9:
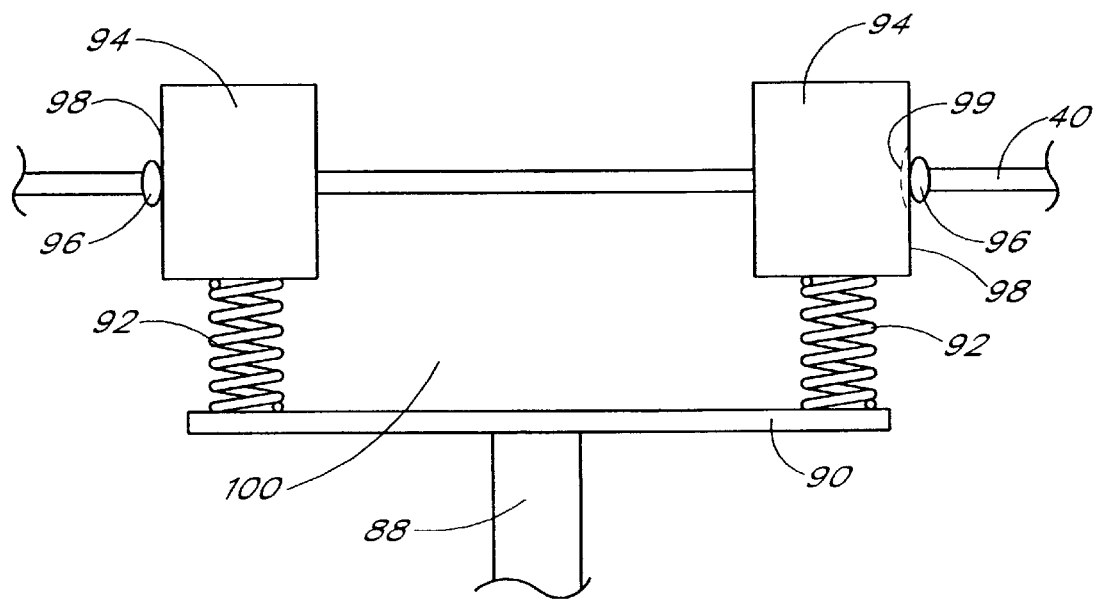
FIG. 9 is an enlarged elevational view of another configuration of a suture clasp.

FIG. 9 shows another configuration of the suture clasps 32. In this configuration, the arm 28, 30 comprises a shaft 88 extending to a plate or bar 90. A resilient element 92, such as a spring, is attached at each end of the bar 90, and tips 94 are attached to the end of each resilient member 92. The tips 94 have slots as previously described and shown by FIG. 7. The suture 40 has beads 96 fixed thereto or knots tied therein. The beads are spaced apart by a distance just less than the distance between the outer edges 98 of the tips 94. With this distance between the beads 96, the tips 94 must be slightly bent toward each other thereby loading the resilient members 92 to receive the suture 40. When the tips 94 are pulled inwardly and the resilient members 92 loaded, the suture 40 is held in place by the force from the resilient members 92. Therefore, the suture 40 is held in tension between the tips 94.

Figure 10:
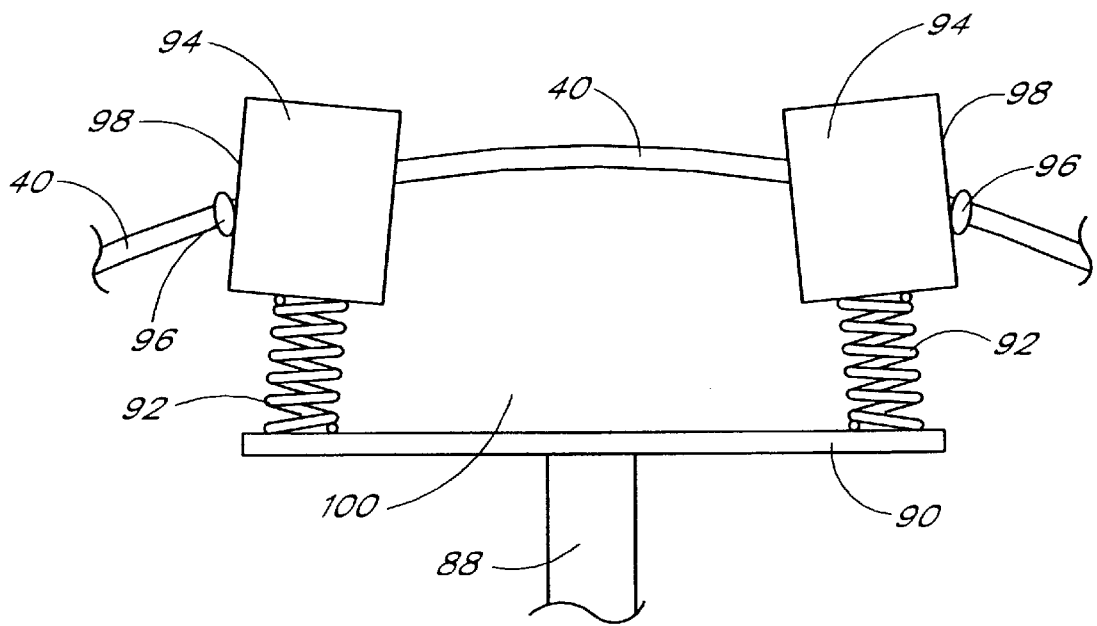
FIG. 10 is an elevational view of the suture clasp of FIG. 9 illustrating the action of a suture and the suture clasp as the suture is being removed from the suture clasp.

When the suture catch 38 is guided through the suture catch receiving area 100, the resilient members 92 are further deformed as the suture 40 is forced to make an arc to receive the suture catch 38 as illustrated in FIG. 10. The resilient members 92 then bend in the direction that the suture catch 38 is retracted, so that the suture 40 slides smoothly out of the clasp 32. If desired, the outer edges 98 of the tips may be indented 99 to receive and more securely hold the beads 96 or knots on the suture 40.

Figure 14:
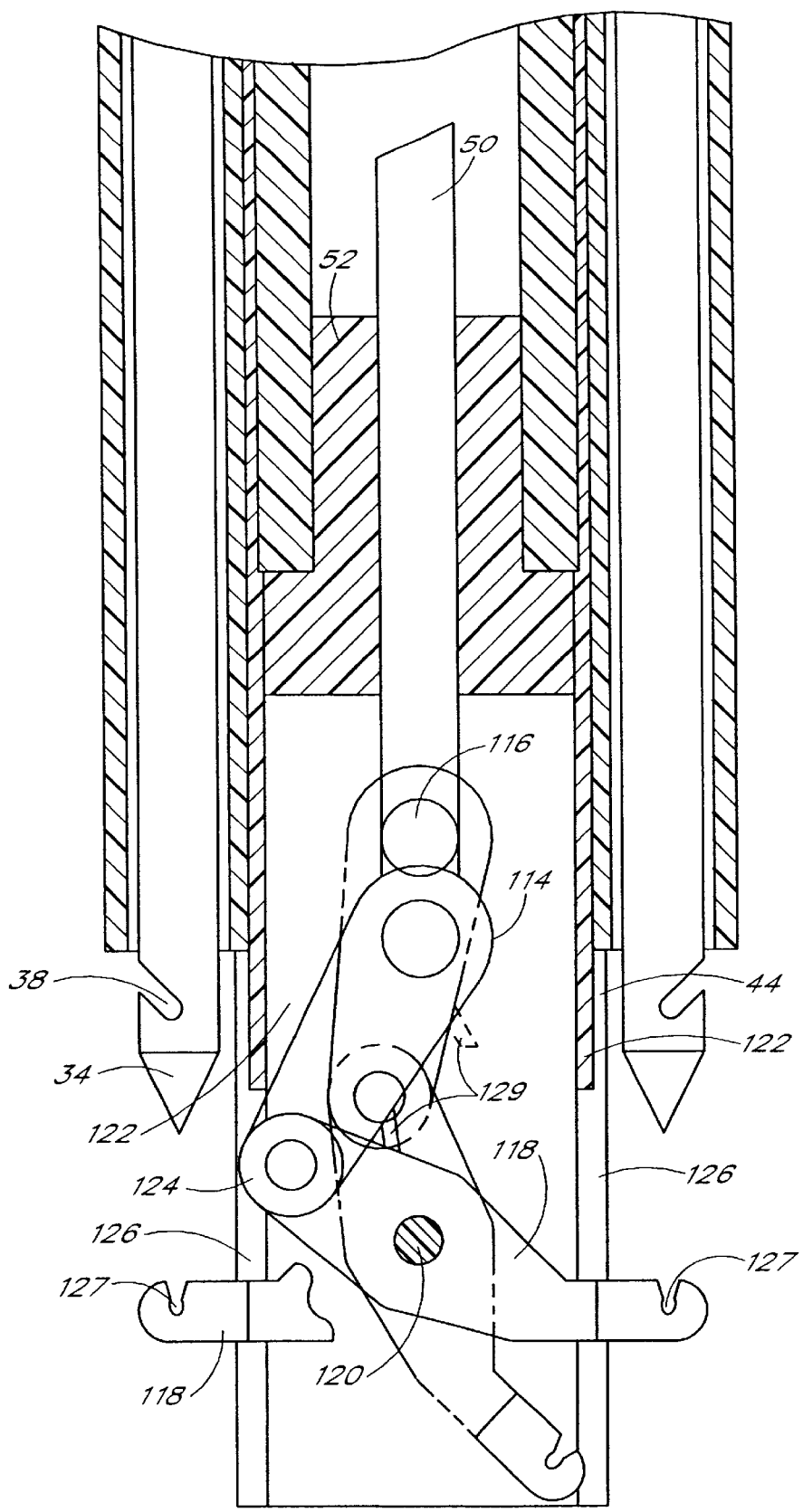
FIG. 14 is a partial cross-sectional view of an alternate configuration of the device for deploying the suture clasp arms.

FIG. 14 illustrates an alternate configuration of the suture clasp slot. The slot 127 opens upwardly toward the penetrating mechanism instead of transverse to the penetrating mechanism as in the previous configuration.

Figure 11A:
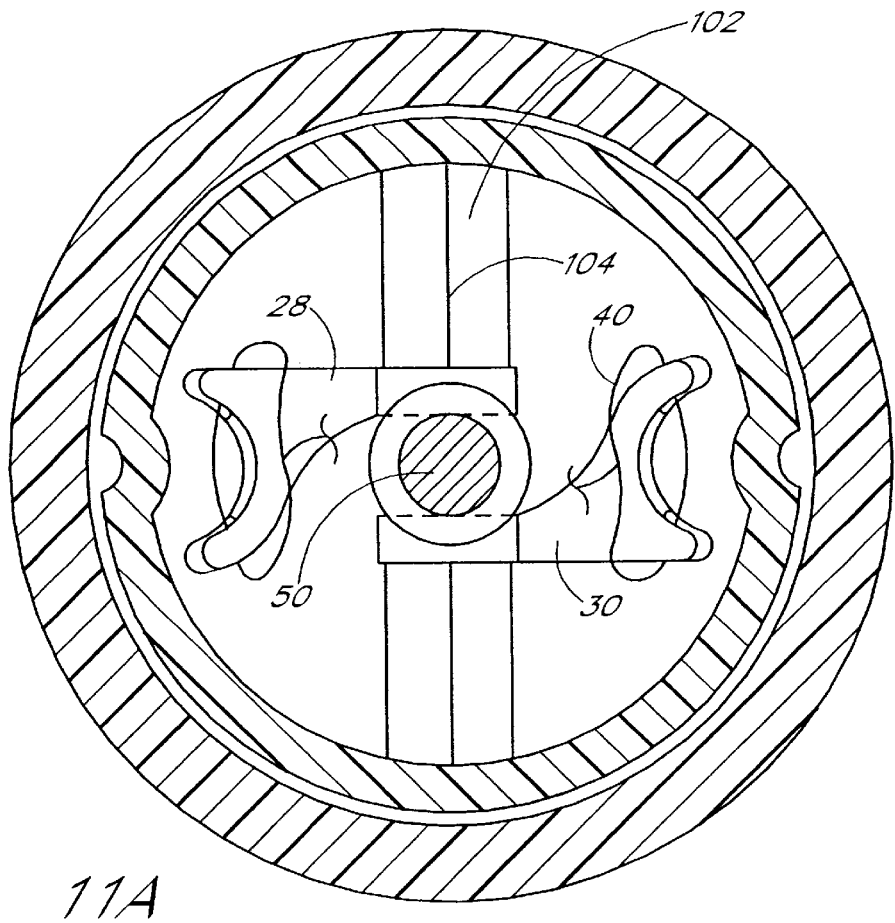
FIG. 11A is a cross-sectional top view of one configuration of a suture introducer housing, suture clasp arms, a suture, and a triangular spreader.

In FIG. 2, the suture clasp arms 28, 30 are deployed when the actuation rod 50 forces the arms 28, 30 downward to a triangular spreader 102. FIG. 11A is a cross-sectional top view of one configuration of the suture introducer housing 24, the clasp arms 28, 30, the suture 40, and a triangular spreader 102. FIG. 11A shows the triangular spreader 102 extending across a diameter line of the suture introducer housing 24. The spreader 102 may be shaped in alternative forms other than a triangle.

Figure 11B:
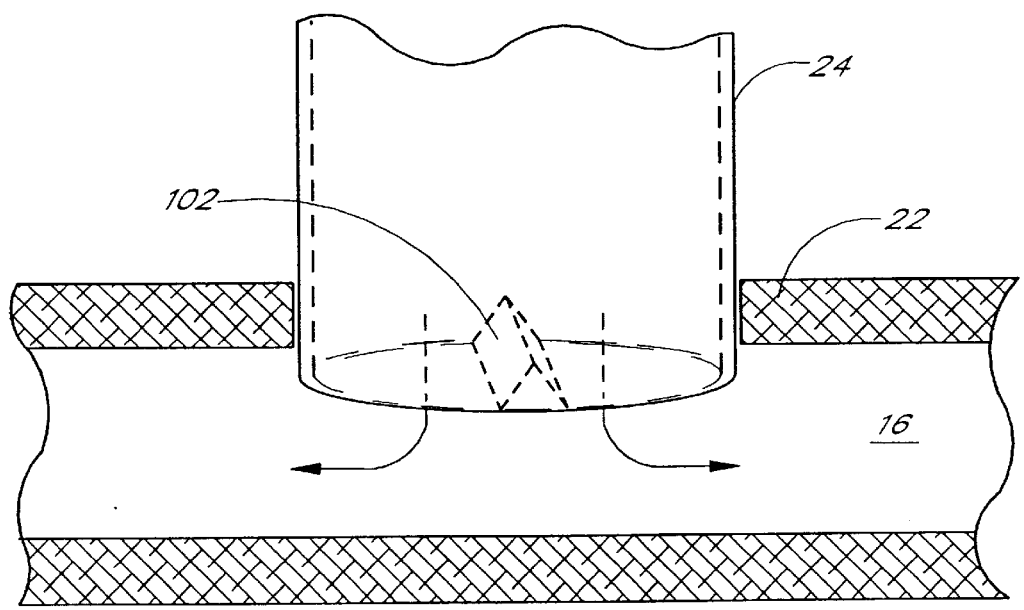
FIG. 11B is a cross-sectional side view of the suture introducer housing and triangular spreader of FIG. 11A.

FIG. 11B is a side view of one configuration of the suture introducer housing 24, the triangular spreader 102 and the direction of the clasp arms 28, 30 as they extend downward into the blood vessel 16. One vertex 104 of the triangular spreader 102 is positioned centrally in the housing 24 and extends upwardly. The triangle is preferably isosceles with respect to the upward extending vertex 104, so that the arms 28, 30 spread uniformly when they engage the spreader 102 and pivot about the pivot shaft 56. Each arm 28, 30 ultimately extends the same distance beyond the circumference of the housing 24. The surfaces of the spreader 102 and arms 28, 30 which engage to deploy the arms are preferably smooth, so that the deployment of the arms 28, 30 is smooth.

Another configuration for deploying the suture clasp arms is shown in FIGS. 12 and 13. The arms 106 are pivotally attached to the actuating rod 50 with a pivot shaft 109, and a circular spreader bar 108 or cam pin extending across a diameter line of the housing 110. When the actuating rod 50 forces the suture clasp arms 106 to engage the circular spreader 108, they are forced into the deployed position of FIG. 13. To obtain smooth deployment of the arms 106, the bottom surface 107 of the arms 106 forms a curved camming surface for engaging the circular spreader 108. The housing 110 has two slit shaped openings 112 evenly spaced around the circumference of the housing 110 through which the arms 106 extend into the deployed position. The end of the openings 112 also forms a stop 113 to prevent the arms 106 from moving past the deployed position. With the openings 112 in the housing 110, the shape of the arms 106 is simplified. Because the arms 106 do not have to curve down out of the housing 110, the arms 106 are straighter than in the previous configurations.

An alternative means for deploying the clasp arms is illustrated in FIG. 14. Each clasp arm comprises an upper lever arm 114 pivotally attached at one end to the actuating rod 50 with a pivot shaft 116 and a lower pivot arm 118 pivotally attached to the other end of the upper lever arm 114. The lower pivot arm 118 rotates around a pivot shaft spreader 120 which is attached to the housing 122 and extends across a diameter line of the housing 122. When the actuating rod 50 is forced distally farther down the housing 122, the lower pivot arms 118 are forced to pivot around the pivot shaft spreader 120, and the arms 118 are deployed to the position shown in solid lines. As the lower pivot arm 118 rotates, the upper lever arm 114 rotates relative to the pivot shaft 116, and the junction 124 between the upper and lower arms is translated downward (distally) and outwardly toward the circumference of the housing. When the actuating rod 50 is retracted from the housing, the junction is moved upward and centrally in the housing 122, and the lower pivot arm 118 is rotated to the retracted position shown in partial dashed lines.

The housing 122, similar to the configuration of FIG. 13, has slit openings 126. The openings 126 extend a greater distance along the length of the housing 122 than in FIG. 13 to allow room for the lower pivot arm 118 to exit the housing 122 and provide sufficient room for the junction 124 to move outwardly.

A stop 129 attached to the upper lever arm 114 is placed between the upper lever arm 114 and the lower pivot arm 118 to prevent the arms from moving past the deployed position. Alternatively, the stop 129 can be inherent in the lower pivot arm 118 and upper lever arm 114. This would include a notch on the side of one of the arms which the other arm would contact to limit the movement of the arms.

FIG. 14 illustrates the use of a sealing member 52 inside the suture introducer housing 24. The sealing member 52 prevents blood flow back through the housing 122.

Figure 16:
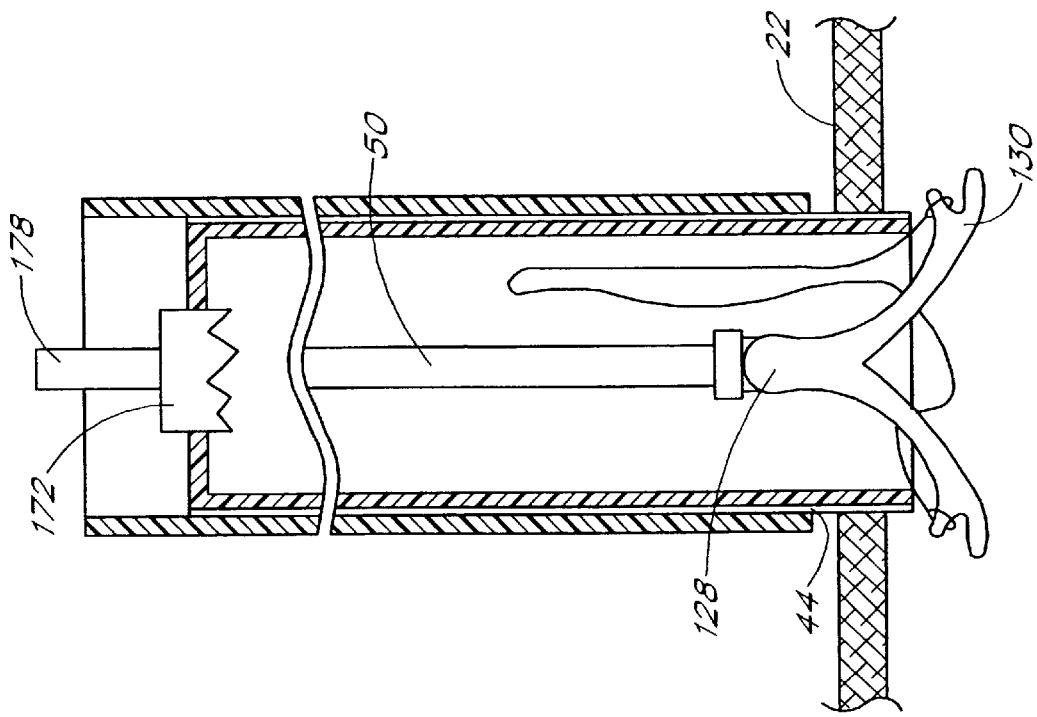
FIG. 16 is a partial cross-sectional view of the device of FIG. 15 illustrating the suture clasp arms in a deployed position.
Figure 15:
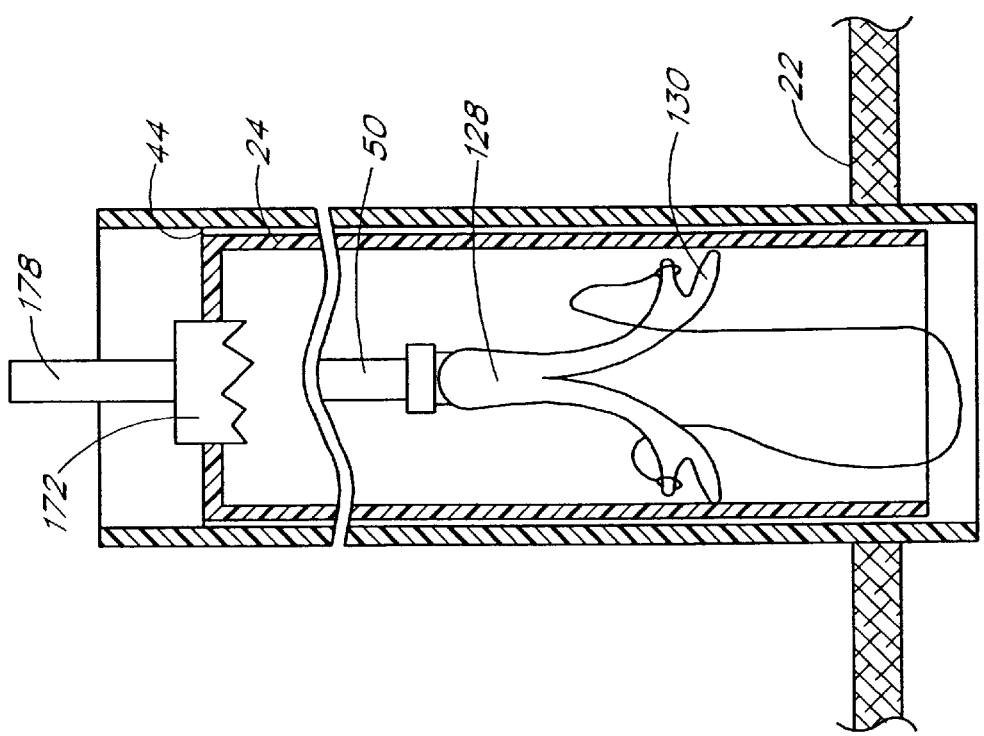
FIG. 15 is a partial cross-sectional view of an alternate configuration of suture clasp arms.

Still another configuration of the clasp arm deployment mechanism is illustrated in FIGS. 15 and 16. In this configuration, a single resilient arm 128 is attached to the actuating rod 50. The resilient arm 128 is predisposed in a deployed configuration shown in FIG. 16. When the arm 128 is retracted into the housing 24, the prongs 130 of the arm 128 are elastically deformed inwardly. When the arm 128 is moved out of the housing 24 by the actuating rod 50, the prongs 130 expand to the predisposed deployed position. This configuration is easily adaptable to having four prongs 130 spaced at ninety degrees. Thus, any configuration and number of prongs can be incorporated into the device depending on the specific needs of the application.

Figure 17:
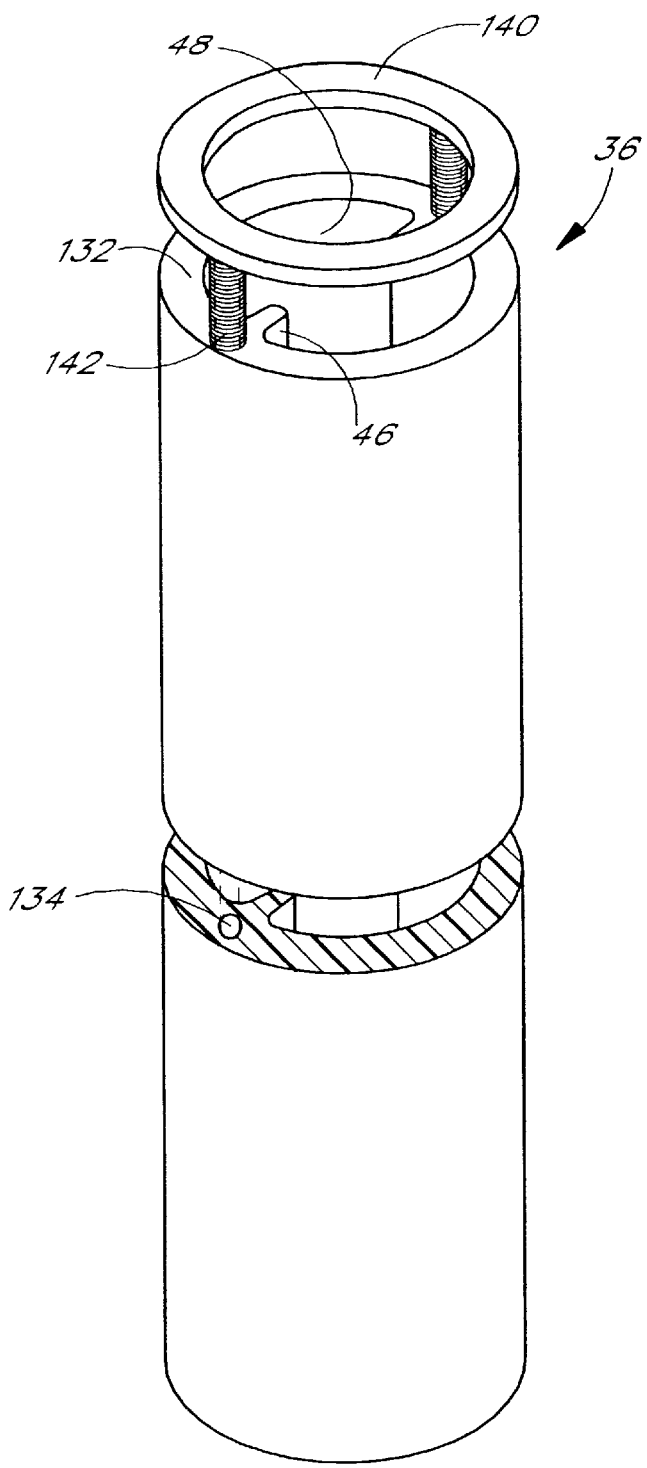
FIG. 17 is a bifurcated perspective view of the suture catch assembly of FIG. 2.

FIGS. 2 and 17 illustrate a preferred configuration of the suture catch assembly 36 with a generally cylindrical outer tube 132, which, as described above, includes a key 46 to mate with the key way groove 44 of the suture introducer housing 24. The inner diameter of the tube 132 is sized to fit over the outer diameter of the suture introducer housing 24 without any interference. This fit does not need to be tight because the suture catch assembly 36 is not inserted into the opening 26 of the vessel 16. Therefore, there is no need to prevent the flow of blood between the suture housing 24 and the suture catch assembly 36. Also, the fit between the suture catch assembly 36 and the suture introducer housing 24 does need to be close enough to assure that the suture catch 38 is properly aligned with respect to the suture clasps 32. Proper alignment is accomplished by a close fit between the key 46 and the key way groove 44.

The catch assembly 36 comprises a plurality of, preferably two, apertures 134 for slidably receiving respective needles 136 or other penetration members. The apertures 134 extend through the length of the tube 132 and may be equally spaced around the circumference of the tube 132 in one configuration of the device.

The blunt ends 138 of the needles 136 are connected to an activation ring 140, and springs 142 are interposed between the activation ring and the tube 132. The springs 142 hold the needles in a retracted position so that the needle points are within the tube 132. With the needles 136 biased in a retracted position by the springs, the suture catch assembly 36 can be handled without the chance of inflicting an unintentional puncture wound.

At least one stop 144 is fixed on the inner surface 48 of the tube 132 and engages the top 146 of the suture housing 24 to fix the relative position between the suture housing 24 and the catch assembly 36. Because the spring 142 can only be compressed a certain distance, the depth of entry of the needles 136 into the vessel 16 is controlled to prevent puncturing the opposite side of the vessel 16. Furthermore, the fixed relative position between the suture housing 24 and catch assembly 36 assures that the needles 136 pass far enough into the suture catch receiving area 80 to catch the suture 40.

Near the end of each needle 136 is the suture catch 38. The suture catch 38 is an aperture extending to the outer edge on one side of the needle 136. The aperture is slot shaped and angled upwardly toward the proximal end of the device. While the needles are being pulled from the vessel 16, the suture 40 is pulled to the bottom of the suture catch 38 where it cannot come loose.

Figure 18:
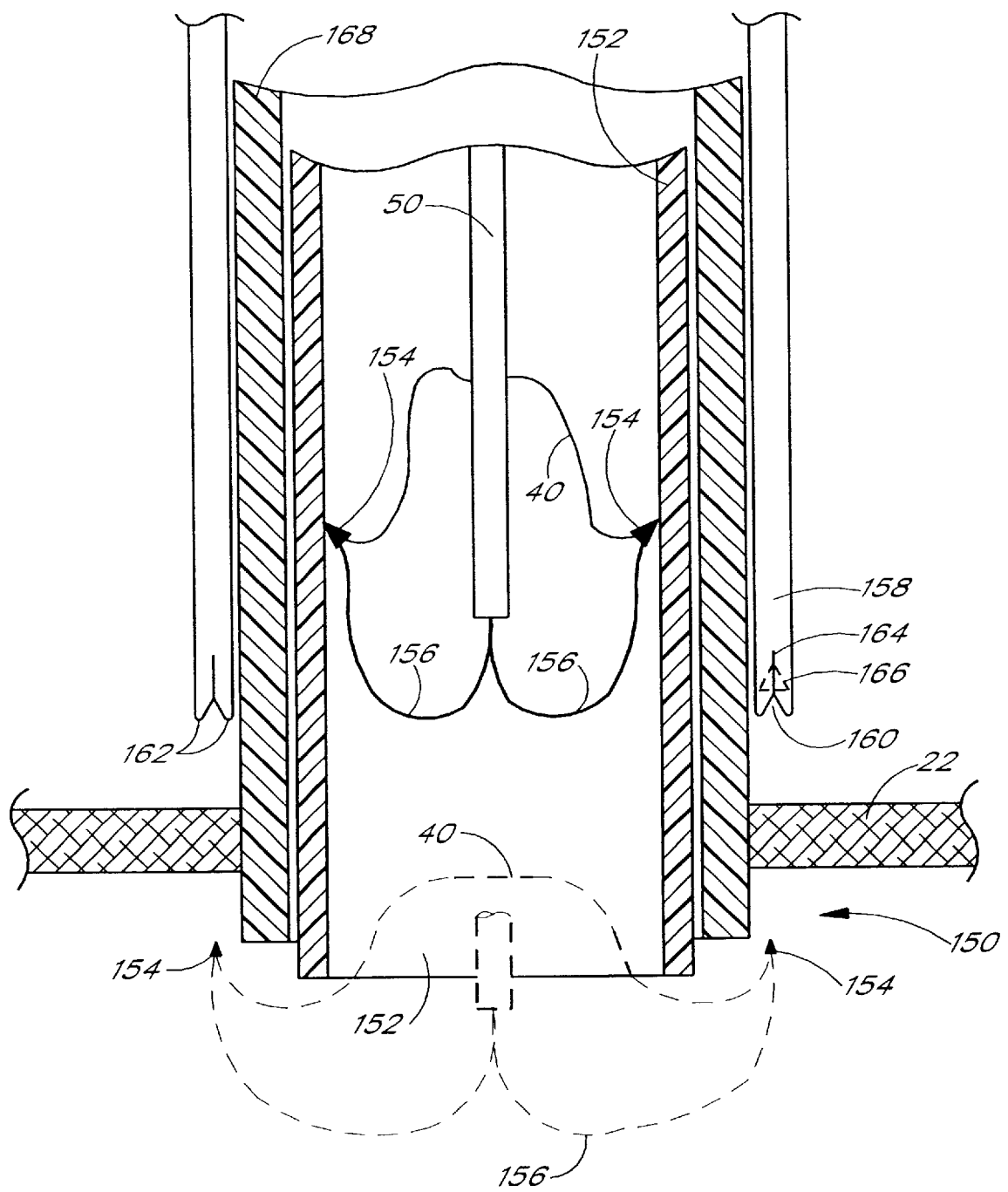
FIG. 18 is a partial cross-sectional view of an alternate configuration of the suture catches and the suture clasp arms.

FIG. 18 shows an alternate configuration of a penetrating mechanism, generally designated 150, with the suture introducer housing 152. The penetrating mechanism comprises needle points 154 press fit onto arms 156. The end of the arms 156 opposite the needle points 154 are fixed to the actuating rod 50. The arms 156 are made of a resilient material exhibiting shape memory such as NITENOL, and the arms 156 are at rest in a deployed position shown in dashed lines. When the arms 156 are within the suture housing 152, they are deformed to fit within the housing 152. When the actuating rod 50 pushes the needle points 154 beyond the suture housing, the arms 156 return to their at-rest position with the needle points 154 beyond the circumference of the housing 152. The suture 40 is attached to the needle points 154. The needle points 154 are then pulled upward by the actuating rod 50 toward the vessel wall 22, thereby penetrating the vessel wall 22 from within the vessel 16.

The suture catch 158 has a V-shaped notch 160 with rounded tips 162. There is a slit 164 extending up from the vertex of the notch 160. The rounded tips 162 prevent the suture catch 158 from inadvertently puncturing the vessel wall 22. The needle points 154 fit into the notches 160 and cause the notches 160 to open farther along the slits 164. After the needle points 154 are inside a cavity 166 within the suture catch 158, the notch 160 collapses to its original shape and traps the needle points 154 inside. The suture catch 158 is then pulled proximally until the press fit between the needle points 154 and the arms 156 is overcome, and the needle points 154 are separated from the arms 156. The actuation rod 50 is then moved proximally to pull the arms 156 both into the housing 152.

For this configuration, an alignment mechanism can be provided such as the key way described above. But in the configuration shown, the notch is circumferential. Thus, no alignment mechanism is needed, and any number of arms 156 extending from the actuating rod can be provided.

The suture catch 158 can be positioned over an introducer 168 if desired. If the proximal end of the introducer 168 is too large for the suture catch 158 to fit over, the suture catch 158 could be made of a flexible material with a longitudinal slit over its entire length allowing it to be expanded to fit around the diameter of the introducer 168. The arms 156 would be modified so that the needle points 154 extend beyond the circumference of the introducer 168.

FIGS. 19 through 23 illustrate an alternate configuration of the suture catch and suture clasp. A needle 400 is provided with a slotted opening 402 having a peg 404 extending from the top of the opening 402 through a portion thereof. The peg 404 has a narrow and rounded front peg surface 406 with an identical radial location on the needle 400 as the outer surface of the needle 400. The back peg surface 408 of the needle 400 is relatively wide, rounded, and located toward the radial center of the needle 400. The peg sides 410 are flat and angled relative to the walls 412 of the slotted opening 402. The slotted opening 402 receives suture fitting 414 having a shaft 416 connected, preferably by crimping, to the suture 40 and an enlarged termination 418 which is preferably spherical.

The alternate suture fitting 420 of FIG. 22 has a half spherical termination 422 with rounded edges. The half spherical termination 422 does not protrude beyond the diameter of the needle 400. This half spherical termination 422 reduces the trauma to the vessel wall 22 when the needle 400 is retracted. The shaft in either configuration has a length short enough not to protrude from the diameter of the needle 400 when the suture fitting is held by the needle 400. This also reduces trauma to the vessel wall 22 during retraction.

The suture fitting 414 is held by a modified suture clasp arm 424 having an aperture 426 to receive the shaft 416 of the suture fitting 414. The wall 428 of the aperture is slowly tapered so that the diameter decreases as the aperture 426 moves inwardly in the arm 424. This frustoconical shape provides a secure press fit with the suture fitting shaft 416. Other aperture shapes are possible so long as the press fit is secure and is of a force which can be overcome by the retraction of the arm 424. The shaft 416 of the suture fittings can also be tapered to better mate with the aperture 426.

When the suture clasp arm 424 is deployed, the termination 418, 422 engages the peg 404 forcing it to one side allowing the termination 418, 422 to slide against the peg 404 until the termination 418, 422 is past the peg 404. When the termination 418, 422 slides past the peg 404, the peg 404 snaps toward its at rest central position thereby capturing the termination 418, 422 and hence the suture 40. When the suture clasp arm 424 is retracted, the press fit is overcome and the suture fitting 414 is pulled from the arm 424. When the peg 404 snaps back into its central position, it tends to pull the suture fitting 414 away from the suture clasp arm 424. This can be utilized to help overcome the press fit. With the suture filling securely held, the needles are retracted, the suture fittings 414 cut from the suture 40, and the suture 40 tied.

FIGS. 24 and 25 illustrate another configuration of the suture catch. A needle 450 is provided with a slot shaped opening 451 with a U-shaped raised portion 452 in the lower front of the slot 451. The opening 451 also defines a suture fitting receiving area 454 at the top of the opening 451 for receiving a suture fitting 456 and a suture fitting catch area 458 in the lower back of the slot adjoining the raised portion 452. The suture fitting 456 has a spherical tip 459, and an arcuate neck 460 which tapers down to a cylindrical shaft 462. The spherical tip 459 is sized to fit through the suture fitting receiving area 454 but not through the U-shaped raised potion 452. Thus, the raised portion 452 holds the suture fitting 456 in the suture fitting catch area 458. The raised portion 452 angles toward the back of the needle 450, so that it becomes larger as it extends farther down the needle 450.

FIGS. 26 and 27 show another configuration of the suture clasp arms 464, which comprises an upwardly facing key hole shaped opening 466 for holding the suture fitting 456. The opening 466 faces upwardly, that is in the direction of needle retraction, to aid in the removal of the suture fitting 456 from the suture clasp arm 464.

In operation, the suture catch is activated to penetrate the tissue to be sutured. The suture clasp arms 464 are deployed directing the suture fitting 456 into the suture fitting receiving area 454. As the suture catch needle 450 is retracted, the neck 460 of the suture fitting 456 is engaged by the raised portion 452, and the angled surface of the raised portion 452 pulls the suture fitting 456 farther and farther toward the back of the needle. Thus, the suture fitting 456 is being pulled out of the suture clasp arm 464 as the needle 450 is retracted. If the suture fitting 456 is not completely removed from the suture clasp arm 464 when it contacts the bottom of the opening 451, it is snapped upwardly pass a neck 468 of the key hole opening 466 and out of the suture clasp arm 464.

The control of the distal and proximal translation of the actuating rod 50 is preferably performed by the three sector, arm actuator assembly, generally designated 170, which is attached to the suture introducer housing 24 (see FIG. 3). Each sector of the arm actuator assembly 170 is substantially identical. FIGS. 28–31 show that the arm actuator handle is comprised of three pieces: a button 172, a cylindrical guide 174, and a catch 176.

The button 172 comprises an actuation post 178 extending centrally from a closed end of a cylindrical body 180. The cylindrical body 180 is sized to longitudinally slide in the guide 174. Three button tabs 182 are spaced equally around the outer surface of the cylindrical body at the end opposite the actuation post 178. Thus, there is one button tab 182 in each sector.

The catch 176 comprises three catch tabs 184 corresponding to the three button tabs 182, a cylindrical body 186 which is sized to fit rotatably inside the cylindrical body 180 of the button 172, and a control ring 188 at an end of the cylindrical body 186 for engaging the three button tabs 182. The control ring 188 is at the end of the catch 176 corresponding to the end of the button 172 having the button tabs 182, and the catch tabs 184 which rotate from sector to sector extend radially from the central ring 188.

The guide 174, which is attached at its proximal end to the housing, has three channels 190 and three notches 192, and the guide 174 is open at both ends; so that the button 172 protrudes from the proximal end, and the catch 176 can extend from the opposite (distal) end. There is one channel 190 in each sector with a notch 192 adjacent thereto. The button tabs 182 and the catch tabs 184 are slidable within the channels 190, each button tab 182 stays in the same channel 190 while each catch tabs 184 is rotated from a channel 190 to a notch 192 and to another channel 190 during operation.

As indicated, the outer diameter of the button 172 is sized to slide inside the guide 174. Preferably, there is a button gap 194 between the button 172 and the guide 174. The diameter of the control ring 188 is sized to rotate freely within the guide 174 with minimum clearance, and the catch cylindrical body 186 is sized to rotate and slide longitudinally inside the button cylindrical body 180 with minimum clearance. This leaves a relatively large catch gap 196 between the catch cylindrical body 186 and the guide 174. Therefore, the length of the catch cylindrical body 186 is preferably long enough so that it is never withdrawn from the button cylindrical body 180 during operation.

Because there is a button gap 194 between the button cylindrical body 180 and the guide 174, the button tabs 182 have a thickness sufficient to extend across the gap 194 and into the channels 190. Thus, the button tabs 182 also overlap the diameter of the control ring 188, so that the button tabs 182 can engage the control ring 188. The bottom surface 195 of the button 172 is contoured to mate with the control ring 188. The catch tabs 184 have a diameter and thickness so that they slide in the channels 190 and fit into the notches 192. Preferably, the outer diameter of the guide 174 is the largest diameter thereby assuring adequate clearance for translation of the button 172 and catch tabs 184.

Figure 28:
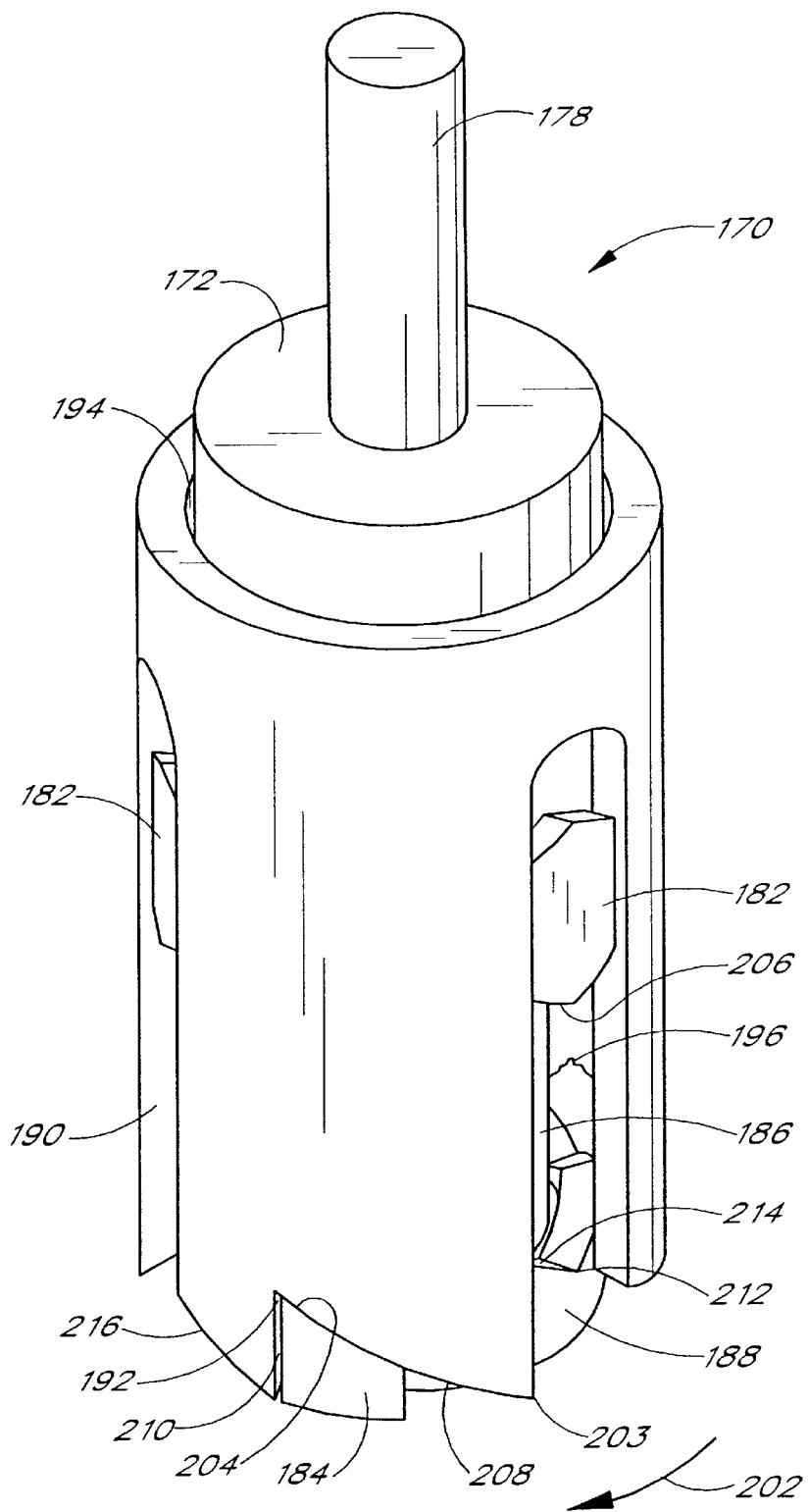
FIG. 28 is a perspective view of a three-sector arm actuator assembly with a catch in a distal position.
Figure 29:
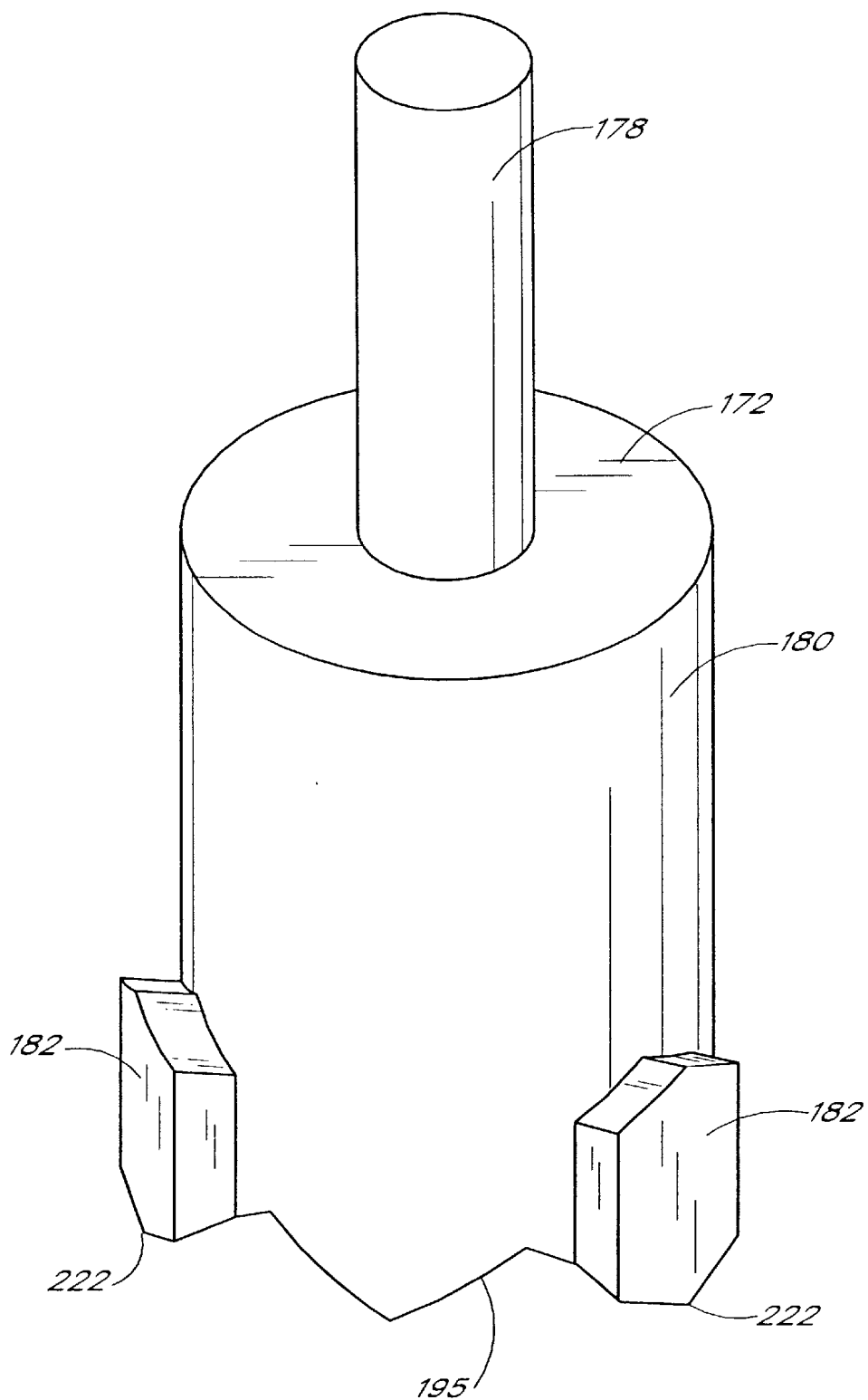
FIG. 29 is a perspective view of a button of the assembly of FIG. 28.
Figure 30:
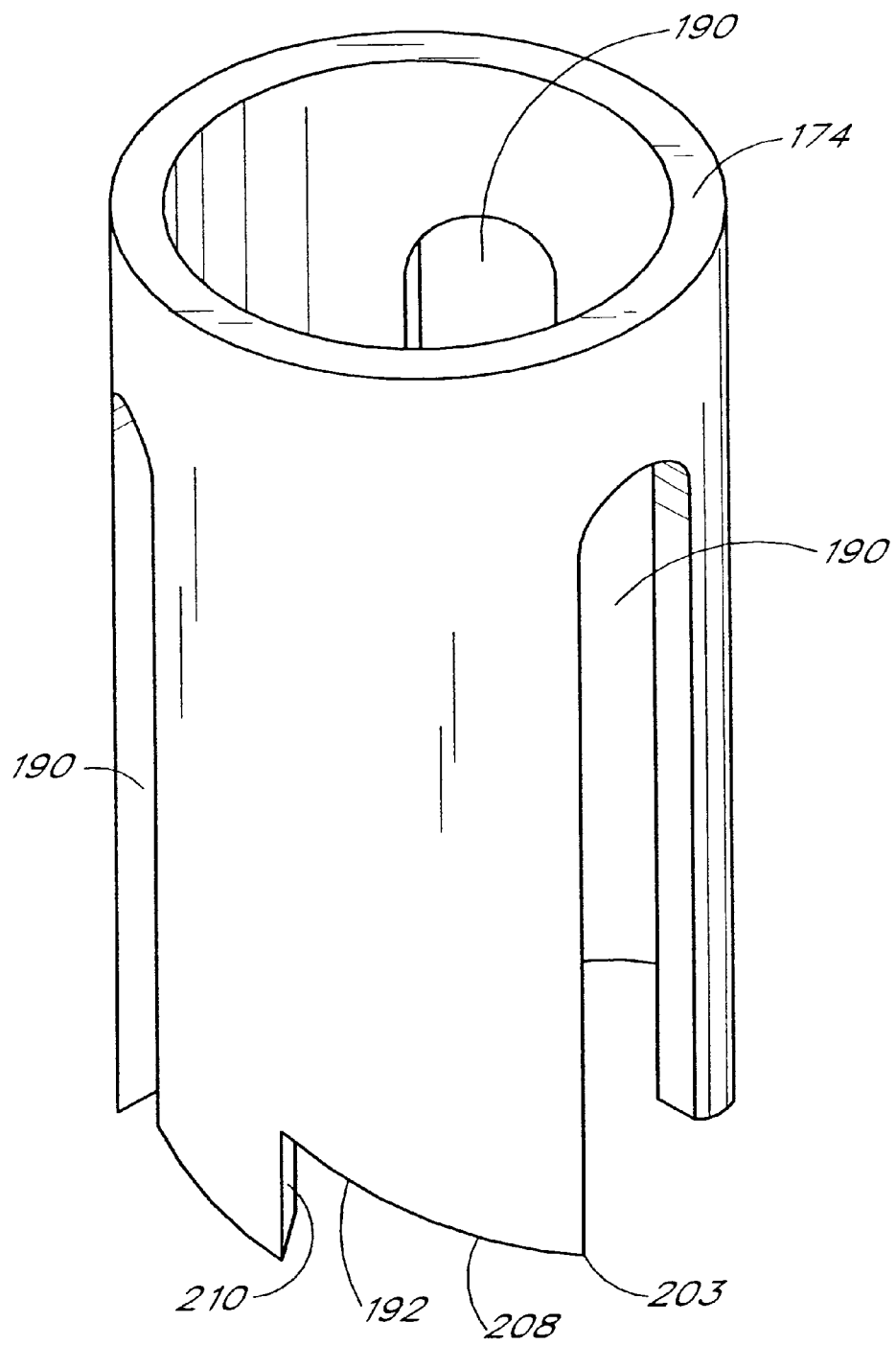
FIG. 30 is a perspective view of a guide of the assembly of FIG. 28.
Figure 31:
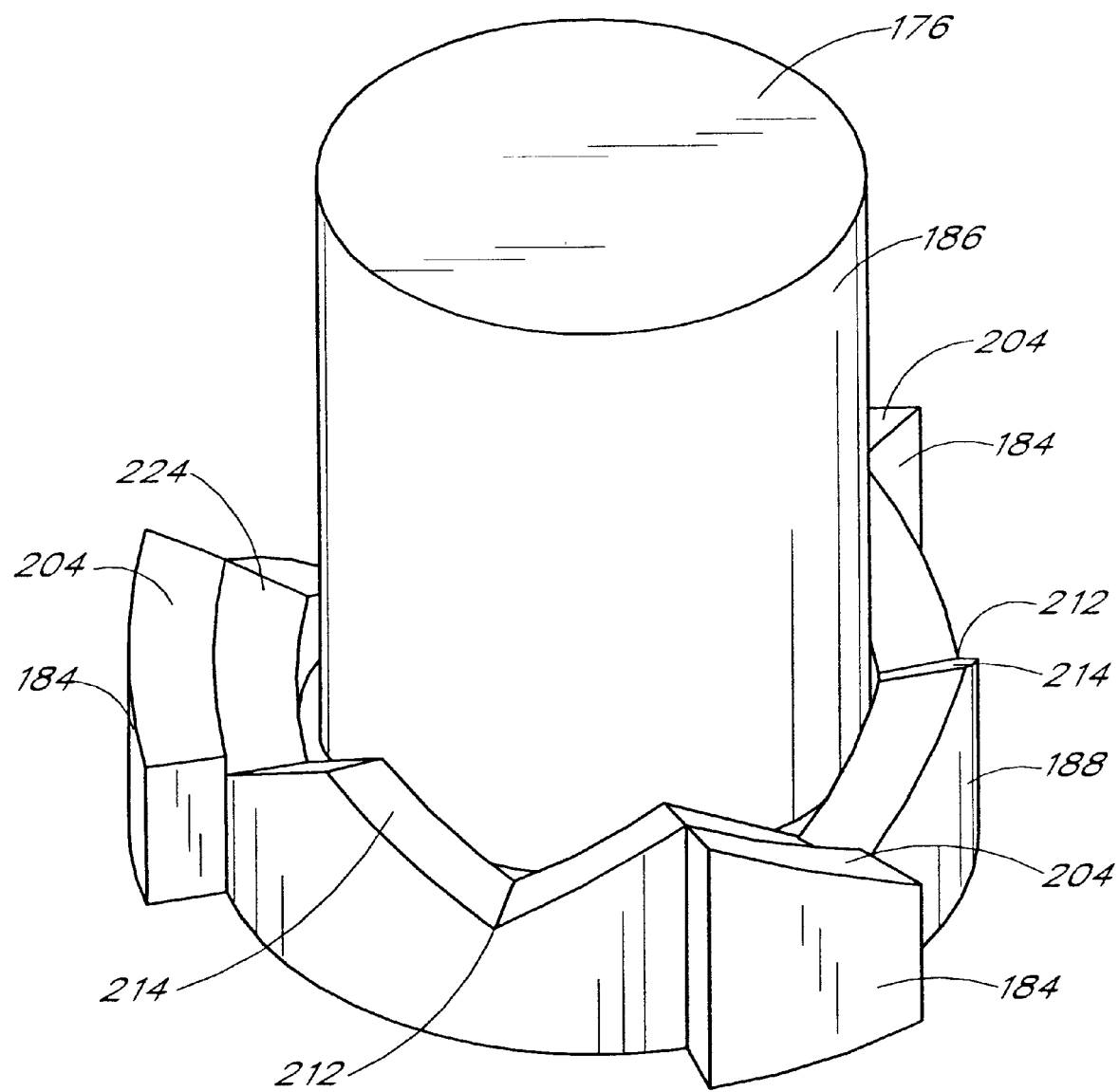
FIG. 31 is a perspective view of the catch of the assembly of FIG. 28.
Figure 32:
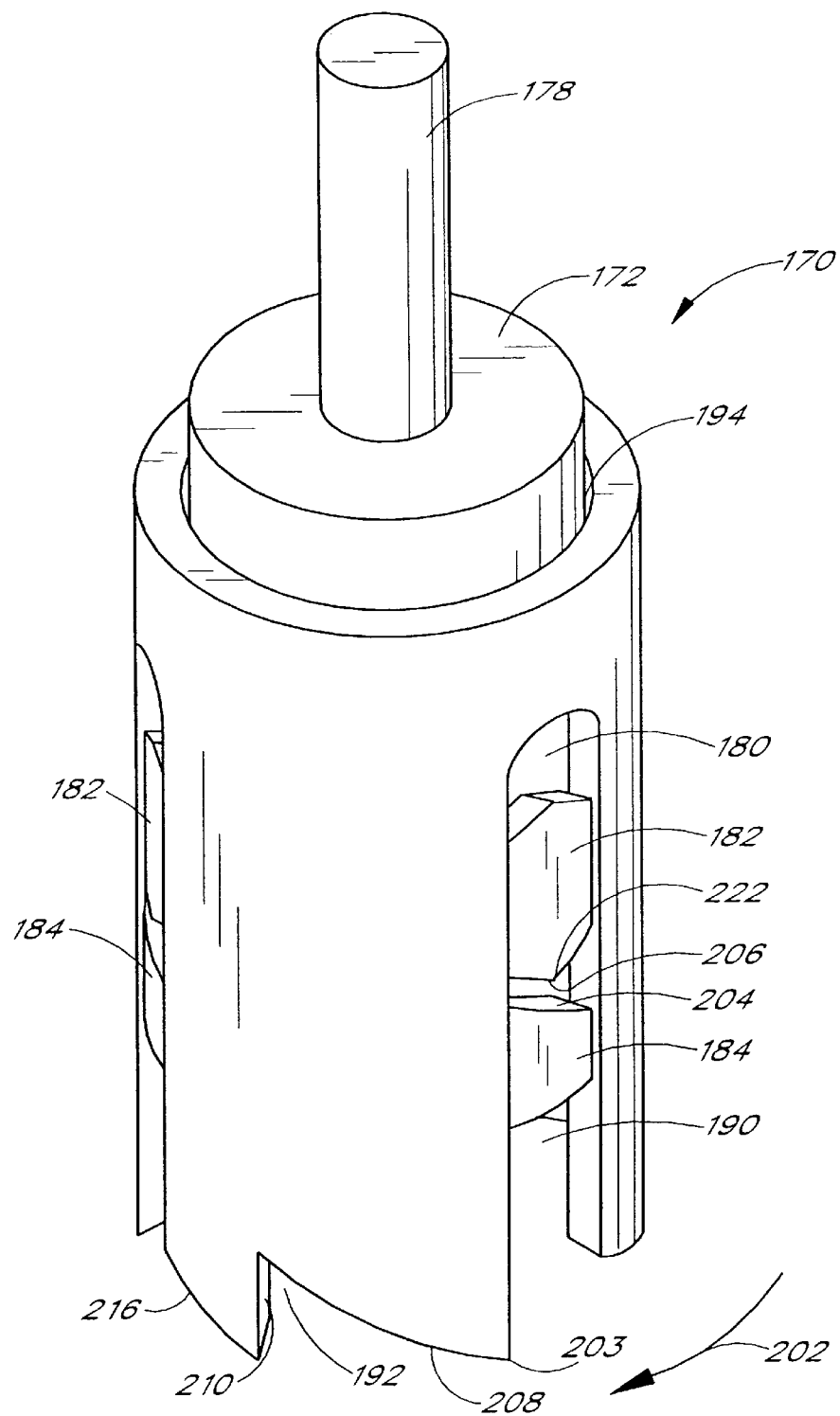
FIG. 32 is a perspective view of the assembly of FIG. 28 with the catch in a proximal position.
Figure 33:
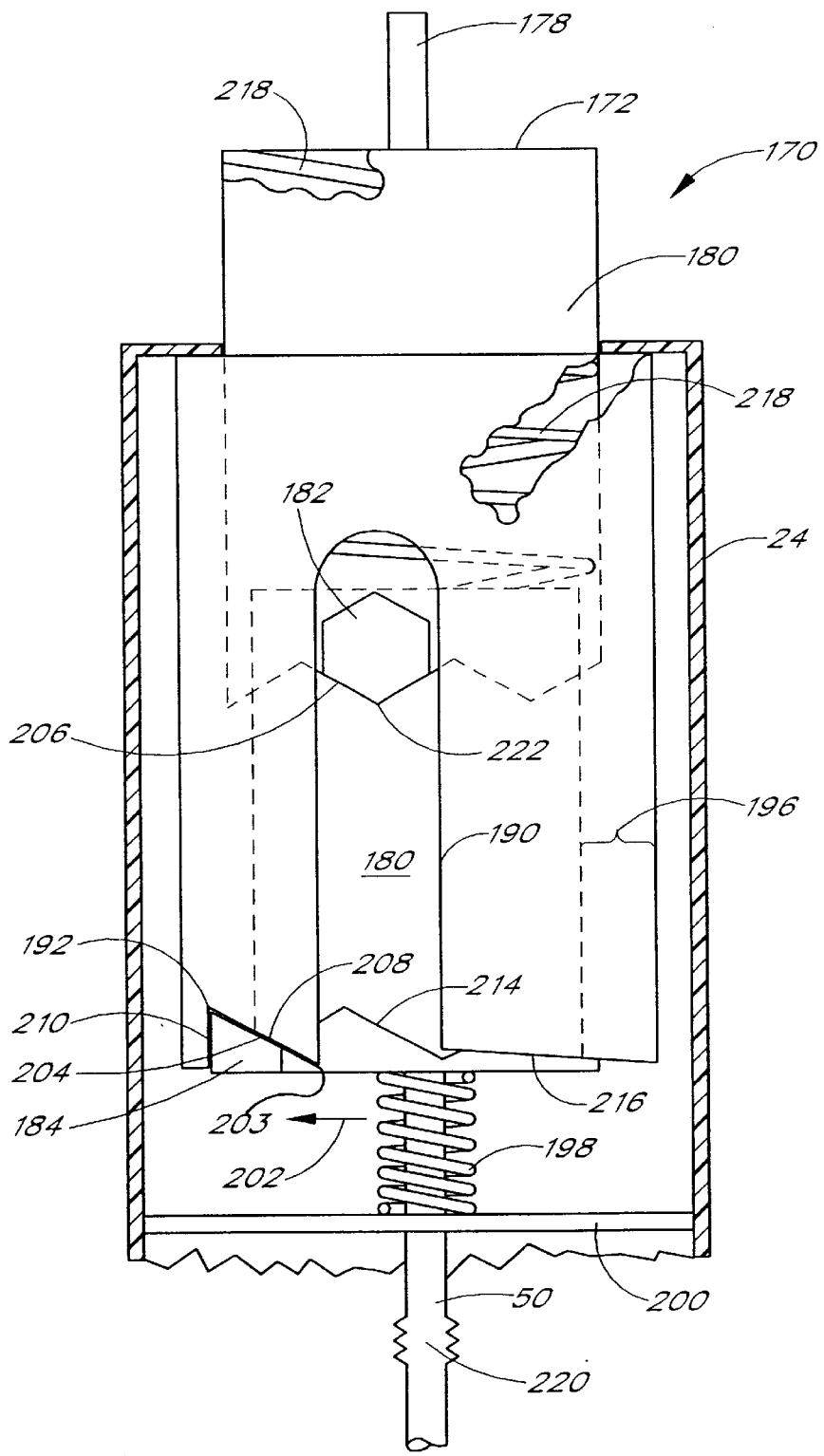
FIG. 33 is a schematic partial cross-sectional view of the assembly of FIG. 28 with the catch in a distal position.
Figure 35:
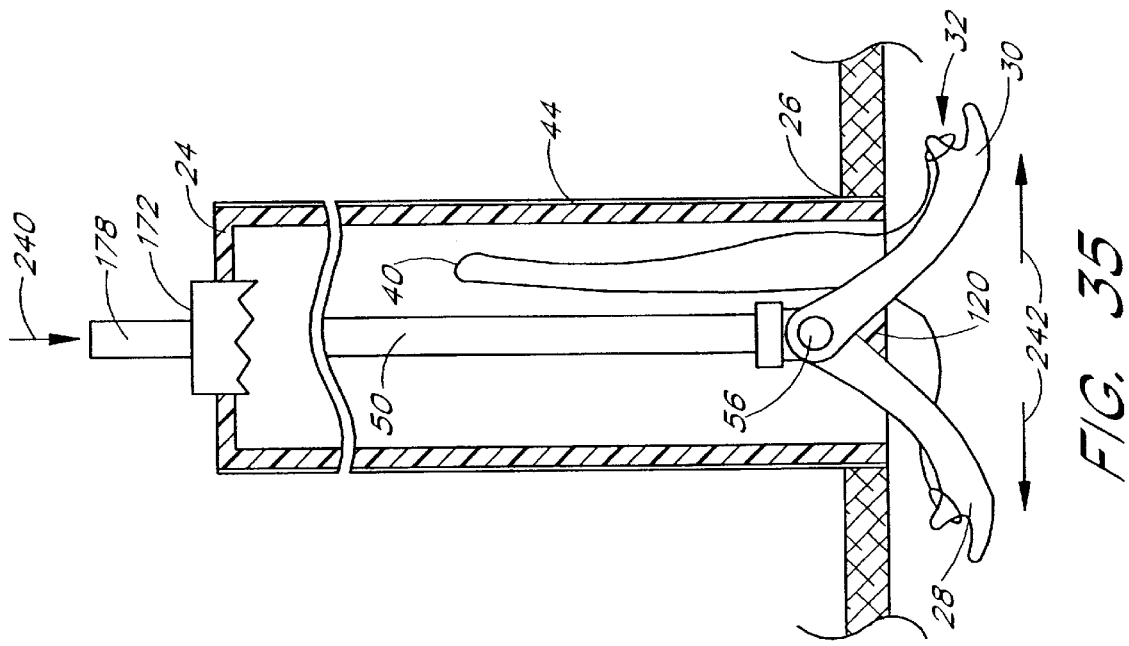
FIG. 35 is a partial cross-sectional view of the suture introducer housing of FIG. 2 with the suture clasp arms deployed.
Figure 34:
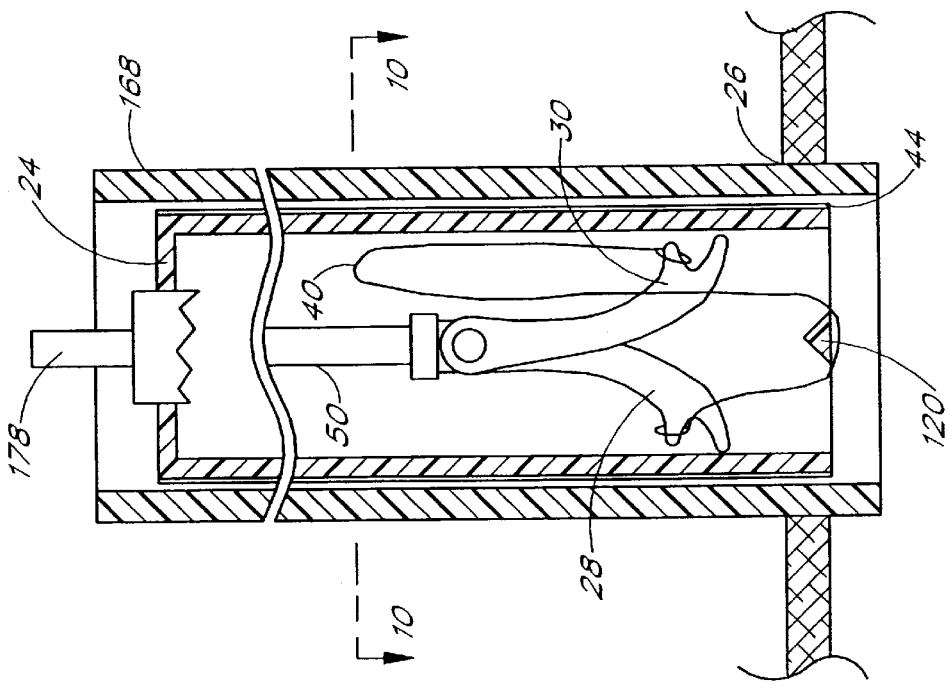
FIG. 34 is a partial cross-sectional view of the suture introducer housing of FIG. 2 with the introducer over the housing.

In FIGS. 28, 32, and 33, the catch 176 starts out in a proximal position with the catch tabs 184 in the channels 190 as shown in FIG. 32. A rotation spring 198 is held in compression between fixed plate 200, which is attached to the housing 24, and the catch 176. The rotation spring 198 biases the catch 176 in the proximal direction, which corresponds to a retracted suture clasp arm position.

The physician presses down on the actuation post 178 of the button 172 causing the button tabs 182 to move distally pressing against the catch tabs 184 and control ring 188 thereby moving the catch tabs 184 distally until the catch tabs 184 are beyond the distal edge 203 of the channels 190. At this point, the catch 176 rotates in the direction of arrow 202 in FIG. 32. The rotation is created by the rotation spring 198 pushing a top angled surface 204 of the catch tab 184 against the bottom angled surface 206 of the button tabs 182. As the catch 176 rotates, it also translates upwardly because of the angled surfaces. This prevents the catch 176 from rotating past the notch 192.

The physician then releases the actuation post 178 allowing the rotation spring 198 to push the catch tabs 184 against the angled notch surface 208 and rotate the catch tabs 184 until they contact the vertical notch stops 210 as illustrated in FIG. 28. In this rotational position, V-shaped depressions 212 on the control ring 188 are aligned with the channels 190 of the guide 174. When the catch tabs 184 are in the notches 192, the suture clasp arms 28, 30 are in a deployed position.

To retract the needles 136, the physician again depresses the actuating post 178, so that the button tabs 182 engage the V-shaped depressions 212 in the control ring 188 located between the catch tabs 184. This pushes the catch tabs 184 below the bottom of the guide 174. The rotation spring 198 pushing upward on the guide 174 causes the slide surface 214 of the V-shaped depression 212 to slide across the bottom surface of the button tab 182 causing the catch tabs 184 to rotate and move upwardly until they engage the angled bottom return surfaces 216 of the guide 174. After the physician releases the actuation post 178, the rotation spring 198 continues to force the catch tab 184 to slide over the return surface 216 until the catch tab 184 reaches the channel 190 and the spring 198 forces the catch tab 184 upwardly into the channel 190 thereby retracting the suture clasp arms 28, 30. As shown in FIG. 33, a button spring 218 can be provided between the catch 176 and the button 172 to return the button 172 to an upward position after it is released. If the button spring 218 is used, the button tabs 182 contact the tops of the channels 190 preventing the button 172 from coming off the assembly.

The suture clasp arms 28, 30 are completely deployed when the catch tab 184 is in the notch 192 against the notch stop 210. For the operation of the actuator assembly, the catch tab 184 is pushed below this level several times. To prevent the arms 28, 30 from going past a fully deployed position, a resilient member 220 is placed in the actuating rod 50. Once the suture clasp arms 28, 30 reach the fully deployed position, their further motion is restricted as described above. As the catch tab 184 is pushed below the position corresponding to the fully deployed position, the resilient member 220 is compressed allowing the catch tab 184 to be moved the rest of the way below the bottom surface of the guide so that it can rotate to the next position. This prevents damage to the spreader 102, bending the actuating rod 50, and risk of injury to the vessel 16.

To allow the catch 176 to begin rotating after it clears the bottom of the channel 190 or the bottom of the vertical notch stop 210. The vertex 222 of the button tab 182 is not aligned with the bottom of the V-shaped depression 212 when the V-shaped depression 212 is aligned with the channel 190. The vertex of the depressions 212 is positioned to a side of the vertex of the button tab 182 in the rotational direction, so that the catch 176 is allowed to rotate until it is underneath the shallow end of the return surface 216 of the guide 174. Similarly, when the catch tab 184 is inside the channel 190, the angled surfaces 224 of the control ring 188 corresponding to the catch tab 184 continue past the catch tabs 184 to again allow initial rotation of the catch 176 until the catch tab 184 is beneath the shallow end of the notch surface. Thus, the catch tab 184 can rotate underneath the shallow end of the notch 192 before the button tabs 182 contact the lowest point of the control ring surfaces 224 and rotation is restricted. When the rotation is restricted, the actuation post 178 is released raising the button tab 182 out of the way, and the catch 176 can complete its rotation.

The operation of the device is illustrated in sequence by FIGS. 1, 2 and 34 through 36. After the medical procedure, the introducer sheath 6 is left in place, and the suture introducer housing 24 is inserted into the introducer 6 and introduced into the artery 16 as shown in FIGS. 1A and 1B. The actuation post 178 is then depressed, as illustrated by arrow 240 in FIG. 35 to deploy the suture clasp arms 28, 30 outwardly as illustrated by arrows 242 so that portions, preferably the ends, are positioned on opposite sides of the opening 26 with the suture 40 extending transverse to the flow of blood.

The introducer 6 is then removed, leaving the suture introducer housing 24 with the suture clasp arms 28, 30 deployed inside the artery 16. The opening 26 in the vessel 16 closes around the housing 24 after the introducer 6 is removed. In FIG. 38, the suture introducer housing 24 is then oriented so that the arms 28, 30 extend transversely to the flow of blood through the vessel 16 which is illustrated by arrow 244. The suture catch assembly 36 is then inserted over the housing 24 and the stop 144 is brought into contact with the top 146 of the housing 24 as shown in FIG. 2. A physician depresses the activation ring 140 as illustrated by arrows 246 (FIG. 36) pushing the needles 136 through the vessel wall 22 and puncturing holes 248 in the vessel wall 22. The suture catch 38 catches the suture 40, and the suture catch assembly 36 is pulled proximally as illustrated by arrows 250 (FIG. 37). The needles 136 can be retracted inside the suture catch assembly 36 or left deployed. The suture 40 is cut from the suture catch 38 and pulled tight to remove it from the housing 24.

The suture clasp arms 28, 30 are retracted by depressing the actuation post 178 again, and the suture 40 is pulled tight simultaneously with the housing 24 being pulled out of the artery 16. Alternatively, the length of the actuation post 178 is set to correspond with the height of the depressed activation ring 140. Thus, when the activation ring 140 is depressed, the actuation post 178 is simultaneously depressed for the second time thereby retracting the arms 28, 30 simultaneously with pulling the suture catch assembly 36 proximally.

With the suture catch 38 removed, the pattern of holes shown in FIGS. 38 and 39 is left. As stated above, the suture 40 closes the artery vessel opening 26 transverse to the flow of blood. This is the most efficient direction to close the opening 26. If additional suture clasp arms are utilized, it is preferred that they make additional holes around the circumference of the opening as shown in dashed lines in FIG. 38, so that sutures again pull the opening 26 closed in a direction transverse to the flow of blood.

The present invention could be similarly used to close a patent ductus arteriosus, a patent foramen ovale, a heart defect, a puncture wound in the skin, and other tissues requiring suturing. For example, for closure of a heart septal defect such as an atrial septal defect (ASD), the suturing device may be used to close the defect opening by approximating the tissue surrounding the defect opening. Access to such heart septal defects can be provided by inserting a catheter including the suturing device into the right atrium via the inferior vena cava and the femoral artery. Alternatively, access to such heart septal defects can be provided by inserting the catheter including the suturing device into the right atrium via the superior vena cava and the subclavian vein or internal jugular vein. Once the suture clasp arms 28, 30 are deployed and the suture 40 is positioned on the left-atrial side of the ASD, the needles 136 can be extended to puncture through the tissue of the septal wall surrounding the ASD to engage the suture 40 with the suture catches 38. Retracting the needles 136 then pulls the suture 40 through the septal wall, and further tension applied to the suture 40 closes the ASD by approximating the surrounding tissue of the septal wall. Similar procedures can be used to repair other septal defects such as patent foramen ovales, ventricle septal defects (VSD), endocardial cushion defects, or septal defects existing in conjunction with Tetralogy of Fallot. As discussed below in conjunction with FIGS. 82–84, where the size of the septal defect is so large that approximation of the tissue surrounding the septal defect would result in excessive distortion of the cardiac tissue, the suturing device may be used in conjunction with a patch.

Figure 40:
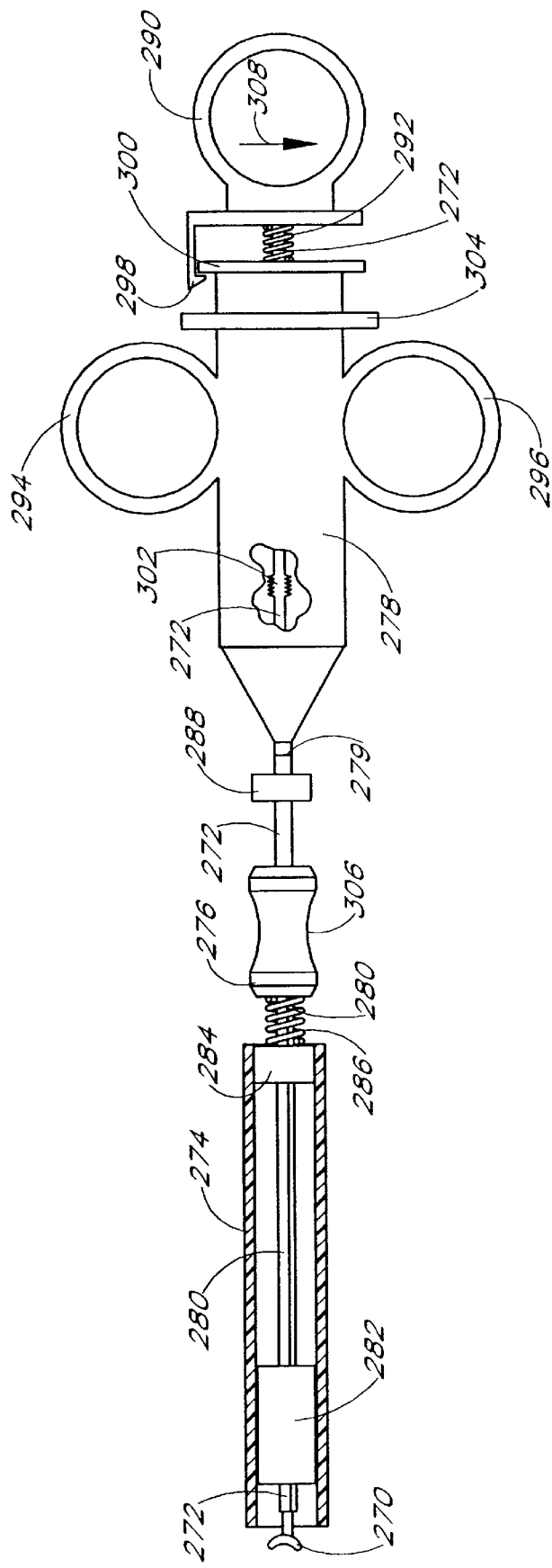
FIG. 40 is a partial schematic cross-sectional view of one configuration of the suturing device having a detachable arm deployment handle.

An alternate configuration of the suturing device is shown in FIG. 40. The device comprises a pair of suture clasp arms 270 attached to the end of an actuating rod 272 in accordance with one of the above described configurations. The actuating rod extends through a needle cover 274 and slidably through a needle actuator 276 to a suture arm deployment handle 278. Near the deployment handle 278 the actuating rod 272 has, a severable junction 279. The junction 279 is threaded or snap fit allowing the actuating rod 272 to be quickly separated and joined thereby quickly removing or attaching the handle 278 from the remainder of the device. The actuating rod 272 can, in the alternative, have a junction where it enters the needle cover 274.

Needles 280 are held near their distal ends by a needle guide 282 and pass through a stop 284 that limits the deployment distance of the needles 280. The needles 280 fixably attaching to the needle actuator 276. A spring 286 is interposed between the stop 284 and the needle actuator 276 to bias the needles 280 in a retracted position. A second stop 288 is fixed to the actuating rod 272 on the opposite side of the needle actuator 276 to prevent the needles 280 from being pulled out of the needle guide 282.

The actuating rod 272 terminates at a thumb ring 290 separated from the distal end of the suture arm deployment handle 278 by a thumb ring spring 292 which biases the thumb ring 290 in a proximal position which corresponds to a retracted position of the suture clasp 270. The handle 278 also comprises two finger rings 294, 296 on opposite sides of the handle allowing a physician to smoothly overcome the force of the thumb ring spring 292.

In operation, the distal portion of the device, from the needle cover 274 to the suture clasp arms 270, is inserted into the introducer 6 with the handle 278 detached. The introducer 6 is removed and the handle 278 is attached to the device by connecting the actuating rod 272. The thumb ring 290 is pushed distally to deploy the suture clasp arms 270. A clip 298 hooks onto a clip ring 300 to lock the suture clasp arms 270 in the deployed position.

The actuating rod 272 includes a resilient member 302 (shown schematically), which functions, as described in the previous configurations, to prevent the suture clasp arms 270 from moving past their deployed position. The resilient member 302 can simply comprise a spring, or a spring housing can be provided on one part of the actuation rod 272 to receive a spring and a slidable plunger therein. The plunger, which is provided on the opposite part, slides to a maximum distal position defined by the spring housing and is biased in that position by the spring. When the suture clasp arms 270 reach a deployed position, the plunger is then forced into the spring housing, compressing the spring and allowing the upper portion of the actuation rod 272 to travel distally without forcing the suture clasp arms 270 past a deployed position or bending the actuation rod 272. A thumb ring stop 304 prevents the thumb ring 290 from being pushed beyond a point for which the resilient member 302 could compensate.

With the suture clasp arms 270 deployed, the physician grasps the needle actuator 276, which has a central curved indented surface 306 to make it easy to grasp, and pushes the needle actuator 276 distally. The needles 280 are pushed into the vessel 16 and catch the suture 40 as described in one of the above configurations. The stop 284 prevents the needles 280 from penetrating too far and damaging the vessel 16. The spring 286 pushes the needles 280 back to a retracted position when the needle actuator 276 is released.

With the suture 40 held by the needles 280, the thumb ring 290 is pushed in a direction transverse to the length of the actuating rod and away from the clip 298 as illustrated by arrow 308 to release the clip 298 and retract the suture clasp arms 270. The entire device is retracted, the suture 40 cut from the needles 280, and the suture 40 tied to close the opening 26. Because the handle 278 is detachable, the handle 278 could be used in conjunction with the above described configurations. In such a case, the arm actuator assembly would be removed, and the actuating rod 50 would extend through the top of the housing 24. The end of the actuating rod 50 would be modified to connect to the handle 278.

Embodiments of FIGS. 1C–1D and 41–50

In the embodiments described above, the suture introducer housing 24 and the suture catch assembly 36 consist of two separate pieces, wherein the suture catch assembly 36 operatively fits around the suture introducer housing 24. As described above with reference to FIGS. 1A–1B, in these embodiments, the physician fully removes the original CSI 6 before inserting the suture catch assembly 36 to penetrate the blood vessel wall and catch the ends of a suture. The removal of the CSI 6 and the introduction of the suture catch assembly 36 may disturb the flesh 14 or enlarge the incision 20 and add to the complexity of the procedure.

Figure 41:
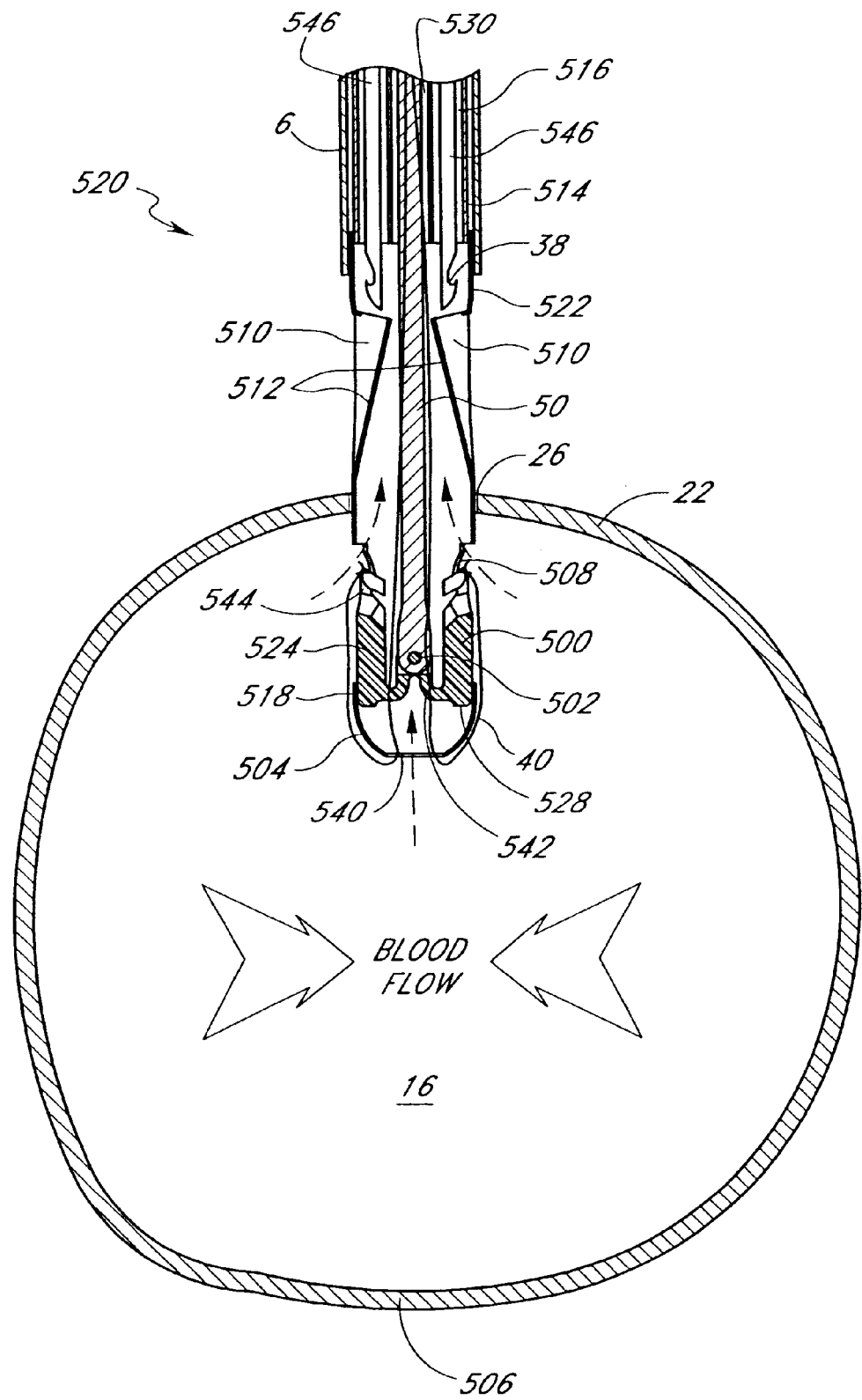
FIG. 41 is a cross-sectional view of the embodiment depicted in FIG. 1C with the distal end inserted through an arterial wall.

The embodiments illustrated in FIGS. 1C–1D and 41–50, however, do not require the full removal of the original CSI 6 (used for the original percutaneous approach procedure, such as an angioplasty/angiography procedure) in order for the device to catch the ends of a suture. Rather, as depicted in FIG. 41, the distal portion of the device 520 passes through the CSI 6 and the flesh 14 of the patient's thigh 12 with minimal disturbance to the flesh 14, and through the second incision 26 into the femoral artery 16. Any disturbance to the flesh 14 is significantly reduced because the CSI 6 is not removed and a suture catch assembly is not slid down over a suture introducer housing through the flesh 14, as in the embodiments described above with reference to FIGS. 1A–1B and 240.

Figure 46:
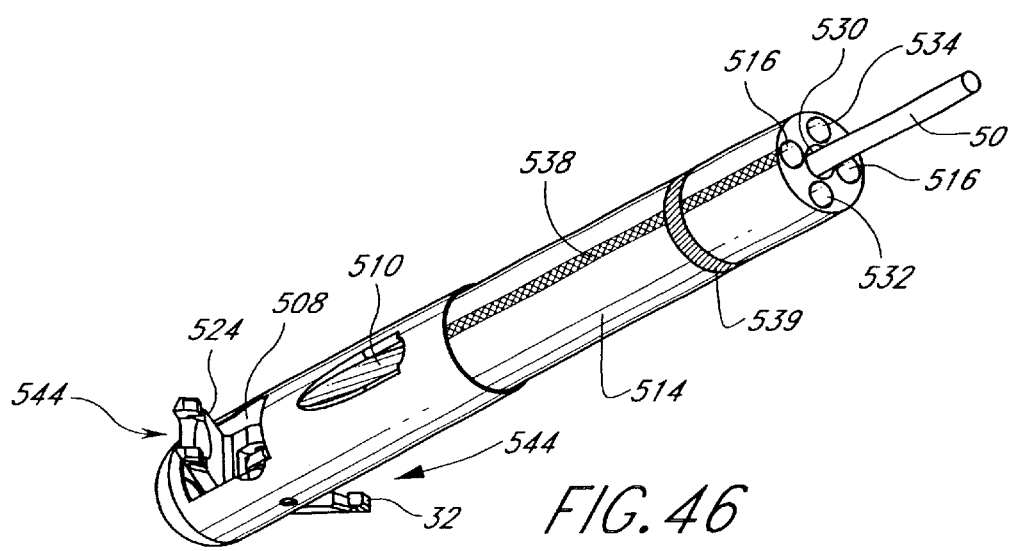
FIG. 46 is a rear perspective view of the device of FIG. 44.
Figure 47:
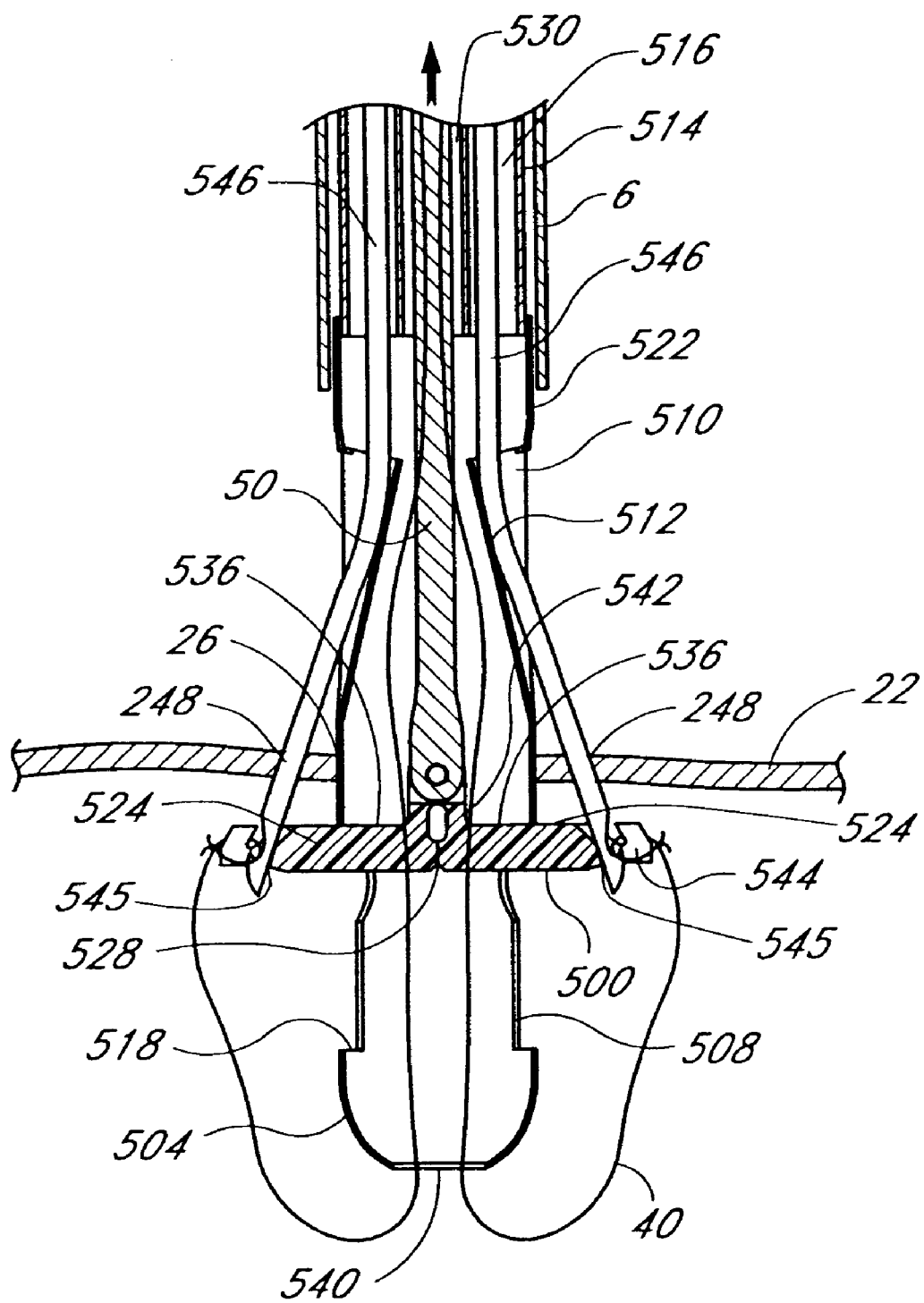
FIG. 47 is cross-sectional view of the device of FIG. 41 with the suture clasp member fully deployed.
Figure 48:
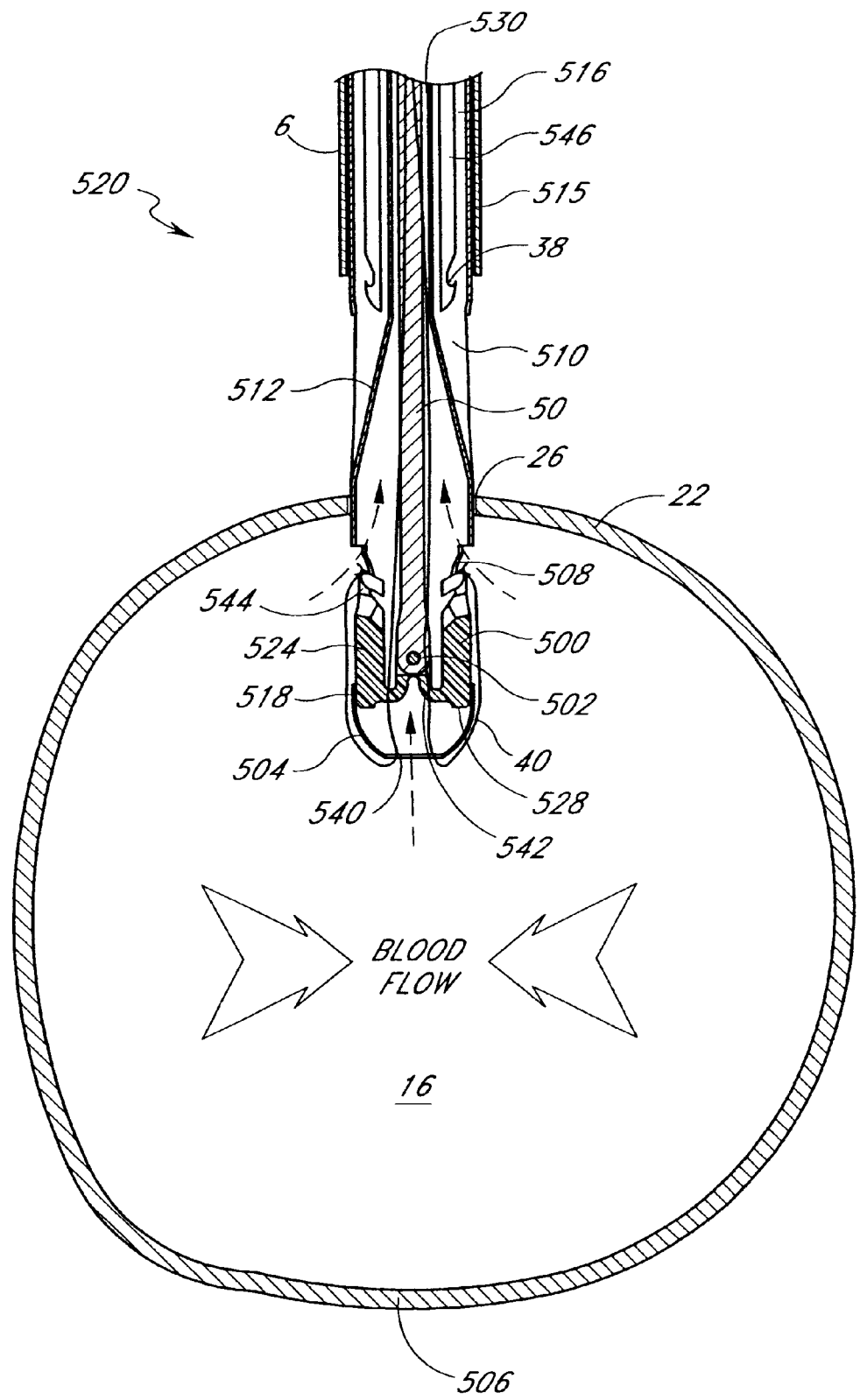
FIG. 48 is a cross-sectional view of another embodiment of the present invention.

FIGS. 41–48 illustrate the device 520 depicted in FIGS. 1C–1D where the suture introducer housing and the suture catch assembly are integrated into a single suture insertion and retraction device 520. This suturing device 520 may comprise a one-piece suture insertion and retraction housing 515 as shown in FIG. 48, or may comprise a suture introducer head 522 attached to the distal end of a hollow elongated body 514 as shown in FIG. 41.

With reference to FIG. 41, the suture introducer head 522 and the hollow body 514 are narrower in diameter than the configurations illustrated in FIGS. 1A–1B and 2–40 because the suture clasp member 500 and the needles 546 reside in the same longitudinal space. In other words, the needles 546 share the same housing as the suture clasp member 500 (while they are all in their retracted state), but are higher up (proximally) in the suturing device 520 than the suture clasp member 500. An important feature of this embodiment is that it uses flexible needles 546 which bend outward, away from the axis of the device 520, when in the extended position (as shown in FIG. 47).

The dimensions of the suturing device 520 may vary according to the suture site and the biological tissue intended to be sutured. In one configuration, the diameter of the suture introducer head 522 is about 0.105 inches, and the diameter of the hollow elongated body 514 is about 0.098 inches.

Figure 42:
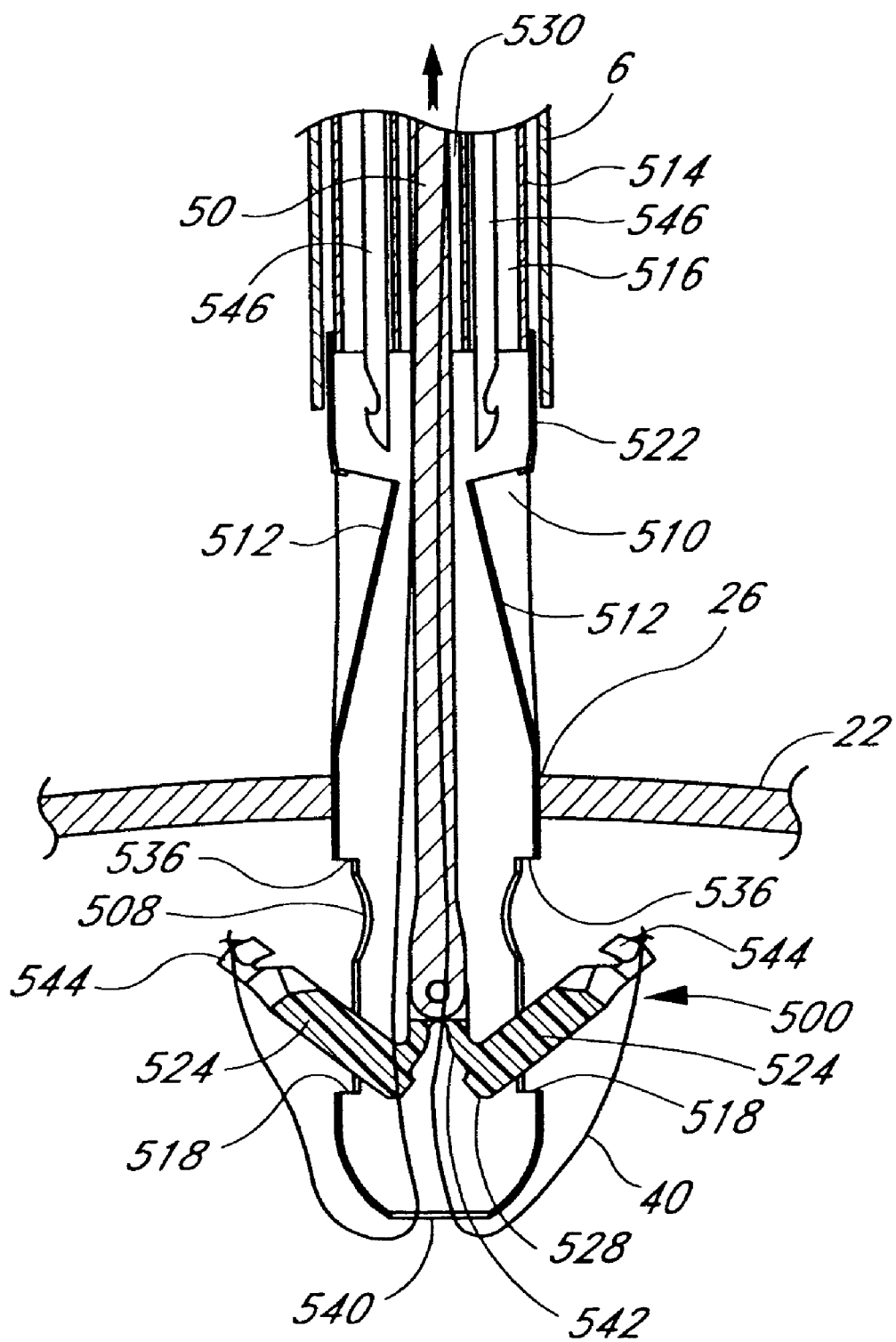
FIG. 42 is a cross-sectional view of the device of FIG. 41 with the suture clasp member partially deployed.

As shown in FIGS. 42, 46 and 47, the suture introducer head 522 has two needle ports or apertures 510 formed therein (one per needle 546) proximal to the suture clasp arms 524. Each needle port includes a needle guiding portion 512 ("needle guide"), in the form of an outwardly curved groove or channel, which guides the corresponding needle 546 along a particular path. The needle guides 512 may be formed within the suture introducer head 522 (as shown in FIG. 41) as part of a mold, or may be separate pieces (not shown) that are inserted into the suture introducer head 522 during manufacture.

Another advantage of the embodiments illustrated in FIGS. 41–48 is the required size of the initial incision 20 into the patient's body and the diameter of the introducer sheath 6 used to insert the device 520 may be reduced. The size of the suture device 520 may vary depending on the application and the size of the vessel incision 26.

FIG. 46 shows a preferred configuration of the hollow elongated body 514 with five lumens. Two of the lumens 516 are used to house the needles 546 (FIG. 41). Another lumen 530 is used to house the actuating rod 50. Another lumen 532 is used to hold the length of the suture 40 to prevent the suture 40 from becoming tangled. Alternatively, the suture 40 may be stored in the actuating rod lumen or in a hole drilled into the suture clasp arm 500.

The fifth lumen 534 is preferably used for 'bleed back,' which lets the physician determine whether the distal end 504 of the suture introducer head 522 is still positioned in the artery 16 after the physician removes the catheter sheath introducer (CSI) 6. Bleed back is accomplished by the hole 540 (FIG. 45) at the distal end 504 of the suture introducer head 522, the suture clasp arm apertures 508 and any other openings in the suture introducer head 522. The direction of blood flow for bleed back is shown by the dashed arrows in FIGS. 41 and 48. If the distal end 504 of the introducer head 522 is still in the artery 16, the blood pressure measured by the blood coming up into the hole 540 will be much greater than if the distal end 504 is not in the artery 16. In one embodiment, the bleed back lumen 534 extends to a port (not shown) at a proximal portion of the device, and the physician can observe the blood pressure through bleed back lumen 534 by monitoring blood flow from the port. For example, the bleed back lumen may be attached to a balloon which inflates when the distal portion 504 of the suture introducer head 522 is within the blood vessel 16. In another embodiment, a pressure sensor is associated with the blood flow lumen 534 to provide the physician with a numeric reading. Alternatively, the fifth lumen 534 may be used to inject medication or for diagnostic purposes.

In a preferred embodiment, two thin stripes 538 (only one shown in FIG. 46) are marked on the exterior of the elongated body 514 which denote the circumferential location of the two needles 546. These stripes extend along a portion of the elongated body 514 which is outside the patient's body. These stripes help the physician to align the needles 546 with the axis of the blood vessel 16, so that the needle incisions 248 (FIG. 47) will be longitudinally aligned. As described above for FIG. 38, the suture 40 closes the artery vessel opening 26 transverse to the flow of blood. This is the most efficient direction to close the opening 26. Proper insertion of the needles 546 reduces the risk of damage to the vessel walls 22, 506. Alternatively, there may be only one stripe to denote the circumferential location of one of the two needles 546. The physician will know the circumferential location of the other needle 546 because the needles 546 are 180 degrees apart.

As illustrated in FIG. 46, the exterior surface of the elongated body 514 includes a marker 539 which denotes the proximal position to which the CSI 6 should be partially withdrawn (after the distal portion of the suturing device 520 has been inserted into the blood vessel 16) to expose the needle apertures 510. The partial withdrawal of the CSI 6 is described below. The marker 539 is shown as a visual marker, but may additionally or alternatively be in the form of a ridge, groove, or other physical structure which interacts with a corresponding structure of the CSI to allow the physician to position the CSI using the sense of feel. For example, the CSI 6 and elongated body 514 could be configured to releasably engage or interlock with one another when the CSI reaches the proper position along the body 514. A specially formed CSI which includes such an interlocking structure is included within the scope of the invention. One or more additional longitudinal markers (not shown) could be provided along the body 514, distal to marker 539, to indicate other relative positions of the CSI and the body 514, such as the position at which the retractable arms 524 are exposed outside the CSI.

As illustrated in FIGS. 41–43, the device 520 includes a single, resilient suture clasp member 500 attached to the actuating rod 50. This resilient suture clasp member 500 is preferably of a unitary construction as shown. The suture clasp member 500 comprises a center or hinge portion 542 and two suture clasp arms 524 (one for each needle 546). Each suture clasp arm 524 has a suture clasp 544 at the end thereof.

The hinge portion 542 of the suture clasp member 500 acts as a "living hinge" because it has a memory which causes the member 500 to return to a partially open, unretracted position (FIG. 42) when a force (applied via rod 50) is released. This can be seen in FIGS. 41 and 42. In FIG. 42, the suture clasp member 500 is deployed in the artery 16 in its predisposed (relaxed or natural) position. In FIG. 41, the suture clasp member 500 is retracted into the suture introducer head 522 in its compressed (stressed or tensed) position. The arms 524 are moved to the retracted position by applying a distal force to the actuator rod 50, which causes the arms to contact deflection surfaces 518 (FIG. 42).

This suture clasp member 500 is preferably composed of a resilient shape memory material such as NITENOL. The suture clasp member 500 may alternatively be composed of another material with spring-like characteristics, such as plastic, spring steel, stainless steel or any variations thereof. Further, the suture clasp member 500 could be composed of two arms that are hingedly connected to the actuating rod 50 without the use of a resilient hinge, as shown in FIGS. 43C and 43D and described below.

The living hinge configuration is easily adaptable to having three arms spaced at 120 degrees or four arms (as in FIGS. 58 and 59) spaced at ninety degrees. If there are three arms, then there are preferably 3 needles 546 and six lumens in the elongated body 514. Thus, other configurations and numbers of arms can be incorporated into the device to accomplish the specific needs of the application.

The needles 546 are flexible and preferably made from a material with shape memory, such as SUPERFLEX NITENOL. Alternatively, the needles 546 may be composed of spring steel, surgical stainless steel or any variation thereof. The diameter of the needles 546 is preferably about 0.019 inches, but needles with other diameters may be used in accordance with the present invention.

When the needles 546 are advanced distally and come in contact with the needle insertion guides 512, the needle insertion guides cause the needles 546 to bend radially outward. The needles 546 also preferably further bend slightly (radially outward) when they come in contact with the angled surfaces 545 of the suture clasp arms 524, as shown in FIG. 47. When the needles 546 are retracted into the needle lumens 516, they resume a straight configuration as a result of their resiliency. Although the embodiment of FIGS. 41–48 preferably uses flexible needles which bend during deployment, it is contemplated that non-bending needled, which may be either straight or curved, could alternatively be used.

Figure 43A:
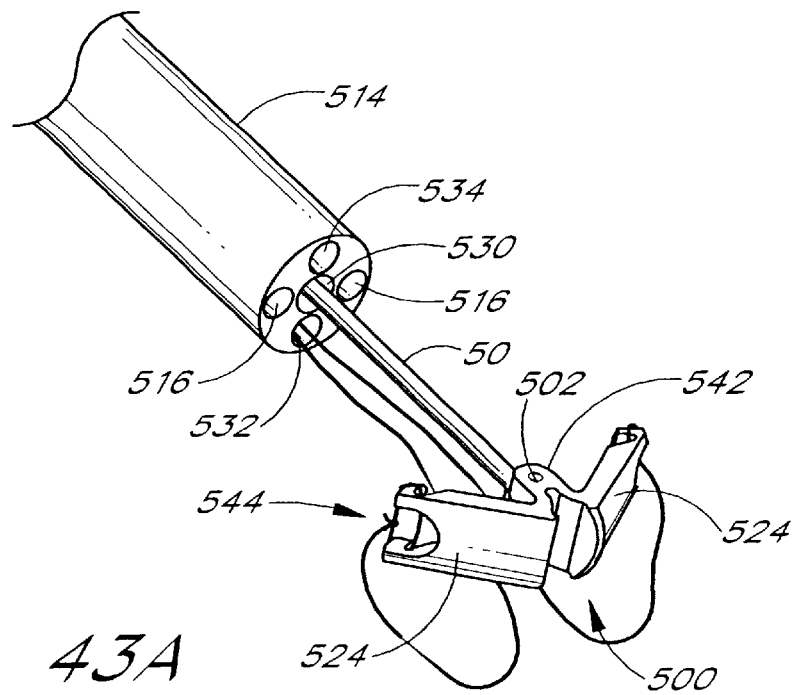
FIG. 43A is a perspective view of a suture clasp member, an actuator and a hollow elongated body of FIG. 41.
Figure 43B:
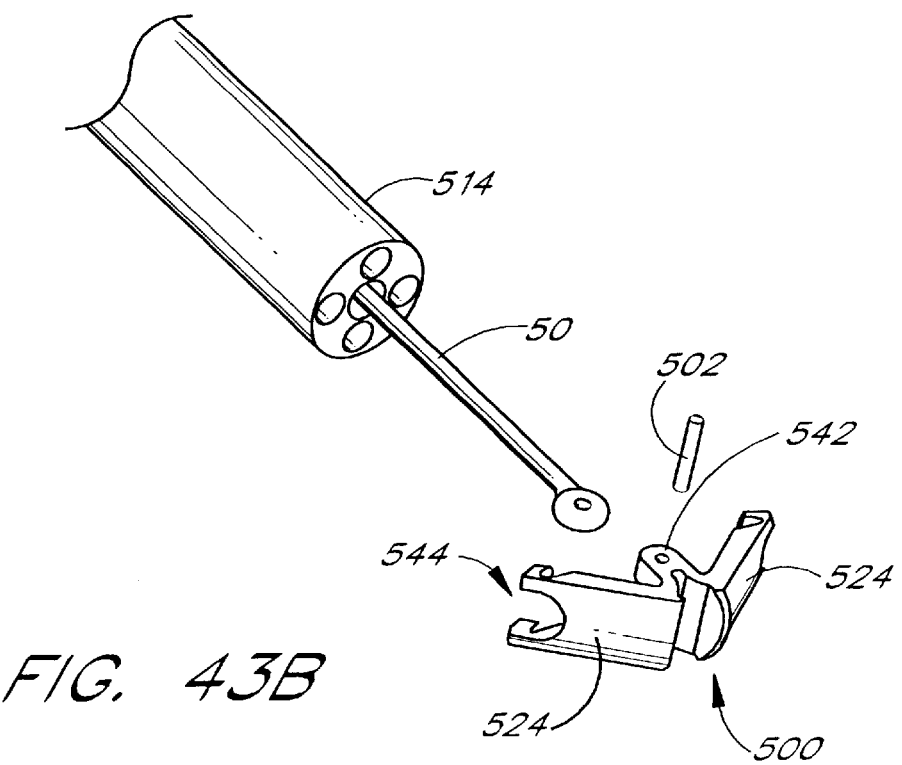
FIG. 43B is an exploded view of the suture clasp member, pivot pin and actuator of FIG. 42.
Figure 43C:
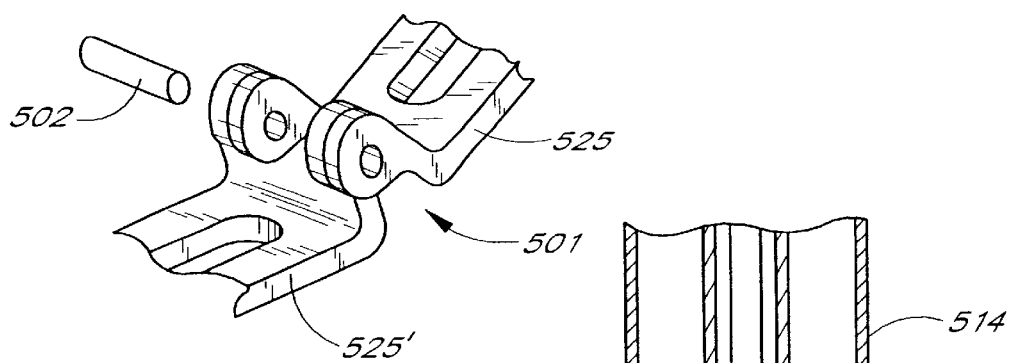
FIG. 43C is a perspective view of a two-piece suture clasp member.
Figure 43D:
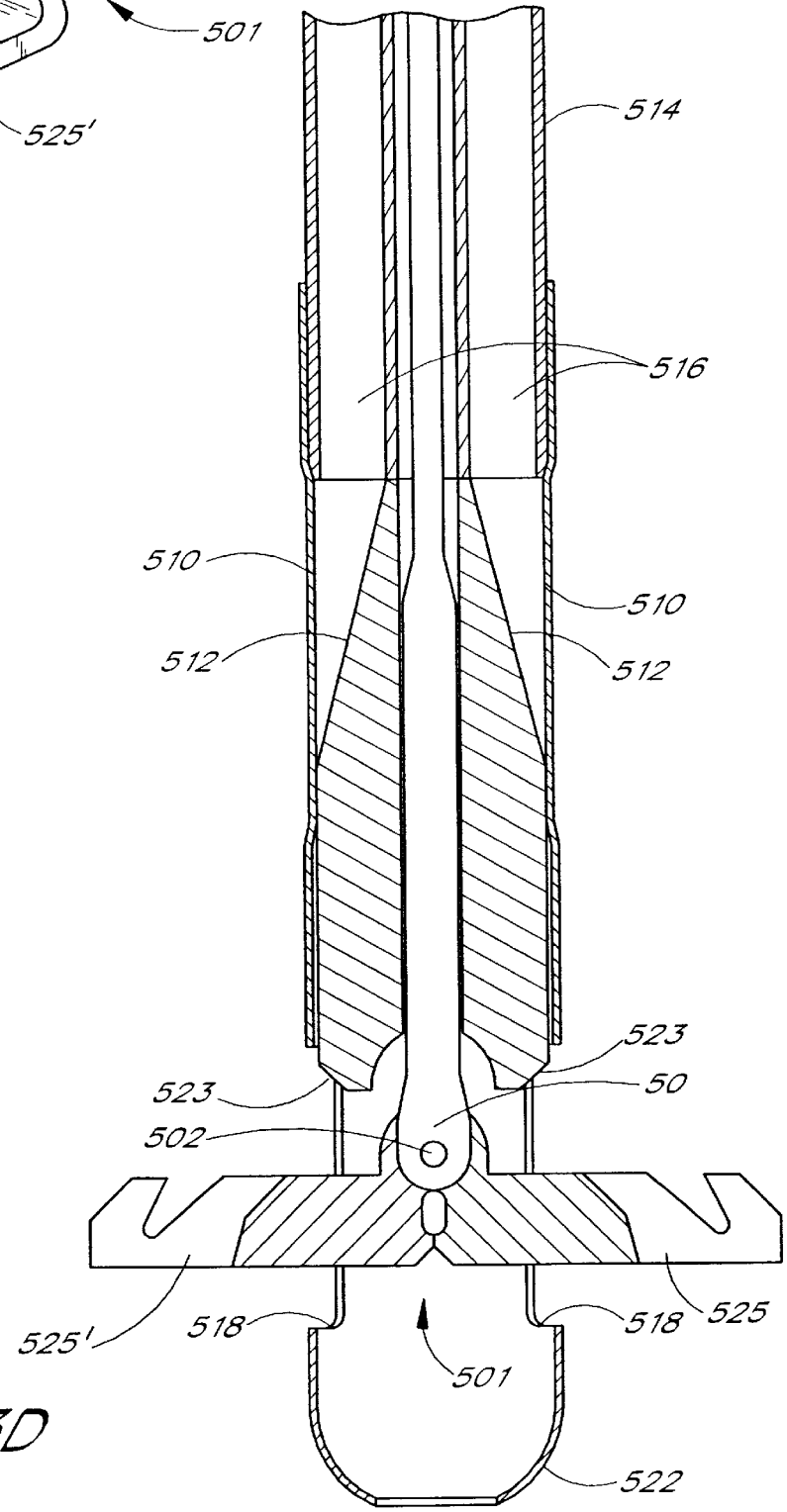
FIG. 43D is a cross-sectional view of the two-piece suture clasp member of FIG. 43C and a spreader within the suture introducer head of FIG. 41.

As illustrated by the cut-away views of FIGS. 43A and 43B, the actuating rod 50 attaches to the resilient suture clasp member 500 by a pivot pin 502. The actuating rod 50 in this configuration preferably comprises a single shaft (as shown), but may comprise a plurality of shafts in other configurations.

FIG. 43C is a perspective view of a non-living hinge embodiment or a two-piece suture clasp member 501. FIG. 43D is a cross-sectional view of the two-piece suture clasp member 501 and a ramp or spreader 523 within the suture introducer head 522. Alternatively, the hinge portion of the suture clasp arms 525, 525' with suture clasps 544 may be similar to a hinge portion shown in FIG. 53, which is described below. The spreader 523 may be a separate piece attached within the suture introducer head 522. Alternatively, the spreader and suture introducer head 522 may comprise a single molded piece.

The length of the suture clasp arm 525 is preferably about 0.174 inches. The length of both of the suture clasp arms 525, 525' together in their fully extended position (deployed with both arms parallel to each other) is preferably about 0.288 inches. In other configurations of the suture clasp arms 525, 525', the dimensions may vary.

In FIG. 43D, when the actuating rod 50 pulls the two-piece suture clasp member 501 proximally (while the suture clasp member 501 is in its retracted position), the distal edges of the spreader 523 come in contact with the tips of the suture clasp arms 525, 525'. The spreader 523 causes the two suture clasps arms 525, 525' to open radially outward relative to the actuating rod 50. In a preferred method of operation, the actuating rod 50 continues to pull the suture clasp member 501 proximally until the center of the suture clasp member 501 fits into the center of the spreader 523. To retract the suture clasp arms 525, 525' into the suture clasp member's retracted position, the actuating rod 50 is advanced distally, and the interior edges 518 of introducer head 522 come in contact with the suture clasp arms 525, 525.' The interior edges 518 of introducer head 522 cause the two suture clasp arms 525, 525' to retract radially inward relative to the actuating rod 50. The general use and operation of the two-piece suture clasp member 501 is similar to the use and operation of the suture clasp member 500 shown in FIG. 43A, as described below.

The proximal portion of the suturing device 520 preferably includes a handle which allows the physician to externally operate the suture clasp arms 524 and the needles 546 inside the blood vessel 16. This handle preferably has three actions: a first action in which the actuating rod 50 applies a proximal force to the hinge portion 542 to deploy and maintain the arms 524 in a fully outward position (FIG. 47); a second action to advance the needles 546 distally (FIG. 47) and pull the needles 546 back proximally using one or more springs; and a third action in which the actuating rod 50 applies a distal force to the hinge portion 542 to retract the arms 524 (FIG. 41 or 48).

Alternatively, the handle may be a 2-action handle in which one of the two actions is a combination of two of the three actions described above for the 3-action handle. For example, in a first action, the actuating rod 50 applies a proximal force to the hinge portion 542 to deploy and maintain the suture clasp arms 524 in a fully extended state of FIG. 47. With the arms 524 in this fully extended position, the needles 546 automatically advance distally (FIG. 47) and retract proximally to capture the looped ends of the suture 40. In a second action for this 2-action handle, the actuating rod 50 applies a distal force to the hinge portion 542 to retract the arms 524 (FIG. 41 or 48). This 2-action handle is suited for physicians with more experience in operating this suture device 520. It will be apparent to one of ordinary skill in the art that a 1-action handle or a 4-action handle (inserting and withdrawing the needles 546 as two separate actions) could be used, or that separate handles or triggers could be provided for different actions.

Figure 49:
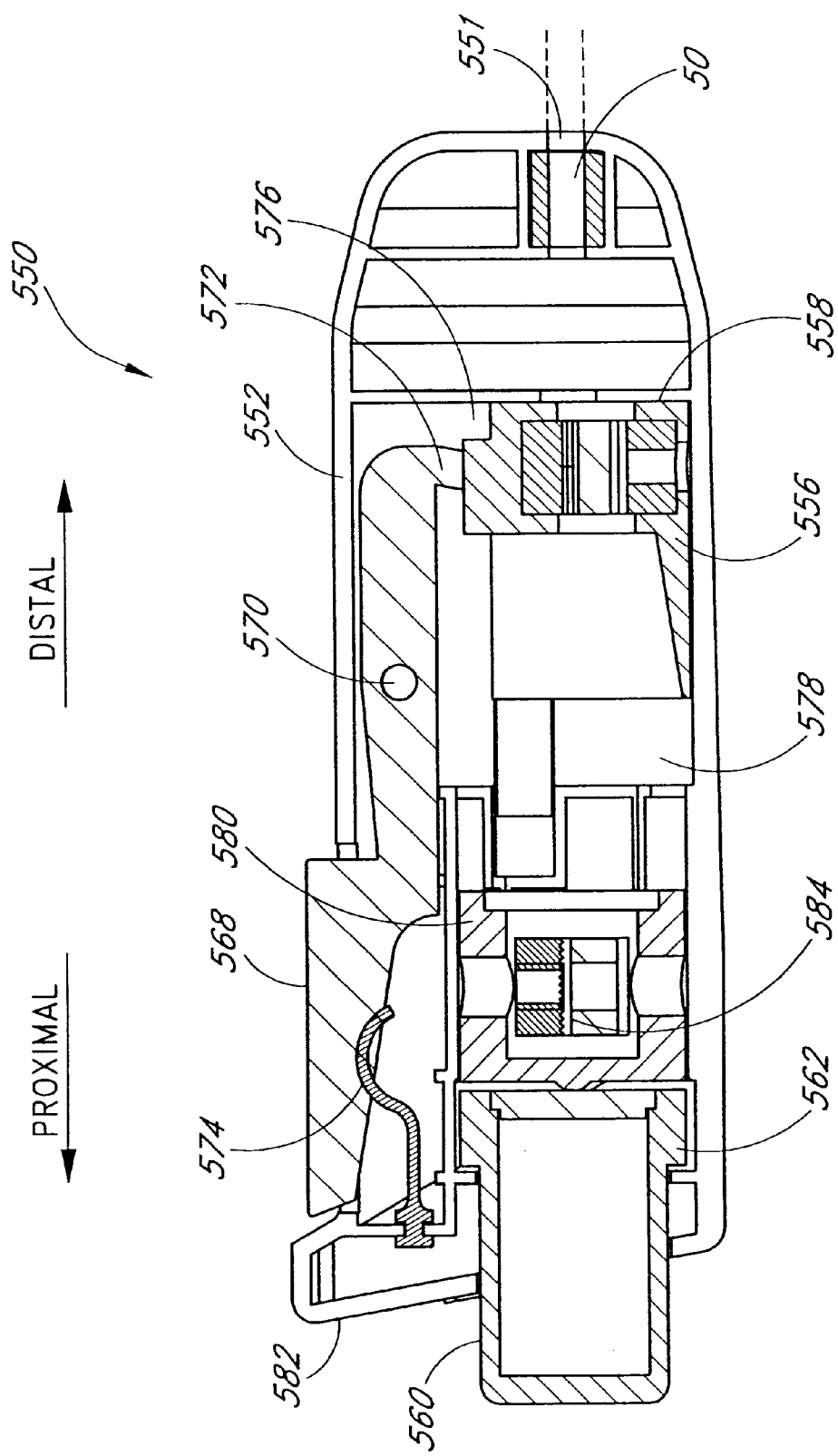
FIG. 49 is a cross-sectional view of one embodiment of a handle capable of being attached to the proximal end of the device of FIG. 41, the device of FIG. 48 or the device of FIG. 52A.
Figure 50:
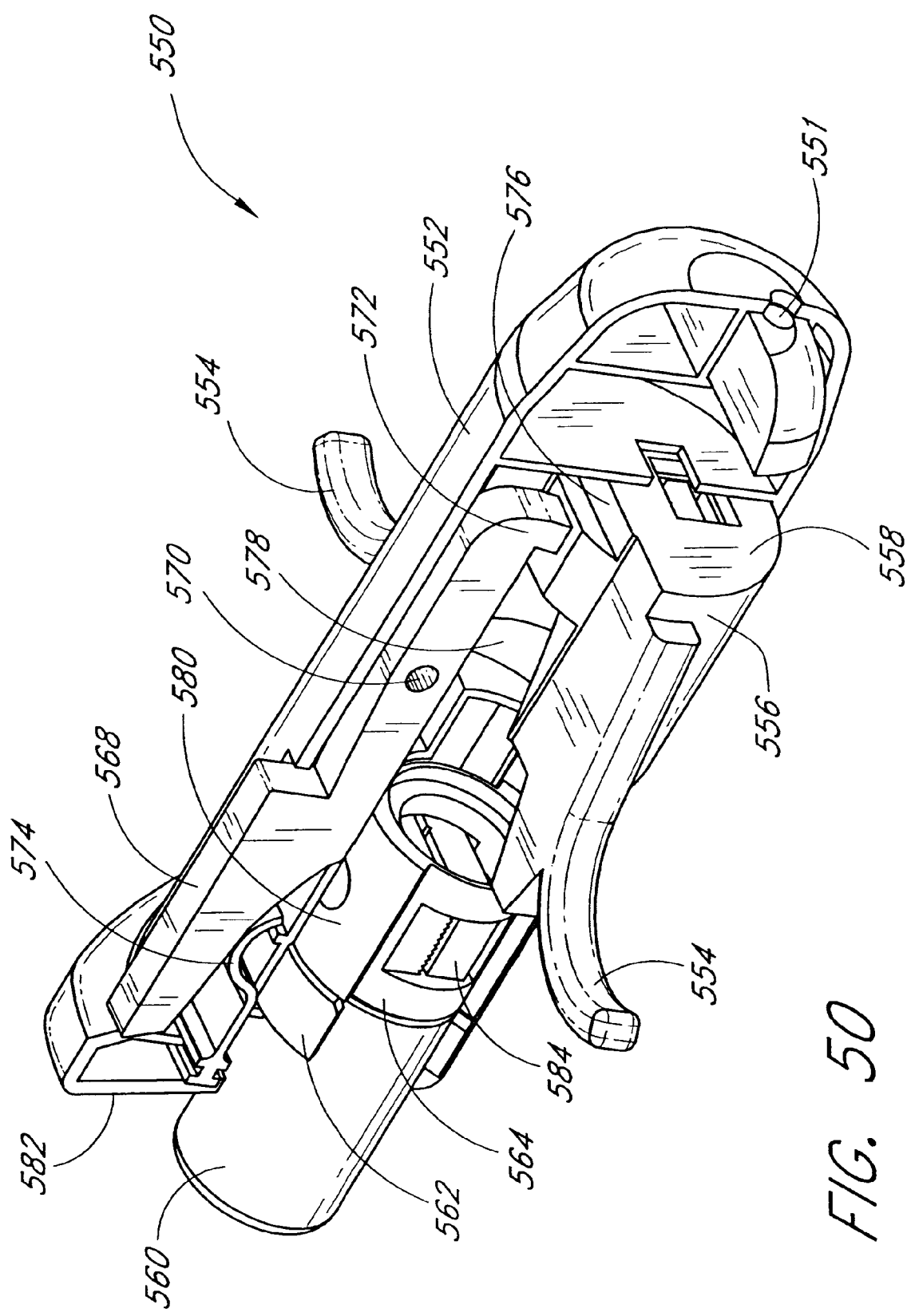
FIG. 50 is a perspective view of the handle of FIG. 49.
Figure 52B:
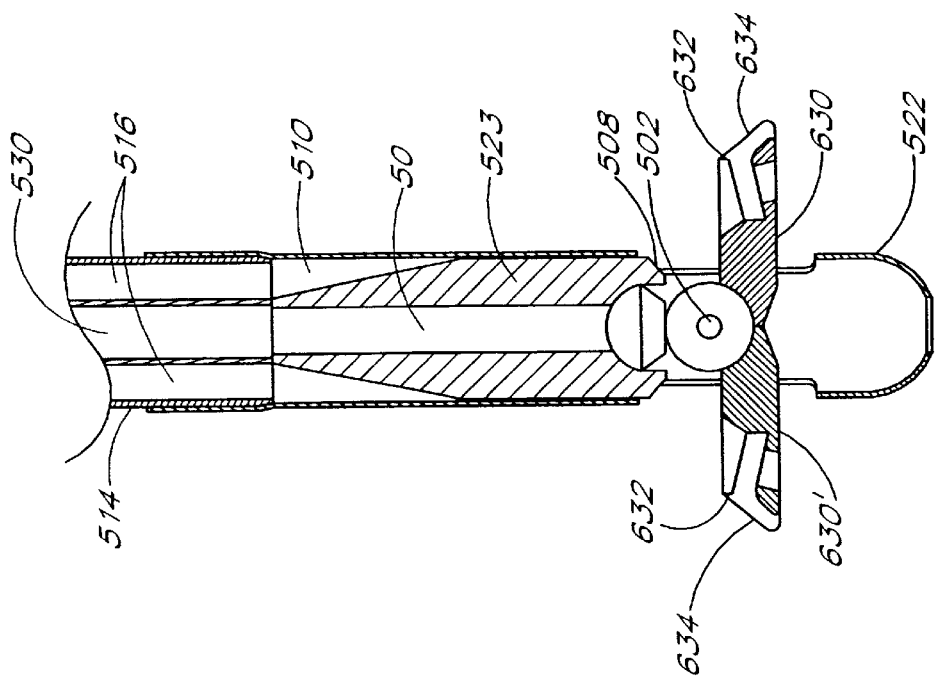
FIG. 52B is a cross-sectional view of the device of FIG. 52A.
Figure 52A:
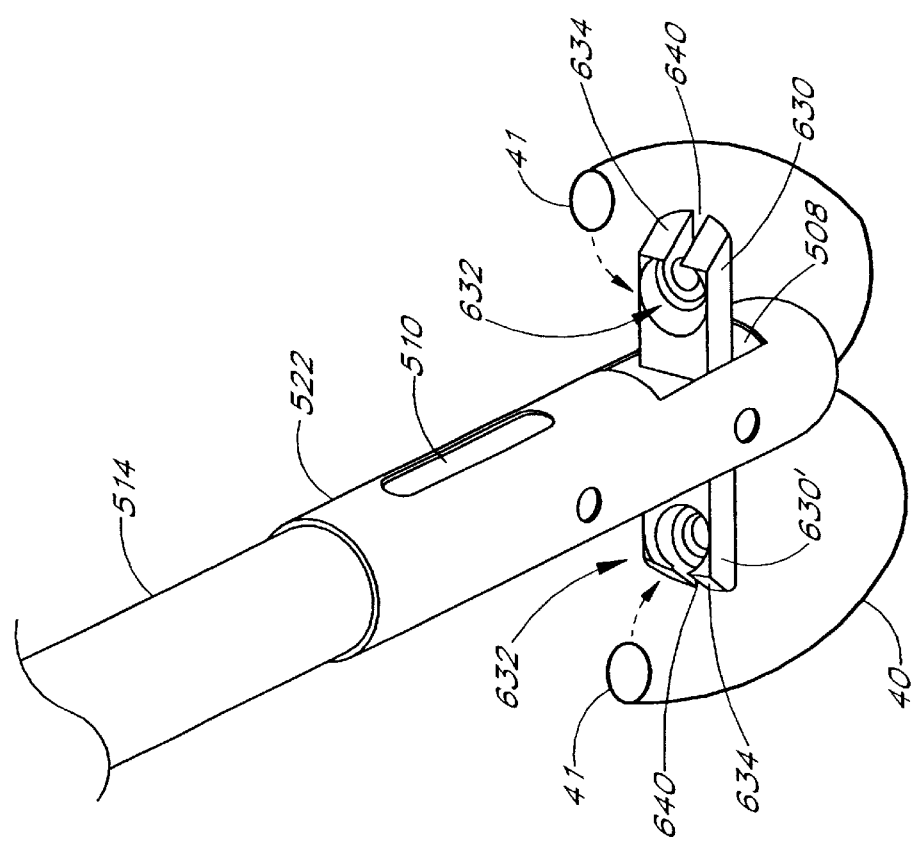
FIG. 52A is a perspective view of the suture introducer head and the hollow elongated body of FIG. 41 with another embodiment of the suture clasp arms.
Figure 57:
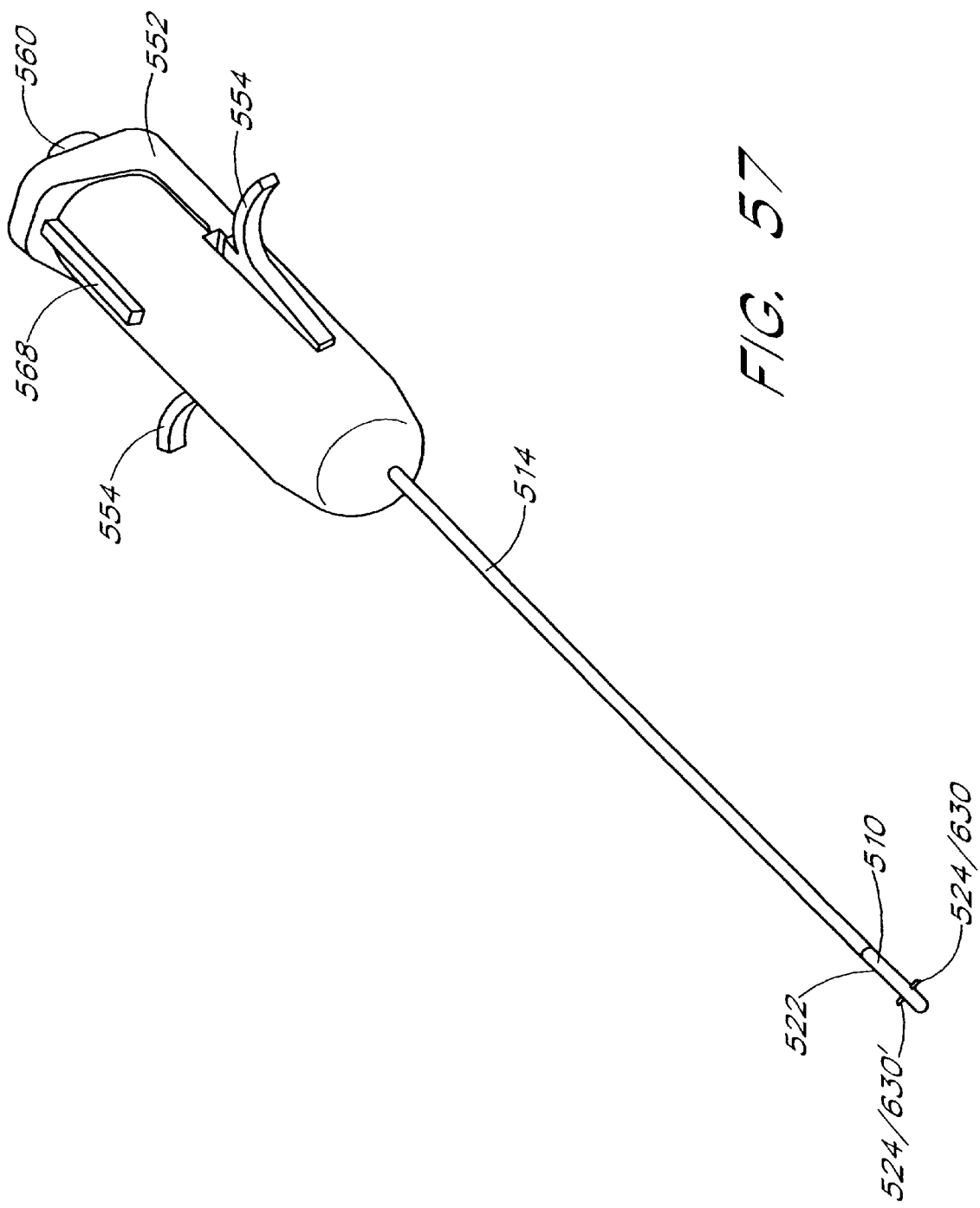
FIG. 57 is a perspective view of the handle of FIG. 49.

FIG. 49 is a cross-sectional view of one embodiment of a handle 550 operatively attached to the proximal end of the hollow elongated body 514 of FIG. 41 or the single suture insertion and retraction housing 515 of FIG. 48 or the device of FIG. 52A. FIG. 50 is a perspective view of the handle 550. FIG. 57 is a perspective view of the handle 550 of FIG. 49. The handle 550 comprises an actuating rod aperture 551, a main housing 552, a pair of finger grips 554, a suture clasp arm piston 556 with a locking groove 576, a needle piston 560 with at least one raised key portion 562, a releasor 568 with a locking stopper 572, a pivot pin 570, a releasor support 574, a compression spring (not shown) operatively positioned in a spring recess 578 between the suture clasp arm piston 556 and the needle piston 560, a needle piston support cylinder 580 with at least one grooved recess 564 and needle clamps 584.

In one configuration, the housing 552 is attached to or is a continuation of the hollow elongated body 514 of FIG. 41 or the single suture insertion and retraction housing 515 of FIG. 48. In another configuration, the housing 552 is separate from the hollow elongated body 514 or single suture insertion and retraction housing 515. In this configuration, the actuating rod 50 connects the housing 552 with the hollow elongated body 514 or single suture insertion and retraction housing 515.

A proximal portion of the actuating rod 50 (FIGS. 41 and 48) slides through the actuating rod aperture 551 at the distal end of the housing 552. The proximal end of the actuating rod 50 is attached to the distal end 558 of the suture clasp arm piston 556, which is slidably received within the main housing 552. A compression spring (not shown) resides in the spring recess 578 of the housing 552 between the suture clasp arm piston 556 and the needle piston 560 and simultaneously exerts two forces: a distal force on the suture clasp arm piston 556; and a proximal force on the needle piston 560.

The needle clamps 584 of the needle piston 560 hold the proximal ends of the needles 546. The needle piston 560 is slidably received within a distal portion of the housing 552. The needle piston support cylinder 580 is attached to the housing 552 and preferably does not move relative to the housing 552.

The releasor 568 pivots radially inward and outward on the pivot pin 570. The releasor support 574 exerts a radially outward force on the releasor 568. This force causes the releasor 568 to pivot and the locking stopper 572 to fall into the locking groove 576 of the suture clasp arm piston 556 when the locking groove 576 is aligned to receive the locking stopper 572. The releasor support 574 is preferably made of a resilient shape memory material such as NITENOL. The releasor support 574 may alternatively be composed of another material with spring-like characteristics, such as plastic, spring steel, stainless steel or variations thereof. Other embodiments of the handle are described below with reference to FIGS. 57, 60 and 61.

The use and operation of the device 520 and the handle 550 will now be described with reference to FIGS. 1C–1D and 41–50. In operation, with the CSI extending into the patient's artery 16, the physician inserts the suture introducer head 522 through a catheter sheath introducer (CSI) 6 and into the artery 16 (FIGS. 1C–1D). The CSI 6 is then partially withdrawn along the body 514 of the suturing device 520 to remove the CSI 6 from the artery 16 and expose the needle apertures 510, as shown in FIG. 41. There are one or more markings 539 (FIG. 46) on the exterior surface of the elongated body 514 which indicate how far the physician should withdraw the CSI 6 to expose the needle apertures 510.

The distal end 504 of the introducer head 522 has a smooth, rounded surface to prevent injury to the opposite vessel wall 506 when inserting the introducer head 522. In addition, the blood flow in the artery 16 is uninterrupted because the introducer head 522 does not occlude the artery 16. The physician may use the aperture 540 at the distal end of the suture introducer head 522 and the bleed back lumen 534 to determine when the distal end 504 of the suture introducer head 522 is in the artery 16.

While the introducer head 522 is inserted into the artery 16 in FIG. 41, the actuating rod 50 holds the resilient suture clasp member 500 in its compressed position within the introducer head 522. The actuating rod 50 applies a downward force while the interior edges 518 of the introducer head 522 apply an inward force on the two suture clasp arms 524. The combination of these two forces cause the hinge portion 542 of suture clasp member 500 between the two arms 524 to elastically deform or compress. The suture clasps 544 hold the looped ends of a suture 40 in the angled slot of the suture clasps 544 as shown in FIGS. 41–43A. The looped ends of the suture 40 are held securely by the suture clasps but are positioned for easy removal by the suture catches 38 of the needles 546.

When the distal portion of the device 520 (FIGS. 41 and 48) is properly positioned in the blood vessel 16, the physician may deploy the suture clasp arms 524 (FIG. 42) by pulling the finger grips 554 in a proximal direction relative to the housing 552 (FIG. 50). A physician may pull the suture clasp arm piston 556 proximally by placing the physician's index and middle finger around the finger grips 554 and pushing on the proximal end 582 of the housing 552. This action is similar to operating a standard syringe. This motion compresses the spring (not shown) in the spring recess 578 of the handle 550 in a proximal direction. As the suture clasp arm piston 556 moves proximally, the actuating rod 50 moves in a proximal direction relative to the elongated body 514 or housing 515. This is shown by the arrows in FIG. 42. This motion causes the suture clasp member 500 to deploy or open to its predisposed or natural position as shown in FIG. 42. The suture clasp arms 524 deploy out of the introducer head 522 into the blood vessel 16 through two suture clasp arm apertures 508 (FIG. 42), one on either side of the introducer head 522.

When the physician pulls the suture clasp arm piston 556 a certain proximal distance relative to the housing 552, the locking stopper 572 at the distal end of the releasor 568 moves radially inward and falls into the locking groove 576 of the piston 556. The locking stopper 572, in combination with the locking groove 576, prevents the suture clasp arm piston 556 from advancing distally. The force of the spring in recess 578 prevents the suture clasp arm piston 556 from moving proximally. The locking of the suture clasp arm piston 556 stabilizes the suture clasp arms 524 in a locked position before the needles 546 are advanced distally.

In this locked position, the suture clasp arms 524 preferably have reached their fully extended position, as shown in FIG. 47. In the fully extended position, the actuating rod 50 (attached to the suture clasp arm piston 556) has pulled the resilient suture clasp member 500 up, and the proximal inside edges 536 of the aperture 508 have come in contact with the arms 524 of the suture clasp member 500. This is shown in FIG. 47. The pulling of the actuating rod 50 and the stationary inside edges 536 of the apertures 508 cause the arms 524 to bend backward until the arms 524 are longitudinally aligned with each other, as shown in FIG. 47. Thus, the resilient suture clasp member 500 is deformed from its natural configuration again, but this time in an extended position instead of a compressed position. In this extended position, the physician may move the suturing device 520 proximally so that the arms 524 touch the interior of the vessel wall 22 while the needles 546 advance distally and capture the ends of the suture 40 from the suture clasps 544.

Next, the physician twists the needle piston 560 clockwise or counter-clockwise until the raised key portion 562 of the needle piston 560 matches the grooved recess 564 of the needle piston support cylinder 580. The grooved recess 564 of the needle piston support cylinder 580 allows the raised key portion 562 of the needle piston 560 to advance distally. Otherwise, the needle piston 560 may not be advanced distally if the raised key portion 562 does not match the grooved access 564. The needle piston support cylinder 580 and the raised key portion 562 of the needle piston 560 prevent the needles 546 from advancing distally prematurely or improperly. Premature or improper insertion of the needles may cause damage to the patient's surrounding tissue 14 (FIGS. 1B and 1D) or the blood vessel 16.

When the raised key portion 562 of the needle piston 560 matches the grooved recess 564 of the needle piston support cylinder 580, the physician may advance the proximal end of the needle piston 560 (with the physician's thumb or palm) in a distal direction relative to the proximal end 582 of the housing 552. This motion compresses the spring in the spring recess 578 in a distal direction. When the needle piston 560 advances distally, the needles 546 and the suture catches 38 on the needles (FIG. 47) also advance distally.

The paths taken by the needles 546 are illustrated in FIG. 47. The needles 546 slide along the needle housings 516 (or needle lumens) and out of the suture device 520 through needle apertures 510. When the needles 546 come in contact with the needle insertion guides 512, the needles 546 begin to bend radially outward. As the needles 546 exit, they are guided at a radially outward, acute angle away from the actuating rod 50 by the needle insertion guides 512. The angle of the needle deflection is preferably 13.2 degrees. Deflection angles in the ranges of 10 to 15 degrees and 5 to 20 degrees are also contemplated.

The needles 546 then penetrate the vessel wall 22 at an angle by creating incisions 248 on either side of the main vessel incision 26. The needles 546 also preferably bend slightly (radially outward) when they come in contact with the suture clasp arms 524. The combination of the suture clasps 544 and the suture catches 38 on the needles 546 creates a lock on the looped ends of the suture 40, such that the suture ends will not fall off while the needle 546 engages the suture clasp member 500.

The physician advances the needle piston 560 distally until the resistance of the compression spring prevents the needle piston 560 from advancing any further distally. In this position, the needles 546 are sufficiently advanced in the blood vessel 16 such that when the needles 546 are pulled back proximally, the suture catches 38 on the needles 546 will catch the looped ends of the suture 40 from the suture clasps 544. As shown in FIG. 47, the clasp arms 524 hold the suture loops away from the suture introducer head 522, so that the needles 546 pierce the vessel 22 and catch the suture loops outside the perimeter of the suture introducer head 522.

After the physician advances the needle piston 560 to its farthest distal position, the physician releases the needle piston 560. The compressed spring causes the needle piston 560 to immediately spring back proximally. This motion causes the distal portion of the needles 546 to immediately spring back proximally into the needle housing 516 with the looped ends of the suture 40 attached to the suture catches 38.

The suture catches 38 on the needles 546 catch the suture loops held by the suture clasps 544 and pull the ends of the suture 40 up through the punctured holes 248 when the needles 546 are retracted proximally. When the needles 546 are retracted into the needle lumens 516, they resume a straight configuration. As the needles 546 retract, a segment of the suture 40 is released (as a result of the tension caused by the retracting needles 546) through an aperture 540 at the distal end 504 of the suture introducer head 522 and into the artery 16.

Figure 44:
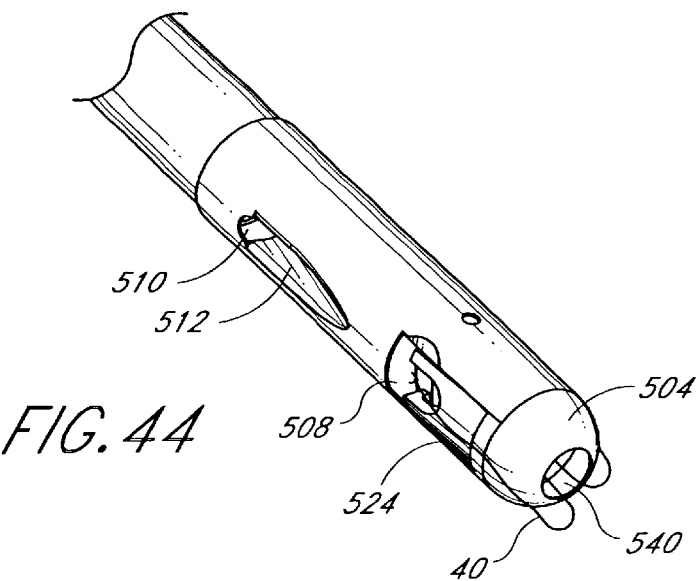
FIG. 44 is a perspective view of the suture introducer head and suture clasp member of FIG. 41.
Figure 45:
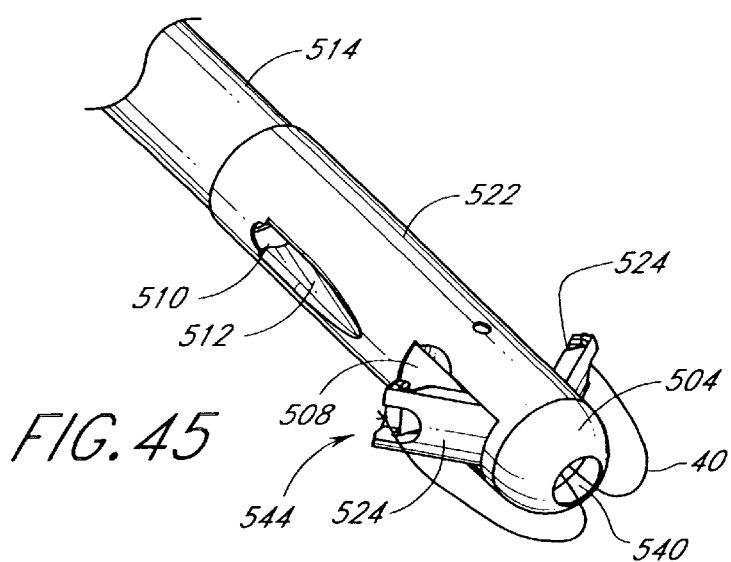
FIG. 45 is perspective view of the device of FIG. 44 with the suture clasp member partially deployed.

To retract the suture clasp arms 524 (FIGS. 41 and 48), the physician presses the proximal portion of the releasor 568 in a radially inward direction. This motion causes the releasor 568 to pivot. The locking stopper 572 moves radially outward and releases the locking groove 576. The force of the compressed spring causes the suture clasp arm piston 556 and the actuating rod 50 to advance distally. Together with the proximal interior edges 518 of the introducer head 522, the downward force of the actuating rod 50 causes the resilient suture clasp member 500 to retract into its compressed position. As shown in FIGS. 44 and 45, the suture clasp arms 524 retract into respective apertures or grooves 508 on the exterior surface of the introducer head 522. In this retracted state, the arms 524 are substantially parallel with the elongated body 514. As FIG. 44 illustrates, the exterior surfaces of the arms 524 are flush with the exterior surface of the introducer head 522. This reduces the likelihood that the arms 524 will catch on the vessel wall 22 or flesh 14 during withdrawal. The device 520 is now ready for removal from the blood vessel 16.

The physician withdraws the device 520 out of the blood vessel 16 and out of the flesh 14 of the patient's thigh 12. After the device 520 is withdrawn (and with the CSI 6 still in the flesh 14), the physician pulls the ends of the suture 40 and closes the main vessel incision 26. The physician then ties at least one knot with the ends of the suture 40 and slides or pushes the knot(s) down through the CSI 6 to the vessel incision 26. Alternatively, the physician may fasten a small, circular or flat stainless steel clip (not shown) to the ends of the suture 40 and slide the clip down through the CSI 6 to the vessel opening 26 to close the opening 26. The physician then cuts the unused ends (extra length) of the suture 40 and removes the cut portions. The physician then removes the CSI 6 from the patient's thigh 12.

Some of the advantages of the suturing device 520 shown in FIGS. 41–48 will now be described in greater detail. First, the radial deployment of the suture clasp arms 524 (FIGS. 41–42 and 47) from the sides of the suturing device's body, instead of deployment from the distal tip, provides an advantage over other embodiments. The device 520 shown in FIGS. 41–48 deploys its suture clasp arms 524 in a radial direction without extending beyond the distal end 504 of the device 520. Thus, this device 520 reduces the likelihood that the suture clasp arms 524 will contact and damage the inner vessel wall 506 opposite the incision 26.

Second, the locked position of the suture clasp arms 524 (as described above with reference to FIG. 47) provides a stable base or foundation for holding the looped ends of the suture 40 while the needles 546 come in contact with the suture clasp arms 524 and capture the suture 40. The suture clasp arms 524 are locked in the locked position by the proximal force of the actuating rod 50, the stationary inside edges 536 of the apertures 508 and the protrusions 528 at the 'elbow' end of each arm 524 (FIG. 47). Specifically, when the suture clasp arms 524 become substantially parallel with each other (i.e., each arm 524 is at an angle of approximately 90 degrees from the actuating rod 50), the protrusions 528 at the 'elbow' end of each arm 524 come into contact with each other and prevent the arms 524 from bending any further than the configuration shown in FIG. 47. The suture clasp member 500 cannot open any farther, even when the needles 546 are inserted distally and come in contact with the suture clasp arms 524. The protrusions 528 prevent the suture clasp member 500 from moving unintentionally (opening any farther) when the needles 546 come in contact with the suture clasp arms 524. This reduces the risk of the looped ends of the suture 40 being accidentally displaced from the suture clasps 544 when the needles 546 engage the suture clasps 544. Thus, the combination of forces asserted by the actuating rod 50, the proximal inside edges 536 of the aperture 508 and the two protrusions 528 sustain the suture clasp arms 524 in a rigid, locked position to facilitate the proper removal of the suture looped ends from the suture clasps 544.

Third, the shape and position of the angled slits of the suture clasps 544 in FIGS. 41–48 provide another advantage. The slits of the suture clasps 544 in FIGS. 41–48 are angled in a proximal, radially inward direction. Thus, the face of the looped ends of the suture 40 face in a proximal, radially inward direction. In this configuration, there is less chance of the looped ends of the suture 40 falling off the suture clasps 544 improperly or prematurely. When the needles 546 engage the suture clasp arms 524, the only direction the looped ends may move is in a proximal, radially inward direction, which is in the opposite direction of the inserted needles 546. When the needles 546 retract proximally (as shown in FIG. 47), the looped ends reliably fall into the suture catches 38 of the needles 546. It is the proximal movement of the needles 546 in the embodiments in FIGS. 41–48 which causes the suture catches 38 on the needles 546 to catch the looped ends of the suture 40. This configuration does not rely on a radially outward tension in the looped ends to fasten the looped ends onto the suture catches 38 when the needles 546 are inserted distally.

In the various embodiments described with reference to FIGS. 1C–1D and 41–48, retractable suture clasp arms are used to hold the suture 40 beyond the outer circumference of the tubular housing (and thus beyond the boundaries of the incision 26), and flexible needles 546 are used to capture the held suture 40 outside the outer circumference. In other implementations (not shown), the suture clasp assembly may be in the form of a fixed (non-moving) member which holds the suture near or within the circumference of the housing. In such implementations, curved needles may be used which pierce the vessel wall outside the circumference of the housing and then "curve in" to capture the suture. The curved needles may then be withdrawn to pull the ends of the suture out of the vessel wall.

Figure 51:
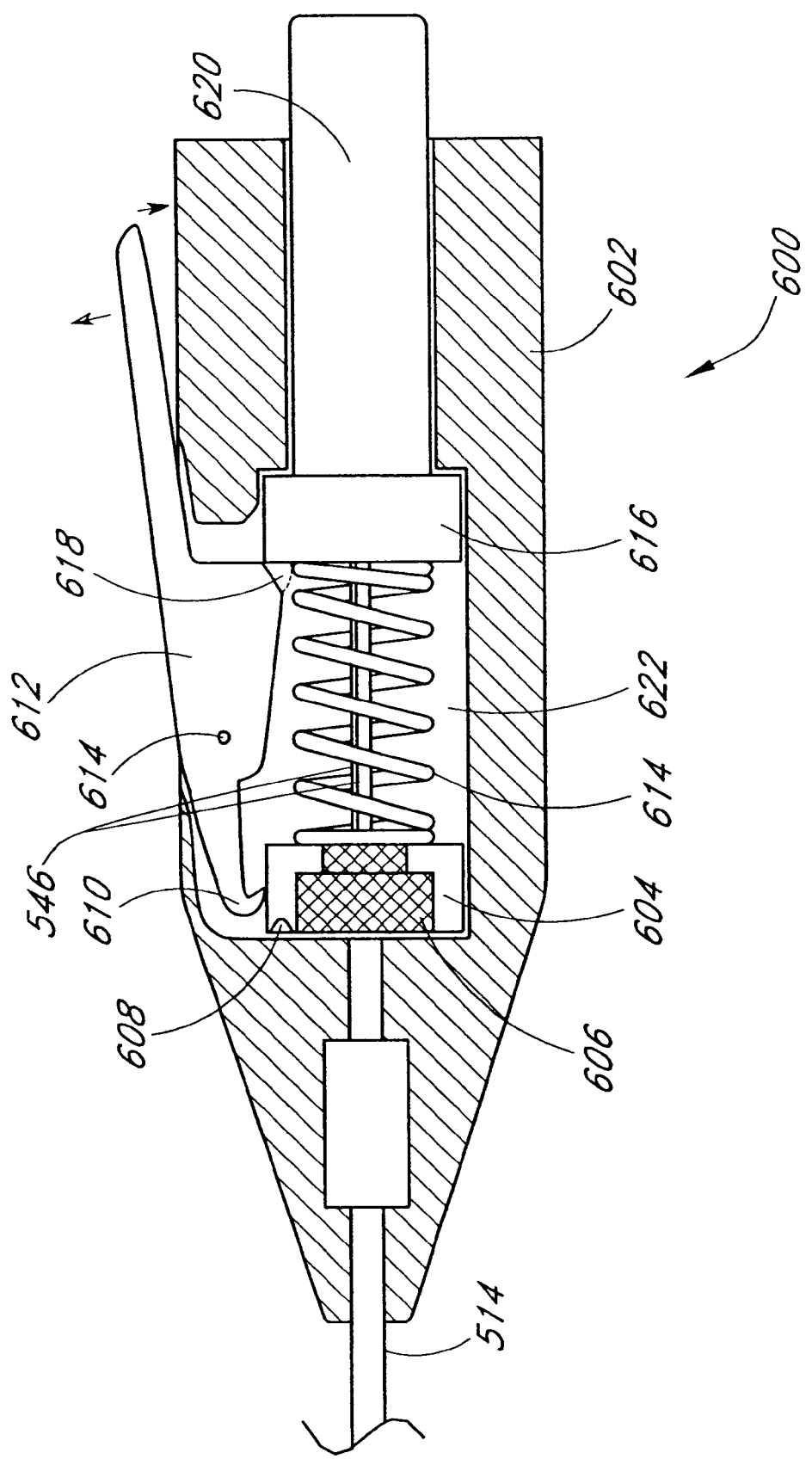
FIG. 51 is a cross-sectional view of another embodiment of a handle capable of being attached to the proximal end of the device of FIG. 41, the device of FIG. 48 or the device of FIG. 52A.

FIG. 51 is a cross-sectional view of another embodiment of a handle 600 attached to the proximal end of the hollow elongated body 514 of FIG. 41 or the single suture insertion and retraction housing 515 of FIG. 48 or the device of FIG. 52A. The handle 600 of FIG. 51 comprises a housing 602 with a spring recess 622, a pair of external finger grips 604 (only one shown in FIG. 51), a suture clasp arm piston 606 with a locking groove 608, a releasor 612 with a locking head 610 and a needle piston stopper 618, a pivot pin 614, a needle piston 620 with needle clamps 616 and a spring 624.

The handle 600 also includes a second spring (not shown) which biases the releasor 612 toward a position in which the locking head 610 is engaged with the groove 608. Similar to the handle 550 shown in FIG. 50, the finger grips 604 extend outside the housing 602 to allow a physician to move the piston 606 relative to the housing 602. The needles 546 in FIG. 51 are attached to the needle clamps 616, which is attached to the needle piston 620. The actuating rod 50 (FIG. 41) is attached to the suture clasp arm piston 606 in FIG. 51.

The general operation of the handle 600 shown in FIG. 51 is similar to the operation of the handle 550 shown in FIGS. 49–50. In FIG. 51, the needle piston stopper 618 prevents the needle piston 620 from distally advancing prematurely or improperly. This function is similar to the function of the raised key portion 562 and grooved recess 564 of the handle 550 shown in FIGS. 49–50. In FIG. 51, the physician advances the suture clasp arm piston 606 proximally against the biasing force of the spring 614 (by pulling the finger grips 604 proximally) to deploy the suture clasp arms 524 (FIG. 42) until the locking head 610 of the releasor 612 moves radially inward and falls into the locking groove 608. At this point, the clasp arms 524 are in the fully deployed or open position as in FIG. 47. This motion causes the proximal portion of the releasor 612 to advance radially outward until the needle piston stopper 618 is no longer blocking the needle piston 620. At this time, the physician may advance the needle piston 620 distally into the recess 622 to cause the needles 546 to advance distally and capture the suture 40. When the physician releases the needle piston 620, the spring 614 moves the needle piston proximally to the outward position, causing the needles 546 to retract with the suture 40. Finally, the physician presses the external lever portion of the releasor 612 to release the suture clasp arm piston 606; this causes the suture clasp arms 524 to return to the retracted position, so that the device can be withdrawn from the artery 16.

One of ordinary skill in the art will appreciate that there are many possible configurations of this handle attached to the proximal end of the device 520. In one configuration (not shown), there are at least two springs or sets of springs (not shown), instead of the single compression spring as used by the handle 550 in FIGS. 49–50 and the handle 600 in FIG. 51. In this embodiment with two springs, a first spring exerts a proximal force on the needles 546 while a second spring exerts a distal force on the actuating rod 50 inside the handle. In another configuration (not shown), instead of a second set of springs or a trigger, the physician manually retracts the needles 546 proximally back into the needle housing 516. In another configuration, a handle (not shown) attached to the proximal end of the device 520 is similar to the handle as shown in FIG. 40.

Embodiments of FIGS. 52A–59

Figure 54:
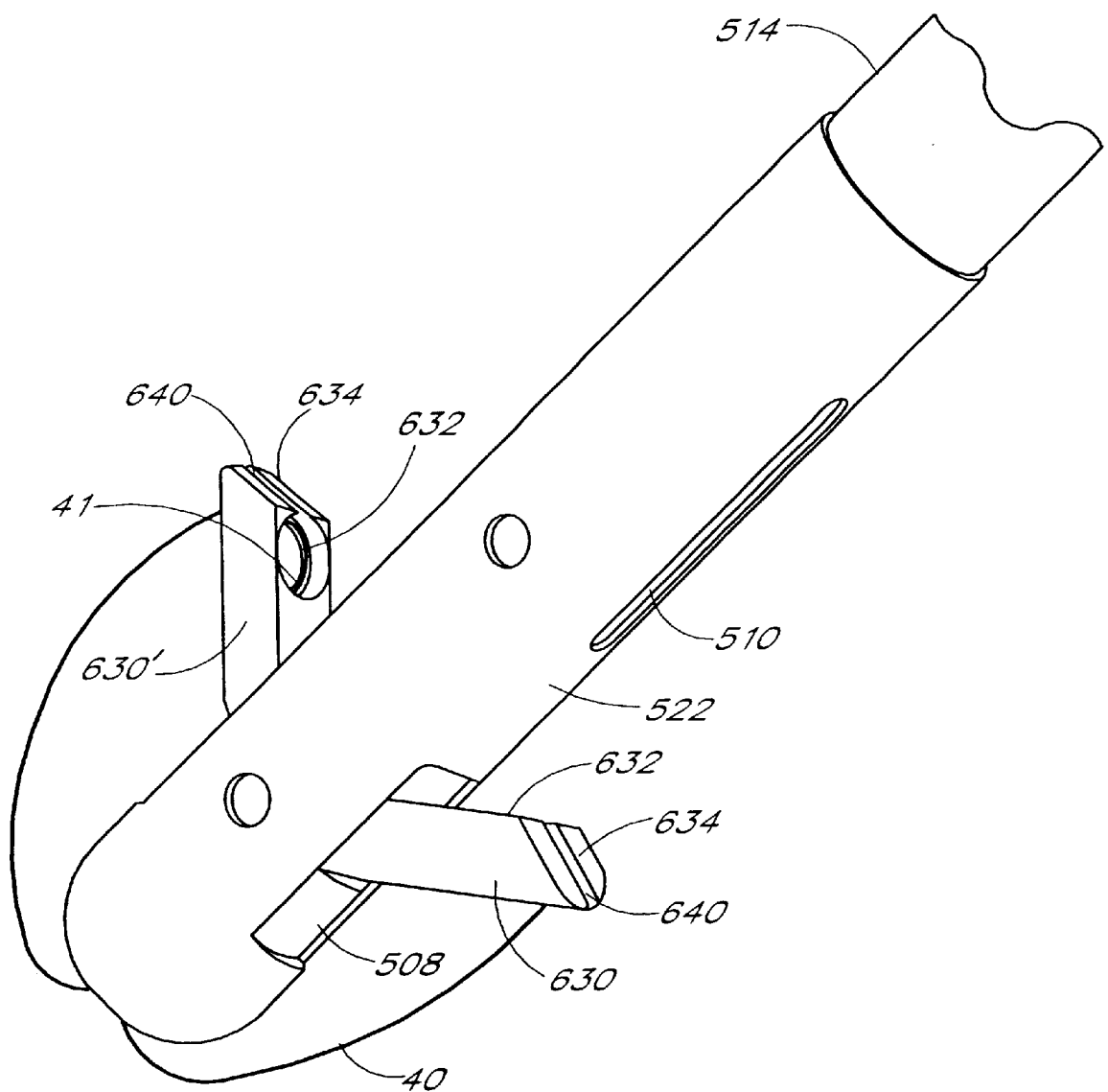
FIG. 54 is a perspective view of the device of FIG. 52A with the suture clasp member partially deployed.
Figure 55:
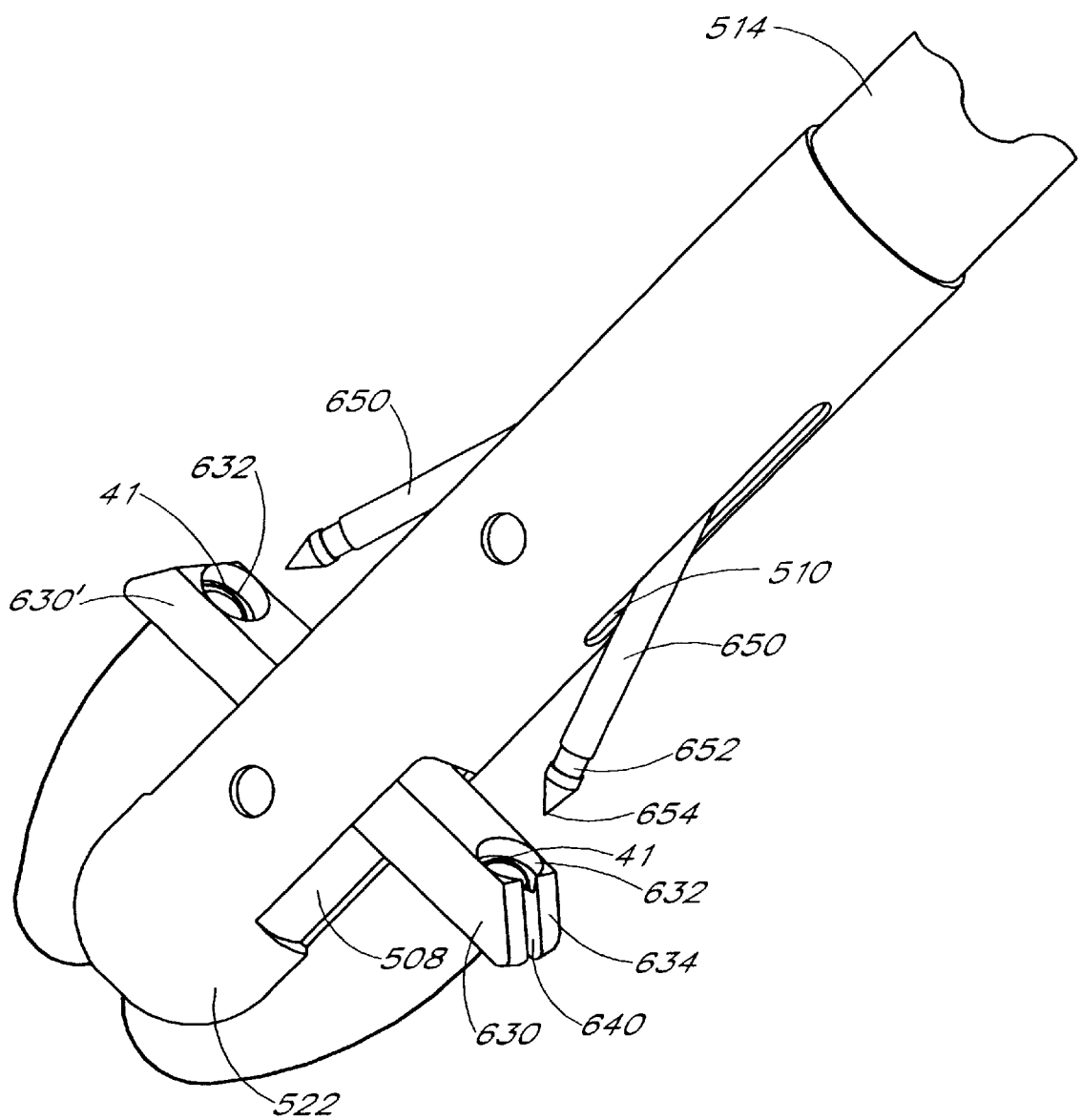
FIG. 55 is a perspective view of the device of FIG. 52A with the suture clasp member fully deployed.
Figure 56:
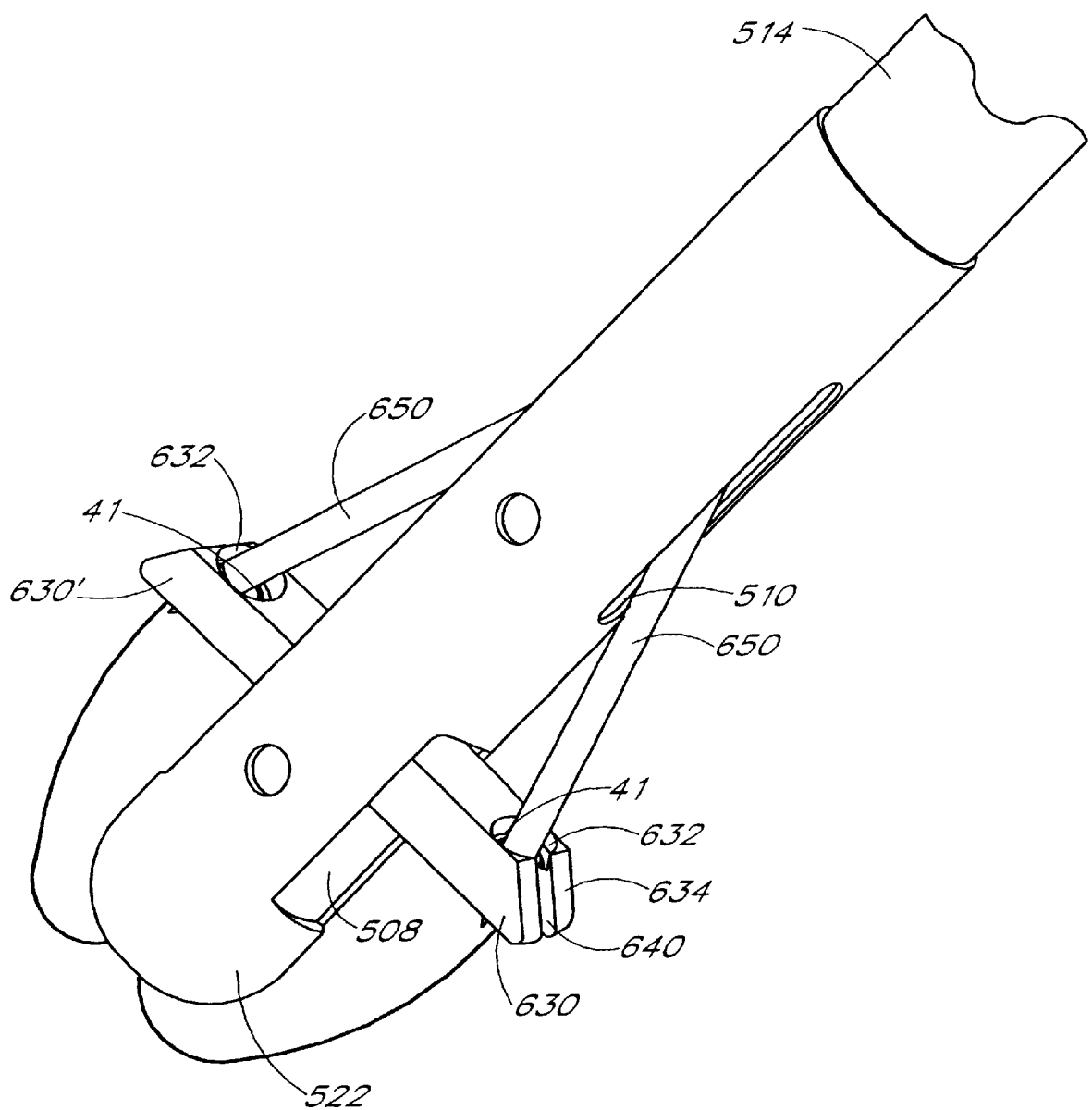
FIG. 56 is a perspective view of the device of FIG. 52A with the suture clasp member fully deployed and needles engaging the suture clasp member.

FIG. 52A is a perspective view of the suture introducer head 522 and the hollow elongated body 514 of FIG. 41 with another embodiment of the suture clasp arms 630, 630'. In this embodiment, the ends of the suture are provided with special loops 41 that are configured to engage with the needles (as described below). FIG. 52B is a cross-sectional view of the device of FIG. 52A. FIGS. 53A–53B are perspective views of one configuration of the suture clasp arms 630, 630' shown in FIG. 52A. FIG. 54 is a perspective view of the device of FIG. 52A with the suture clasp arms 630, 630' partially deployed. FIGS. 55–56 are perspective views of the device of FIG. 52A with the suture clasp arms 630, 630' fully deployed. FIG. 56 further shows two flexible needles 650 engaging the suture clasp arms 630, 630'.

As shown in FIG. 52A, a first suture clasp arm 630 comprises a hinge portion 636 at a distal side with an aperture 642 for a pivot pin 502 (FIG. 43C). The first suture clasp arm 630 further comprises a curved portion 638 for the distal end of an actuating rod 50 (as in FIG. 43B) and the hinge portion 636 at a distal side of the second suture clasp arm 630' (FIG. 53B). The first suture clasp arm 630 further comprises an annular recess 632 for holding a suture looped end 41 and for receiving the distal portion of a needle. The arm 630 further comprises a slit 640 for the length of the suture 40, and a sloped end 634. The distal side of the arms 630, 630' are connected to the actuating rod 50 via a pivot pin 502 (FIG. 43C) such that the proximal sides of the arms 630, 630' may move away from the suture introducer head 522, as shown in FIG. 54, to a position where the proximal sides are fully extended outwardly away from the distal sides of the arms 630, 630' shown in FIGS. 52A–52B. The extended proximal sides may also be retracted towards and into the suture introducer head 522 to a retreated position (similar to the position shown in FIG. 41).

FIG. 53B illustrates the second suture clasp arm 630', which is the other half of a two-arm suture clasp member. The second suture clasp arm 630' is similar to first suture clasp arm 630 except the second suture clasp arm 630' does not have a curved portion 638 for the distal end of an actuating rod 50 (as in FIG. 43B).

In one embodiment, the length of the first suture clasp arm 630 is about 0.174 inches. In one embodiment, the length of both of the suture clasp arms 630, 630' together in their fully extended position (deployed with both arms parallel to each other) is preferably about 0.288 inches. In other configurations of the suture clasp arms 630, 630', the dimensions may vary.

As shown in FIGS. 55–56, each of the flexible needles 650 comprises an elongated shaft, a pointed, generally conical penetrating distal tip 654, and a groove or shoulder 652 at the base of the distal tip 654 near the distal end. The circumference of the looped end 41 is slightly smaller than that of the base of the conical tip 654, so that the needle groove 652 acts as a detent mechanism or suture catch. In a preferred configuration, the grooves 652 extend around the complete circumference of the needles 650. In other configurations, the grooves 652 are partially circumferential along the radial edge of the needles 650. The loops 41 correspond generally in circumference to grooves 652 of the needles 650, and are sufficiently resilient to expand in circumference in response to the downward force of the needles 650, so as to slide over the conical tip 654.

In one embodiment, the looped end 41 comprises an eyelet that is formed as a unitary, integral part of the suture 40. The suture eyelet comprises a flat, thin portion of suture material having a central opening that is slightly smaller than the base of the tip 654. The periphery of the disc is contoured to match that of the recess 632 of the clasp arms. The disc is sized to fit within the recess and to be retained therein by interference fit. The looped end 41 of the suture 40 may be formed by heating one end of a length of suture such as by a stream of hot gas until the end becomes a ball-shape and pliable. The ball-shaped end is then deformed by compressing it into a disc shape while the suture material is still pliable. A sharpened hypotube is then used to punch out the hole near the center of the disc-shaped end such that the disc-shaped end forms the eyelet. If desired, the disk may be bent relative to the strand while the material is pliable to put a permanent set in the bent suture. In one configuration, the suture comprises a monofilament or plastic suture material, such as prolene or declene. In one method of forming the looped end, instead of heating the end of a suture length, the suture end is simply compressed and a hole is formed thereafter. The end may be further cut or stamped into a circle shape.

In another configuration, instead of pre-forming the hole in the suture end, the actuation of the needles 650, as described below with reference to FIG. 56, is used to form the hole and fasten the ends of the suture to the needles 650.

In another configuration, a separately-formed loop is insert-molded, glued, crimped or otherwise attached to the end of a length of suture. The loop may be in the shape of a circle, oval, triangle, rectangle, hexagon, octagon, etc.

The general use and operation of the suture clasp arms 630, 630' in FIGS. 52A–56 is substantially similar to the use and operation of the suture clasp arms 524 described above with reference to FIGS. 41–48. Specifically, the looped ends 41 of the suture 40 are placed within the annular recess 632 of the suture clasp arms 630, 630' (FIGS. 52A and 54). The suture introducer head 522 is inserted into biological tissue (similar to FIG. 47), and the suture clasp arms 630, 630' are deployed radially outward (FIG. 55). The penetrating flexible needles 650 pass through the biological tissue to be sutured (similar to FIG. 47) and engage the suture clasp arms 630, 630' (FIG. 56).

When the needle points 654 pass through the looped ends 41 of the suture 40, the looped ends 41 elastically stretch slightly, so as to circumferentially flex momentarily. As the needles 650 continue to advance distally, the looped ends 41 relax, fall into the grooves 652, and fasten around the needle grooves 652, such that pulling the needles 650 proximally causes the suture ends 41 to follow the proximal movement of the needles 650. Thus, the grooves 652 provide the same general function as the suture catches 38 (FIG. 41) described above with reference to FIGS. 41–42 and 47. In an alternative embodiment, the needles are formed without a groove or shoulder, and the shaft of the needle is sized relative to the opening in the eyelet to provide an interference fit therebetween.

Figure 58:
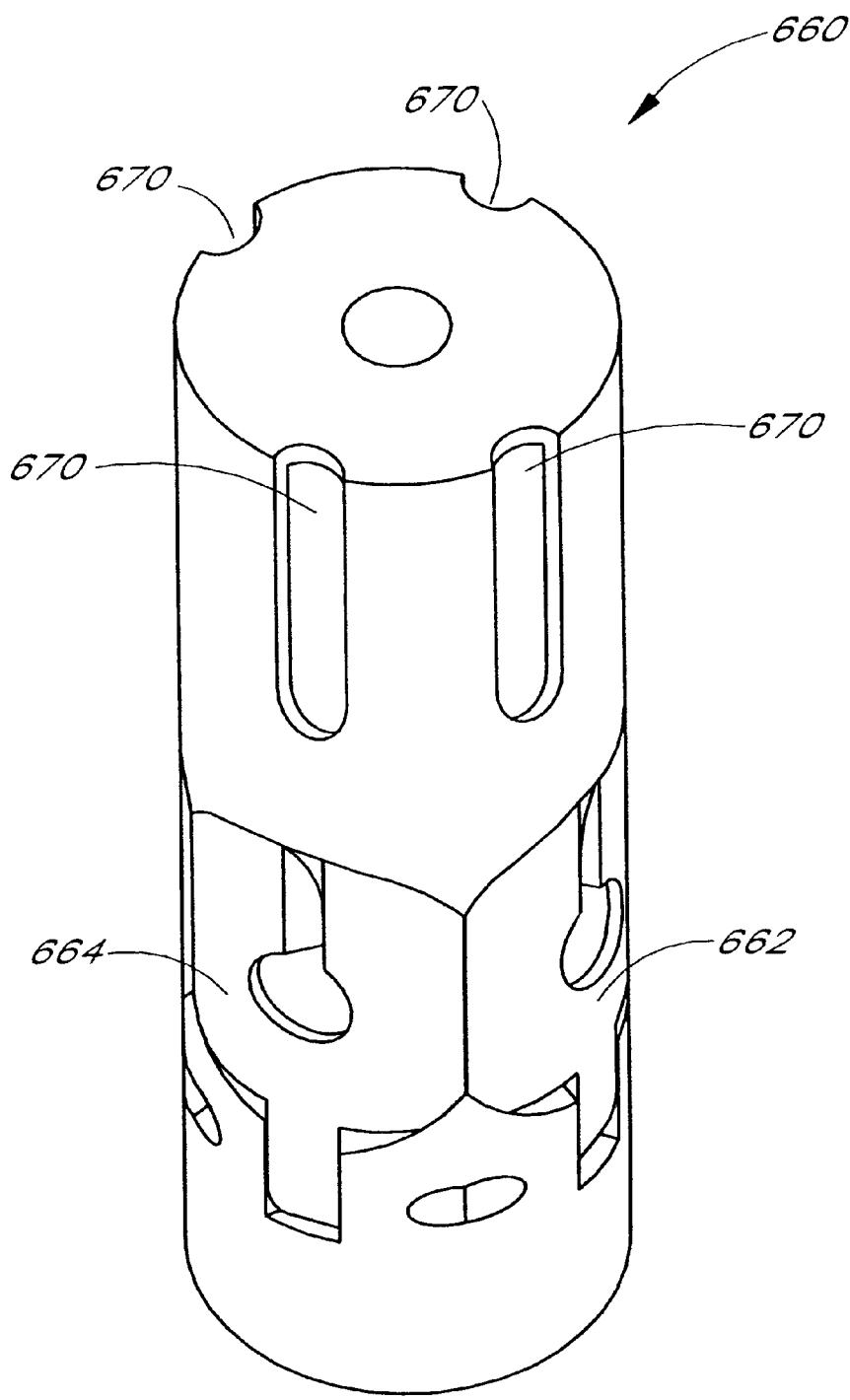
FIGS. 58–59 are perspective views of a four-arm suture clasp member used with the device of FIG. 1C–1D.
Figure 59:
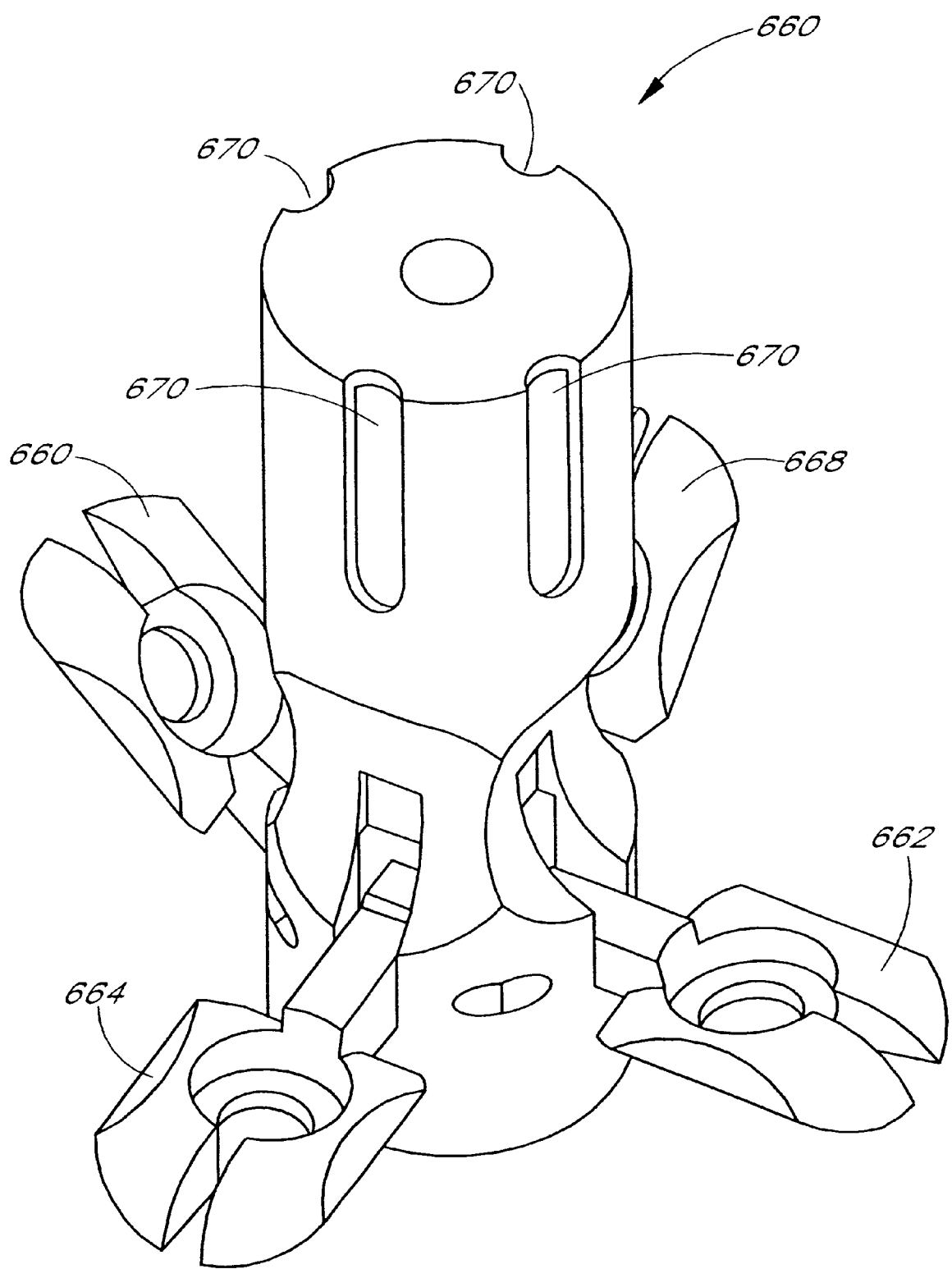

FIGS. 58–59 are perspective views of a suturing device 660 with a four-arm suture clasp member used with the device of FIGS. 1C–1D. The suturing device 660 shown in FIGS. 58–59 comprises four needle apertures 670 and four suture clasp arms 662–668. Each of the four suture clasp arms 662–668 comprises an annular recess and a slit for the length of the suture. In one embodiment, two sutures are used with the device shown in FIGS. 58–69, each of which is held by a pair of suture clasp arms. Each suture has a loop at either end which is placed within one of annular recesses of a suture clasp arm. The arms 662–668 may alternatively be provided with one of the other types of suture clasp structures disclosed herein.

Figure 60:
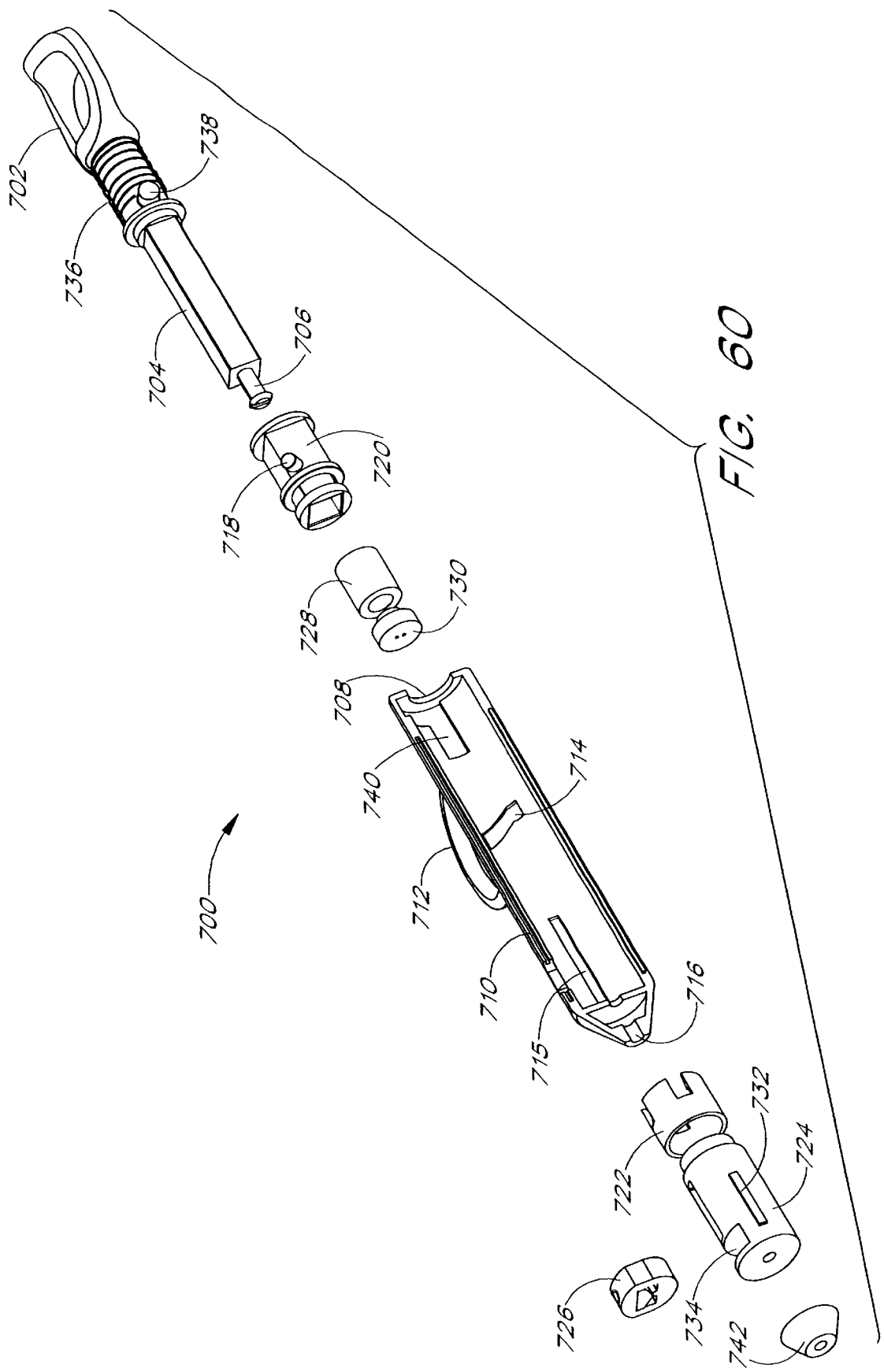
FIG. 60 is an exploded view of another embodiment of a handle capable of being attached to the proximal end of the device of FIG. 41, the device of FIG. 48 or the device of FIG. 52A.
Figure 61:
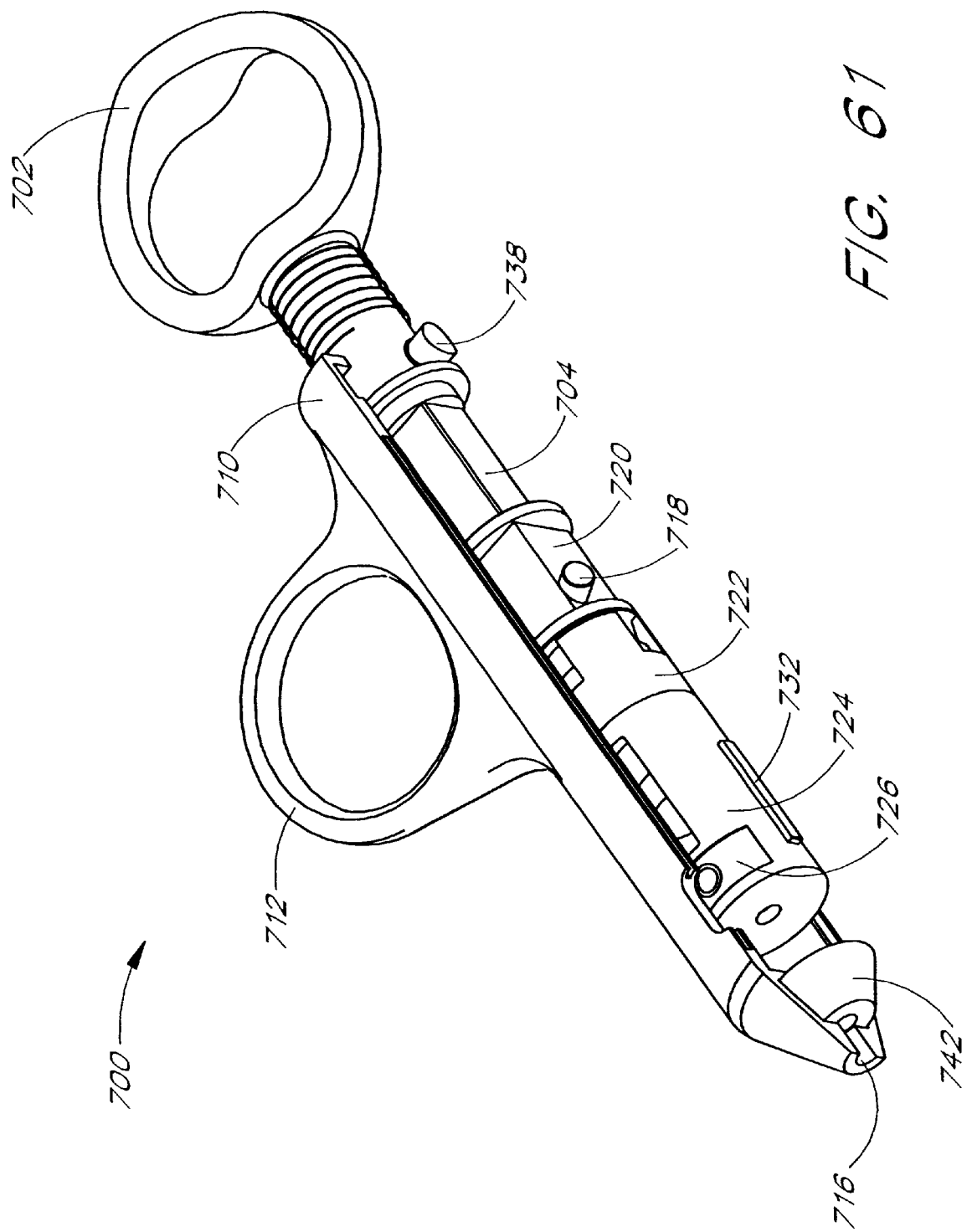
FIG. 61 is a perspective view of the handle of FIG. 60.

FIG. 60 is a perspective, exploded view of another handle configuration 700 attached to the proximal end of the device of FIG. 41, the device of FIG. 48 or the device of FIG. 52A. FIG. 61 is a perspective view of the handle of FIG. 60. In FIG. 60, the handle 700 comprises a thumb ring 702, a plunger 704, a plunger distal end 706, a main housing 710, a proximal aperture 708, a finger ring 712, a sloped floater peg slot 714, a floater clamp slot 715, a distal end aperture 716, a floater 720, a peg 718, a floater clamp lock 722, a floater clamp 724, a drive wire (actuating rod 50) clamp 726, a needle holder backer 728, a needle holder 730, a floater clamp peg 732, a floater clamp aperture 734, a spring 736, at least one plunger peg 738, L-shaped lock recess 740 and an extrusion (hollow elongated body 514) clamp 742.

The spring 736, the floater 720, the floater clamp lock 722, the floater clamp 724, the drive wire clamp 726, the needle holder backer 728, the needle holder 730 and the extrusion clamp 732 are operatively received within the main housing 710. The shaft of the plunger 704 is slidably received through the floater 720, the floater clamp lock 722 and the floater clamp 724.

The square- or rectangular-shaped shaft of the plunger 704 fits within the square- or rectangular-shaped axial recess of the floater 720, such that rotating the plunger 704 clockwise causes the floater 720 to rotate clockwise as well. The plunger distal end 706 is adapted to snap into or otherwise attach itself into the needle holder backer 728. The plunger pegs 738 are slidably received along the L-shaped lock recess 740 formed on the interior of the main housing 710.

In a preferred configuration, the L-shaped recess lock 740, the floater peg slot 714 and the floater clamp slot 715 are all molded, carved or otherwise formed on the interior of the main housing 710. The spring 736 provides a proximal biasing force on the plunger pegs 738 and the plunger 704. The spring 736 also provides a distal biasing force on the floater 720.

The floater peg 718 is slidably received along the sloping floater peg slot 714. The distal end of the floater 720 snaps and locks into the proximal portion of the floater clamp lock 722. The floater clamp lock 722 is preferably glued, bonded or otherwise attached to the floater clamp 724. The drive wire clamp 726 fits within the aperture 734 of the floater clamp 724. The drive wire clamp 726 is glued, bonded or otherwise attached to a proximal portion of a drive wire or the actuating rod 50 of FIG. 52B.

The extrusion (hollow elongated body 514) clamp 742 is glued, bonded or otherwise attached to a proximal portion of the hollow elongated body 514 of FIG. 52A. The needle holder 730 is preferably glued, bonded or otherwise attached to the needle holder backer 728. The proximal portion of the needles 546 of FIG. 47 or the needles 650 of FIG. 55 are preferably glued, bonded, molded into or otherwise attached to the needle holder 730.

The use and operation of the handle 700 will now be described with reference to FIG. 60. While the handle 700 is in its initial state and shipped to end-users, the plunger pegs 738 within the L-shaped lock recess 740 prevent the plunger 704 from moving distally relative to the main housing 710. When a physician rotates the plunger 704 clockwise by twisting the thumb ring 702, the plunger pegs 738 move circumferentially along the L-shaped lock recess until the plunger pegs 738 are positioned to slide distally down the longitudinal part of the L-shaped lock recess 740.

As the physician rotates the plunger 704, the floater 720 also rotates clockwise. The peg 718 moving within the sloped floater peg slot 714 causes the floater 720 to move proximally. Because the drive wire clamp 726 is attached to the drive wire or actuating rod 50 (FIG. 52A), the proximal movement of the floater 720 causes the floater clamp lock 722, the floater clamp 724, the drive wire clamp 726, and the actuating rod 50 to move proximally, such that the suture clasp arms 630, 630' deploy radially outward (FIGS. 52A–52B).

Once the plunger 704 is fully rotated and the plunger pegs 738 are positioned to slide distally down the longitudinal part of the L-shaped lock recess 740, the physician may advance the plunger 704 distally. The distal movement of the plunger 704 causes the needles 546 (FIG. 47) or the needles 650 (FIG. 55) to advance distally, penetrate the biological tissue, and engage the suture clasp arms 524, 630, 630' (FIG. 47 and FIG. 55).

One of the advantages of the handle 700 is that the L-shaped lock recess 740 prevents the plunger 704 and the needles 546 (FIG. 47) or the needles 650 (FIG. 55) from advancing prematurely. This prevents unintentional deployment of the needles 546, 650 which may cause damage to the patient's tissues 14, 22 (FIG. 1D).

Six-Arm and Eight-Arm Embodiments

Figure 62:
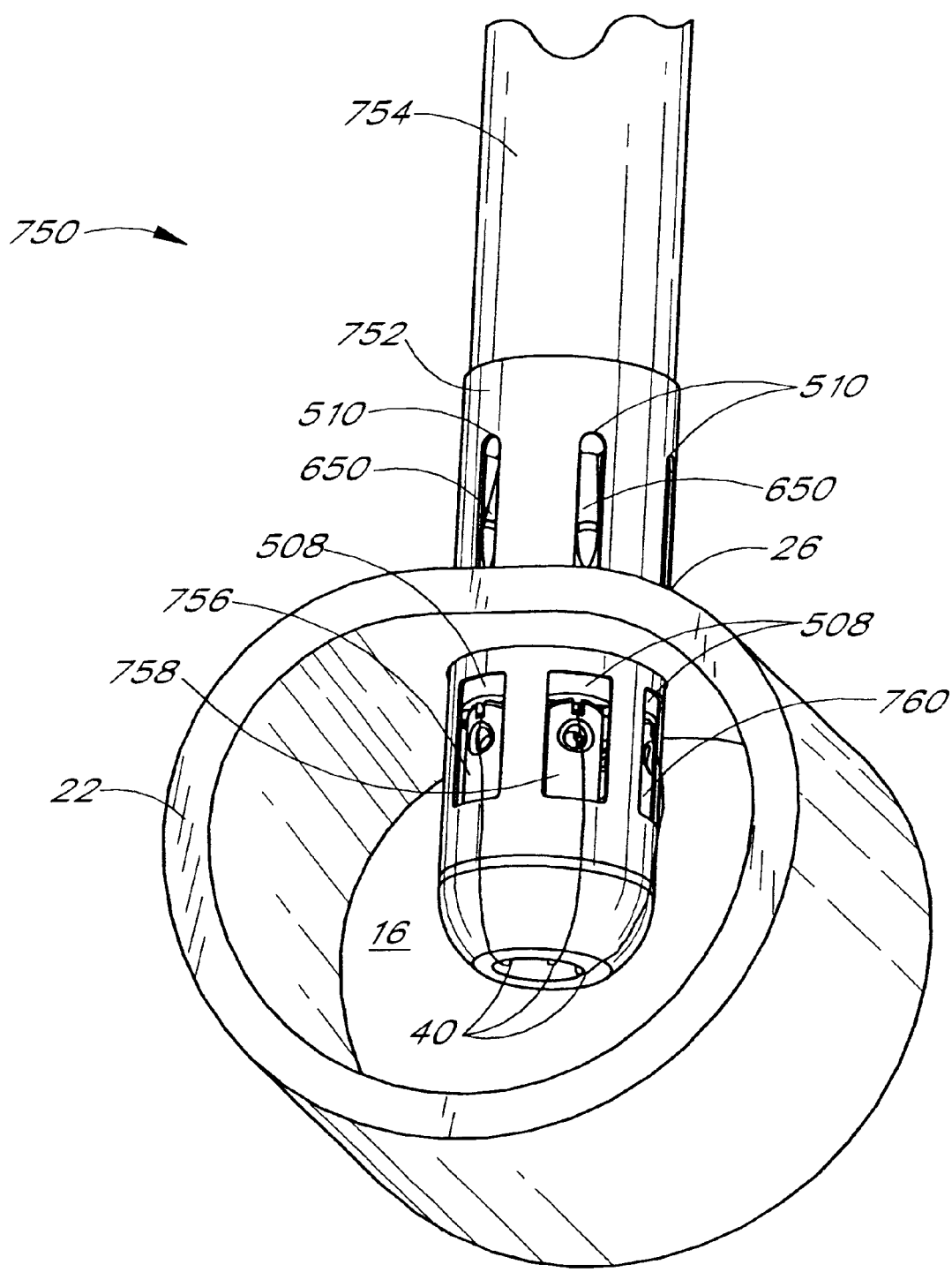
FIG. 62 is a perspective view of another configuration of the suture introducer head and the hollow elongated body of FIG. 52A with six suture clasp arms.
Figure 63:
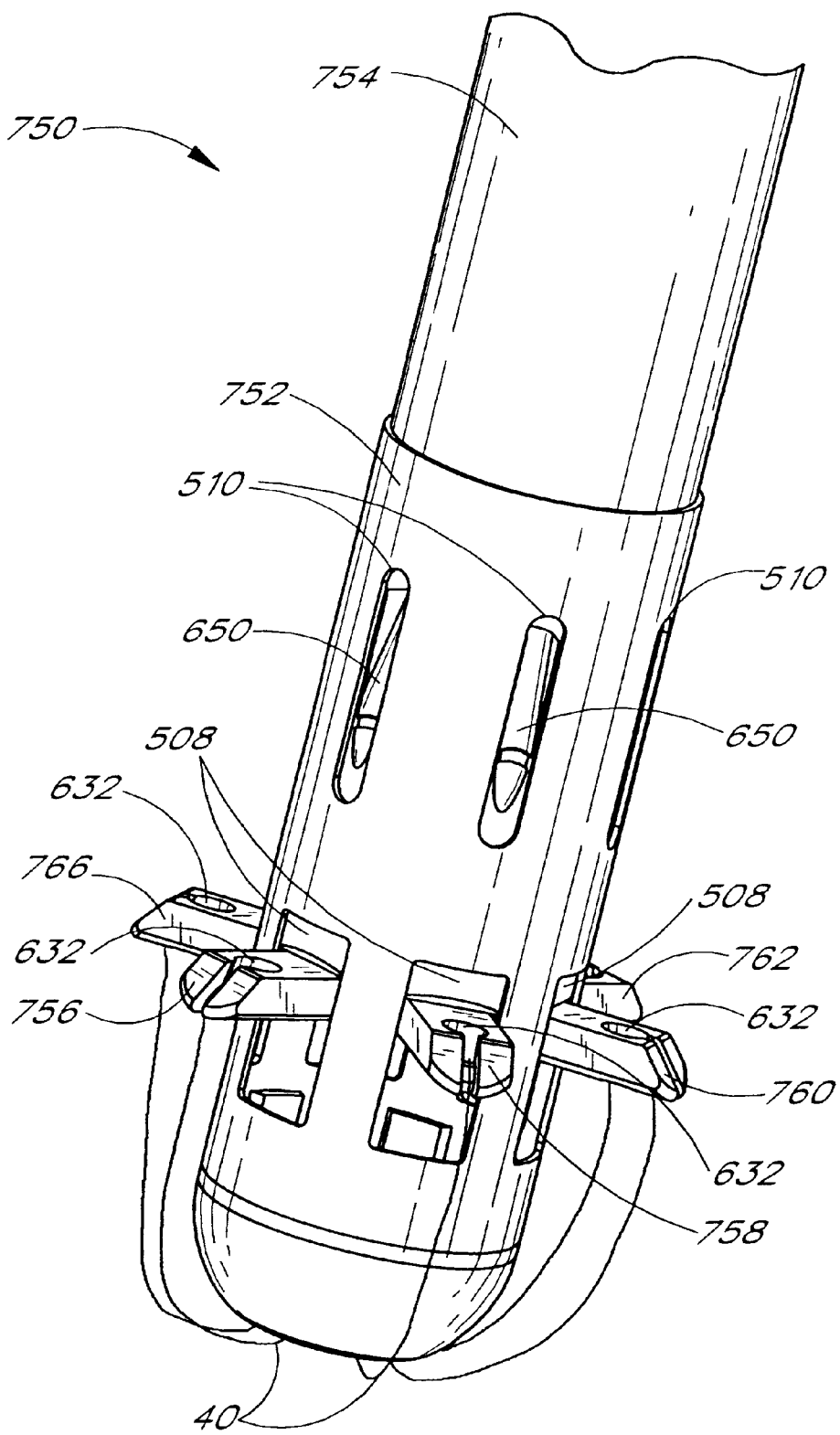
FIG. 63 is a perspective view of the device of FIG. 62 with the suture clasp arms fully deployed.
Figure 64:
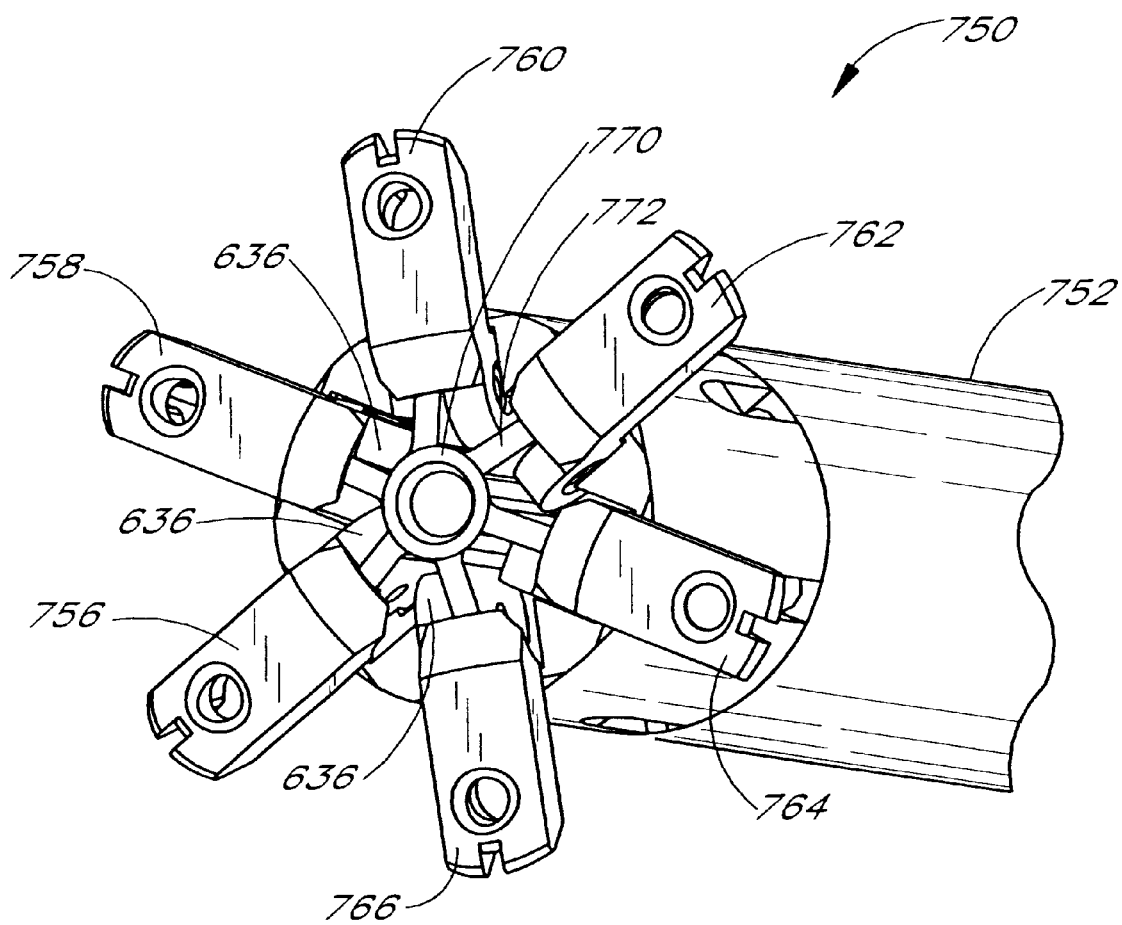
FIG. 64 is a perspective view from the distal end of the device of the six suture clasp arms of FIG. 62.
Figure 65:
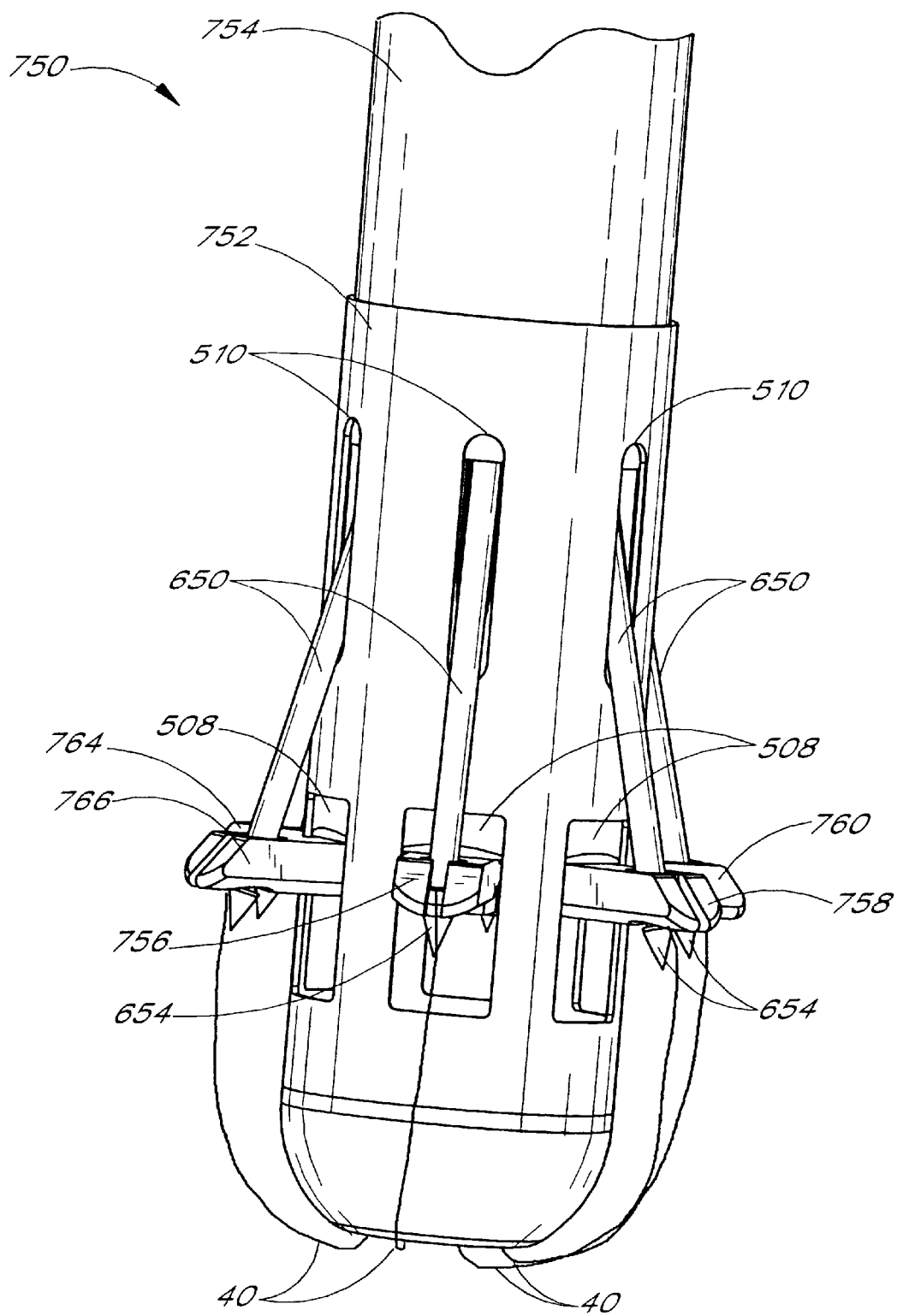
FIG. 65 is a perspective view of the device of FIG. 62 with the suture clasp arms fully deployed and a set of needles engaging the suture clasp arms.

FIGS. 62–65 illustrate another suture device configuration 750. FIG. 62 is a perspective view of the suture device 750 with six suture clasp arms 756–766 (only three of which are visible in FIG. 62). FIG. 63 is a perspective view of the device 750 of FIG. 62 with the suture clasp arms 756–766 fully deployed. FIG. 64 is a perspective view from the distal end of the device 750 of the six suture clasp arms 756–766 of FIG. 62. FIG. 65 is a perspective view of the device of FIG. 62 with the suture clasp arms fully deployed and a set of needles engaging the suture clasp arms.

In FIG. 62, the structure of the suture introducer head 752 is substantially similar to the suture introducer head 522 of FIG. 52A, except the suture introducer head 752 in FIG. 62 comprises six suture arm apertures 508 and six needle apertures 510. Similarly, the structure of the hollow elongated body 754 in FIG. 62 is substantially similar to the structure of the hollow elongated body 514 in FIG. 52A, except the hollow elongated body 754 in FIG. 62 comprises six needle lumens (not shown) to house the needles 650. Alternatively, the hollow elongated body 754 and the suture introducer head 752 may be one integrated piece, similar to the device 515 in FIG. 48.

In another embodiment, the suture device may have eight suture clasp arms, eight suture clasp arm apertures, eight needles, eight needle apertures, eight needle lumens and four sutures.

In a preferred embodiment, there is a handle (not shown) at the proximal end of the suture device 750 which allows a physician to operate the suture device 750. The handle may be similar to any one of the handle embodiments described above and below, except that the handle for suture device 750 is adapted to operate six suture clasp arms and six needles.

The structure of the suture clasp arms 756–766 of FIG. 62 is substantially similar to the structure of the suture clasp arm 630' in FIG. 53B. Alternatively, the structure of the suture clasp arms 756–766 is substantially similar to the suture clasp arm 630 (with a curved portion 638) in FIG. 53A. As shown in FIG. 63, each suture clasp arm 756–766 comprises an annular recess 632 for holding a looped end 41 of a suture 40. As shown in FIG. 64, each suture clasp arm 756–766 comprises a hinge portion 636, which is similar to the hinge portion 636 shown in FIG. 53B.

In FIG. 64, the suture introducer head 752 comprises a center ring 770 with six spokes 772. Each hinge portion 636 is operatively attached to a spoke 772 by a pivot pin (not shown), which is substantially similar in structure and function to the pivot pin 502 in FIG. 52B. The center ring 770 is attached to an actuating rod (not shown), which is substantially similar in structure and function to the actuating rod 50 in FIG. 52B.

In addition, the structure of the suture 40 and the needles 650 in FIG. 62 is substantially similar to the structure of the suture 40 and the needles 650 in FIG. 52A. In FIG. 62, there are six needles 650 and three sutures 40. Each suture 40 has a loop 41 at each end of the suture 40.

The general use and operation of the suture device 750 in FIGS. 62–65 is substantially similar to the use and operation of the suture devices described above with reference to FIGS. 41–48 and FIGS. 52A–56. Specifically, in FIG. 63, a first looped end 41 of a first suture 40 is placed within the annular recess 632 of a first suture clasp arm 756, and the second looped end 41 of the same suture 40 is placed within the annular recess 632 of a second suture clasp arm 762. The second suture clasp arm 762 is on the opposite side (180 degrees) of the suture introducer head 752 in relation to the first suture clasp arm 756. Similarly, a first looped end 41 of a second suture 40 is placed within the annular recess 632 of a third suture clasp arm 766, and the other looped end 41 of the second suture 40 is placed within the annular recess 632 of a fourth suture clasp arm 760. The third suture clasp arm 766 is on the opposite side (180 degrees) of the suture introducer head 752 in relation to the fourth suture clasp arm 760. Lastly, a first looped end 41 of a third suture 40 is placed within the annular recess 632 of a fifth suture clasp arm 758, and the other looped end 41 of the third suture 40 is placed within the annular recess 632 of a sixth suture clasp arm 764 (FIG. 64).

To assist a user in placing the six suture loops 41 properly, the suture clasp arms 756–766 may be colored to distinguish each suture clasp arm pair. For example, suture clasp arms 756 and 762 may be colored red, suture clasp arms 760, 764 may be colored white, and suture clasp arms 758 and 766 may be colored blue. Alternatively, instead of colors, the suture clasp arm pairs may have another type of indication, such as a marking. Alternatively, the suture introducer head 752 or the elongated body 754 may include an indication, such as coloring or markings to indicate the suture clasp arm pairs.

In operation, the suture introducer head 752 of FIG. 62 is inserted into biological tissue 22 (similar to FIG. 47). The physician preferably uses a handle to deploy the six suture clasp arms 756–766 radially outward (FIG. 63). The physician uses the handle to advance the six penetrating flexible needles 650 through the biological tissue 22 to be sutured (similar to FIG. 47) and to engage the suture clasp arms 756–766 (FIG. 56) simultaneously. Alternatively, in another method, the three pairs of needles 650 advance distally through the tissue 22 and engage the suture clasp arms 756–766 at different times.

When the needles 650 engage the suture clasp arms 756–766, the needles 650 capture the ends 41 of the sutures 40. The needles 650 are then withdraw proximally with the ends 41 of the sutures 40 attached. Once the needles 650 are drawn into the needle apertures 510, the combination of the circular detents or grooves of the needles 650 and the inside surface of the suture introducer head 752 securely holds the sutures 40 or creates a lock on the sutures 40 such that withdrawing the suture device 750 will not cause the suture ends 41 to slip out of the apertures 510.

After the needles 650 pull the ends 41 of the three sutures 40 proximally out of the tissue 22, the physician removes the suture device 750 from the patient's tissues 22, 14 (FIG. 1B). The physician then releases the suture ends 41 from the needles 650 and ties three knots to secure the three sutures 40 at the suture site 26 (FIG. 1B).

Compact, Four-Arm Embodiment

Figure 66:
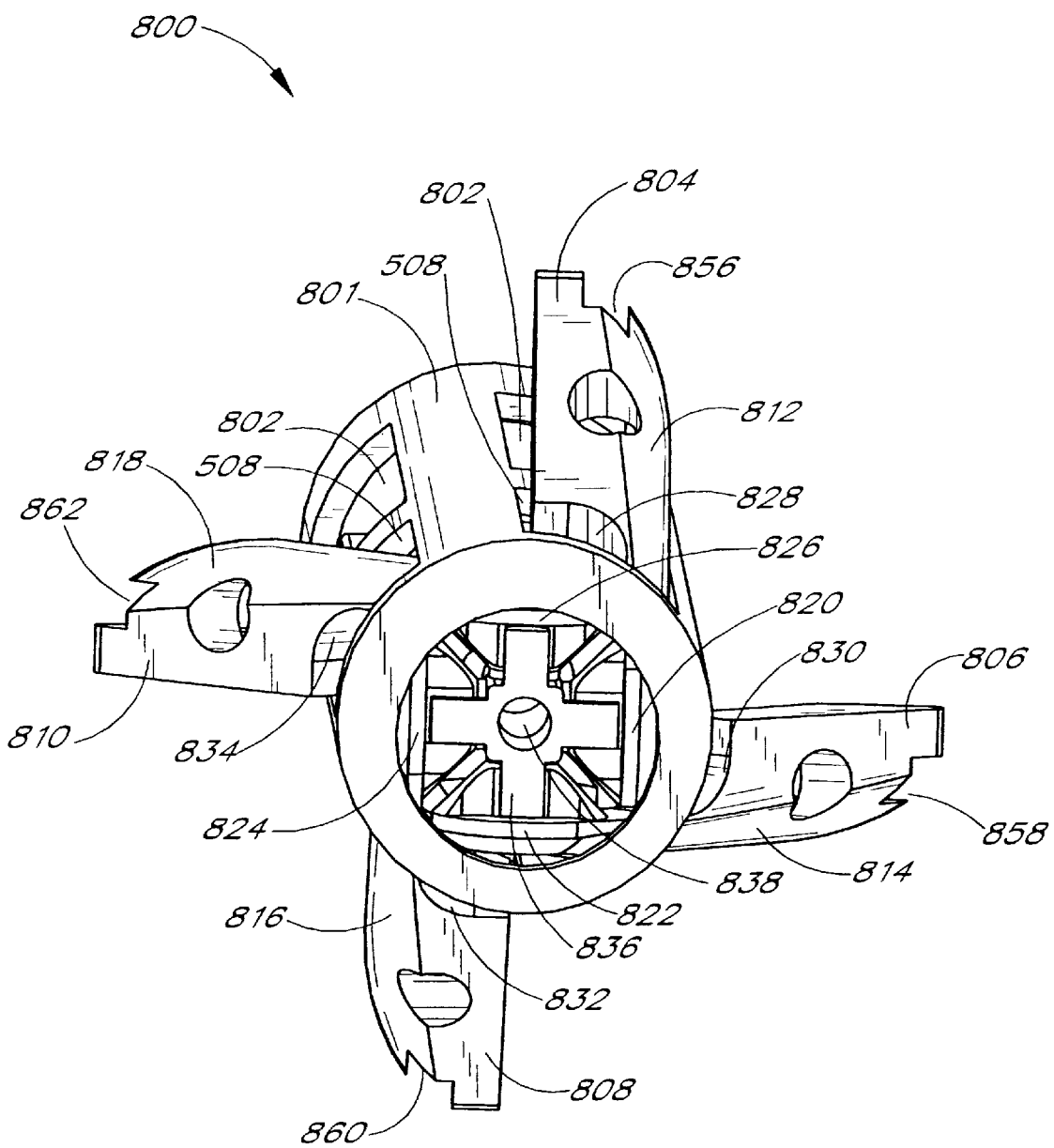
FIG. 66 is a perspective view from the distal end of another suture device configuration of the present invention with four suture clasp arms.
Figure 67:
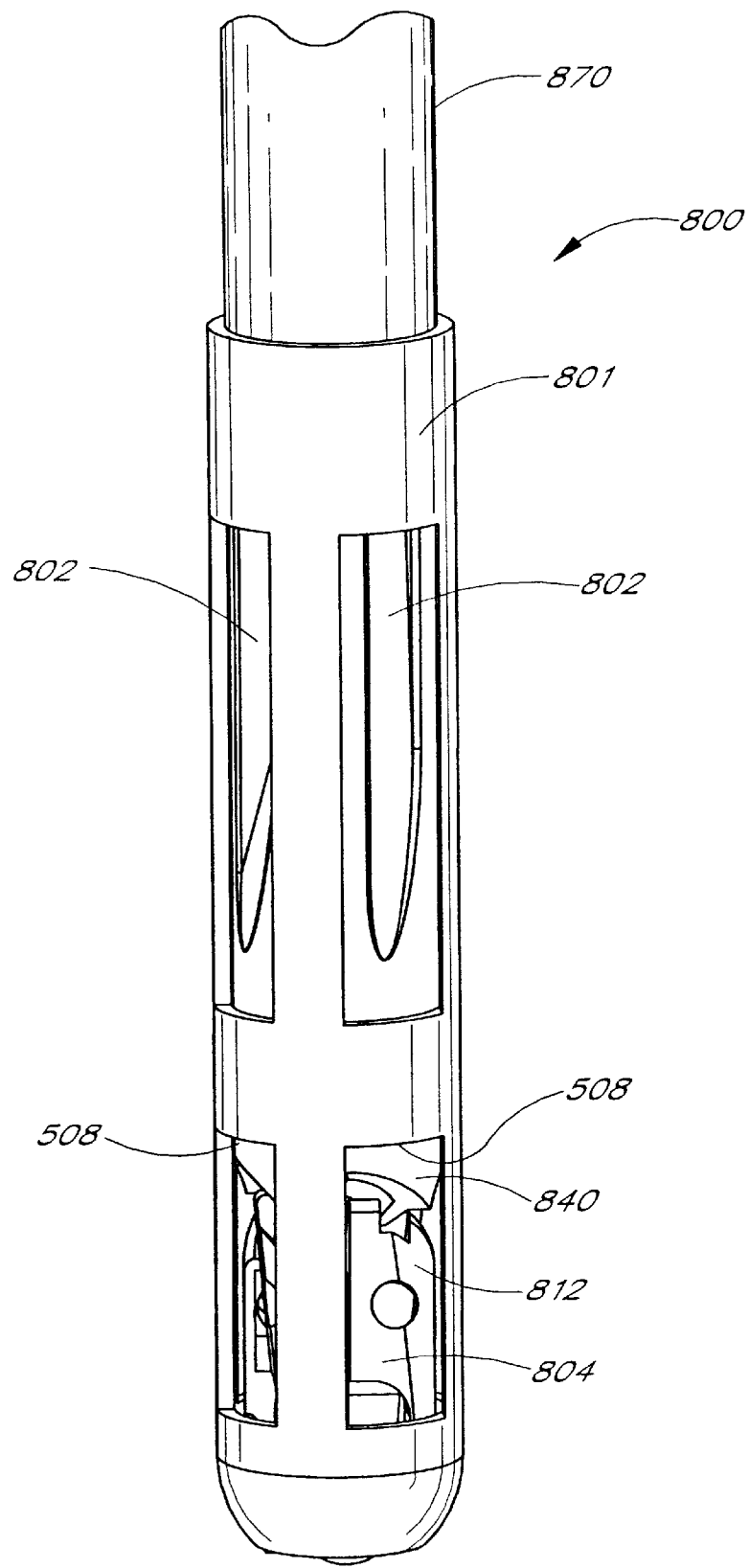
FIG. 67 is a perspective view of the suture device of FIG. 66 with the suture clasp arms fully retracted.
Figure 68:
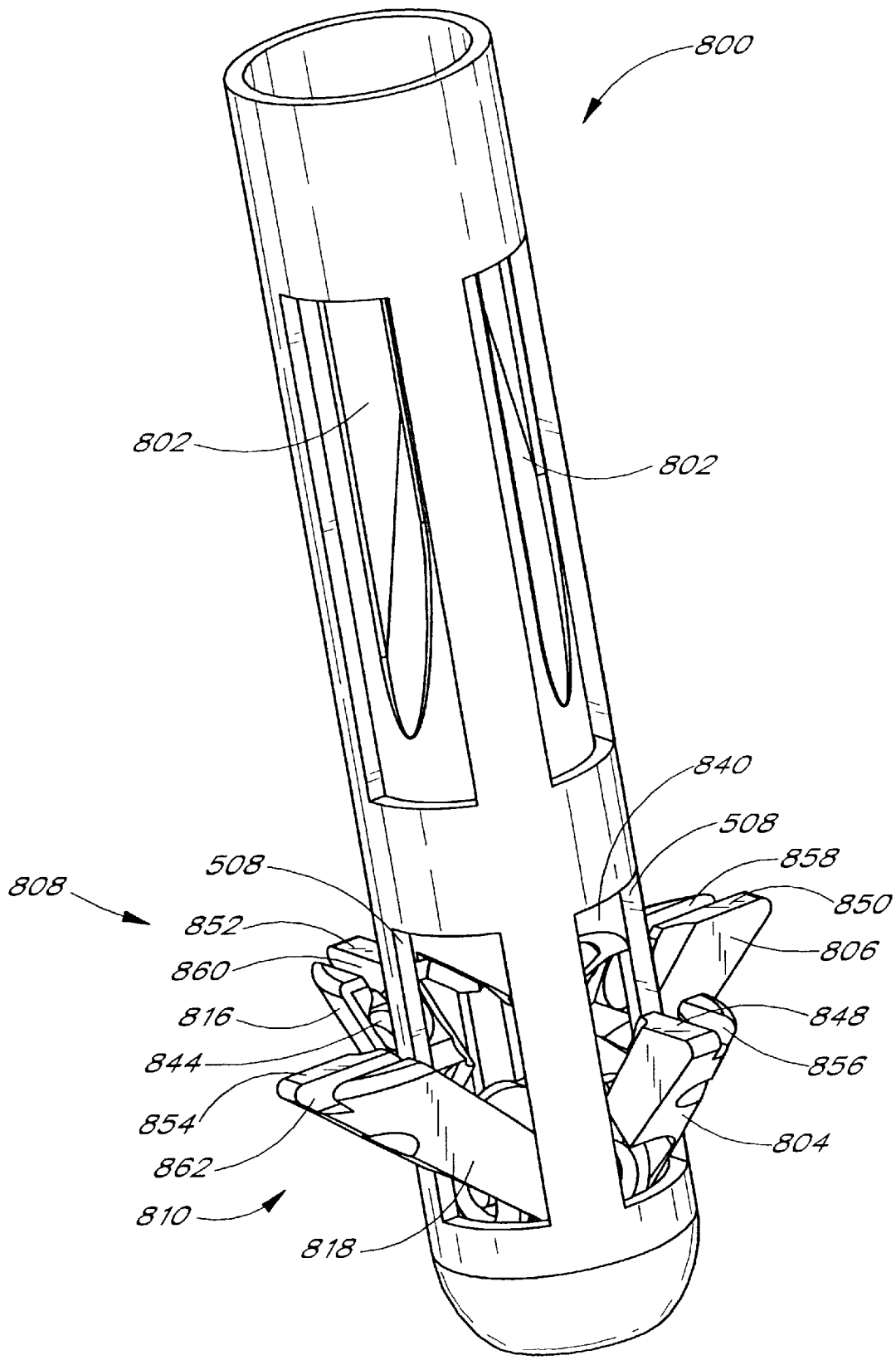
FIG. 68 is a perspective view of the suture device of FIG. 66 with the suture clasp arms partially deployed.
Figure 69:
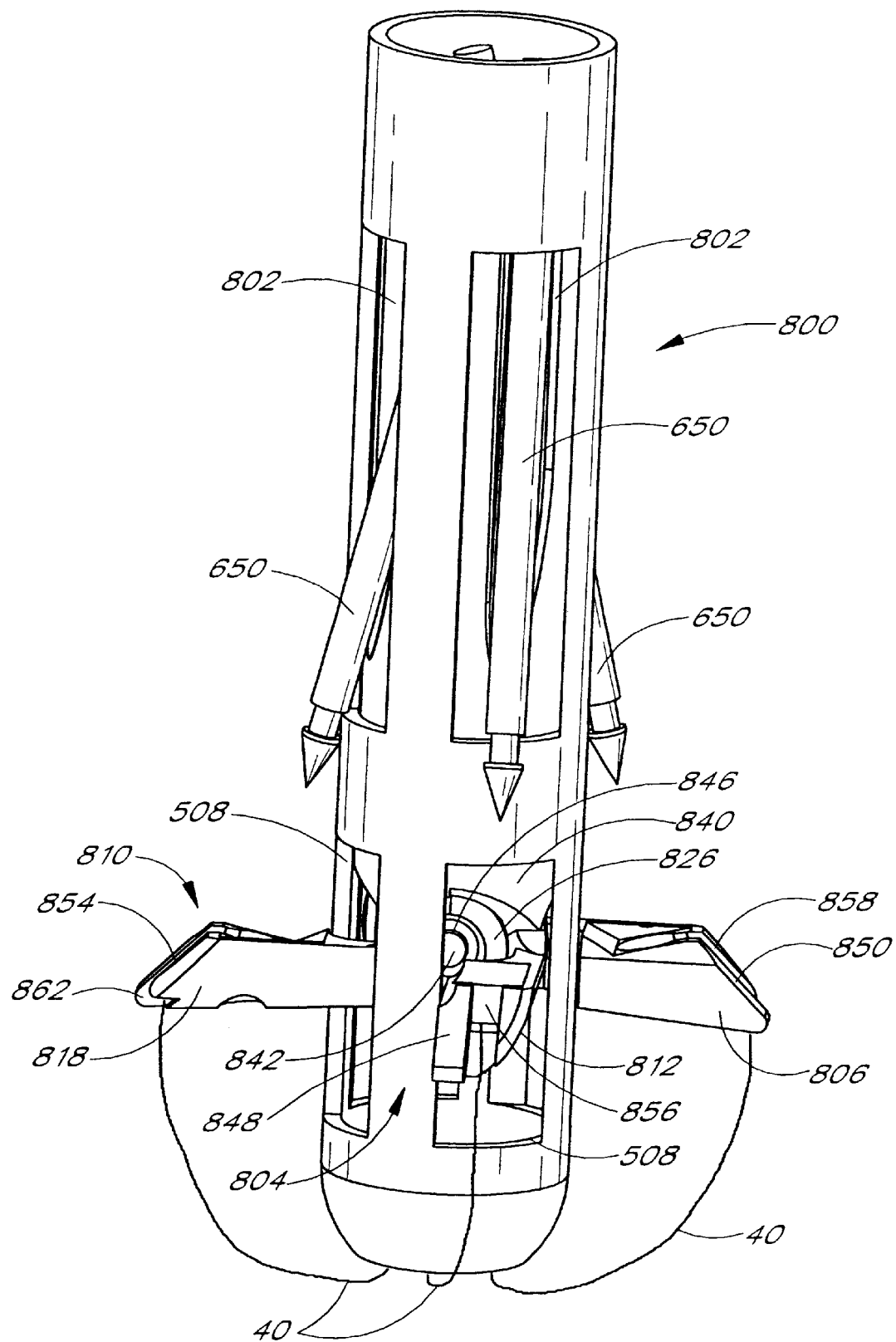
FIG. 69 is a perspective view of the suture device of FIG. 66 with the suture clasp arms fully deployed and a set of needles.

FIGS. 66–69 illustrate another suture device configuration 800 of the present invention. FIG. 66 is a perspective view from the distal end of the suture device 800 with four suture clasp arms 804–810. FIG. 67 is a perspective view of the suture device 800 of FIG. 66 with the suture clasp arms 804–810 fully retracted. FIG. 68 is a perspective view of the suture device 800 of FIG. 66 with the suture clasp arms 804–810 partially deployed. FIG. 69 is a perspective view of the suture device 800 of FIG. 66 with the suture clasp arms 804–810 fully deployed and a set of needles 650.

In FIG. 66, the structure of the suture introducer head 801 is substantially similar to the suture introducer head 522 of FIG. 52A, except the suture introducer head 801 of FIG. 66 has four suture clasp arm apertures 508, four needle apertures and four needle guides 802. Similarly, the structure of the hollow elongated body 870 attached to proximal end of the suture introducer head 801 of FIG. 66 is substantially similar to the elongated body 514 of FIG. 52A, except the elongated body 870 attached to the suture introducer head 801 has four needle lumens (not shown). Alternatively, the hollow elongated body 870 and the suture introducer head 801 may be one integrated piece, similar to the device 515 in FIG. 48.

In a preferred embodiment, there is a handle (not shown) at the proximal end of the suture device 800 which allows a physician to operate the suture device 800. The handle may be similar to any one of the handle embodiments described above and below, except that the handle for suture device 800 is adapted to operate four suture clasp arms and four needles.

Like the suture clasp arm 630 in FIG. 52A, the suture clasp arms 804–810 of FIGS. 66–69 comprise hinge portions 820–826, apertures for pivot pins (e.g., an aperture 846 and a pivot pin 842 are shown in FIG. 69), annular recesses for holding looped ends of a suture 40 (e.g., an annular recess 844 is shown in FIG. 68), sloped ends 848–854 for facilitating deployment of the suture clasp arms 804–810, and slits 856–862 for the lengths of sutures 40.

The suture clasp arms 804–810 further comprise sloped side surfaces 812–818 and curved recesses 828–834. The sloped side surfaces 812–818 facilitate deployment and/or retraction of the suture clasp arms 804–810 when the sloped side surfaces 812–818 come in contact with the edges of the suture clasp arm apertures 508. The curved recesses 828–834 are configured to accommodate the hinge portions 820–826 of the suture clasp arms 804–810. For example, the curved recess 828 accommodates the hinge portion 826 and provides sufficient space for both suture clasp arms 804, 810 to deploy and retract without hindering each other.

In FIG. 66, the suture device 800 comprises a central hinge member 836 which is attached to an actuating rod (not shown, but similar to the actuating rod 50 in FIG. 52B) via an actuating rod aperture 838. The center hinge member 836 comprises four pivot pins, such as the pin 848 shown in FIG. 69. The hinge portions 820–826 of the suture clasp arms 804–810 rotate or pivot about the pivot pins. From a perspective view, such as FIG. 66, the suture clasp arms 804–810 and the central hinge member 836 resemble a pin-wheel.

The suture device 800 further comprises a spreader 840 (FIGS. 67–69). The structure of the spreader 840 is slightly different than the spreader 523 in FIGS. 43D and 52A, but the function is the same. Like the spreader 523 described above with reference to FIGS. 43D and 52A, the distal end of the spreader 840 in FIG. 67 is configured to spread the four suture clasp arms 804–810 into their deployed position when the central hinge member 836 is moved proximally.

The general use of the suture device 800 in FIGS. 66–69 is substantially similar to the use and operation of the suture devices described above with reference to FIGS. 41–48, 52A–56 and 62–65. Specifically, a first looped end 41 of a first suture 40 is placed within the annular recess of a first suture clasp arm 804, and the second looped end 41 of the same suture 40 is placed within the annular recess of a second suture clasp arm 808. The second suture clasp arm 808 is on the opposite side (180 degrees) of the suture introducer head 801 in relation to the first suture clasp arm 804. Similarly, a first looped end 41 of a second suture 40 is placed within the annular recess of a third suture clasp arm 806, and the other looped end 41 of the second suture 40 is placed within the annular recess of a fourth suture clasp arm 810. The third suture clasp arm 806 is on the opposite side (180 degrees) of the suture introducer head 801 in relation to the fourth suture clasp arm 810.

As shown in FIG. 66, the suture clasp arms 804–810 do not deploy and retract in the same manner as the four suture clasp arms 660–668 of the suturing device 660 shown in FIG. 59 (and other suturing devices disclosed herein, such as the suturing device 520 shown in FIG. 41 and the suturing device shown in FIG. 52A). In FIG. 59, each suture clasp arm 660–668 (and a needle associated with each suture clasp arm 660–668) deploys and retracts within a two-dimensional plane, and the central longitudinal axis of the suturing device 660 lies within each plane.

By comparison, in FIG. 66, the suture clasp arms 804–810 deploy and retract off-center in relation to the central longitudinal axis of the suture device 800. In other words, each suture clasp arm 804–810 (and a needle 650 (FIG. 69) associated with each suture clasp arm 804–810) deploys and retracts within a two-dimensional plane, and the central longitudinal axis of the suturing device 800 is offset or displaced from each plane. The plane associated with a first suture clasp arm 804 is preferably parallel to the plane associated with a second suture clasp arm 808. Likewise, the plane associated with a third suture clasp arm 806 is preferably parallel to the plane associated with a fourth suture clasp arm 810. All of these planes are preferably parallel to the longitudinal axis.

This pin-wheel configuration of the suture clasp arms 804–810 shown in FIG. 66 allows the suture device 800 to be built compactly with a relatively small diameter. In one embodiment, the suture device 800 is sized to fit an 8 french catheter or tube. Alternatively, in other embodiments, the suture device 800 may be sized to fit a catheter or tube that is smaller than or larger than 8 french.

In another embodiment of the suturing device 800, the central longitudinal axis is angularly offset from at least one of the four planes such that the central longitudinal axis intersects at least one of the four planes.

In another embodiment, the plane associated with a first suture clasp arm 804 intersects the plane associated with a second suture clasp arm 808. In addition, the plane associated with a third suture clasp arm 806 may intersect the plane associated with a fourth suture clasp arm 810.

The needle guides 802 shown in FIG. 69 preferably direct the tips of the needles 650 such that they deploy distally and retract proximally along a path that is curved in three dimensional space and which is offset from the central longitudinal axis of the suture device 800. In effect, the needletips move both sideways and outwardly relative to the central axis. Stated another way, if the needle tips in their retreated position lie in respective planes in which the central longitudinal axis also lies, then the path of these needle tips will diverge from the planes as the tips move from their retracted position to their extended position.

Alternatively, in another embodiment, each suture clasp arm 804–810 (FIG. 66) deploys and retracts within a two-dimensional plane which is offset from the central longitudinal axis of the suture device 800, but each needle 850 deploys distally and retracts proximally in a two dimensional plane.

Alternatively, in another embodiment, each needle 850 (FIG. 69) deploys distally and retracts proximally within a two-dimensional plane which is offset from the central longitudinal axis of the suture device 800, but each suture clasp arm 804–810 deploys distally and retracts proximally in an arc or curve.

Alternatively, in other embodiments, this pin-wheel configuration (where the central longitudinal axis of the suturing device 800 is offset from each plane associated with a suture clasp arm 804–810) and the related variations described above are embodied in suturing devices with less than or greater than four suture clasp arms, such as two, six or eight suture clasp arms.

In operation, the suture introducer head 802 of FIG. 66 is inserted into biological tissue with the suture arms 804–810 withdrawn, as shown in FIG. 67 (similar to FIG. 47). The physician preferably uses a handle to deploy the four suture clasp arms 804–810 radially outward, as shown in FIGS. 68 and 69. The physician uses the handle to advance the four penetrating flexible needles 650 through the biological tissue to be sutured (similar to FIG. 47) and to engage the suture clasp arms 804–810 (FIG. 69) simultaneously. Alternatively, in another method, the two pairs of needles 650 advance distally through the tissue and engage the suture clasp arms 804–810 at different times.

Once the needles 650 pull the ends 41 of the two sutures 40 proximally out of the tissue 22, the physician ties two knots to secure the two sutures 40.

Movable Sheath

Figure 70:
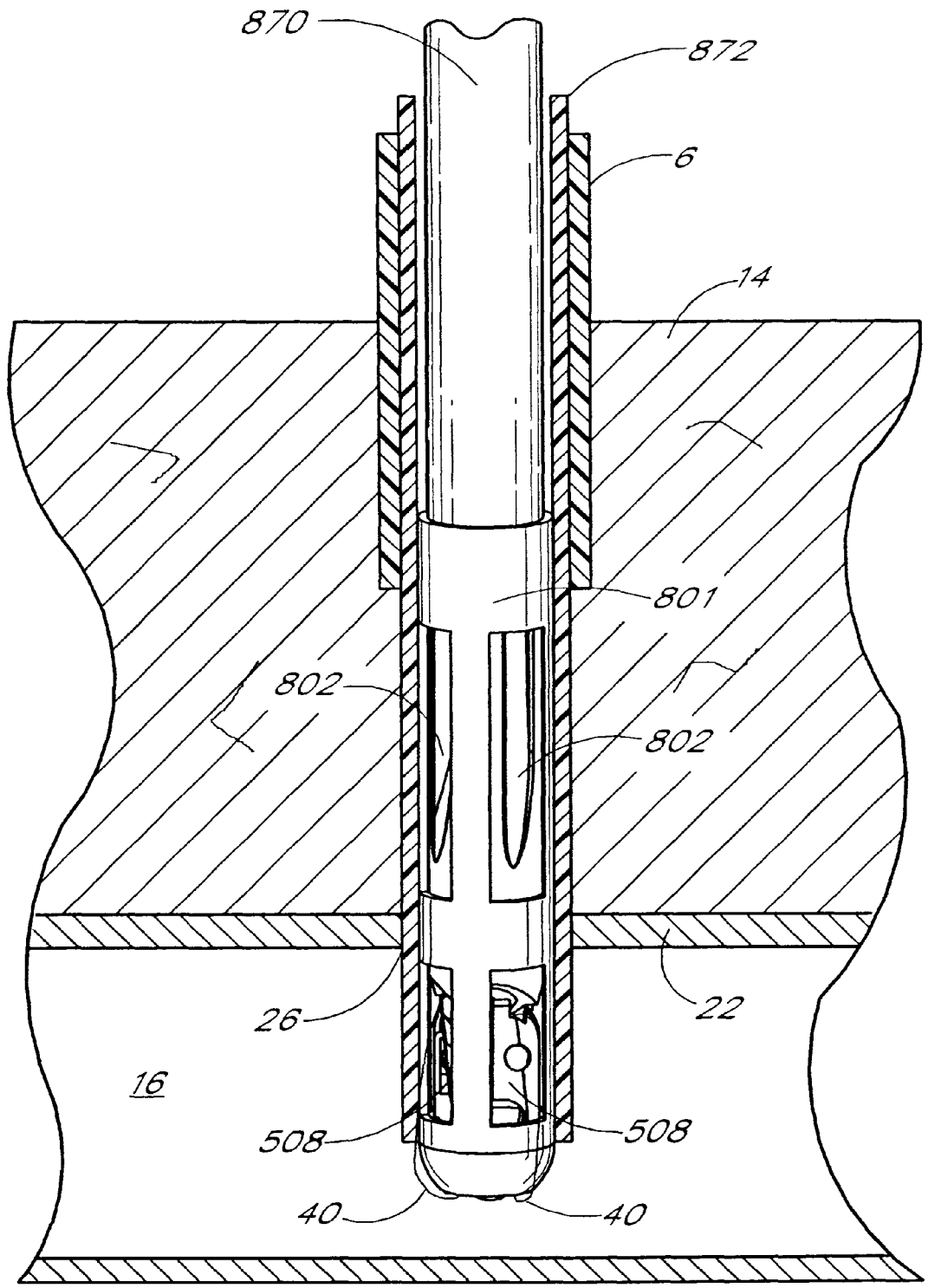
FIGS. 70–71 illustrate a removable sheath that may be used with the suture devices shown in FIG. 1A–69.
Figure 71:
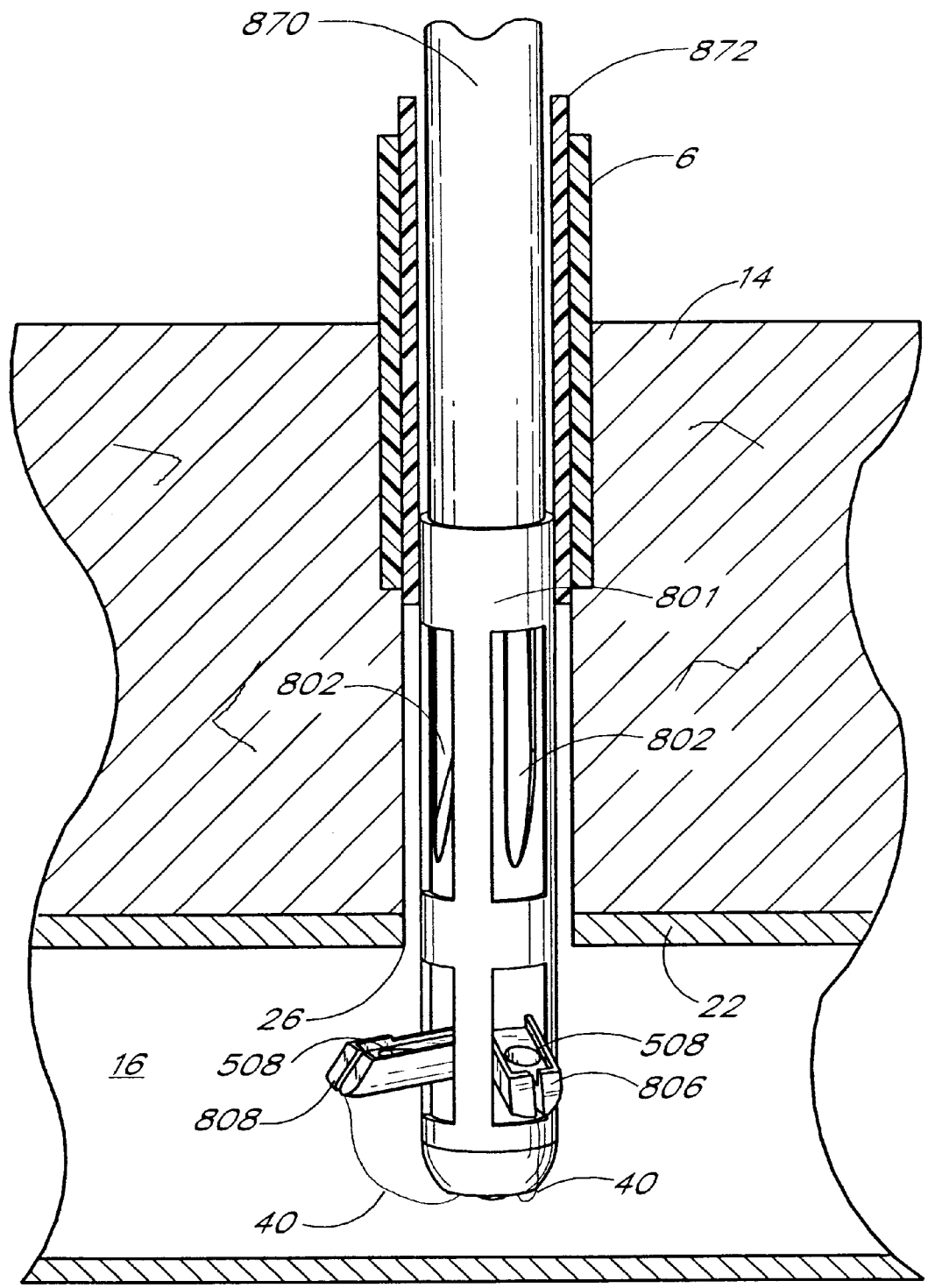

FIGS. 70–71 illustrate a movable sheath 872 that may be used with the suture devices described above. For purposes of illustration, the sheath 872 is shown in FIGS. 70–71 in use with the suture device 800 of FIG. 67. Alternatively, the sheath 872 may be adapted for use with any of the suture devices described above with reference to FIGS. 1A–69.

In FIG. 70, the sheath 872 comprises a thin-wail catheter which covers the entire suture device 800 or at least a distal portion of the suture device 800. In one configuration, the sheath 872 includes an opening at its distal end. In another configuration, the sheath 872 does not include an opening at its distal end, but may have a perforation which can be torn by downward pressure of the suture device 800 to create an opening. The sheath 872 is preferably formed or placed on the suture device 800 during manufacturing. In one configuration, the sheath 872 comprises polyimide. Alternatively, other materials may be used instead of or in addition to polyimide.

One of the advantages to the sheath 872 is that it protects the exposed portions of the sutures 40 from premature displacement as the suture device 800 is inserted distally through the CSI 6, the patient's tissue 14 and the vessel 22. The sheath 872 may also protect other exterior parts of the suturing device 800 and/or the tissue 14 and incision 26 (FIG. 70). In one embodiment, the sheath 872 also protects the exposed portions of the sutures 40 as the suture device 800 is withdrawn proximally through the CSI 6, the patient's tissue 14 and the vessel 22.

In operation, after the suture device 800 is inserted through the CSI 6, the patient's tissue 14 and the vessel 22, the user removes the sheath 872 at least partially from the suture introducer head 801. This is shown in FIGS. 70–71. There may be a number of ways to remove the sheath 872. In one embodiment, the user manually removes the sheath 872 by sliding it proximally along the suture device 800. In another embodiment, the plunger 704 of the handle 700 in FIG. 60 is attached to the sheath 872, such that rotating the plunger 704 causes the sheath 872 to slide proximally.

In addition, in one embodiment, the sheath 872 may be advanced distally over the suture introducer head 801 after the needles 650 have captured the ends 41 of the sutures 40 and retracted into the needle lumens. In this manner, the sheath 872 protects the exposed portions of the sutures 40 as the suture device 800 is withdrawn proximally through the CSI 6, the patient's tissue 14 and the vessel 22.

Occlusion Devices

Figure 72:
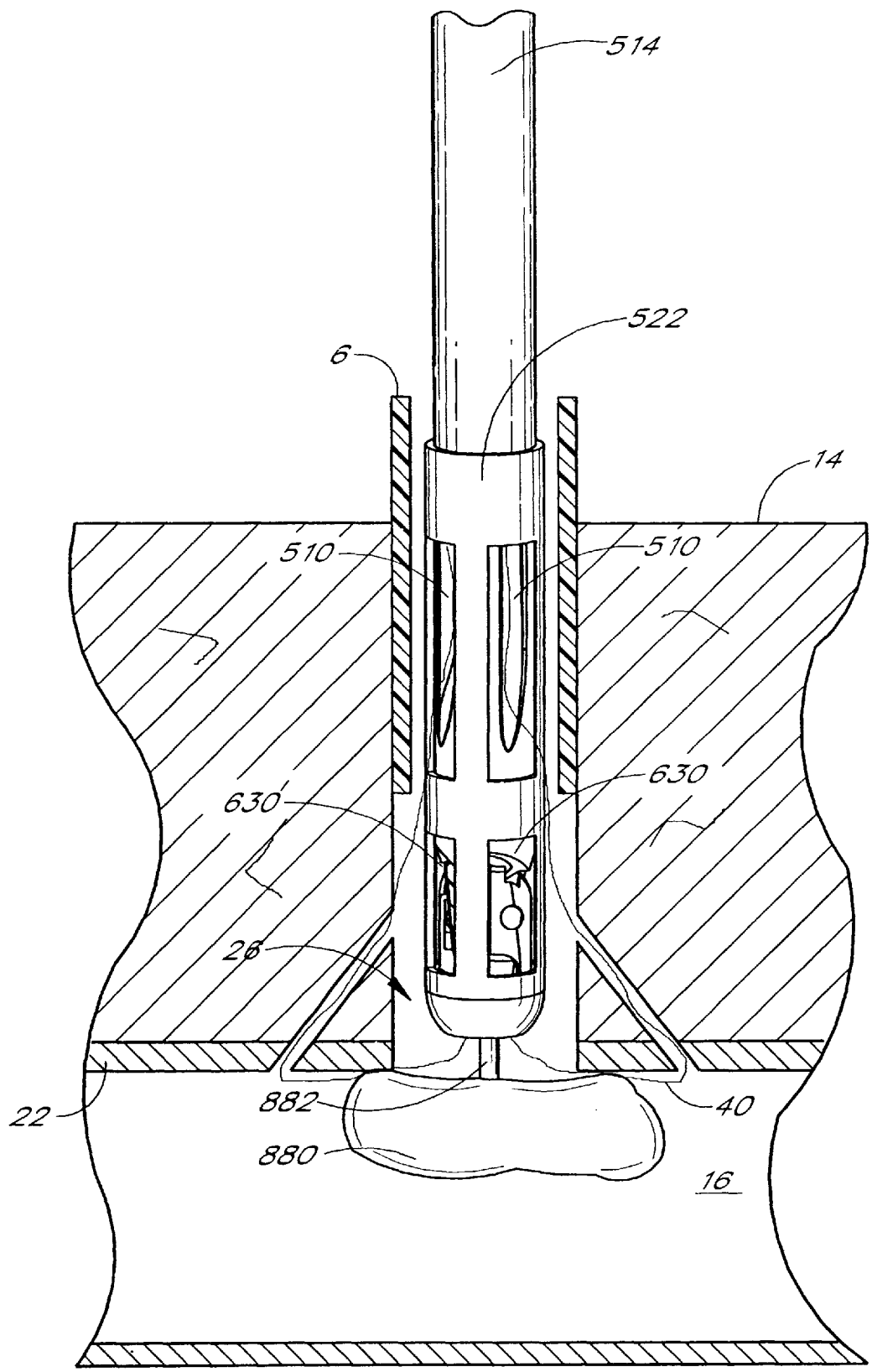
FIGS. 72–73 illustrate occlusion devices that may be used with the suture devices shown in FIGS. 1A–69.
Figure 73:
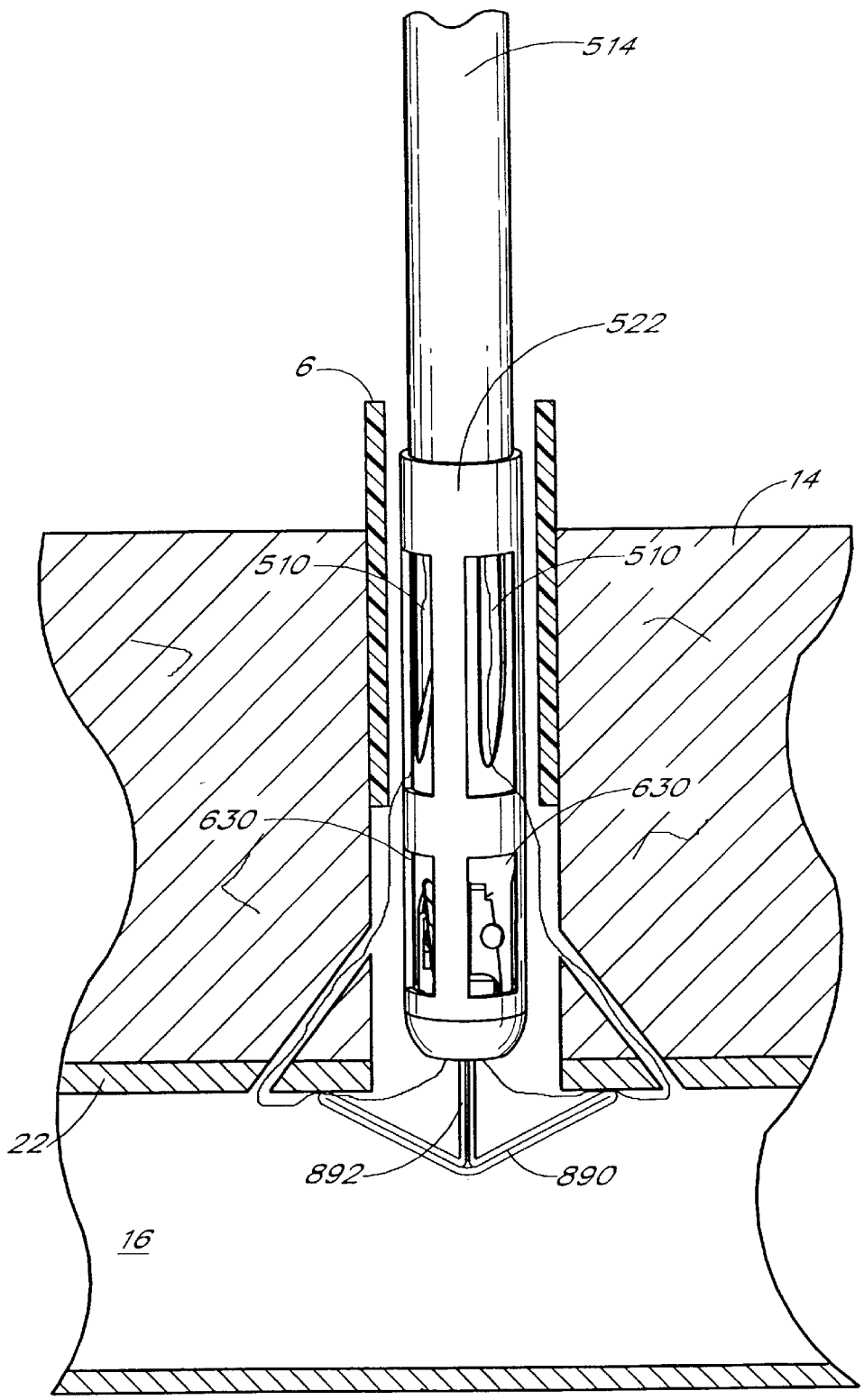

FIGS. 72–73 illustrate occlusion devices 880, 890 that may be used with the suture devices described above to temporarily occlude the incision 26 and minimize the amount of blood escaping from the blood vessel 16 through the incision 26. The occlusion devices 880, 890 are preferably adapted to allow blood to flow through the blood vessel 16 itself uninterrupted. Alternatively, in another embodiment, the occlusion devices 880, 890 are adapted to occlude the entire blood vessel 16, including the incision 26.

For purposes of illustration, the occlusion devices 880, 890 are shown in FIGS. 72–73 in use with the suture device of FIG. 52A. Alternatively, the occlusion devices 880, 890 may be adapted for use with any of the suture devices described above with reference to FIGS. 1A–69.

In FIG. 72, the occlusion device comprises a balloon 880 which is adapted to temporarily occlude the incision 26 to be sutured. The balloon 880 may comprise polyethylene, polyurethane, other polymers or any other material with similar properties. The balloon 880 is attached to a hollow tube 882 which is attached to a lumen (not shown) within the suture introducer head 522 and the hollow elongated body 514. Alternatively, the hollow tube 882 may extend through the lumen within the suture introducer head 522 and the hollow elongated body 514, and may slide within such lumen. The hollow tube 882 may be flexible or substantially rigid. The hollow tube 882 is used to inflate the balloon 880. The balloon 882 may be inflated with saline solution or any fluid that is safe for internal occlusion devices.

In operation, inflation of the balloon 880 is initiated after (1) the needles capture the ends of the suture 40 from the suture clasp arms 630, 630' and (2) the suture clasp arms 630, 630' are retracted into the suture introducer head 522. This is shown in FIG. 72. The balloon 880 temporarily occludes the incision 26 while the suture introducer head 522 is being withdrawn proximally from the tissue 14 and the physician is tying a knot with the suture ends. The physician slides the knot distally toward the incision 26. Before the physician tightens the knot, the physician deflates the balloon 880 and withdraws the balloon 880 from the vessel 16 and the tissue 14. Finally, the physician then tightens the knot to close the incision 26.

In FIG. 73, the occlusion device comprises an inverting member 890, such as the inverting members shown and described in U.S. Pat. No. 5,944,730 entitled "DEVICE AND METHOD FOR ASSISTING END-TO-SIDE ANASTOMOSIS" filed on Mar. 6, 1997, the entirety of which is incorporated by reference herein. The inverting member 890 is attached to an actuator 892 which extends through a lumen (not shown) within the suture introducer head 522 and the hollow elongated body 514. As described in the above-referenced patent, the inverting member 890 comprises: an elongated shaft or tube and an expandable inverting member which forms a cup or umbrella-like structure that can be used to form a sealed pocket against the inner wall 22 of the vessel 16.

Like the occlusion balloon 880 described above with reference to FIG. 72, the inverting member 890 is adapted to temporarily occlude the incision 26 to be sutured. In operation, the inverting member 890 protrudes from the distal tip of the suture introducer head 522. The inverting member 890 is expanded from a collapsed configuration to an expanded configuration after (1) the needles capture the ends of the suture 40 from the suture clasp arms 630, 630' and (2) the suture clasp arms 630, 630' are retracted into the suture introducer head 522. This is shown in FIG. 73. The inverting member 890 temporarily occludes the incision 26 while the suture introducer head 522 is being withdrawn proximally from the tissue 14 and the physician is tying a knot with the suture ends. The physician slides the knot distally toward the incision 26. Before the physician tightens the knot, the physician collapses the inverting member 890 so that the expanded cup is contracted against the shaft, and withdraws the inverting member 890 from the vessel 16 and the tissue 14. Finally, the physician then tightens the knot to close the incision 26.

Alternate Handle Embodiment

Figure 74A:
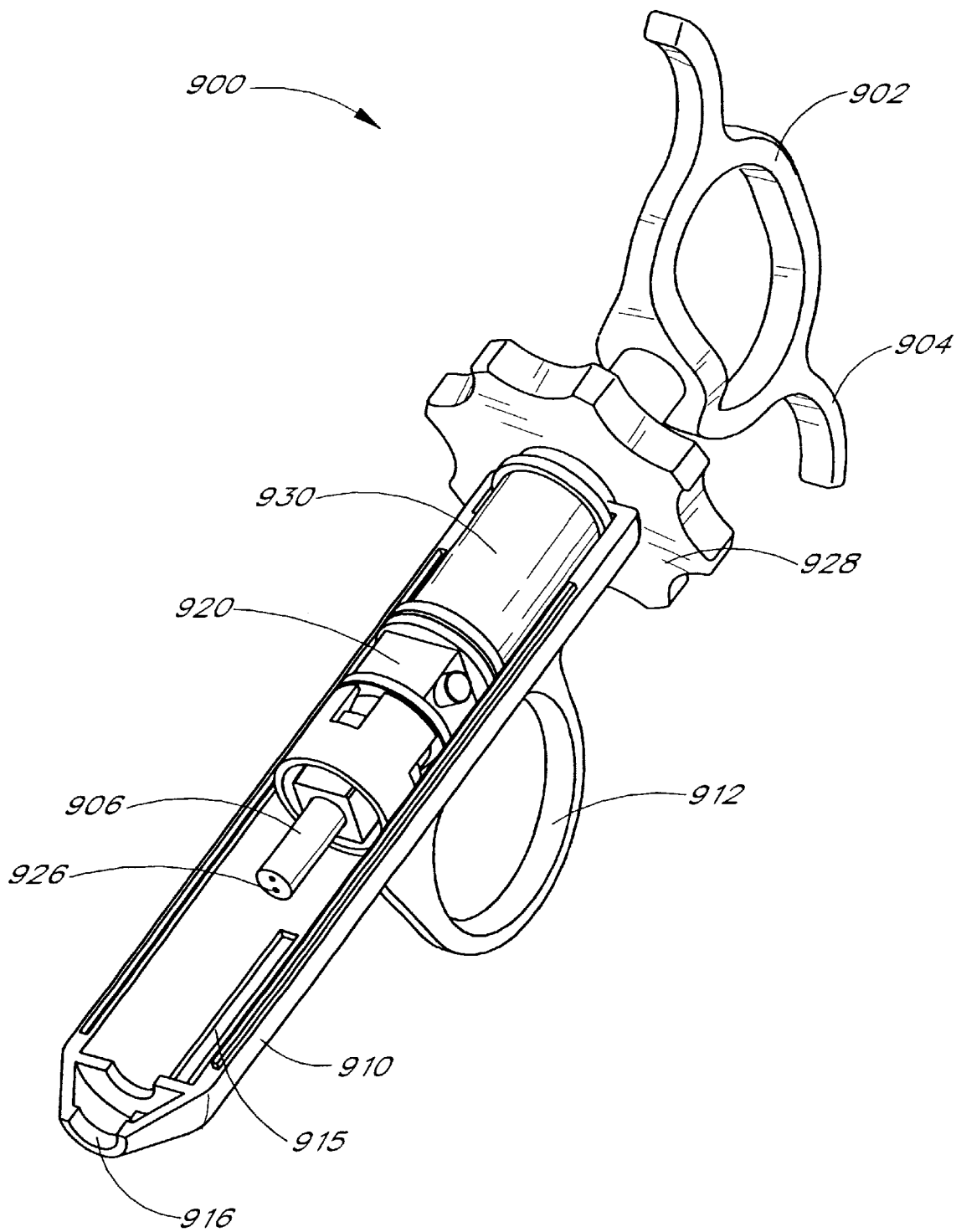
FIG. 74A is an exploded cross-sectional view of another embodiment of a handle capable of being attached to the proximal end of the device of FIG. 41, the device of FIG. 48 or the device of FIG. 52A.
Figure 74B:
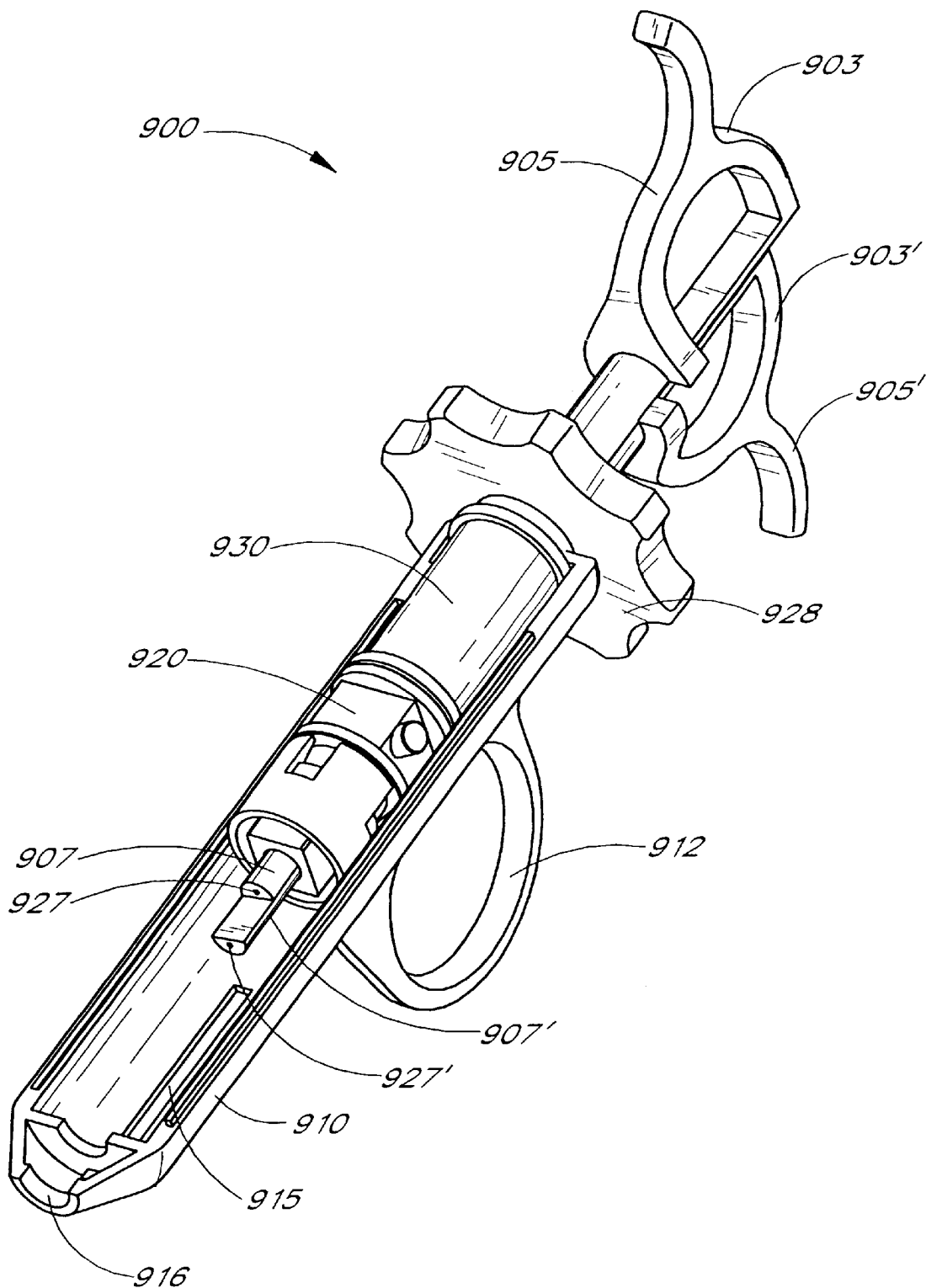
FIG. 74B is an exploded cross-sectional view of another embodiment of a handle adapted to separately actuate the first and second needles.
Figure 75A:
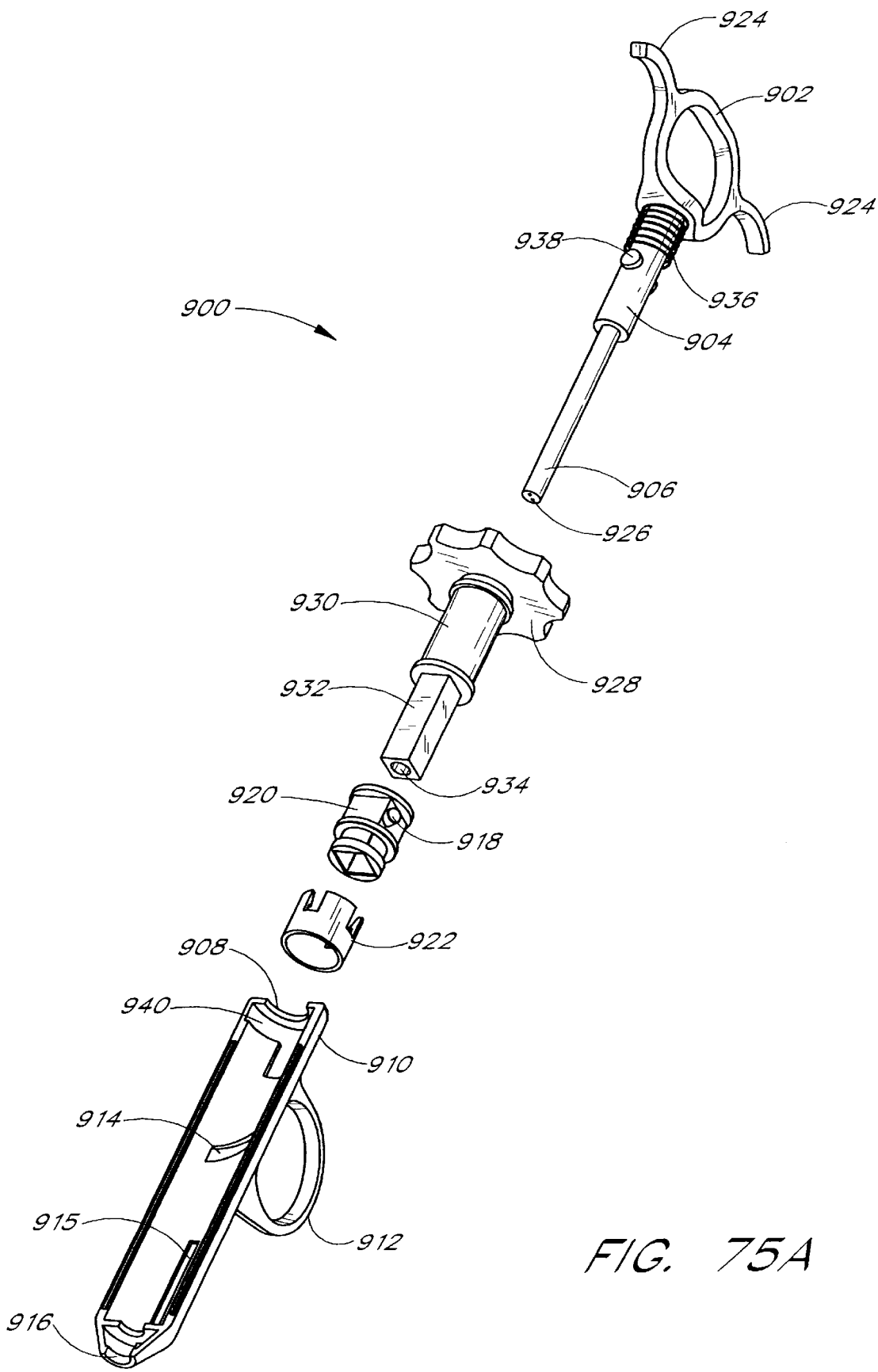
FIGS. 75A and 75B are exploded, cross-sectional, perspective views of the handle of FIG. 74A.
Figure 75B:
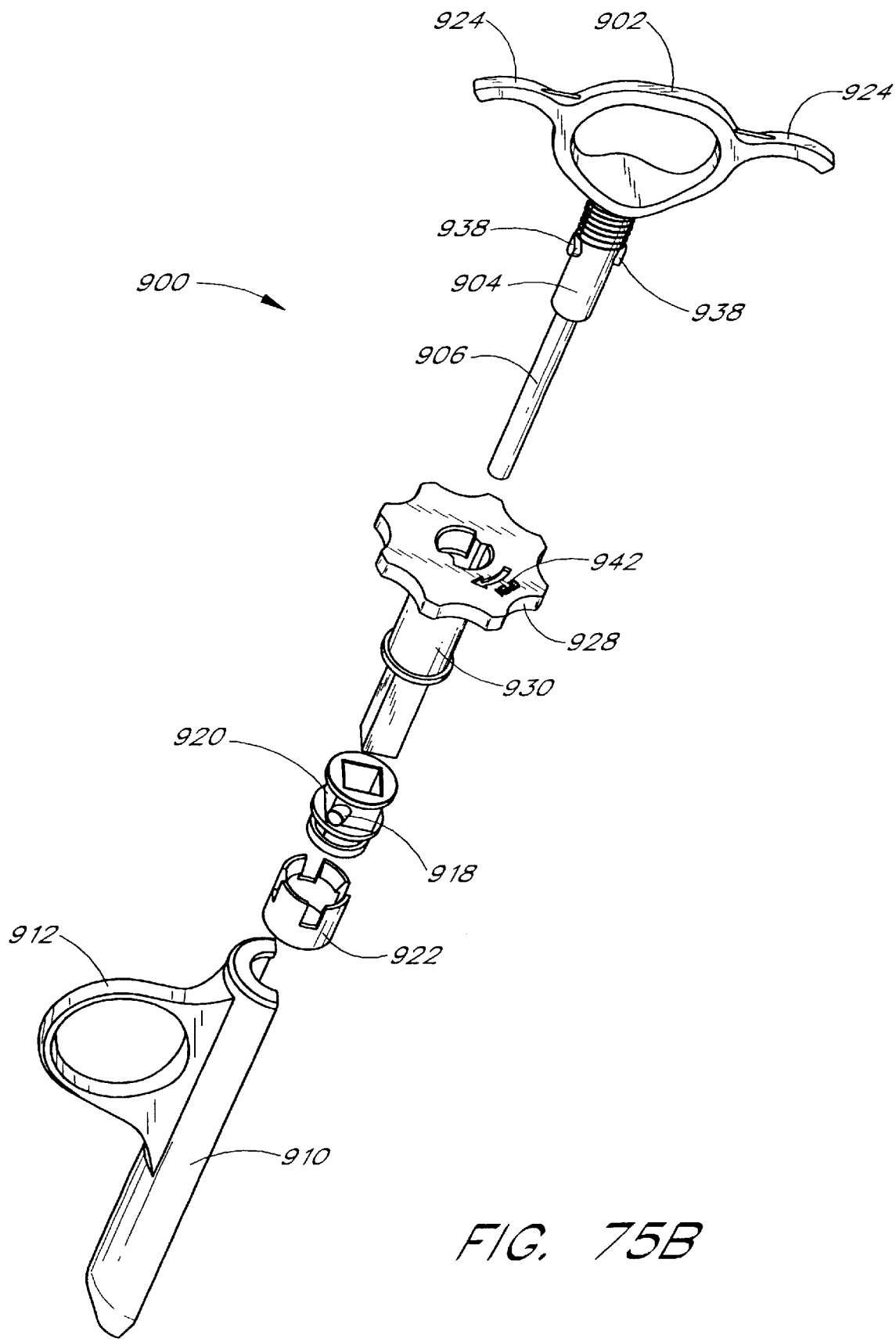
Figure 76A:
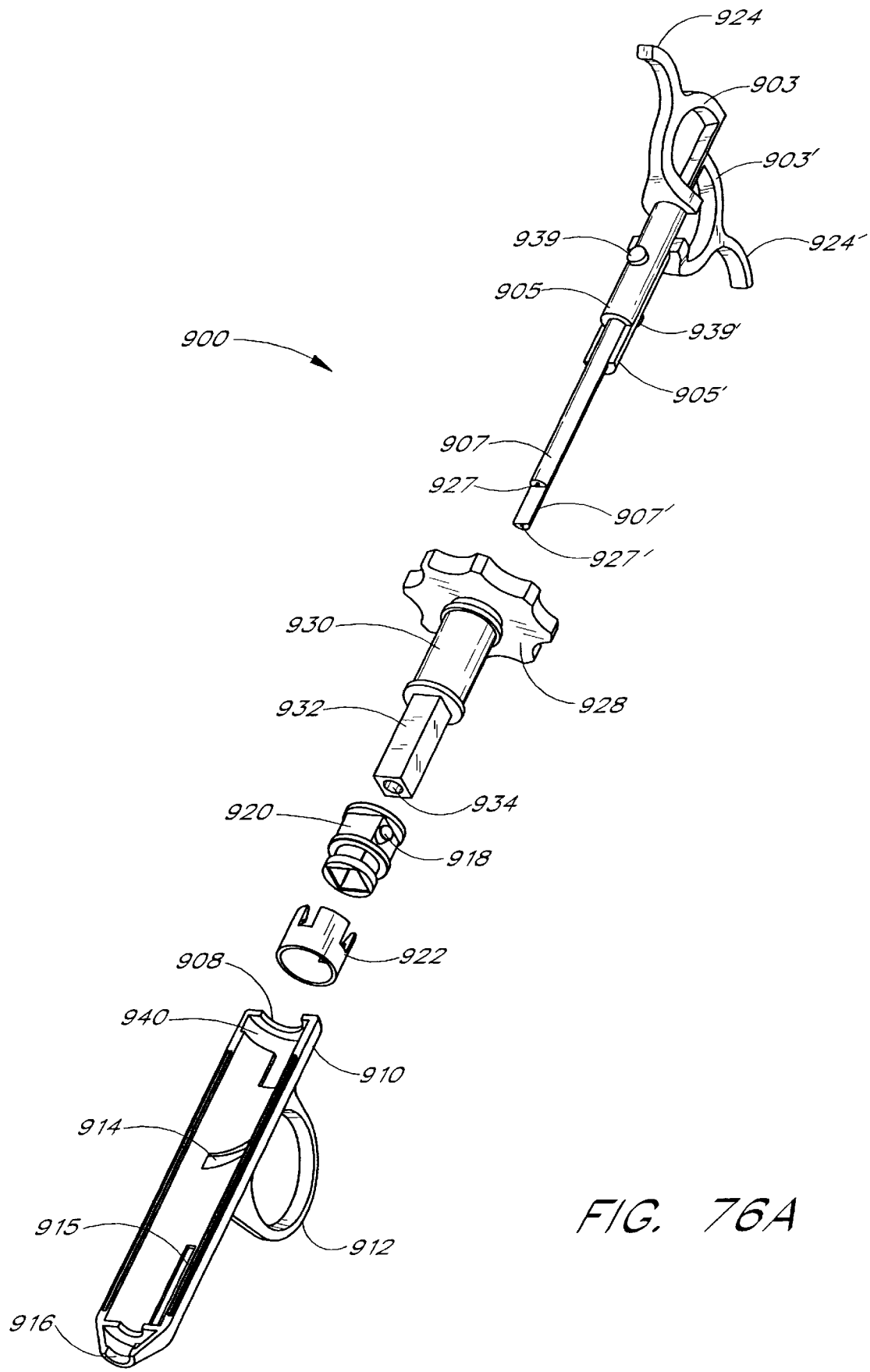
FIG. 76A is an exploded, cross-sectional, perspective view of the handle of FIG. 74B.

FIG. 74A is a perspective view of another embodiment of a handle 900 capable of being attached to the proximal end of the device of FIG. 41, the device of FIG. 48 or the device of FIG. 52A. Similarly, FIG. 74B is a perspective view of another embodiment of a handle 900 adapted to separately actuate the first and second needles. A portion of the main housing 910 has been removed in FIGS. 74A and 74B to expose the interior. FIGS. 75A and 75B are exploded, perspective views of the embodiment shown in FIG. 74A. FIG. 76A is an exploded, perspective view of the embodiment shown in FIG. 74B, and FIGS. 76B–D schematically illustrate various embodiments of the needle drivers adapted to separately actuate the first and second needles. FIGS. 74B and 76A–D will be described more fully below in connection with the non-simultaneous actuation of the first and second needles.

In FIGS. 74A, 75A, and 75B, the handle 900 comprises a thumb ring 902, a plunger 904, a plunger distal end 906, a main housing 910, a proximal aperture 908, a finger ring 912, a sloped floater peg slot 914, a floater clamp slot 915, a distal end aperture 916, a floater 920, a peg 918, a floater clamp lock 922, a pair of finger grips 924, a pair of needle holding apertures 926, a rotator 930, a 928 rotator grip, a distal portion 932 of the rotator 930, a central lumen 934 in the rotator 930, a spring 936, at least one plunger peg 938, and an L-shaped lock recess 940.

In a preferred embodiment, the handle 900 further comprises other members which are substantially similar to the members of the handle 700 described above with reference to FIGS. 60 and 61. These members include a floater clamp (not shown), a drive wire clamp for an actuating rod 50 (e.g., FIG. 52B), a floater clamp peg, a floater clamp aperture, and an extrusion clamp for a hollow elongated body 514 (e.g., FIG. 52B).

As shown in FIG. 74A, at least a portion of the spring 936, the plunger 904, the rotator 930, the floater 920, the floater clamp lock 922, the floater clamp (not shown), the drive wire clamp (not shown), and the extrusion clamp (not shown) are operatively received within the main housing 910, similar to FIG. 60. The distal portion 906 of the plunger 904 is slidably received through the rotator 930, the floater 920, the floater clamp lock 922 and the floater clamp (not shown), similar to FIG. 60.

The square- or rectangular-shaped distal portion 932 of the rotator 930 fits within the square- or rectangular-shaped axial recess of the floater 920, such that rotating the rotator 930 clockwise causes the floater 920 to rotate clockwise as well. The plunger pegs 938 are slidably received along the L-shaped lock recess 940 formed on the interior of the main housing 910.

In a preferred configuration, the L-shaped recess lock 940, the floater peg slot 914 and the floater clamp slot 915 are all molded, carved or otherwise formed on the interior of the main housing 910. The spring 936 provides a proximal biasing force on the plunger peg 938 and the plunger 904. The spring 936 also provides a distal biasing force on the floater 920.

The floater peg 918 is slidably received along the sloping floater peg slot 914. The distal end of the floater 920 snaps and locks into the proximal portion of the floater clamp lock 922. The floater clamp lock 922 is preferably glued, bonded or otherwise attached to the floater clamp, similar the one shown in FIG. 60. Similar to the handle 700 of FIG. 60, the drive wire clamp fits within the aperture of the floater clamp. The drive wire clamp (not shown) is glued, bonded or otherwise attached to a proximal portion of a drive wire or an actuating rod 50 (e.g., FIG. 52B).

The extrusion clamp (not shown) is glued, bonded or otherwise attached to a proximal portion of a hollow elongated body 514 (e.g., FIG. 52A). The proximal portion of the needles 546 of FIG. 47 or the needles 650 of FIG. 55 are preferably glued, bonded, molded into or otherwise attached to the needle holding apertures 926 of the plunger 904.

The use and operation of the handle 900 will now be described with reference to FIGS. 74A, 75A, and 75B. While the handle 900 is in its initial state and shipped to end-users, the plunger pegs 938 within the L-shaped lock recess 940 prevent the plunger 904 from moving distally relative to the main housing 910. When a physician rotates the rotator 930 clockwise by twisting the rotator grip 928, the plunger pegs 938 move circumferentially along the L-shaped lock recess 940 until the plunger pegs 938 are positioned to slide distally down the longitudinal part of the L-shaped lock recess 940.

As the physician rotates the rotator 930, the floater 920 also rotates clockwise. The peg 918 moving within the sloped floater peg slot 914 causes the floater 920 to move proximally. Because the drive wire clamp is attached to the drive wire or actuating rod 50 (e.g., FIG. 52A), the proximal movement of the floater 920 causes the floater clamp lock 922, the floater clamp, the drive wire clamp, and the actuating rod 50 to move proximally, such that the suture clasp arms 630, 630' deploy radially outward (FIGS. 52A–52B). As shown in FIG. 75B, the proximal side of the rotator grip 928 preferably has a marking 842 which indicates the direction of rotation (e.g., clockwise) required to deploy the suture clasp arms 630, 630'.

Full rotation of the rotator 930 disables the lock so as to allow the plunger 902 to move longitudinally relative to the main housing 910. When the rotator 930 is fully rotated, the plunger pegs 938 are positioned to slide distally down the longitudinal part of the L-shaped lock recess 940, and the physician may advance the plunger 904 distally. The distal movement of the plunger 904 causes the needles 546 (FIG. 47) or the needles 650 (FIG. 55) to advance distally, penetrate the biological tissue, and engage the suture clasp arms 524, 630, 630' (FIG. 47 and FIG. 55).

One of the advantages of the handle 900 is that the L-shaped lock recess 940 prevents the plunger 904 and the needles 546 (FIG. 47) or the needles 650 (FIG. 55) from advancing prematurely. This prevents unintentional deployment of the needles 546, 650 which may cause damage to the patient's tissues 14, 22 (FIG. 1D).

Moving Arms And/Or Needles At Different Times

Figure 77:
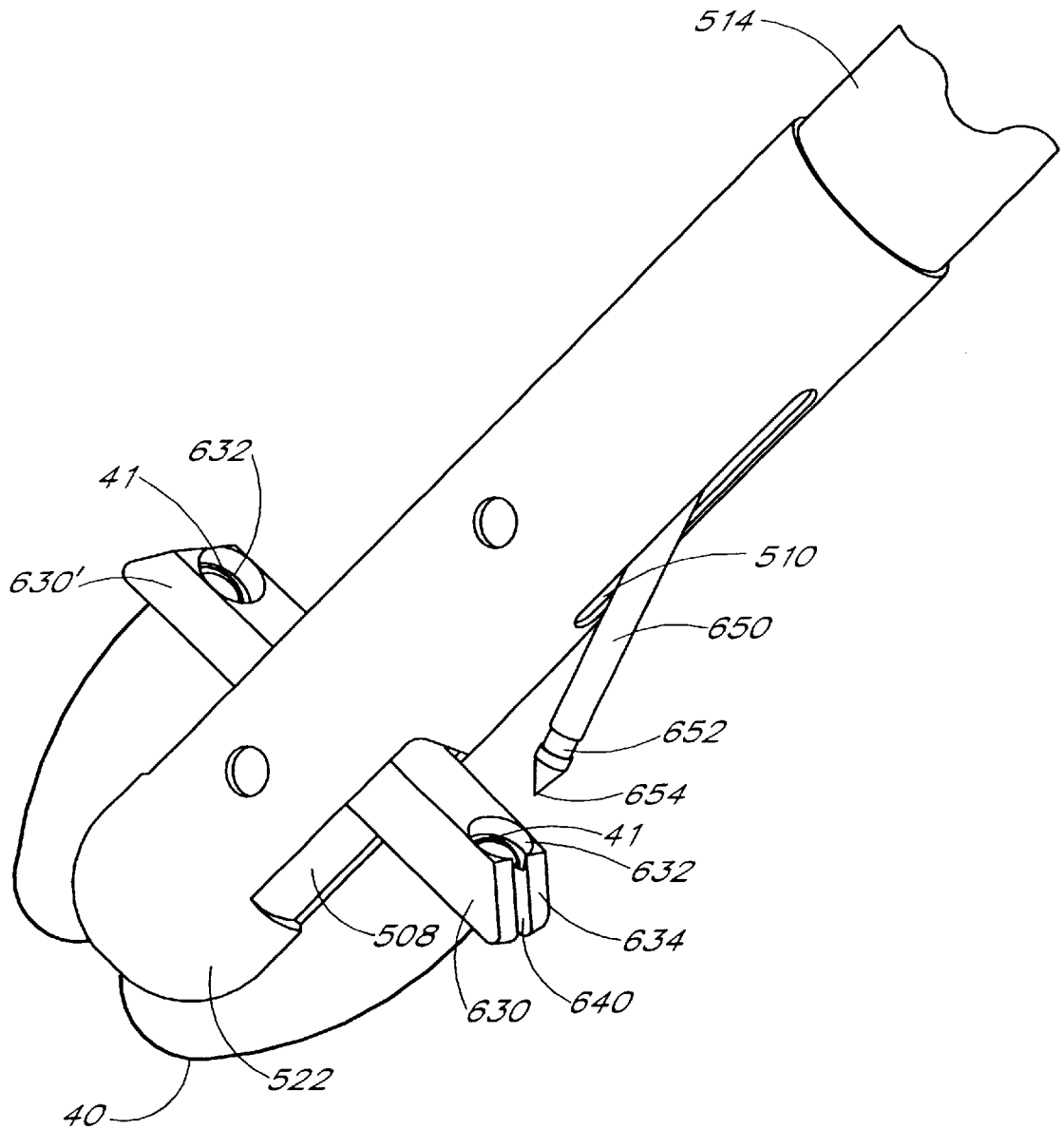
FIG. 77 illustrates the suture device of FIG. 56 adapted to move a first needle distally to engage a first suture clasp arm before moving a second needle distally to engage a second arm.
Figure 78:
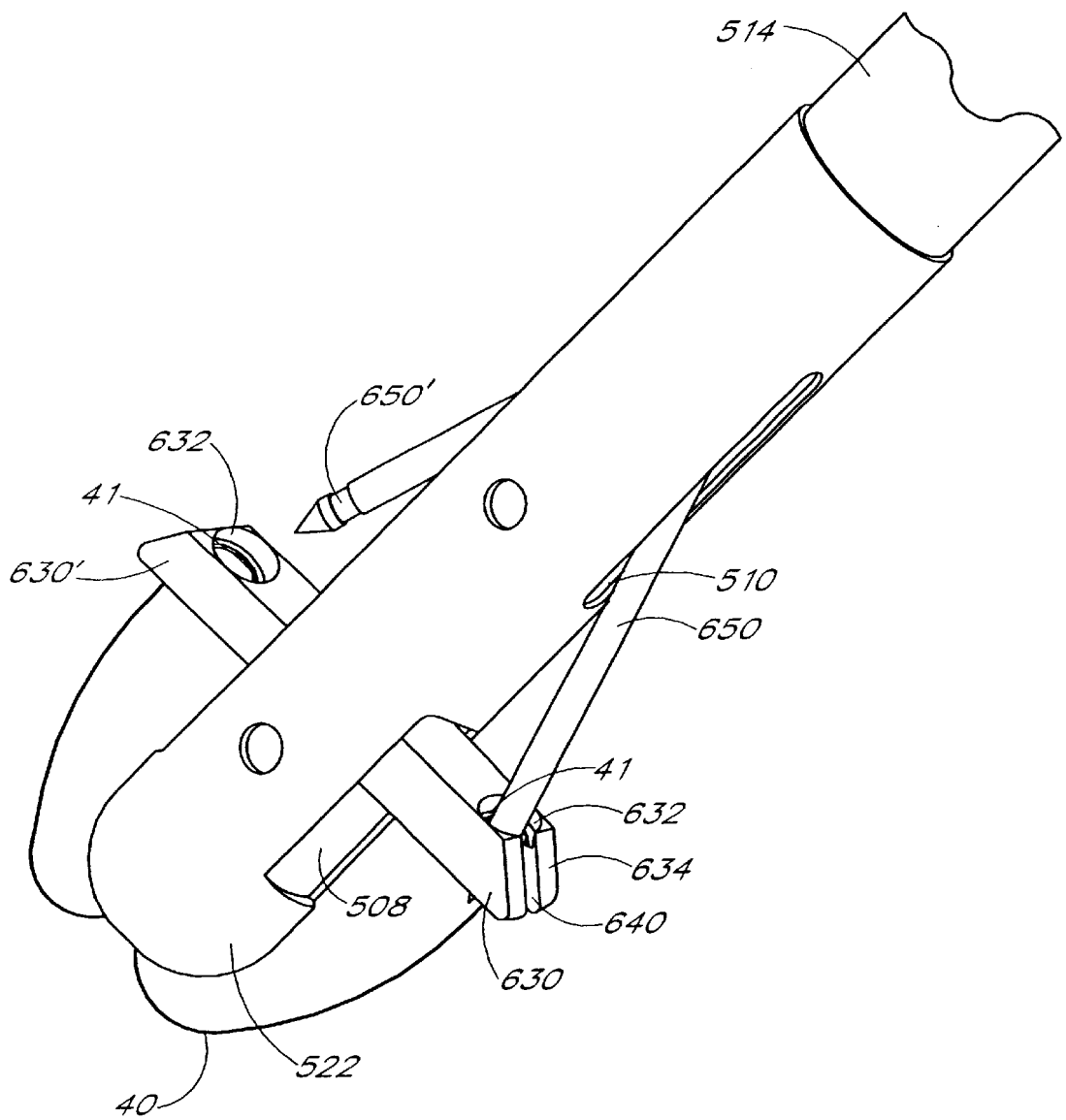
FIG. 78 illustrates the suture device of FIG. 77 with the second needle moving distally.

In the embodiments described herein, the suturing device may be configured to deploy the arms at different times, to deploy the needles to engage the suture at different times or to deploy one arm and its associated or corresponding needle and then deploy another arm and its associated or corresponding needle. For example, FIG. 77 illustrates the suture device of FIG. 56 adapted to move a first needle 650 distally to engage a first suture clasp arm 630 before moving a second needle 650' (FIG. 78) distally to engage a second clasp arm 630'. FIG. 78 illustrates the suture device of FIG. 77 with the second needle 650' moving distally to engage the second suture clasp arm 630'. In certain embodiments, the first needle 650 engages the first suture clasp arm 630 before the second needle 650' engages the second suture clasp arm 630'. In other embodiments, the first needle 650 engages the first suture clasp arm 630 before the second needle 650' moves distally. In still other embodiments, the first and second suture clasp arms 630, 630' are deployed non-simultaneously. For example, the second suture clasp arm 630' is deployed after the first suture clasp arm 630 is deployed and after the first needle 650 engages the first suture clasp arm 630.

Likewise, the first and second needles 650, 650' may be moved proximally at different times. For example, the first needle 650 may be withdrawn proximally after it captures one end of the suture 40 before the second needle 650' is withdrawn proximally after the second needle 650' captures the other end of the suture 40. In one embodiment, the first and second needles 650 and 650' are separably actuatable such that each needle is deployed independently of the other needle at different times. Alternatively, in other embodiments, the first and second needles 650 and 650' are deployed by a common actuator adapted to first deploy one needle, and then to deploy the other needle.

One embodiment in which the first and second needles 650 and 650' are separately actuable such that each needle is deployed independently of the other needle at different times is schematically illustrated in FIGS. 74B and 76A. The handle 900 of FIGS. 74B and 76A closely mirrors that of FIGS. 74A, 75A, and 75B, but includes a pair of needle drivers 905, 905' each with a thumb ring 903, 903', a needle driver distal end 907, 907', and a needle holding aperture 927, 927', respectively. Each needle driver 905, 905' also has a driver peg 939, 939'. The needle drivers 905, 905' each have a needle (not shown) connected to the needle holding aperture 927, 927' of its needle driver distal end 907, 907'. The combination of the needle drivers 905, 905' of the embodiment of FIGS. 74B and 76A is similar to the plunger 904 of FIGS. 74A, 75A and 75B. However, the needle drivers 905, 905' are adapted to be slidably displaced relative to one another and to the handle 900, thereby separately actuating the two needles 650, 650'.

As shown in FIG. 74B, the needle driver distal ends 907, 907' of the needle drivers 905, 905' are slidably received through the rotator 930, the floater 920, the floater clamp lock 922 and the floater clamp (not shown), similar to the single plunger 704 of the embodiment of FIG. 60 and the single plunger 904 of the embodiment of FIG. 74A. The driver pegs 939, 939' are slidably received along the L-shaped lock recess 940 formed on the interior of the main housing 910.

While the handle 900 is in its initial state and shipped to end-users, the driver pegs 939, 939' within the L-shaped lock recess 940 prevent the needle plungers 905, 905' from moving distally relative to the main housing 910. When a physician rotates the rotator 930 clockwise by twisting the rotator grip 928, the driver pegs 939, 939' move circumferentially along the L-shaped lock recess 940 until the driver pegs 939, 939' are positioned to slide distally down the longitudinal part of the L-shaped lock recess 940. In this position, the needle drivers 905, 905' can be moved longitudinally relative to the main housing 910 and relative to each other. The distal movement of the needle drivers 905, 905' cause the needles 650, 650' to advance distally, penetrate the biological tissue, and engage the suture clasp arms 630, 630' (FIGS. 77 and 78). In this way, the needles 650, 650' can be non-simultaneously actuated by individually advancing the needle drivers 905, 905' at different times. The driver pegs 939, 939' of the embodiment illustrated in FIGS. 74B and 76A operate in a similar manner as do the plunger pegs 938 described above for the use and operation of the embodiment illustrated in FIGS. 74A, 75A, and 75B.

Figure 76B:
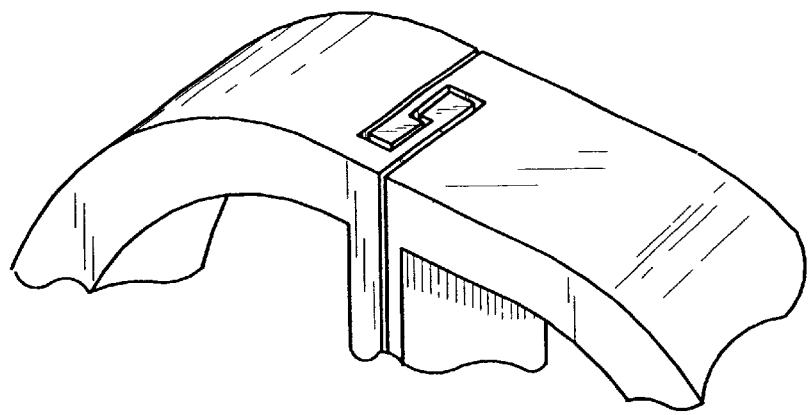
FIGS. 76B–D schematically illustrate various embodiments of the needle drivers adapted to separately actuate the first and second needles.
Figure 76C:
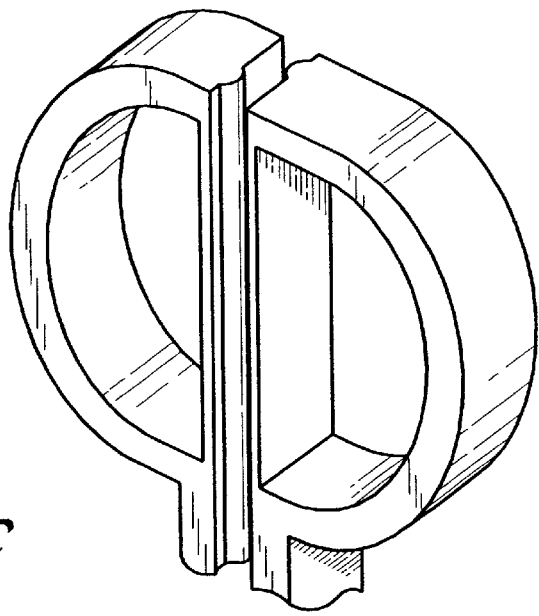
Figure 76D:
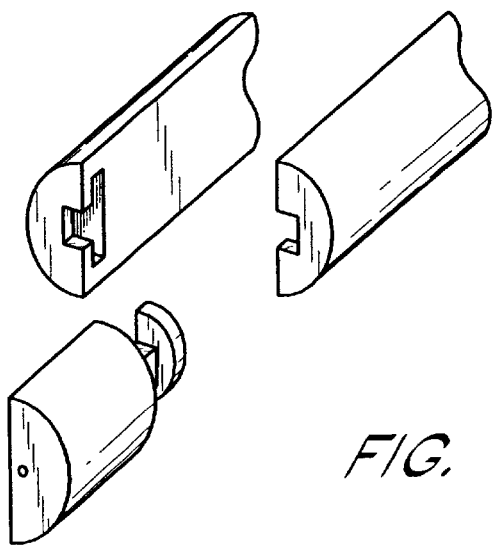

FIGS. 76B–D schematically illustrate various embodiments of the needle drivers 905, 905'. In certain embodiments, the two needle drivers 905, 905' are slidably interlocked with one another along at least a portion of their length. The embodiment illustrated in FIG. 76B has needle drivers 905, 905' which utilize a interlocking clasp configuration. Other embodiments may utilize tongue-in-groove configurations, or axially concentric needle drivers 905, 905'. Persons skilled in the art can select an appropriate interlocking configuration for the needle drivers 905, 905'.

In other embodiments, as schematically illustrated in FIG. 76C, one or both needle drivers 905, 905' can have a raised area 909 on the surface which is in proximity to the other needle driver. Such a raised area 909, 909' can serve to reduce the sliding friction between the two needle drivers 905, 905', thereby facilitating the independent actuation of the needle drivers 905, 905'. While the raised areas 909, 909' illustrated in FIG. 76C extends along the surface of the needle driver in the axial direction, other embodiments can utilize raised bumps on this surface. Persons skilled in the art can select an appropriate raised area 909, 909' for the needle drivers 905, 905'.

In other embodiments, each needle driver 905, 905' is configured to have a needle holder 911, 911' which is separately manufactured from the remaining portion of the needle driver 905, 905'. As schematically illustrated in FIG. 76D, each needle driver distal end 907, 907' includes a recess 913 which is configured to mate and lock with a flange 917, 917' of the needle holder 911, 911'. In this way, the needle holders 911, 911' can be fixedly attached to needles, and the needle drivers 905, 905' can be releasably attached to the needle holders 911, 911'.

Figure 79:
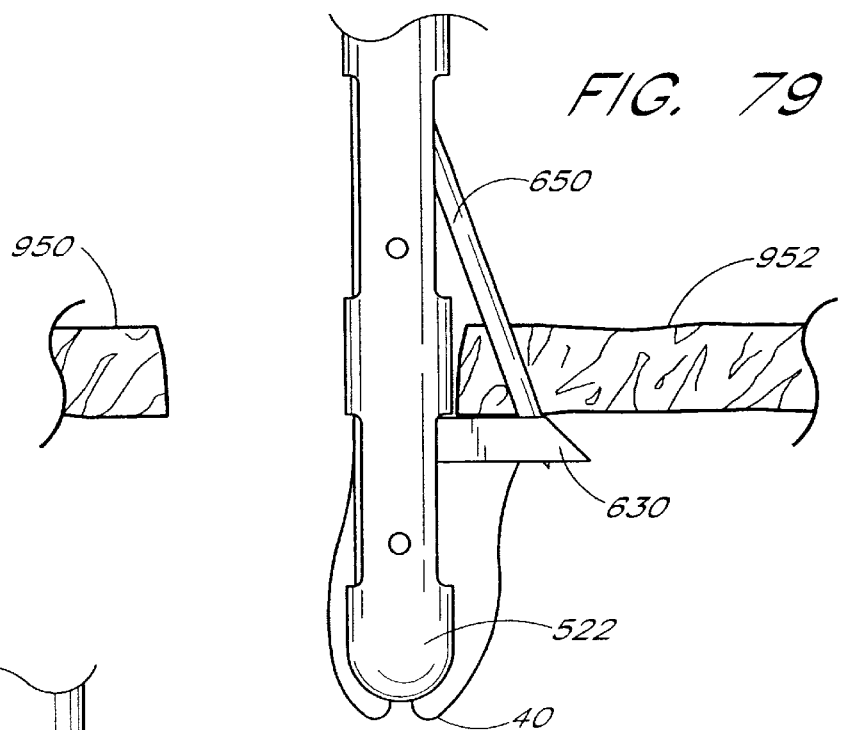
FIG. 79 illustrates the suture device of FIG. 77 with the first needle piercing a first biological tissue portion and engaging the first suture clasp arm.
Figure 80:
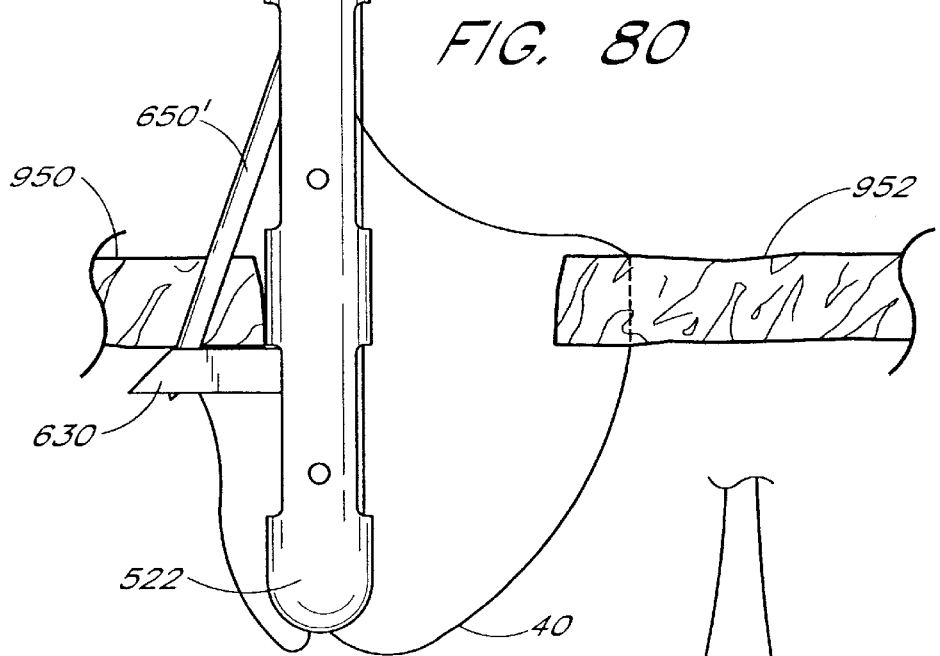
FIG. 80 illustrates the suture device of FIG. 77 with the second needle piercing a second biological tissue portion and engaging the second suture clasp arm.
Figure 81:
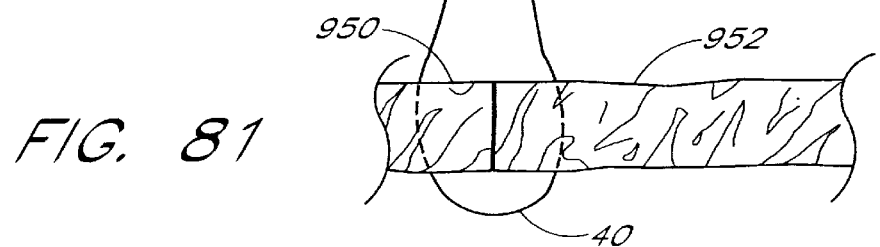
FIG. 81 illustrates the first and second biological tissue portions being drawn together by a suture inserted by the suture device of FIG. 77.

The suturing device of FIGS. 77–78 may be advantageously used to suture two biological tissue portions that are not proximal to one another, as shown in FIGS. 79–81. FIG. 79 illustrates the suture device of FIG. 77 with the first needle 650 penetrating a first surface of a first biological tissue structure or portion 952 and advancing through a second surface of the tissue portion 952. The distal end portion of the needle 650 is circumferentially surrounded by the suture material (end portion of the suture 40) held by the first suture clasp arm 630.

As described herein, the end portion of the suture 40 may be, for example, a loop with an opening or some other molded shape with or without an opening. In one embodiment, the opening formed in the end portion of the suture 40 has a diameter that is approximately the same as the diameter of the distal end portion of the needle 650. In another embodiment, the opening formed in the end portion of the suture 40 has a diameter that is smaller than the diameter of the distal end portion of the needle 650

As described above, the needle 650 captures the end of the suture 40 lying within the suture clasp arm 630. The needle 650 then moves proximally into the suture introducer head 522 and withdraws the end of the suture 40 from the second surface and the first surface of the first tissue portion 952 and into the suture introducer head 522.

FIG. 80 illustrates the suture device of FIG. 77 with the second needle 650' piercing a second biological tissue portion 950 and engaging the second suture clasp arm 630'. The needle 650' captures the end of the suture 40 lying within the suture clasp arm 630' and withdraws the end of the suture 40 into the suture introducer head 522 as the needle 650' moves proximally into the suture introducer head 522.

FIG. 81 illustrates the first and second biological tissue portions 950, 952 being drawn together by a suture inserted by the suture device of FIG. 77. A knot or clip may be slid down the suture 40 to secure the suture site. In another embodiment, the suture ends may be melted near the suture site to secure the suture site.

The four-, six- and eight-arm suture device embodiments described herein may also be configured to move each needle at different times. In some embodiments, the needles may be configured to move two or more at a time.

In the embodiments described above, the needles may be drawn proximally all the way until they are completely removed from the hollow tubular body 514 while the suture introducer head 522 is still proximal to the suture site.

Patch

Figure 82A:
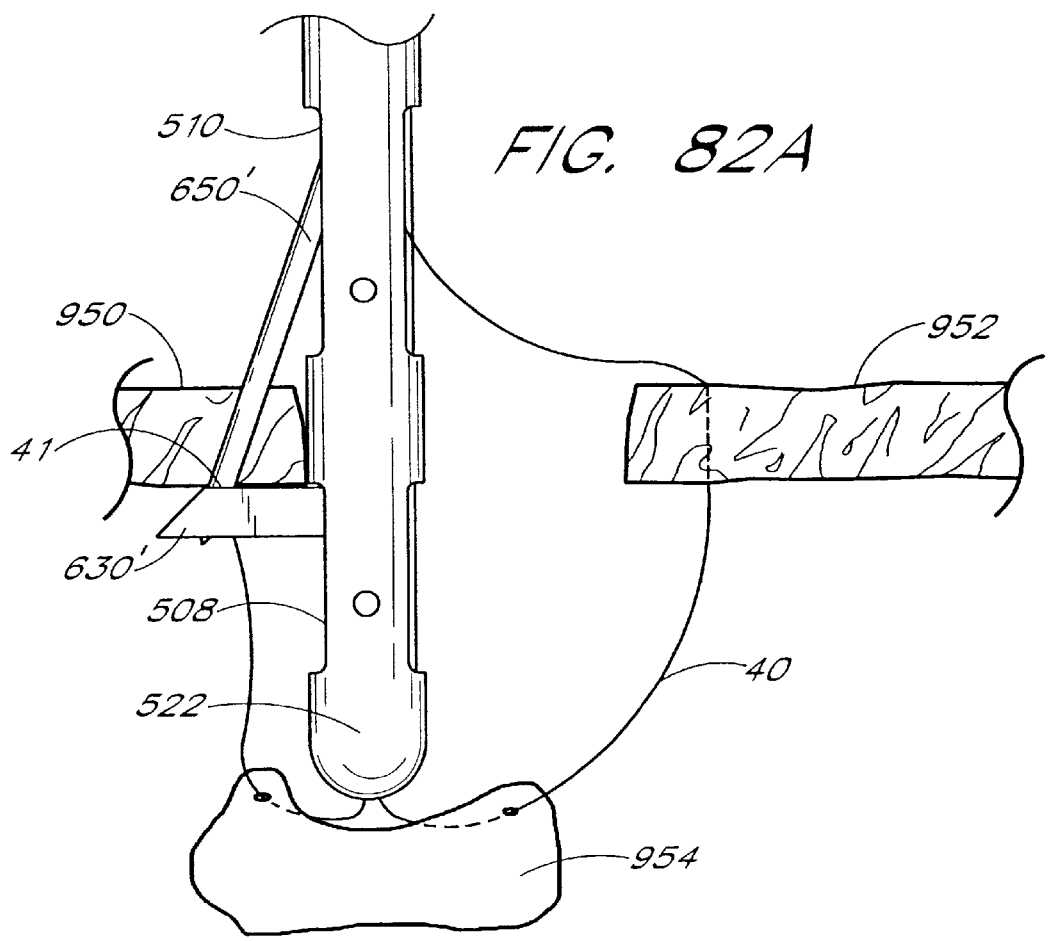
FIG. 82A illustrates the suture device of FIG. 77 with a patch deployed from the elongated body.
Figure 82B:
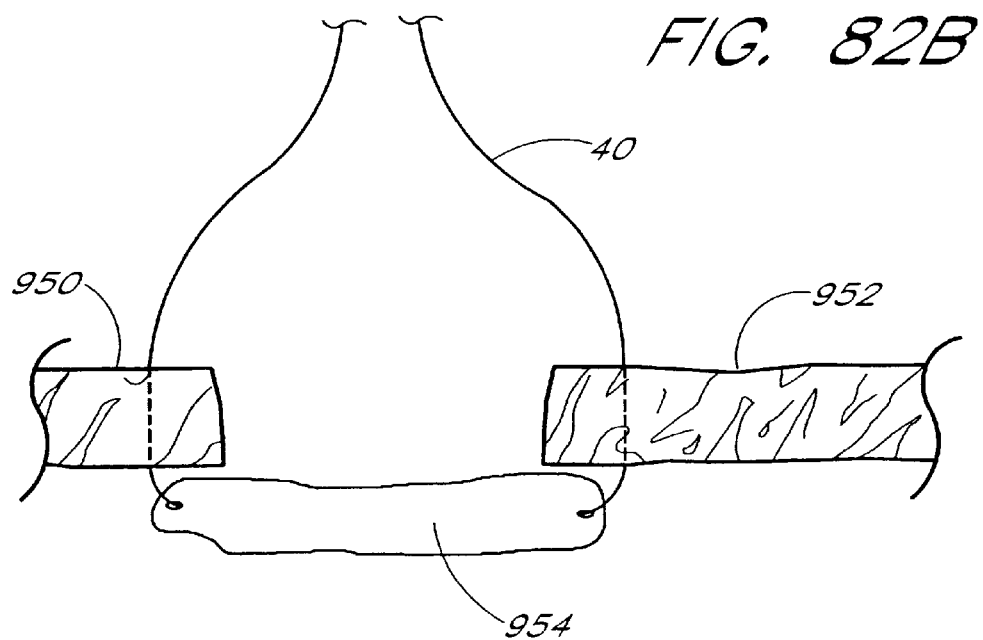
FIG. 82B illustrates the patch of FIG. 82A occluding the suture site.

In the embodiments described herein, the suturing devices may be used with a patch to facilitate closure, for example, of a surgical site, or other opening, including natural openings that are the result of a congenital defect, such as cardiac septal defects. For example, FIG. 82A illustrates the suture device of FIG. 77 with a patch 954. The patch 954 may comprise a flexible synthetic material, such as, for example, Gortex or Dacron, or a harvested piece of natural tissue. In one embodiment, the patch 954 is preloaded within the suture introducer head 522, threaded onto the suture 40, and deployed from the distal end of the suture introducer head 522. FIG. 82B illustrates the patch 954 of FIG. 82A occluding the suture site as the ends of the suture 40 are drawn proximally. When the ends of the suture 40 are drawn and a knot or clip is slid down to secure the suture site, the patch 954 provides an improved suture closure site.

Figure 83A:
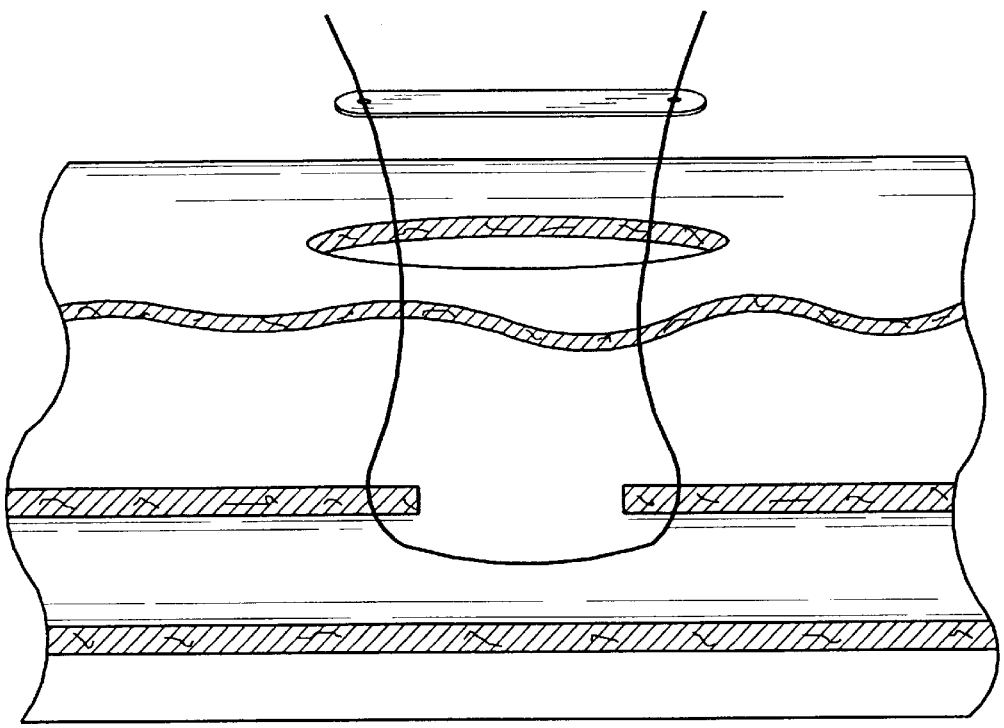
FIG. 83A illustrates a patch connected to the ends of the suture before distally sliding the patch toward the suture site.
Figure 83B:
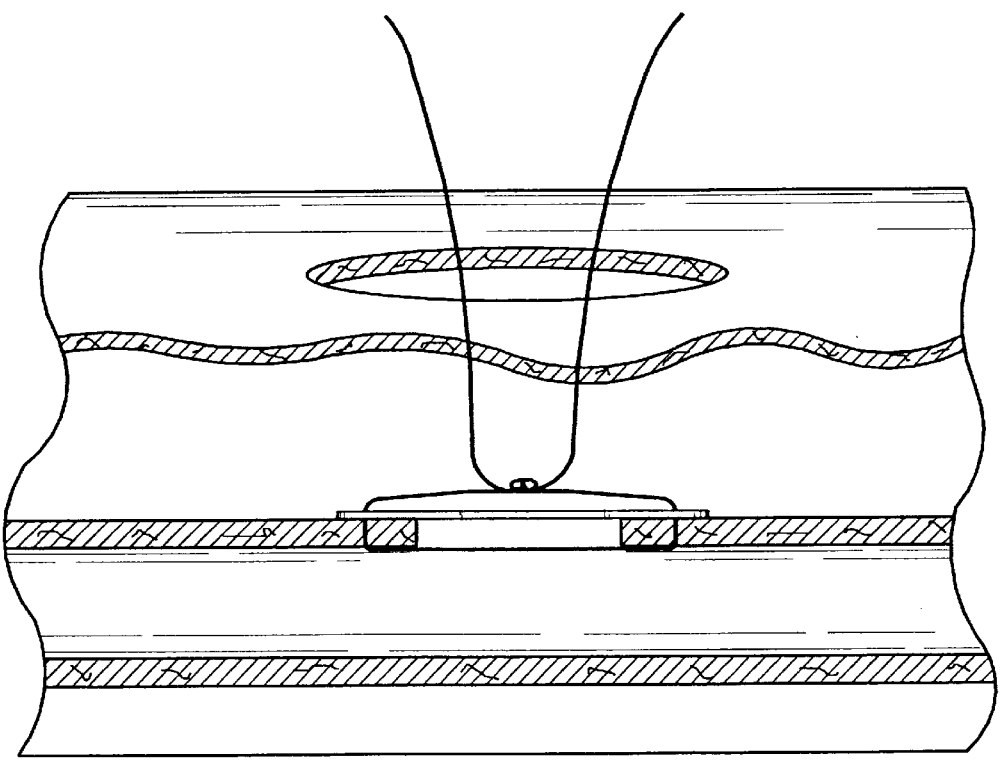
FIG. 83B illustrates the patch of 83A occluding the suture site with a knot securely holding the patch in place.

Alternatively, as illustrated in FIGS. 83A and 83B, a patch 955 can be positioned on the proximal side of tissue structures 950, 952 after the suture 40 has been pulled proximally through tissue structures 950, 952. For example, as described above in conjunction with FIGS. 79–80, the suture 40 extends through both tissue structures 950, 952 and out of the body, as illustrated in FIG. 83A. The physician can thread the suture 40 through corresponding apertures in a patch 955 and then push the patch 955 distally along the suture 40. Once the patch 955 is in proximity to the proximal side of the tissue structures 950, 952, the patch 955 can be secured to the suture site by drawing the suture 40 and sliding distally a knot or clip to securely hold the patch 955 in place, as illustrated in FIG. 83B.

Figure 84:
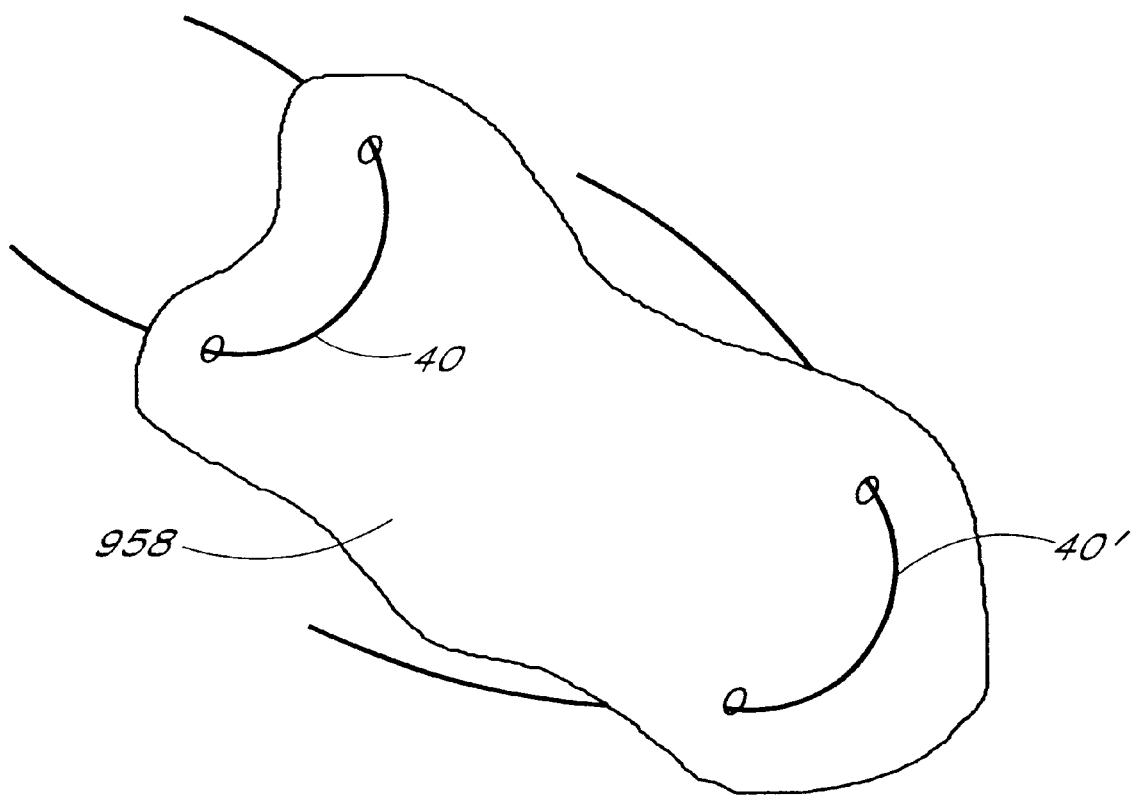
FIG. 84 illustrates a patch with two pairs of sutures through the patch.

The patch may be implemented with the 4, 6, and 8-arm suture device embodiments described above. For example, FIG. 84 illustrates a patch 958 with two pairs of sutures 40, 40' through the patch 958. The patch 958 of FIG. 84 may be used with the four-arm suture device embodiments described above with reference to FIGS. 58–59 or FIGS. 66–69.

Steerable or Guidable Portion

Figure 85:
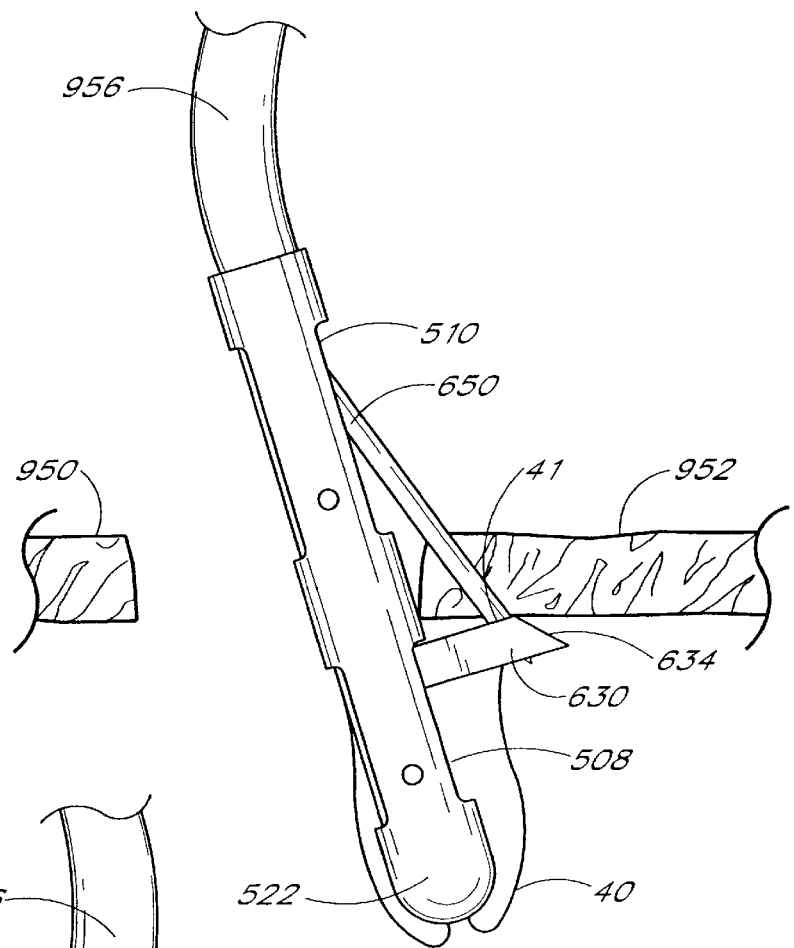
FIG. 85 illustrates a suture device with a steerable portion and a first needle piercing a first biological tissue portion.

In the embodiments described herein, the suturing devices may have a steerable or guidable portion for placing sutures at desired suture sites. The steerable portion is particularly advantageous to place sutures in biological structures that are difficult to suture because the biological structures are either deep within a patient's body, substantially apart from one another and/or at an entry angle that is difficult to access. FIG. 85 illustrates a suture device with a steerable portion 956, such as the hollow elongated body 514 as described above with reference to FIGS. 52A–52B. In FIG. 85, the steerable, hollow elongated body 956 comprises a movable, guide wire within a lumen of the body 956. The guidewire may be remotely manipulated by a physician outside of the patient's body, either by a handle that is similar to the handles described herein or some other control mechanism.

Figure 86:
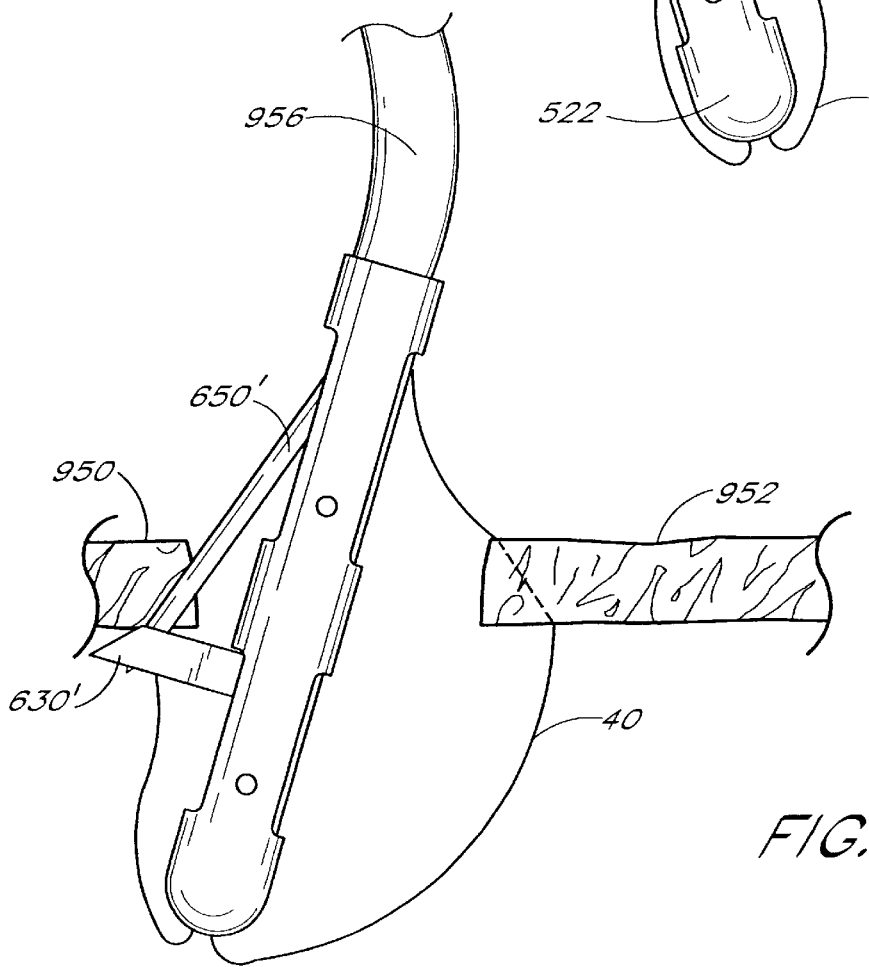
FIG. 86 illustrates the suture device of FIG. 85 with a second needle piercing a second biological tissue portion.

FIG. 85 illustrates the steerable portion bending to the right and a first needle 650 piercing a first biological tissue portion 952. FIG. 86 illustrates the steerable portion bending to the left and a second needle 650 piercing a second biological tissue portion 950. In FIGS. 85–86, the guide wire is configured to move the suture introducer head 522 in 2-dimensions. In another embodiment, the guide wire is configured to move the suture introducer head 522 in 3 dimensions.

Methods of Forming Suture Ends

Figure 87:
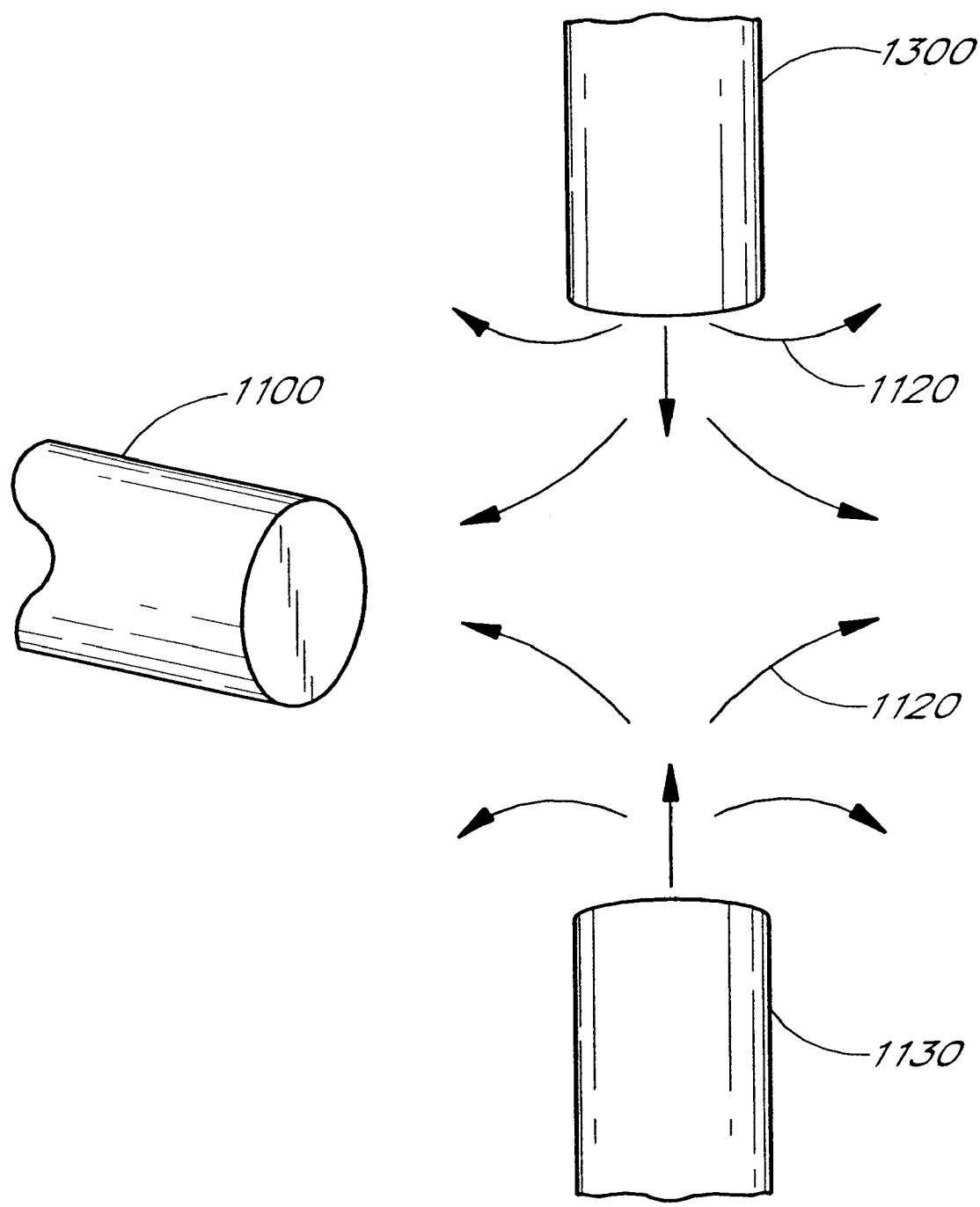

FIGS. 87–102 illustrate methods of forming suture ends of a suture which may be used with the suture devices described herein. In FIG. 87, one embodiment of the suture is a strand 1100 of deformable material that is preferably monofilament, such as Deklene (from Genzyme), Prolene (from Johnson & Johnson), or Nylon (from Johnson & Johnson). In one embodiment, the strand 1100 is advantageously approximately 0.010" thick and has a length that makes it suitable for use in a suture procedure. The strand 1100 is brought near a stream of hot gas 1120, which may be, in one embodiment, 500° F. air ejected from, for example, nozzles 1130.

Figure 88:
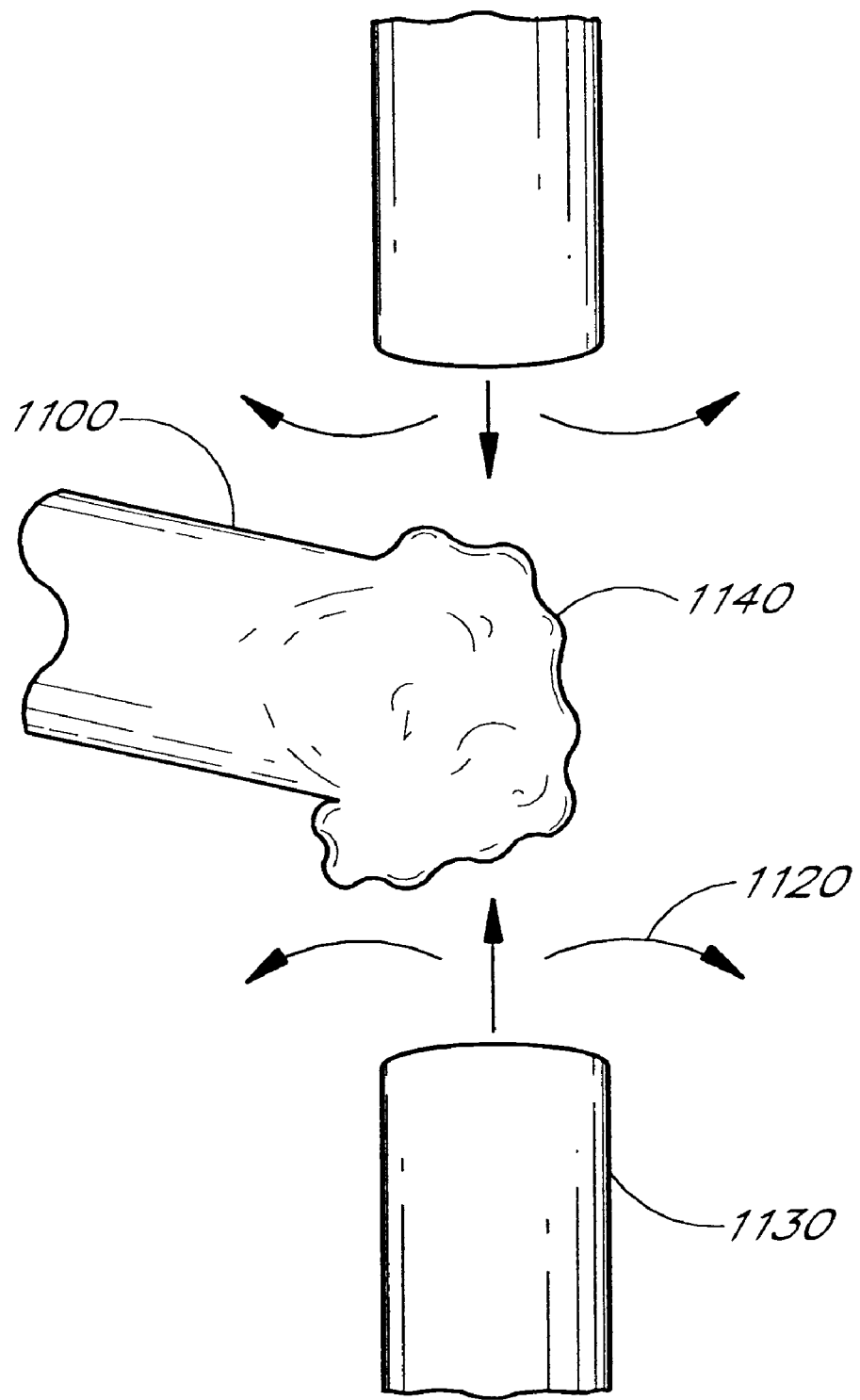

In FIG. 88, as the distal end of the strand 1100 is impacted by the gas 1120, the distal end melts or is otherwise plastically or thermally deformed to form a locally deformed region 1140 (such as a globule) that is broader than the rest of the strand 1100 in at least one dimension (i.e., at least one dimension of the strand 1100 has been increased). By pushing the distal end of the strand 1100 into the stream of gas 1120 (e.g., by about 2 mm), the strand 1100 substantially melts back on itself. Once the deformed region 1140 is formed, the strand 1100 may be removed from the presence of the hot gas 1120 and allowed to cool. As an alternative to using the hot gas 1120, the strand 1100 may be brought into contact with a hot metal or other solid material, such as a soldering iron (not shown), whereupon the strand 1100 is deformed similar to the strand of FIG. 88.

Figure 89:
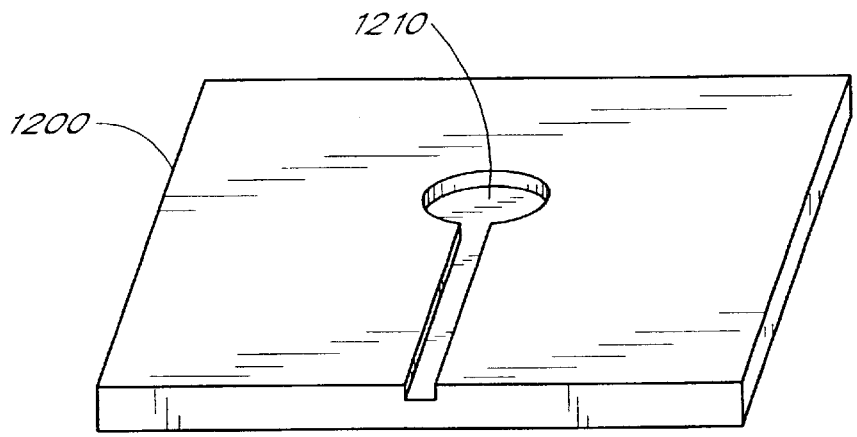
Figure 90:
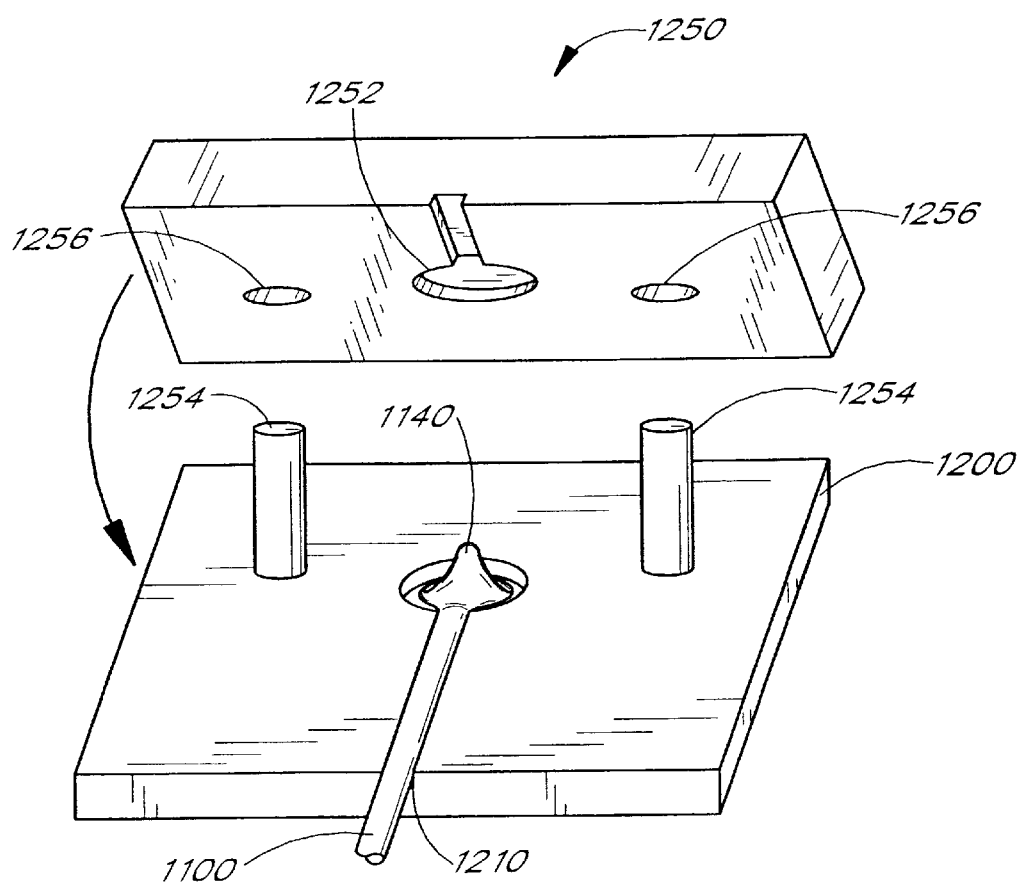
Figure 91:
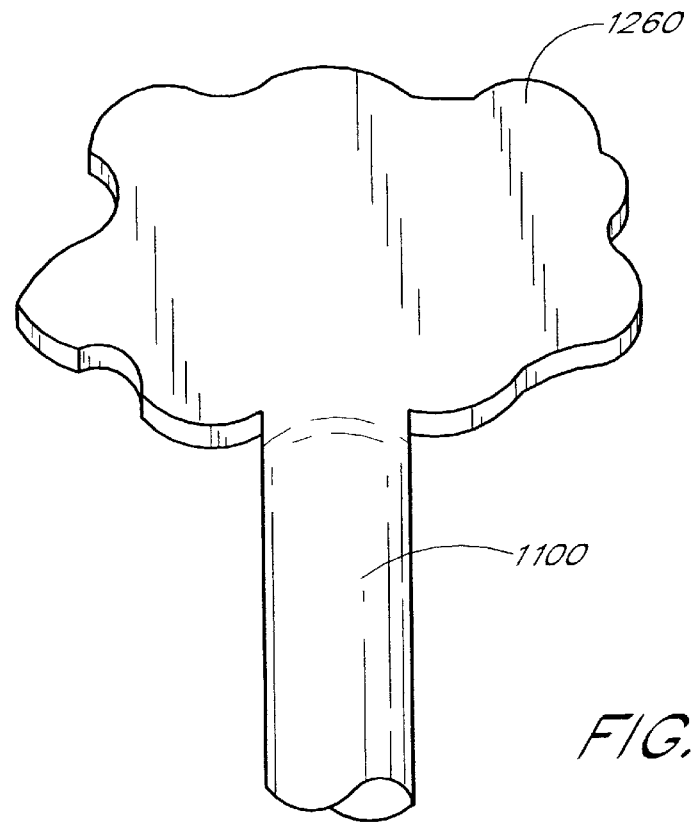
Figure 92:
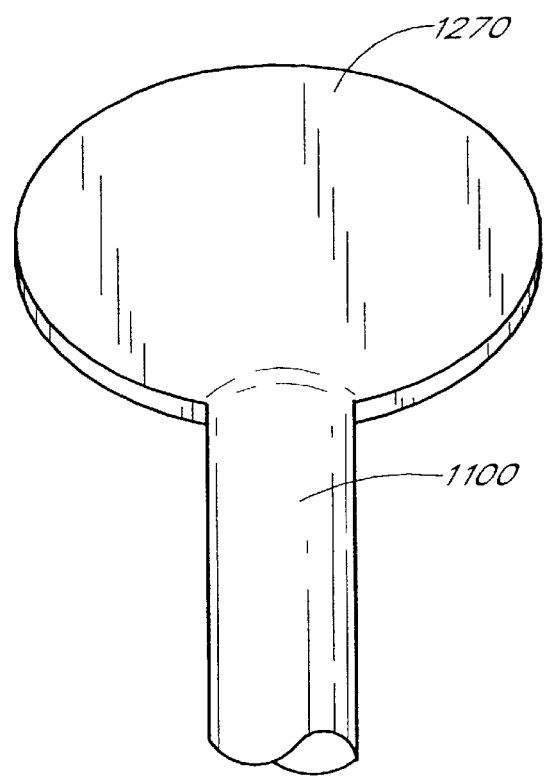

Next, the deformed region 1140 may be flattened, and a hole or eyelet is formed therein, as illustrated in FIGS. 89–94. Alternatively, the deformed region 1140 may be formed into a cup-like member as discussed below in connection with FIGS. 95–98. FIG. 89 illustrates a die 1200 used for flattening the deformed region 1140. The die 1200 has a relief or recessed portion 1210 for accepting the strand 1100 and the deformed region 1140, as illustrated in FIG. 90. A block 1250, which preferably also has a recessed portion 1252 that mates with the recessed portion 1210, may then be placed over the deformed region 1140. The aligning of the respective recessed portions 1210 and 1252 is facilitated by a plurality of posts 1254 in the die 1200 which mate with respective holes 1256 in the block 1250. Thus, the deformed region 1140 is squeezed between the die 1200 and the block 1250, resulting in a flattened distal portion 1260 (FIG. 91) that preferably has a thickness that matches the rest of the strand 1100. The edges of flattened distal portion 1260 may then be trimmed to form a circular, smooth disc portion 1270 (FIG. 92) to reduce the risk of such edges snagging on vessel walls during suturing procedures.

Figure 93:
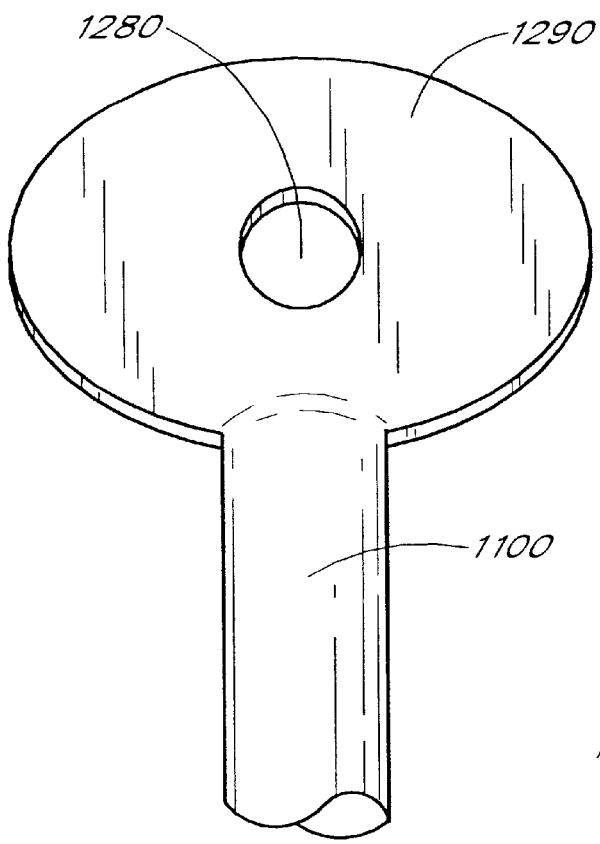

As illustrated in FIG. 93, a hole or eyelet 1280 may be formed out of the distal end of the strand 1100. A punch (not shown) such as a hypotube may be used to poke through the distal portion 1270, thereby leaving the eyelet 1280 in an eyelet portion 1290 at the distal end of the strand 1100. The eyelet 1280 is formed such that a surgical hook or needle as described above may pass through the eyelet in a suturing procedure. The eyelet portion 1290 acts as a connector to the hook or needle, allowing the strand 1100 to be picked up by the hook or needle. The method of forming the eyelet 1280 described herein, including the forming of the deformed region 1140, advantageously results in no significant reduction in the mechanical strength of the strand 1100, with the material throughout the strand 1100 (including the material in the eyelet portion 1290) having substantially uniform mechanical strength.

Figure 94:
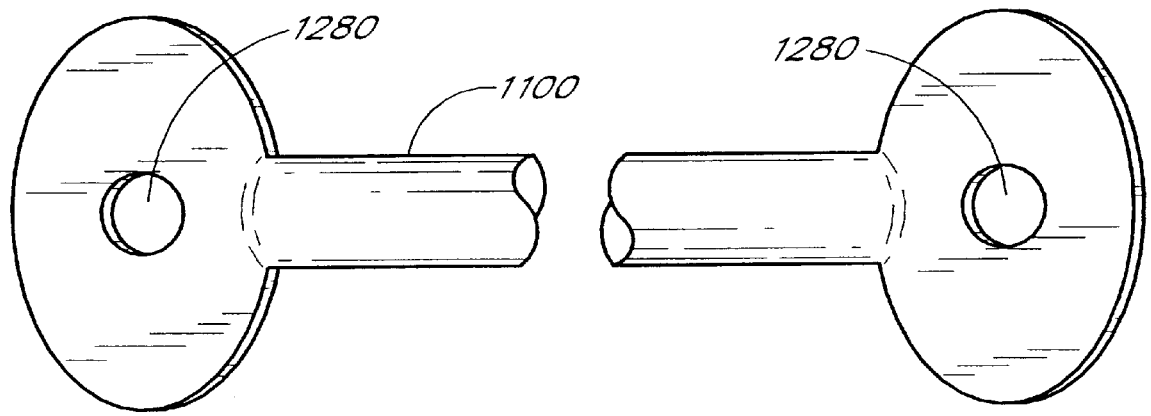

Advantageously, the suture embodiment shown in FIG. 93 has no knots or ties formed therein which might increase the profile of the suture strand 1100 or make it easier for the suture to snag during use. This process may be advantageously repeated at the proximal end of the strand 1100, resulting in eyelets 1280 at both ends of the strand 1100, as illustrated in FIG. 94. The eyelet portion 1290 at one or more of the ends of the strand 1100 may be bent (not shown) at an angle with respect to the rest of the strand to facilitate the guiding of a surgical needle through the eyelet 1280.

Figure 95:
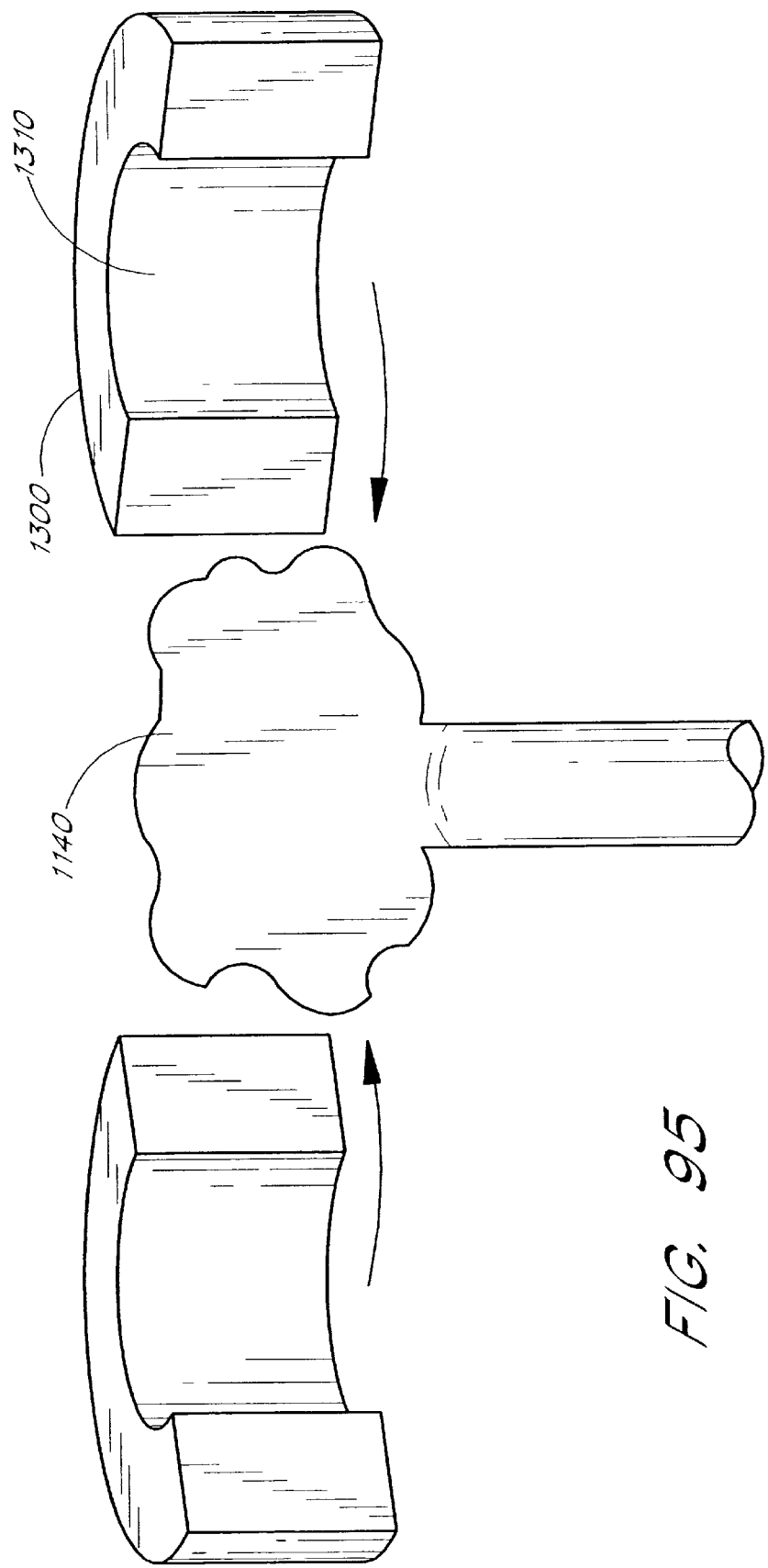
Figure 96:
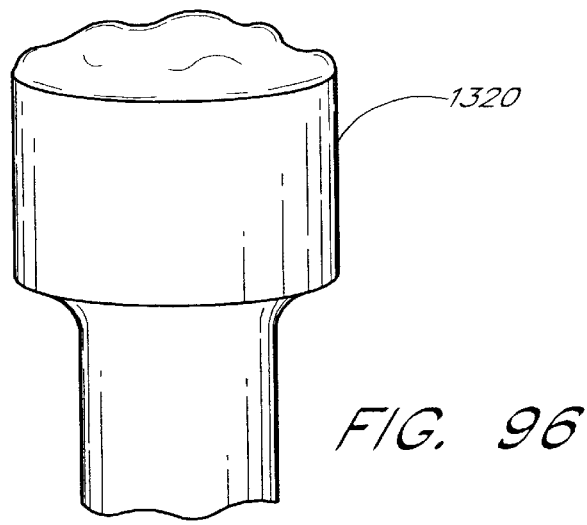

FIGS. 95–102 illustrate another embodiment of forming suture end portions. In FIGS. 95–102, the deformed region 1140 (FIG. 87) may be formed into a cup-like member having a recess therein for receiving a needle. In FIG. 95, the deformed region 1140 is compressed on its sides by blocks 1300 which have recessed portions 1310. The blocks 1300 squeeze the deformed region 1140 to form a substantially cylindrically shaped member 1320, as shown in FIG. 96.

Figure 97:
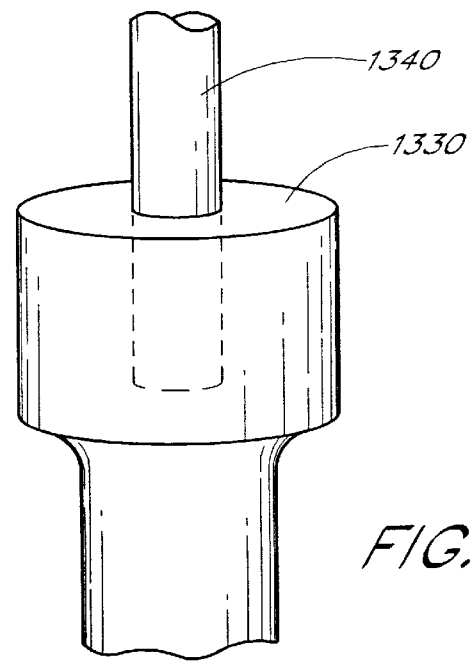
Figure 98:
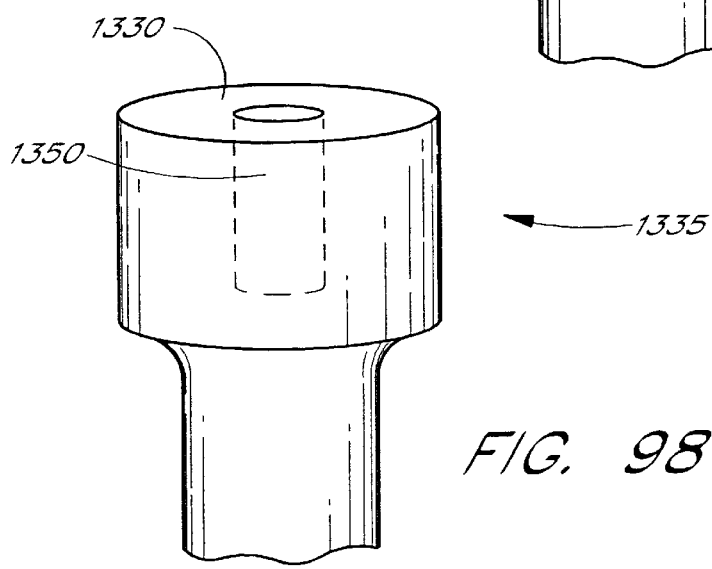
Figure 99:
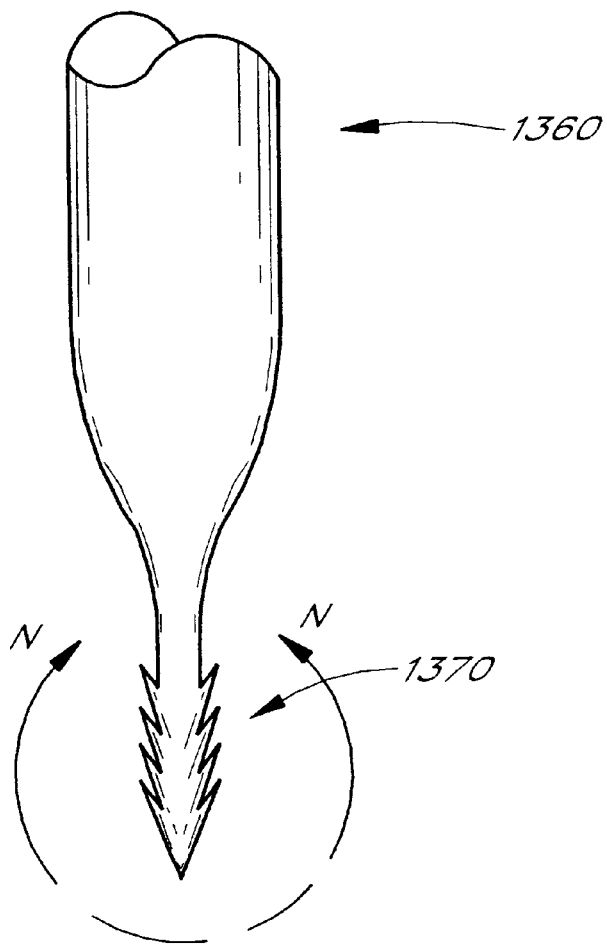
Figure 100:
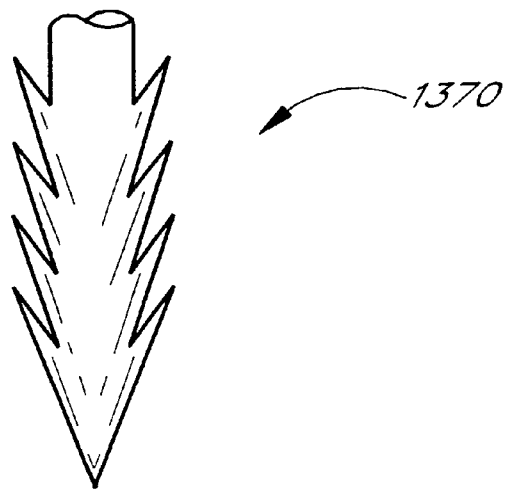
Figure 101:
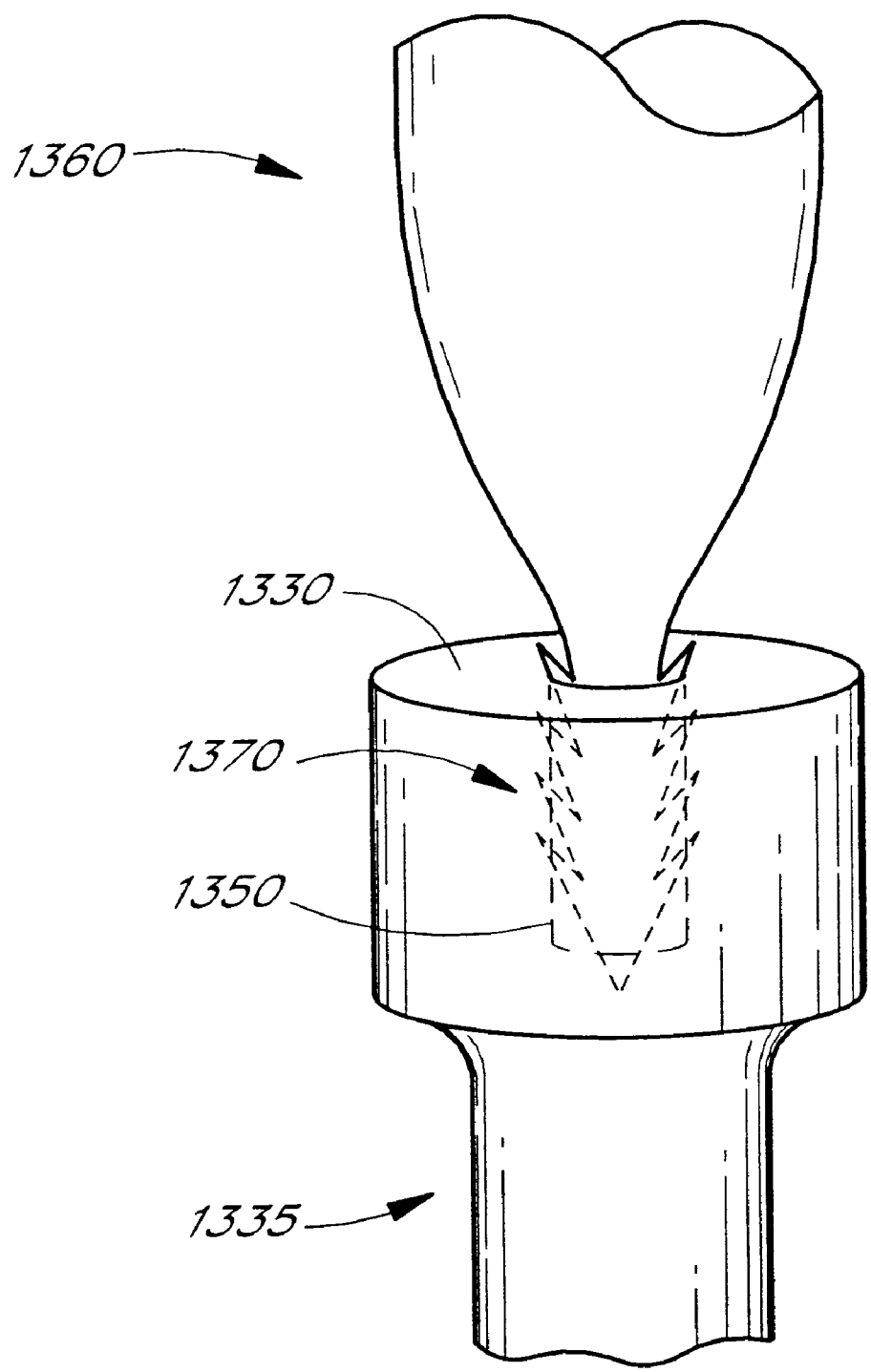

One end of the member 1320 may be cut off to form a flat top 1330, which may then be punched or bored out with a hypotube 1340 to form a suture that comprises a cup-like member 1335 having a recess 1350, as illustrated in FIGS. 97–98. In one embodiment, the cup-like member 1335 has a height of 0.032" and an outside diameter of 0.032±0.010." The recess 1350 is advantageously sized to accept a distal end portion 1370 of a needle 1360 shown in FIGS. 99–101. The surgical needle 1360 has a main shaft portion connected to the distal end portion 1370. Knurling or barbs are provided on the distal end portion 1370. In this way, when the surgical needle is inserted into the member 1320 (see FIG. 101), the surgical needle digs into the sides of the cup shaped recess and resists the tendency to be withdrawn from the member 1320. The outside diameter of the member 1320 and the outside diameter of the shaft portion of the surgical needle 1360 (i.e. the portion proximal to the barbs) may advantageously have substantially the same diameter, so that when the needle 1360/member 1320 combination (see FIG. 101) is withdrawn from the patient, the possibility that the needle/member combination will snag on tissue is reduced.

Figure 102:
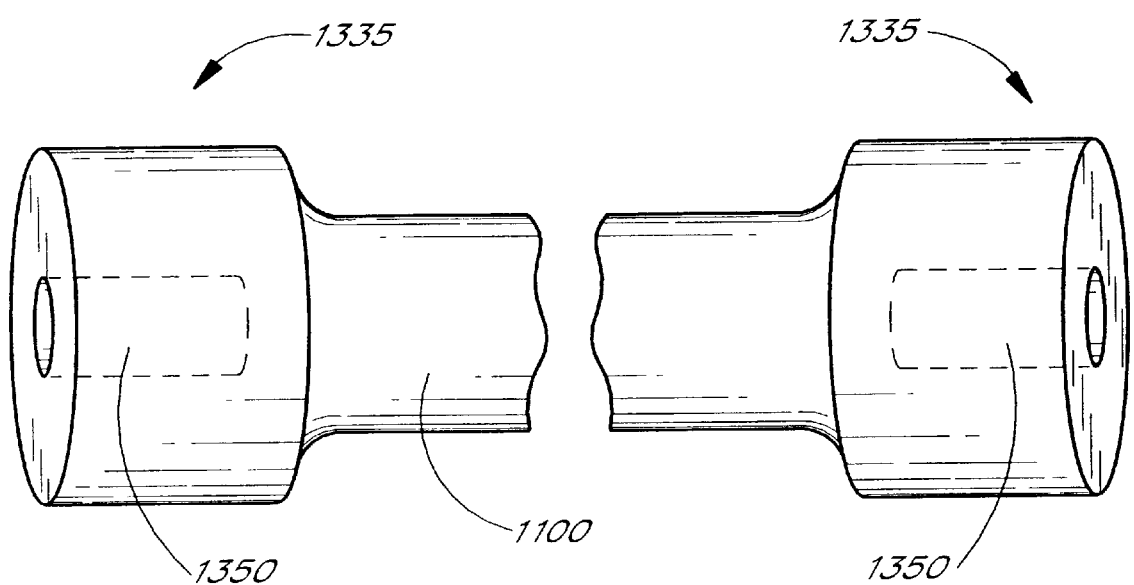

The method of forming the cup-like member 1335 described herein, including the forming of the recess 1350, advantageously results in no significant reduction in the mechanical strength of the strand 1100, with the material throughout the strand 1100 (including the material in the member 1335) having substantially uniform mechanical strength. No knots or ties are necessary. Both ends of the strand 1100 may be formed with cup-like members 1335, as illustrated in FIG. 102. The cup-like member 1335 at one or more of the ends of the strand 1100 may be bent (not shown) at an angle with respect to the rest of the strand to facilitate the guiding of a surgical needle into the recess 1350.

Suspension of Body Tissue

Figure 103A:
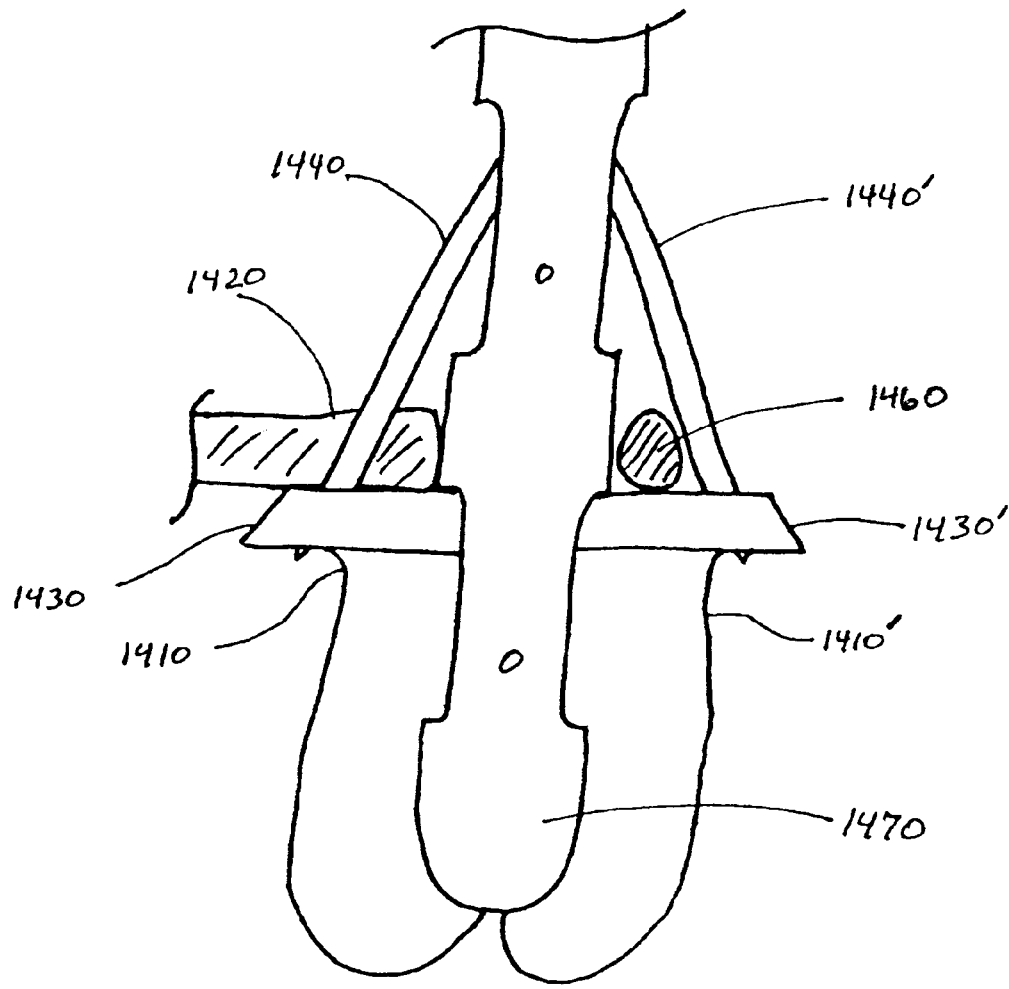
FIG. 103A shows a side view of the distal portion of the device with one end portion of the suture captured by a needle extended through the tissue structure and a second end portion of the suture looped around a second tissue structure.

Independent actuation of the arms can be advantageously used to attach or suspend a biological structure, such as a tissue structure or an implantable material. Examples of such procedures include, but are not limited to, attaching a first tissue structure to a second tissue structure, or attaching an implantable material, which can be a synthetic material or natural tissue, to a tissue structure. The tissue structures used in this method can include bones, ligaments, muscle tissue, and body organs. In operation, a suture portion 1410 is pulled through a tissue structure 1420 for use as an anchor as illustrated in FIG. 103A. One of the arms 1430 is deployed on one side of the tissue structure 1420 and the corresponding needle 1440 is extended through the tissue structure 1420 to capture the suture portion 1410.

Figure 103B:
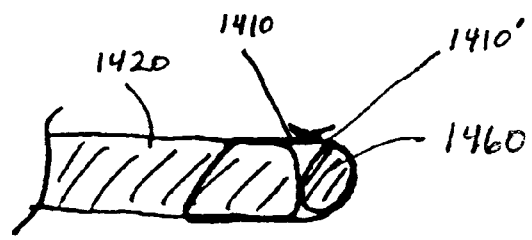
FIG. 103B shows a side view corresponding to FIG. 103A once the end portions of the suture have been tied together and tightened.

A second suture portion 1410' can then be looped around a biological structure 1460. As illustrated in FIG. 103A, the second arm 1430' is deployed on one side of the biological structure 1460, and the corresponding needle 1440' is extended on the other side of the biological structure 1460, such that the arm 1430', the needle 1440', and the elongated body 1470 encircle the biological structure 1460. The second suture portion 1410' is retrieved from the arm 1430' by the needle 1440' to form a suture loop around the biological structure 1460. In certain embodiments, the suture portions 1410, 1410' are pulled and tied together forming a knot, bringing the tissue structure 1420 and biological structure 1460 together as illustrated in FIG. 103B. In certain embodiments, rather than piercing the tissue structure 1420, the first arm 1430 and needle 1440 can be used to loop a suture portion 1410 around the tissue structure 1420.

It will be appreciated that the arms 1430 and 1430' can be deployed in any preferred sequence, and that needles 1440 and 1440' can retrieve the suture portions 1410, 1410' in any preferred sequence. It will also be appreciated that the arms 1430 and 1430' can be deployed either simultaneously or non-simultaneously, and that the needles 1440 and 1440' can be deployed either simultaneously or non-simultaneously.

The embodiment of FIGS. 103A and 103B may also be used for suspending an organ from an adjacent tissue structure, such as, for example, in the treatment of bladder or uterine prolapse. Organ suspension may be accomplished with this embodiment by positioning an arm and extending a needle into an organ to retrieve a first end of a suture, moving the suturing device to traverse a space, and then positioning a second arm and extending a second needle around a ligament to loop the second end of the suture around the ligament. By tightening the suture, the organ is suspended by using the ligament. In other similar embodiments, other biological structures, such as harvested pieces of natural tissue, or synthetic material structures can be suspended or connected to existing body tissue.

While embodiments and applications of this invention have been shown and described, it will be apparent to those skilled in the art that various modifications are possible without departing from the scope of the invention. It is, therefore, to be understood that within the scope of the appended claims, this invention may be practiced otherwise than as specifically described.

What is claimed is:

1. A suturing apparatus, comprising:
   an elongate body;
   first and second arms, each of said arms having a suture mounting portion which mounts an end portion of a suture, said arms being mounted on the elongate body such that said suture mounting portions are movable away from said body to a first position and towards said body to a second position;
   first and second needles, each of said needles having a distal end, and being mounted such that the distal end of the needle is movable (i) in a proximal to distal direction from a position adjacent said elongate body to a position spaced outwardly from said body and (ii) towards the suture mounting portion of one of the arms when in said first position, wherein the respective distal ends of the first and second needles engage respective end portions of said suture; and
   an actuator which drives the needles in said proximal to distal direction such that the engagement of the respective end portions of the suture is non-simultaneous.

2. The apparatus of claim 1, wherein said actuator comprises a pair of independently movable needle drivers coupled to independently advance said needles, respectively, in said proximal to distal direction.

3. The apparatus of claim 2, wherein said needle drivers are slidably coupled to one another.

4. A suturing apparatus, comprising:
   an elongate body;
   first and second arms, each of said arms having a suture mounting portion which mounts an end portion of a suture, said arms being operably connected to the elongate body such that said suture mounting portions are movable away from said body to a first position and towards said body to a second position;
   first and second needles, each of said needles having a distal end, and being mounted such that the distal end of the needle is movable (i) in a proximal to distal direction from a position adjacent said elongate body to a position spaced outwardly from said body and (ii) towards the suture mounting portion of one of the arms when in said first position; and
   an actuator comprising first and second needle drivers connected to drive the first and second needles, respectively, in said proximal to distal direction, said needle drivers being independently actuable such that the first needle is movable independent of the second needle.

5. A device for suturing biological tissue, comprising:
   an elongated body;
   an arm operably connected to the elongated body to move to an extended position away from the elongated body and to a retracted position toward the elongated body, the arm having a mounting portion which mounts a portion of a suture, and having a tissue contacting surface which faces proximally when the arm is in the extended position, said tissue contacting surface having a projecting portion configured to provide intimate contact with said tissue and to thereby inhibit lateral movement of said arm when said tissue contacting surface is pressed against tissue; and
   a needle having a distal end which is movable distally from a position adjacent the elongated body towards said mounting portion of said arm when the arm is in the extended position, such that said distal end engages said portion of the suture mounted by said mounting portion.

6. The device of claim 5, wherein the projecting portion is defined by a curvature in the tissue contacting surface of the arm.

7. The device of claim 5, wherein the projecting portion is at an end of the arm.

8. The device of claim 5, wherein the projecting portion is small compared to the area of the tissue contacting surface of the arm.

9. The device of claim 5, wherein the projecting portion is in proximity to the mounting portion of the arm.

10. The device of claim 5, wherein the distal end of the needle follows a path which diverges from a central axis of the elongated body.

11. The device of claim 5, further comprising:
a second arm operably connected to the elongated body to move to an extended position away from the elongated body and to a retracted position toward the elongated body, the second arm having a mounting portion which mounts a second portion of said suture, and having a tissue contacting surface which faces proximally when the second arm is in the extended position; and
a second needle having a distal end which is movable from a position adjacent the elongated body towards the mounting portion of the second arm when the second arm is in the extended position, such that the distal end engages the second portion of the suture mounted by the mounting portion of the second arm.

12. The device of claim 11, wherein the second tissue contacting surface has a projecting portion configured to provide intimate contact with said tissue and to thereby inhibit lateral movement of said second arm.

13. The device of claim 12, wherein the projecting portion of the second tissue contacting surface is at an end of the second arm.

14. The device of claim 12, wherein the projecting portion of the second tissue contacting surface is small compared to the area of the second tissue contacting surface.

15. The device of claim 12, wherein the projecting portion of the second tissue contacting surface is in proximity to the mounting portion of the second arm.

16. The device of claim 11, wherein the first needle and second needle are configured to move simultaneously.

17. The device of claim 11, wherein the first needle and second needle are configured to move at different times.

18. The device of claim 11, wherein the first needle engages the first portion of the suture before the second needle engages the second portion of the suture.

19. The device of claim 11, wherein the first needle engages the first portion of the suture before the second needle moves towards the mounting portion of the second arm.

20. The device of claim 11, wherein the first arm and second arm are configured to move at different times.

21. The device of claim 5, further comprising:
second, third, and fourth arms operably connected to the elongated body to move to an extended position away from the elongated body and to a retracted position toward the elongated body, the second arm having a mounting portion which mounts a second portion of said suture, the third and fourth arms each having a mounting portion which respectively mounts a first and second portion of a second suture, and the second, third, and fourth arms each having a tissue contacting surface which faces proximally when the respective arm is in the extended position; and
second, third and fourth needles each having a distal end which is movable from a position adjacent the elongated body towards the mounting portions of the second, third, and fourth arms, respectively, when the respective arm is in the extended position, such that the distal end of each needle engages the portion of the sutures mounted by the mounting portion of the respective arm and to thereby inhibit lateral movement of the respective arm when the tissue contacting surface is pressed against the tissue.

22. The device of claim 21, wherein the tissue contacting surface of each arm has a projecting portion configured to provide intimate contact with said tissue and to thereby inhibit lateral movement of the respective arm.

23. A suturing apparatus comprising:
an elongated body;
an arm operably connected to the elongated body and movable relative to the elongated body to an extended position away from the elongated body and to a retracted position towards the elongated body, the arm having a mounting portion which mounts a portion of a suture;
a needle movable relative to the elongated body, the needle having a distal end movable from a position adjacent the elongated body towards the mounting portion of the arm when the arm is in the extended position, such that the distal end engages the portion of the suture mounted by the mounting portion of the arm; and
a patch which is tethered by the suture.

24. The suturing apparatus of claim 23, wherein the patch is stored within the elongated body for deployment from a distal end portion of the elongated body.

25. The suturing apparatus of claim 23, wherein the patch comprises a flexible piece of synthetic material or natural tissue.

26. A method of suturing comprising:
providing an elongate body having first and second arms which mount first and second portions, respectively, of a suture;
engaging the first and second portions of the suture with first and second needles, respectively, by driving the first and second needles towards the first and second arms, respectively, in a proximal to distal direction, the engaging comprising engaging the first portion of suture with the first needle prior to engaging the second portion of the suture with the second needle.

27. The method of claim 26, further comprising moving the first arm away from the elongate body, and moving the second arm away from the elogate body.

28. The method of claim 27, wherein the first arm is moved away from the elongate body before the second arm is moved away from the elongate body.

29. The method of claim 26, wherein the first needle drives towards the first arm before the second needle engages the second portion of the suture.

30. The method of claim 26, wherein the first needle drives towards the first arm before the second needle drives towards the second arm.

31. The method of claim 26, wherein engaging the first portion of the suture with the first needle comprises penetrating a tissue structure with the first needle.

32. The method of claim 31, wherein engaging the second portion of the suture with the second needle comprises penetrating a second tissue structure with the second needle.

33. The method of claim 31, wherein engaging the second portion of the suture with the second needle comprises extending the second needle along a side of a second tissue structure, such that the second arm, second needle, and elongate body encircle the second tissue structure.

34. The method of claim 31, wherein engaging the second portion of the suture with the second needle comprises extending the second needle along a side of an implantable material, such that the second arm, second needle, and elongate body encircle the implantable material.

35. The method of claim 34, wherein the implantable material comprises synthetic material.

36. The method of claim 34, wherein the implantable material comprises natural tissue.

37. The method of claim 26, wherein engaging the second portion of the suture with the second needle comprises penetrating a tissue structure with the second needle.

38. The method of claim 37, wherein engaging the first portion of the suture with the first needle comprises extending the first needle along a side of a second tissue structure, such that the first arm, first needle, and elongate body encircle the second tissue structure.

39. The method of claim 37, wherein engaging the first portion of the suture with the first needle comprises extending the first needle along a side of an implantable material, such that the first arm, first needle, and elongate body encircle the implantable material.

40. The method of claim 39, wherein the implantable material comprises synthetic material.

41. The method of claim 39, wherein the implantable material comprises natural tissue.

42. The method of claim 26, wherein engaging the first portion of the suture with the first needle comprises extending the first needle along a side of a first tissue structure, such that the first arm, first needle, and elongate body encircle the first tissue structure and engaging the second portion of the suture with the second needle comprises extending the second needle along a side of a second tissue structure, such that the second arm, second needle, and elongate body encircle the second tissue structure.

43. The method of claim 26, wherein engaging the first portion of the suture with the first needle comprises extending the first needle along a side of a first tissue structure, such that the first arm, first needle, and elongate body encircle the first tissue structure and engaging the second portion of the suture with the second needle comprises extending the second needle along a side of an implantable material, such that the second arm, second needle, and elongate body encircle the implantable material.

44. A method of occluding a septal defect, the method comprising:
    inserting a distal end portion of an elongated body into an opening in a living being;
    positioning the distal end portion in a first location adjacent a first tissue portion in proximity to the septal defect;
    deploying a first needle within the elongated body so as to draw a first end of a suture through the first tissue portion;
    moving the distal end portion to a second location displaced from the first location and positioning the distal end portion adjacent a second tissue portion in proximity to the septal defect;
    deploying a second needle within the elongated body so as to draw a second end of the suture through the second tissue portion; and
    using the suture to secure a patch across the septal defect.

45. The method of claim 44, wherein securing the patch comprises pulling the ends of the suture to draw the patch against the first and second tissue portions.

46. The method of claim 44, wherein the septal defect is a congenital heart defect.

47. The method of claim 44, wherein using the suture to secure the patch across the septal defect comprises:
    deploying the patch from the distal end of the elongated body, the patch being preloaded and threaded onto the suture; and
    pulling the suture and sliding a knot or clip toward the septal defect to securely hold the patch in place.

48. The method of claim 44, wherein using the suture to secure the patch across the septal defect comprises:
    passing the first and second ends of the suture through the patch;
    pushing the patch distally along the suture toward the septal defect; and
    pulling the suture and sliding a knot or clip toward the septal defect to securely hold the patch in place.

49. A method of suturing, comprising:
    inserting a distal end portion of an elongated body into an opening in a living being;
    positioning the distal end portion in a first location adjacent a first tissue portion;
    deploying a first needle within the elongated body so as to draw a first end of a suture through the first tissue portion;
    moving the distal end portion to a second location displaced from the first location and positioning the distal end portion adjacent a second tissue portion;
    deploying a second needle within the elongated body so as to draw a second end of the suture through the second tissue portion; and
    using the suture to secure a patch to the first and second tissue portions.

50. The method of claim 49, wherein using the suture to secure a patch to the first and second tissue portions comprises pulling the suture through the patch prior to inserting the distal end portion of the elongated body into the opening in the living being.

51. The method of claim 49, wherein the method further comprises:
    pushing the patch distally along the suture to be in proximity to the first and second tissue portions; and
    occluding a space between the first and second tissue portions by sliding a knot or clip toward the patch to securely hold the patch in place.

52. A method of suspending a biological structure, comprising:
    positioning a distal portion of an elongated body adjacent the biological structure to be suspended;
    positioning a first arm operably connected to the elongated body on one side of the biological structure, the first arm releasably holding a first end portion of a suture;
    extending a first needle toward the first end portion of the suture in the first arm, the first needle moving on an opposite side of the biological structure such that when the first needle engages the first end portion of the suture, the biological structure is encircled by the first arm, the first needle, and the elongated body;
    positioning a second arm operably connected to the elongated body adjacent a tissue portion, the second arm releasably holding a second end portion of the suture;
    extending a second needle through the tissue portion to engage the second end portion of the suture in the second arm;
    drawing the first end portion and second end portion of the suture toward the elongated body; and
    tying the first end portion and second end portion of the suture to suspend the biological structure to the tissue portion.

53. A method of placing a suture around the exterior of a biological structure, the method comprising:
    advancing an elongate suturing device having an elongate body distally towards the biological structure;

positioning a first suture portion mounted on the elongate device so that the first suture portion is proximate the biological structure;

advancing a suture retrieving member of the elongate device past the biological structure without piercing the biological structure, said advancing comprising moving the suture retrieving member with the biological structure between the suture retrieving member and the elongate body, said advancing further comprising coupling the suture retrieving member to the first suture portion;

drawing the first suture portion away from the biological structure by moving the suture retrieving member in a direction away from the biological structure; and drawing a second suture portion away from the biological structure by moving at least a portion of the elongate device from the biological structure, whereby the suture extends in a loop around the biological structure.

54. The method of claim 53, wherein advancing the suture retrieving member past the biological structure comprises moving the suture retrieving member in a distal to proximal direction, and drawing the first suture portion away from the biological structure comprises moving the suture retrieving member in a proximal direction.

55. The method of claim 53, wherein advancing the suturing device distally towards the biological structure comprises advancing the suturing device into a body cavity of a living being.

56. The method of claim 55, wherein the biological structure comprises a synthetic material.

57. The method of claim 53, wherein the first and second suture portions are mounted on respective arms extending from the elongate body.

58. The method of claim 53, wherein the biological structure comprises an elongate structure.

59. The method of claim 58, wherein the elongate structure comprises a ligament.

60. The method of claim 53, further comprising tying the first and second suture portions together to form a knot.

61. The method of claim 53, wherein the suture retrieving member comprises a needle.

* * * * *